US012760080B2

(12) United States Patent
Parekkadan et al.

(10) Patent No.: US 12,760,080 B2
(45) Date of Patent: Oct. 13, 2026

(54) PERSONALIZED AND TIMED RELEASE OF BIOMOLECULES

(71) Applicants: The General Hospital Corporation, Boston, MA (US); Rutgers, The State University of New Jersey, New Brunswick, NJ (US)

(72) Inventors: Biju Parekkadan, Cambridge, MA (US); Alexandra Burr, New Brunswick, NJ (US); Alfred Tamayo, West Roxbury, MA (US)

(73) Assignees: Rutgers, The State University of New Jersey, New Brunswick, NJ (US); The General Hospital Corporation, Boston, MA (US)

( * ) Notice: Subject to any disclaimer, the term of this patent is extended or adjusted under 35 U.S.C. 154(b) by 1350 days.

(21) Appl. No.: 17/434,244

(22) PCT Filed: Feb. 27, 2020

(86) PCT No.: PCT/US2020/020125

§ 371 (c)(1),
(2) Date: Aug. 26, 2021

(87) PCT Pub. No.: WO2020/176744

PCT Pub. Date: Sep. 3, 2020

(65) Prior Publication Data

US 2022/0144913 A1 May 12, 2022

Related U.S. Application Data

(60) Provisional application No. 62/811,497, filed on Feb. 27, 2019.

(51) Int. Cl.

| | |
|---|---|
| ***A61P 19/02*** | (2006.01) |
| ***A61K 35/28*** | (2015.01) |
| ***A61K 40/10*** | (2025.01) |
| ***A61K 40/22*** | (2025.01) |
| ***A61K 40/41*** | (2025.01) |
| ***A61P 3/04*** | (2006.01) |
| ***A61P 3/10*** | (2006.01) |
| ***A61P 3/14*** | (2006.01) |
| ***A61P 5/18*** | (2006.01) |
| ***A61P 19/08*** | (2006.01) |
| ***A61P 21/06*** | (2006.01) |
| ***A61P 37/06*** | (2006.01) |
| ***C07K 14/505*** | (2006.01) |
| ***C07K 14/605*** | (2006.01) |
| ***C07K 14/635*** | (2006.01) |
| ***C07K 14/715*** | (2006.01) |
| *A61K 38/00* | (2006.01) |

(52) U.S. Cl.

CPC ............ *C07K 14/605* (2013.01); *A61K 35/28* (2013.01); *A61K 40/10* (2025.01); *A61K 40/22* (2025.01); *A61K 40/416* (2025.01); *A61K 40/418* (2025.01); *A61P 3/04* (2018.01); *A61P 3/10* (2018.01); *A61P 19/02* (2018.01); *A61P 37/06* (2018.01); *C07K 14/505* (2013.01); *C07K 14/635* (2013.01); *C07K 14/7155* (2013.01); *A61K 38/00* (2013.01); *C07K 2319/02* (2013.01)

(58) Field of Classification Search

CPC .. C07K 14/605; C07K 14/505; C07K 14/635; C07K 14/7155; C07K 2319/02; A61K 35/28; A61K 39/461; A61K 39/4621; A61K 39/46433; A61K 39/46434; A61K 38/00; A61P 3/04; A61P 3/10; A61P 19/02; A61P 37/06

See application file for complete search history.

(56) References Cited

U.S. PATENT DOCUMENTS

| | | | |
|---|---|---|---|
| 4,868,116 | A | 9/1989 | Morgan et al. |
| 4,980,286 | A | 12/1990 | Morgan et al. |
| 5,328,470 | A | 7/1994 | Nabel et al. |
| 5,641,670 | A | 6/1997 | Treco et al. |
| 2004/0143104 | A1 | 7/2004 | Wadsworth et al. |
| 2008/0311552 | A1 | 12/2008 | Min |
| 2011/0269817 | A1 | 11/2011 | Sassone-Corsi et al. |

FOREIGN PATENT DOCUMENTS

| | | |
|---|---|---|
| EP | 0043075 | 1/1982 |
| JP | H1047381 | 2/1998 |
| WO | WO 1989/002468 | 3/1989 |
| WO | WO 1989/005345 | 6/1989 |
| WO | WO 1989/007136 | 8/1989 |
| WO | WO 1991/006309 | 5/1991 |
| WO | WO 1992/007573 | 5/1992 |
| WO | WO 2018/075978 | 4/2018 |

OTHER PUBLICATIONS

Papadakis, E.D. et al. “Promoters and control elements: designing expression cassettes for gene therapy”. Current Gene Therapy, vol. 4 (2004), pp. 89-113. (Year: 2004).*

El-Fakharany, E.M. et al. “The use of proteins and peptides based therapy in managing and preventing pathogenic viruses”. International Journal of Biological Macromolecules, vol. 270 (2024), p. 132254. (Year: 2024).*

Yuan, G. et al. “The Circadian Gene Clock Regulates Bone Formation via PDIA3”. Journal of Bone and Mineral Research, vol. 32 (2017), pp. 861-871. (Year: 2017).*

Bozek, K. et al. “Promoter analysis of mammalian clock controlled genes”. Genome Informatics, vol. 18 (2007), pp. 65-74. (Year: 2007).*

(Continued)

*Primary Examiner* — Nancy J Leith
*Assistant Examiner* — Alexandra Geraldine Dace Denito
(74) *Attorney, Agent, or Firm* — Fish & Richardson P.C.

(57) ABSTRACT

Methods and compositions for use in engineering cells to secrete therapeutic biomolecules into the blood stream in vivo in response to an individual’s personal biological needs.

9 Claims, 40 Drawing Sheets

Specification includes a Sequence Listing.

(56) References Cited

OTHER PUBLICATIONS

Patton, J.S. et al. "Inhaling medicines: delivering drugs to the body through the lungs". Nature Reviews, vol. 6 (2007), pp. 67-74. (Year: 2007).*
German, M.S. et al. "The Insulin Gene Contains Multiple Transcriptional Elements That Respond to Glucose". Molecular and Cellular Biology, vol. 14 (1994), pp. 4067-4075. (Year: 1994).*
Rupp, E. et al. "The promoter of the human parathyroid hormone gene contains a functional cyclic AMP-response element", Nucleic Acids Research, vol. 18 (1990), pp. 5677-5683. (Year: 1990).*
Liu, B. et al. "The expression of functional human parathyroid hormone in a gene therapy model for osteoporosis". Cell Tissue Research, vol. 317 (2004), pp. 57-63. (Year: 2004).*
Reis, A. et al. "Cloning and sequence analysis of the human parathyroid hormone gene region." Human Genetics, vol. 84 (1990), pp. 119-124. (Year: 1990).*
Hunninghake, G.W. et al. "The promoer-regulatory region of the Major Immediate—Early gene of Human Cytomegalovirus responds to T-lymphocyte stimulation and contains functional cyclic AMP-response elements". Journal of Virology, vol. 63 (1989), pp. 3026-3033. (Year: 1989).*
White, H.D. et al. "PTH circadian rhythm and PTH target-organ sensitivity is altered in patients with Adult Growth Hormone Deficiency with low BMD". Journal of Bone and Mineral Research, vol. 22, No. 11 (2007), pp. 1798-1807. (Year: 2007).*
Ueda, H.R. et al. "System-level identification of transcriptional circuits underlying mammalian circadian clocks". Nature Genetics, vol. 37, No. 2 (2005), pp. 187-192. (Year: 2005).*
Nakajima, Y. et al. "Identification of Epha4 enhancer required for segmental expression and the regulation by Mesp2". Development , vol. 133 (2006), pp. 2517-2525. (Year: 2006).*
Stern, B. et al. "Improving mammalian cell factories: the selection of signal peptide has a major impact on recombinant protein synthesis and secretion in mammalian cells." Trends in Cell & Molecular Biology, vol. 21 (2007); researchgate.net. (Year: 2007).*
PGL4.24 certificate of analysis obtained from www.promega.com/protocols, updated Nov. 2016. (Year: 2016).*
Mizutani, T. et al. "C/EBPβ (CAAT/enhancer-binding protein β) mediates progesterone production through transcriptional regulation in co-operation with SF-1 (steroidogenic factor-1)." Biochemistry Journal, vol. 460 (2014), pp. 459-471. (Year: 2014).*
Chou, F.-F. et al. "oral gene therapy for Hypothyroidism: A rat model." Human Gene Therapy, vol. 20 (2009), pp. 1344-1350. (Year: 2009).*
Burr et al., "Bioactive, full-length parathyroid hormone delivered using an adeno-associated viral vector," Exp Biol Med (Maywood), Nov. 2022, 247(21):1885-1897.
Al-Janadi et al., "Cytokine profile in systemic lupus erythematosus, rheumatoid arthritis, and other rheumatic diseases," Journal of clinical immunology, 1993, 13(1):58-67.
Arend, "Interleukin-1 receptor antagonist," Advances in Immunology, 1993, 54:167-227.
Armentano et al., "Expression of Human Factor IX in Rabbit Hepatocytes by Retrovirus-Mediated Gene Transfer: Potential for Gene Therapy of Hemophilia B," Proc. Natl. Acad. Sci. USA, 1990, 87:6141-6145.
Aryal et al., "Macromolecular Assemblies of the Mammalian Circadian Clock," Mol Cell., Sep. 2017, 67(5):770-782.e6.
Atreya et al., "Blockade of interleukin 6 trans signaling suppresses T-cell resistance against apoptosis in chronic intestinal inflammation: evidence in crohn disease and experimental colitis in vivo," Nature Medicine, 2000, 6(5):583-588, 7 pages.
Badr et al., "Real-time monitoring of nuclear factor kappaB activity in cultured cells and in animal models," Mol Imaging, Sep. 2009, 8(5):278-90.
Balsalobre et al., "Resetting of circadian time in peripheral tissues by glucocorticoid signaling," Science, Sep. 2000, 289(5488):2344-7.
Berendsen et al., "A simplified subnormothermic machine perfusion system restores ischemically damaged liver grafts in a rat model of orthotopic liver transplantation," Transplant Res., May 2012, 1(1):6, 10 pages.
Binnewies et al., "Understanding the tumor immune microenvironment (TIME) for effective therapy," Nat Med., May 2018, 24(5):541-550, 10 pages.
Bollinger et al., "Circadian clocks in mouse and human CD4+ T cells," PLoS One, Dec. 2011, 6(12):e29801, 11 pages.
Bosio et al., "Isolation and Enrichment of Stem Cells," Adv. Biochem Engin, May 2009, 114:23-72.
Chen et al., "Gene therapy for brain tumors: regression of experimental gliomas by adenovirus-mediated gene transfer in vivo," PNAS USA, Apr. 1994, 91(8):3054-3057.
Chen et al., "Live Cell Imaging of the TGF-β/Smad3 Signaling Pathway In Vitro and In Vivo Using an Adenovirus Reporter System," J Vis Exp., Jul. 2018, 137:e57926, 9 pages.
Chowdhury et al., "Long-term improvement of hypercholesterolemia after ex vivo gene therapy in LDLR-deficient rabbits," Science, Dec. 1991, 254(5039):1802-1805.
Chung et al., "Secreted Gaussia luciferase as a biomarker for monitoring tumor progression and treatment response of systemic metastases," PLoS One, Dec. 2009, 4(12):e8316, 9 pages.
Cohen et al., "Sustained delivery and expression of DNA encapsulated in polymeric nanoparticles," Gene Ther., Dec. 2000, 7(22):1896-1905.
Cooper et al., "Manufacturing of gene-modified cytotoxic T lymphocytes for autologous cellular therapy for lymphoma," Cytotherapy, 2006, 8(2):105-17.
Dai et al., "Gene Therapy via Primary Myoblasts: Long-Term Expression of Factor IX Protein Following Transplantation in vivo," Proc. Natl. Acad. Sci. USA, 1992, 89(22):10892-10895.
Danos and Mulligan, "Safe and Efficient Generation of Recombinant Retroviruses with Amphotropic and Ecotropic Host Ranges," Proc. Natl. Acad. Sci. USA, 1988, 85(17):6460-6464.
De Silva and Bloom, "Gut Hormones and Appetite Control: A Focus on PYY and GLP-1 as Therapeutic Targets in Obesity," Gut Liver, Jan. 2012, 6(1):10-20.
Delrivière et al., "Detailed modified technique for safer harvesting and preparation of liver graft in the rat," Microsurgery, 1996, 17(12):690-6.
Duarte et al., "The interplay of leukemia cells and the bone marrow microenvironment," Blood, Apr. 2018, 131(14):1507-1511.
Dudek and Meng, "Running on time: the role of circadian clocks in the musculoskeletal system," Biochem J, Oct. 2014, 463(Pt 1):1-8.
Eglitis et al., "Gene Expression in Mice After High Efficiency Retroviral—Mediated Gene Transfer," Science, Dec. 1985, 230(4732):1395-1398.
Elman et al., "Pharmacokinetics of Natural and Engineered Secreted Factors Delivered by Mesenchymal Stromal Cells," PLoS One, Feb. 2014, 9(2):e89882, 8 pages.
Feng et al., "Efficient genome editing in plants using a CRISPR/Cas system," Cell Res, Aug. 2013, 23(10):1229-1232, 4 pages.
Ferry et al., "Retroviral-mediated gene transfer into hepatocytes in vivo," Proc. Natl. Acad. Sci. USA, 1991, 88(19):8377-8381.
Fitzsimmons et al., "Mesenchymal Stromal/Stem Cells in Regenerative Medicine and Tissue Engineering," Stem Cells International, 2018, 2018:8031718, 17 pages.
Flotte et al., "Expression of the cystic fibrosis transmembrane conductance regulator from a novel adeno-associated virus promoter," J. Biol. Chem., Feb. 1993, 268(5):3781-3790.
Flotte et al., "Gene expression from adeno-associated virus vectors in airway epithelial cells," Am. J. Respir. Cell. Mol. Biol., Jan. 1992, 7:349-356.
Fraser et al., "The physiology of the circadian rhythm of parathyroid hormone and its potential as a treatment for osteoporosis," Current Opinion in Nephrology and Hypertension, Aug. 2004, 13(4):437-444.
Fuleihan et al., "The parathyroid hormone circadian rhythm is truly endogenous—a general clinical research center study," The Journal of Clinical Endocrinology & Metabolism, 1997, 82(1):281-286.
Gabay et al., "Interleukin 1 receptor antagonist (IL-IRa) is an acute-phase protein," The Journal of clinical investigation, Jun. 1997, 99(12):2930-2940.

(56) References Cited

OTHER PUBLICATIONS

Garaulet et al., "Timing of food intake predicts weight loss effectiveness," Int J Obes (Lond)., Apr. 2013, 37(4):604-11, 8 pages.
Gaucher et al., "Molecular Cogs: Interplay between Circadian Clock and Cell Cycle," Trends Cell Biol., May 2018, 28(5):368-379, 12 pages.
Gekakis et al., "Role of the CLOCK protein in the mammalian circadian mechanism," Science, Jun. 1998, 280(5369):1564-9.
Ghim et al., "The art of reporter proteins in science: past, present and future applications," BMB Rep., Jul. 2010, 43(7):451-60.
Ghivizzani et al., "Direct adenovirus-mediated gene transfer of interleukin 1 and tumor necrosis factor a soluble receptors to rabbit knees with experimental arthritis has local and distal anti-arthritic effects," Proceedings of the National Academy of Sciences, Apr. 1998, 95(8):4613-4618.
Gillessen et al., "A simple method to measure CLOCK-BMAL1 DNA binding activity in tissue and cell extracts," F1000Res., Aug. 2017, 6:1316, 24 pages.
Gratwohl et al., "Hematopoietic stem cell transplantation: a global perspective," JAMA, Apr. 2010, 303(16):1617-24.
Greten et al., "NF-kappaB is a negative regulator of IL-1beta secretion as revealed by genetic and pharmacological inhibition of IKKbeta," Cell, Sep. 2007, 130(5):918-931.
Haj-Ahmand and Graham, "Development of a helper-independent human adenovirus vector and its use in the transfer of the herpes simplex virus thymidine kinase gene," J. Virol., Jan. 1986, 57(1):267-274.
Hanna et al., "Treatment of sickle cell anemia mouse model with iPS cells generated from autologous skin," Science, Dec. 2007, 318(5858):1920-1923.
Hanyu et al., "Per-1 is a specific clock gene regulated by parathyroid hormone (PTH) signaling in osteoblasts and is functional for the transcriptional events induced by PTH," Journal of Cellular Biochemistry, 2011, 112(2):433-438.
Heinrich et al., "Principles of interleukin (IL)-6-type cytokine signalling and its regulation," Biochemical Journal, Aug. 2003, 374(1):1-20.
Heipertz et al., "Circadian Rhythms Influence the Severity of Sepsis in Mice via a TLR2-Dependent, Leukocyte-Intrinsic Mechanism," J Immunol., Jul. 2018, 201(1):193-201.
Hemmers and Rudensky, "The Cell-Intrinsic Circadian Clock Is Dispensable for Lymphocyte Differentiation and Function," Cell Rep., Jun. 2015, 11(9):1339-49.
Hermonat and Muzyczka, "Use of adeno-associated virus as a mammalian DNA cloning vector: transduction of neomycin resistance into mammalian tissue culture cells," Proc. Natl. Acad. Sci. USA, Oct. 1984, 81(20):6466-6470.
Hirota et al., "Identification of small molecule activators of cryptochrome," Science, Aug. 2012, 337(6098):1094-7.
Hockemeyer et al., "Genetic engineering of human pluripotent cells using TALE nucleases," Nat. Biotechnol., Jul. 2011, 29(8):731-734.
Hölsken et al., "Exploiting natural killer cells for therapy of melanoma," Journal der Deutschen Dermatologischen Gesellschaft, Jan. 2015, 13(1):23-28.
Homma et al., "Developing Rods Transplanted into the Degenerating Retina of Crx-Knockout Mice Exhibit Neural Activity Similar to Native Photoreceptors," Stem Cells, Jun. 2013, 31(6):1149-1159.
Huang et al., "Targeting Visceral Fat by Intraperitoneal Delivery of Novel AAV Serotype Vector Restricting Off-Target Transduction in Liver," Molecular Therapy-Methods & Clinical Development, Jun. 2017, 6:68-78.
Huber et al., "Retroviral-mediated gene therapy for the treatment of hepatocellular carcinoma: an innovative approach for cancer therapy.," Proc. Natl. Acad. Sci. USA, Sep. 1991, 88(18):8039-8043.
Hurst et al., "Il-6 and its soluble receptor orchestrate a temporal switch in the pattern of leukocyte recruitment seen during acute inflammation," Immunity, Jun. 2001, 14(6):705-714.
Hutchinson et al., "Peptide hormones and lipopeptides: from self-assembly to therapeutic applications," Journal of Peptide Science, Jan. 2017, 23:82-94.
Imber et al., "Advantages of normothermic perfusion over cold storage in liver preservation," Transplantation, Mar. 2002, 73(5):701-9.
International Preliminary Report on Patentability in International Appln. No. PCT/US2020/20125, dated Aug. 25, 2021, 9 pages.
International Search Report and Written Opinion in International Appln. No. PCT/US2020/20125, dated Jul. 27, 2020, 13 pages.
Invitation to Pay Additional Fees and, Where Applicable, Protest Fee in International Appln. No. PCT/US2020/20125, dated May 18, 2020, 3 pages.
Jinek et al., "RNA-programmed genome editing in human cells," eLife, 2013, 2:e00471, 9 pages.
Jones et al., "Therapeutic strategies for the clinical blockade ofIL-6/gp 130 signaling," The Journal of clinical investigation, Sep. 2011, 121(9):3375-3383.
Kappe et al., "Identification of vascular endothelial growth factor (VEGF) receptor-2 (Flk-1) promoter/enhancer sequences sufficient for angioblast and endothelial cell-specific transcription in transgenic mice," Blood, Jun. 1999, 93(12):4284-4292.
Kay et al., "Hepatic Gene Therapy: Persistent Expression of Human α1-Antitrypsin in Mice after Direct Gene Delivery In Vivo," Human Gene Therapy, Jun. 2008, 3(6):641-647.
Kiessling et al., "Enhancing circadian clock function in cancer cells inhibits tumor growth," BMC Biol., Feb. 2017, 15(1):13, 18 pages.
Kim and Eberwine, "Mammalian cell transfection: the present and the future," Anal Bioanal Chem, Aug. 2010, 397(8):3173-3178.
Kim et al., "Ex vivo gene delivery of IL-1Ra and soluble TNF receptor confers a distal synergistic therapeutic effect in antigen-induced arthritis," Molecular Therapy, Dec. 2002, 6(5):591-600.
Kozmik et al., " The promoter of the CD19 gene is a target for the B-cell-specific transcription factor BSAP," Molecular and Cellular Biology, Jun. 1992, 12(6):2662-2672.
Krevvata et al., "Inhibition of leukemia cell engraftment and disease progression in mice by osteoblasts," Blood, Oct. 2014, 124(18):2834-46.
Kunimoto et al., "A PTH-responsive circadian clock operates in ex vivo mouse femur fracture healing site," Scientific Reports, Feb. 2016, 6:22409, 8 pages.
Lamia, "Ticking time bombs: connections between circadian clocks and cancer," F1000Res., Oct. 2017, 6:1910, 9 pages.
Lawrence, "The nuclear factor NF-kappaB pathway in inflammation," Cold Spring Harbor Perspectives in Biology, Dec. 2009, 1(6):a001651, 10 pages.
Li et al., "Closed loop bioreactor system for the ex vivo expansion of human T cells," Cytotherapy, Jan. 2019, 21(1):76-82, 7 pages.
Lin et al., "Efficient lentiviral transduction of human mesenchymal stem cells that preserves proliferation and differentiation capabilities," Stem Cells Transl Med., Dec. 2012, 1(12):886-97.
Lu et al., "Extracellular matrix degradation and remodeling in development and disease," Cold Spring Harb Perspect Biol., Dec. 2011, 3(12):a005058, 24 pages.
Maguire et al., "Therapeutics from Adult Stem Cells and the Hype Curve," ACS Medicinal Chemistry Letters, 2016, 7(5):441-43.
Mahla, "Stem Cells Applications in Regenerative Medicine and Disease Therapeutics," International Journal of Cell Biology, 2016, 2016(7):1-24.
Marcucci et al., "Natpara for the treatment of hypoparathyroidism," Expert opinion on biological therapy, Nov. 2016, 16(11):1417-1424.
Martin, "Therapeutic application of pluripotent stem cells: challenges and risks," Front Med (Lausanne), Dec. 2017, 4:229, 8 pages.
McCubrey et al., "Advances in targeting signal transduction pathways," Oncotarget, Dec. 2012, 3(12):1505-21.
McLaughlin et al., "Adeno-associated virus general transduction vectors: analysis of proviral structures," J. Virol., Jun. 1988, 62(6):1963-1973.
Mei et al., "Long-term in vivo recording of circadian rhythms in brains of freely moving mice," Proc Natl Acad Sci U S A, Apr. 2018, 115(16):4276-4281.
Meng et al., "Synergistic Effect of Medium, Matrix, and Exogenous Factors on the Adhesion and Growth of Human Pluripotent Stem Cells Under Defined, Xeno-Free Conditions," Stem Cells Dev, Jul. 2012, 21(11):2036-2048.

(56) References Cited

OTHER PUBLICATIONS

Mergental et al., "Development of Clinical Criteria for Functional Assessment to Predict Primary Nonfunction of High-Risk Livers Using Normothermic Machine Perfusion," Liver Transpl., Oct. 2018, 24(10):1453-69.
Meuli et al., "Efficient gene expression in skin wound sites following local plasmid injection," J. Invest. Dermatol., 2001, 116(1):131-135.
Miagkov et al., "NF-kappaB activation provides the potential link between inflammation and hyperplasia in the arthritic joint," Proceedings of the National Academy of Sciences, Nov. 1998, 95(23):13859-13864.
Mizuno et al., "Abstract: Basic research for interferon gene therapy against malignant glioma," No Shinkei Geka—Neurological Surgery, May 1992, 20(5):547-551, 1 page [English Abstract Only].
Morimoto, "Cells in stress: transcriptional activation of heat shock genes," Science, Mar. 1993, 259(5100):1409-1410.
Morimoto, "Regulation of the heat shock transcriptional response: cross talk between a family of heat shock factors, molecular chaperones, and negative regulators," Genes & development, Dec. 1998, 12(24):3788-3796.
Mosser et al., "In vitro activation of heat shock transcription factor DNA-binding by calcium and biochemical conditions that affect protein conformation," Proceedings of the National Academy of Sciences, May 1990, 87(10):3748-3752.
Mure et al., "Diurnal transcriptome atlas of a primate across major neural and peripheral tissues," Science, Mar. 2018, 359(6381):eaao0318, 11 pages.
Muzyczka, "Use of adeno-associated virus as a general transduction vector for mammalian cells," Curr. Topics in Micro. and Immunol., 1992, 158:97-129.
Nakagawa et al., "Generation of induced pluripotent stem cells without Myc from mouse and human fibroblasts," Nat Biotech, 2008, 26:101-106.
Nakagawa et al., "A novel efficient feeder-free culture system for the derivation of human induced pluripotent stem cells," Sci Rep, Jan. 2014, 4:3594, 7 pages.
Nakajima et al., "cDNA cloning and characterization of a secreted luciferase from the luminous Japanese ostracod, Cypridina noctiluca," Biosci Biotechnol Biochem., Mar. 2004, 68(3):565-70.
Nelson et al., "Repair of Acute Myocardial Infarction by Human Stemness Factors Induced Pluripotent Stem Cells," Circulation, Aug. 2009, 120(5):408-416, 9 pages.
Nielsen, "Predicting Secretory Proteins with SignalP," Methods in Molecular Biology, 2017, 1611:59-73.
Nobis et al., "The circadian clock of CD8 T cells modulates their early response to vaccination and the rhythmicity of related signaling pathways," Proc Natl Acad Sci U S A, Oct. 2019, 116(40):20077-20086.
Okubo et al., "Parathyroid hormone resets the cartilage circadian clock of the organ-cultured murine femur," Acta Orthopaedica, 2015, 86(5):627-631.
Owen and Riley, "In vitro Models of Bone Remodelling and Associated Disorders," Front. Bioeng. Biotechnol., Oct. 2018, 6(134): 23 pages.
Padmanabhan and Billaud, "Desynchronization of Circadian Clocks in Cancer: A Metabolic and Epigenetic Connection," Front Endocrinol (Lausanne), Jun. 2017, 8:136, 7 pages.
Parsell et al., "Protein disaggregation mediated by heat-shock protein Hsp104," Nature, 1994, 372(6505):475-478.
Partch et al., "Molecular architecture of the mammalian circadian clock," Trends Cell Biol., Feb. 2014, 24(2):90-9, 10 pages.
Pick et al., "Time-of-Day-Dependent Trafficking and Function of Leukocyte Subsets," Trends Immunol., Jun. 2019, 40(6):524-537.
Potter et al., "Response to continuous and pulsatile PTH dosing: A mathematical model for parathyroid hormone receptor kinetics," Bone, Aug. 2005, 37(2):159-169.
Puram et al., "Core Circadian Clock Genes Regulate Leukemia Stem Cells in AML," Cell, Apr. 2016, 165(2):303-316.
Qin et al., "Systematic comparison of constitutive promoters and the doxycycline-inducible promoter," PLoS One, 2010, 5(5):e10611, 4 pages.
Qin et al., "Parathyroid hormone: a double-edged sword for bone metabolism," Trends in Endocrinology & Metabolism, Mar. 2004, 15(2):60-65.
Redmond et al., "Diurnal rhythms of bone turnover markers in three ethnic groups," The Journal of Clinical Endocrinology & Metabolism, Aug. 2016, 101(8):3222-3230.
Reinders and Hoogduijn, "NK Cells and MSCs: Possible Implications for MSC Therapy in Renal Transplantation," J Stem Cell Res Ther., 2014, 4(2):1000166, 4 pages.
Richmond et al., "Investigating causal relations between sleep traits and risk of breast cancer in women: mendelian randomisation study," BMJ, Jun. 2019, 365:12327, 12 pages.
Roh et al., "Modification of enhanced green fluorescent protein for secretion out of cells," Biotechnol Bioproc E, 2013, 18:1135-1141.
Rosenfeld et al., "In vivo transfer of the human cystic fibrosis transmembrane conductance regulator gene to the airway epithelium," Cell, Jan. 1992, 68(1):143-155.
Rosenfeld et al., "Adenovirus-Mediated Transfer of a Recombinant α1-Antitrypsin Gene to the Lung Epithelium in Vivo," Science, Apr. 1991, 252(5004):431-434.
Saland et al., "A robust and rapid xenograft model to assess efficacy of chemotherapeutic agents for human acute myeloid leukemia," Blood Cancer J, Mar. 2015, 5(3):e297, 7 pages.
Samulski et al., "Helper-free stocks of recombinant adeno-associated viruses: normal integration does not require viral gene expression," J. Virol., 1989, 63:3822-3828.
Schneider et al., "Characterization of EBV-genome negative "null" and "T" cell lines derived from children with acute lymphoblastic leukemia and leukemic transformed non-Hodgkin lymphoma," Int J Cancer, May 1977, 19(5):621-6.
Schofield et al., "Neutrophils—a key component of ischemia-reperfusion injury," Shock, 2013, 40(6):463-70.
Serup et al., "Induction of insulin and islet amyloid polypeptide production in pancreatic islet glucagonoma cells by insulin promoter factor 1," Proceedings of the National Academy of Sciences, 1996, 93(17):9015-9020.
Sever and Brugge, "Signal transduction in cancer," Cold Spring Harb Perspect Med., Apr. 2015, 5(4):a006098, 22 pages.
Shen et al., "Suicide Gene-Engineered Stromal Cells Reveal a Dynamic Regulation of Cancer Metastasis," Sci Rep., Feb. 2016, 6:21239, 8 pages.
Silver and Levi, "Regulation of PTH synthesis and secretion relevant to the management of secondary hyperparathyroidism in chronic kidney disease," Kidney International, 2005, 67:S8-S12.
Silver et al., "Circadian expression of clock genes in mouse macrophages, dendritic cells, and B cells," Brain Behav Immun., Mar. 2012, 26(3):407-13.
Singleton et al., "An engineered biomarker system to monitor and modulate immune clearance of cell therapies," Cytotherapy, Dec. 2017, 19(12):1537-45, 9 pages.
Song et al., "Insights into the Role of Circadian Rhythms in Bone Metabolism: A Promising Intervention Target?," Biomed Res Int, Sep. 2018, 2018:9156478, 11 pages.
Sulli et al., "Pharmacological activation of REV-ERBs is lethal in cancer and oncogene-induced senescence," Nature, Jan. 2018, 553(7688):351-355, 24 pages.
Tak and Firestein, "NF-kappaB: a key role in inflammatory diseases," The Journal of clinical investigation, 2001, 107(1):7-11.
Takahashi and Yamanaka, "Induced pluripotent stem cells in medicine and biology," Development, Jun. 2013, 140(12): 2457-2461.
Takahashi et al., "Induction of pluripotent stem cells from adult human fibroblasts by defined factors," Cell, Nov. 2007, 131(5):861-872.
Tam et al., "Stabilized plasmid-lipid particles for systemic gene therapy," Gene Ther., Nov. 2000, 7(21):1867-74.
Tamayo et al., "Histone monoubiquitination by Clock-Bmall complex marks Perl and Per2 genes for circadian feedback," Nat Struct Mol Biol., Oct. 2015, 22(10):759-66, 10 pages.

(56) References Cited

OTHER PUBLICATIONS

Tamayo et al., "Tracking leukemic T-cell transcriptional dynamics in vivo with a blood-based reporter assay," FEBS Open Bio, Sep. 2020, 10(9):1868-1879.
Tannous, "Gaussia luciferase reporter assay for monitoring biological processes in culture and in vivo," Nat Protoc., 2009, 4(4):582-91.
Tannous et al., "Codon-Optimized Gaussia Luciferase cDNA for Mammalian Gene Expression in Culture and in Vivo," Mol Ther., Mar. 2005, 11(3):435-43.
Teng et al., "Systemic Anticancer Neural Stem Cells in Combination with a Cardiac Glycoside for Glioblastoma Therapy," Stem Cells, Aug. 2014, 32(8):2021-32.
Thim et al., "Secretion and processing of insulin precursors in yeast," Proc Natl Acad Sci U S A, Sep. 1986, 83(18):6766-70.
Timón and Beverley, "Structural and functional analysis of the human CD45 gene (PTPRC) upstream region: evidence for a functional promoter within the first intron of the gene," Immunology, Feb. 2001, 102(2):180-189.
Tolboom et al., "A model for normothermic preservation of the rat liver," Tissue Eng., Aug. 2007, 13(8):2143-51.
Tratschin et al., "A human parvovirus, adeno-associated virus, as a eucaryotic vector: transient expression and encapsidation of the procaryotic gene for chloramphenicol acetyltransferase," Mol. Cell. Biol., Oct. 1984, 4(10):2072-2081.
Tratschin et al., "Adeno-Associated Virus Vector for High-Frequency Integration, Expression, and Rescue of Genes in Mammalian Cells," Mol. Cell. Biol., Nov. 1985, 5(11):3251-3260.
Tratschin et al., "Genetic analysis of adeno-associated virus: properties of deletion mutants constructed in vitro and evidence for an adeno-associated virus replication function," J. Virol., Sep. 1984, 51(3):611-619.
Ueda et al., "A transcription factor response element for gene expression during circadian night," Nature, Aug. 2002, 418(6897):534-9.
Uygun et al., "Diluted Blood Reperfusion as a Model for Transplantation of Ischemic Rat Livers: Alanine Aminotransferase Is a Direct Indicator of Viability," Transplant Proc., Sep. 2010, 42(7):2463-7.
Van Beusechem et al., "Long-term expression of human adenosine deaminase in rhesus monkeys transplanted with retrovirus-infected bone-marrow cells," Proc. Natl. Acad. Sci. USA, Aug. 1992, 89:7640-7644.
Verhaegen and Christopoulos, "Recombinant Gaussia luciferase. Overexpression, purification, and analytical application of a bioluminescent reporter for DNA hybridization," Anal Chem., Sep. 2002, 74(17):4378-85.
Verlande and Masri, "Circadian Clocks and Cancer: Timekeeping Governs Cellular Metabolism," Trends Endocrinol Metab., Jul. 2019, 30(7):445-458, 14 pages.
Vokes et al., "Recombinant Human Parathyroid Hormone Effect on Health-Related Quality of Life in Adults With Chronic Hypoparathyroidism" The Journal of Clinical Endocrinology & Metabolism, Feb. 2018, 103(2):722-731.
Vollmers et al., "A high-throughput assay for siRNA-based circadian screens in human U2OS cells," PLoS One, 2008, 3(10):e3457, 6 pages.
Waage et al., "Interleukin-6 in synovial fluid from patients with arthritis," Clinical immunology and immunopathology, 1989, 50(3):394-398.
Wang et al., "One-step generation of mice carrying mutations in multiple genes by CRISPR/Cas-mediated genome engineering," Cell, 2013, 153(4): 910-918, 13 pages.
Wang et al., "The EF-1α promoter maintains high-level transgene expression from episomal vectors in transfected CHO-K1 cells," J Cell Mol Med., Nov. 2017, 21(11):3044-3054.
Wang et al., "Isolation of neuronal precursors by sorting embryonic forebrain transfected with GFP regulated by the Tα1 tubulin promoter," Nature Biotechnology, 1998, 16(2):196-201.
Watanabe et al., "Multichannel perfusion culture bioluminescence reporter system for long-term detection in living cells," Anal Biochem., Jul. 2010, 402(1):107-9.
Whalen et al., "Adenoviral transfer of the viral IL-10 gene periarticularly to mouse paws suppresses development of collagen-induced arthritis in both injected and uninjected paws," The journal of immunology, 1999, 162(6):3625-3632.
Wilson et al., "Retrovirus-mediated transduction of adult hepatocytes," Proc. Natl. Acad. Sci. USA, May 1988, 85(9):3014-3018.
Winer et al., "Long-term treatment of hypoparathyroidism: a randomized controlled study comparing parathyroid hormone-(1-34) versus calcitriol and calcium," The Journal of Clinical Endocrinology & Metabolism, 2003, 88(9):4214-4220.
Wondisford et al., "Cloning of the Human Thyrotropin β-Subunit Gene and Transient Expression of Biologically Active Human Thyrotropin after Gene Transfection," Mol. Endocrinol., Jan. 1988, 2(1):32-39.
Wu et al., "Dual-reporter assay using two secreted luciferase genes," Biotechniques, Mar. 2007, 42(3):290-292.
Wurdinger et al., "A secreted luciferase for ex vivo monitoring of in vivo processes," Nat Methods., Feb. 2008, 5(2):171-3.
Yamada et al., "Monitoring circadian time in rat plasma using a secreted Cypridina luciferase reporter," Anal Biochem., Aug. 2013, 439(2):80-7.
Yi et al., "Transcriptional repression of type I procollagen genes during adipocyte differentiation," Experimental & molecular medicine, 2001, 33(4):269-275.
Yu et al., "Induced pluripotent stem cell lines derived from human somatic cells," Science, Dec. 2007, 318(5858):1917-1920.
Yu et al., "$T_H$17 cell differentiation is regulated by the circadian clock," Science, Nov. 2013, 342(6159):727-30.
Zhang et al., "A genome-wide RNAi screen for modifiers of the circadian clock in human cells," Cell, Oct. 2009, 139(1):199-210.
Zhang et al., "A circadian gene expression atlas in mammals: implications for biology and medicine," Proc Natl Acad Sci U S A, Nov. 2014, 111(45):16219-24.
Zhang et al., "Salidroside Inhibits Myogenesis by Modulating p-Smad3-Induced Myf5 Transcription," Frontiers in pharmacology, 2018, 9:209, 11 pages.
Zhong et al., "Direct sensing of heat and oxidation by *Drosophila* heat shock transcription factor," Molecular Cell, 1998, 2(1):101-108.
Zielinski et al., "Strengths and limitations of period estimation methods for circadian data," PLoS One, May 2014, 9(5):e96462, 26 pages.

* cited by examiner

| Physiological/Molecular Cue or Induction Mechanism | Pathway | Peptide Drug | Indication |
|---|---|---|---|
| Circadian Rhythms | Core Clock | GLP-1 | Diabetes and Obesity |
| Increased Inflammatory Cytokine Concentration | NFκB | IL-1RA or GP130 | Rheumatoid Arthritis |
| Oxygen Below Physiological Concentration | Hypoxia Inducible Factor | EPO | CKD related Anemia |
| Calcium Concentration | Calcium Response | PTH | Hypoparathyroidism |
| Temperature Above Physiological Norm | Heat Shock Factor | IL-1RA or GP130 | Rheumatoid Arthritis |
| Oral Administration of Dexamethasone | Glucocorticoid Response | Fuzeon | HIV-1 |

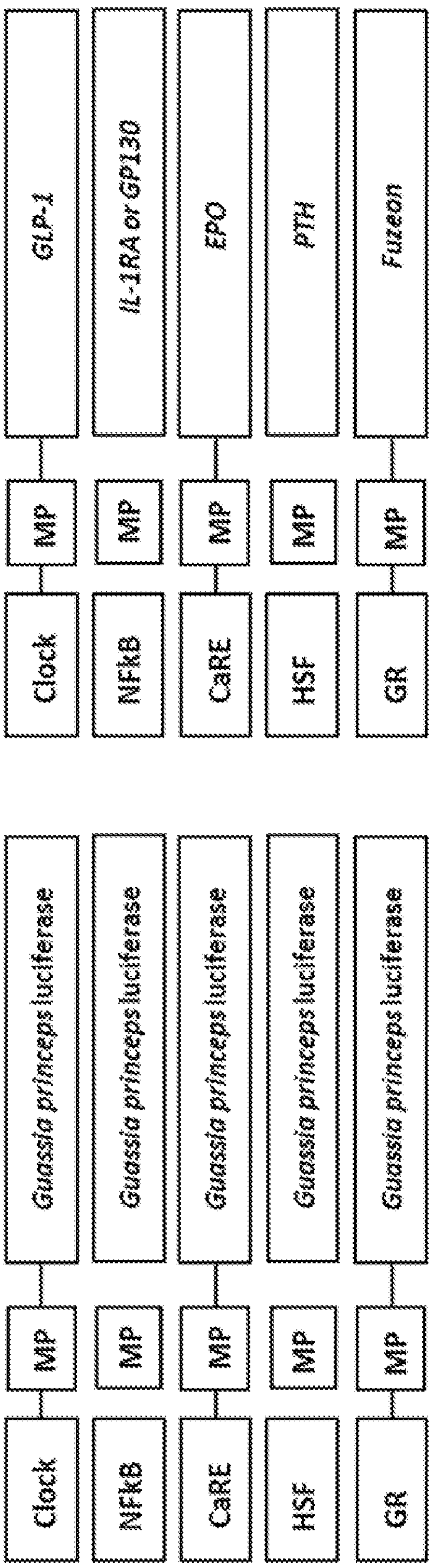

*FIG. 2*

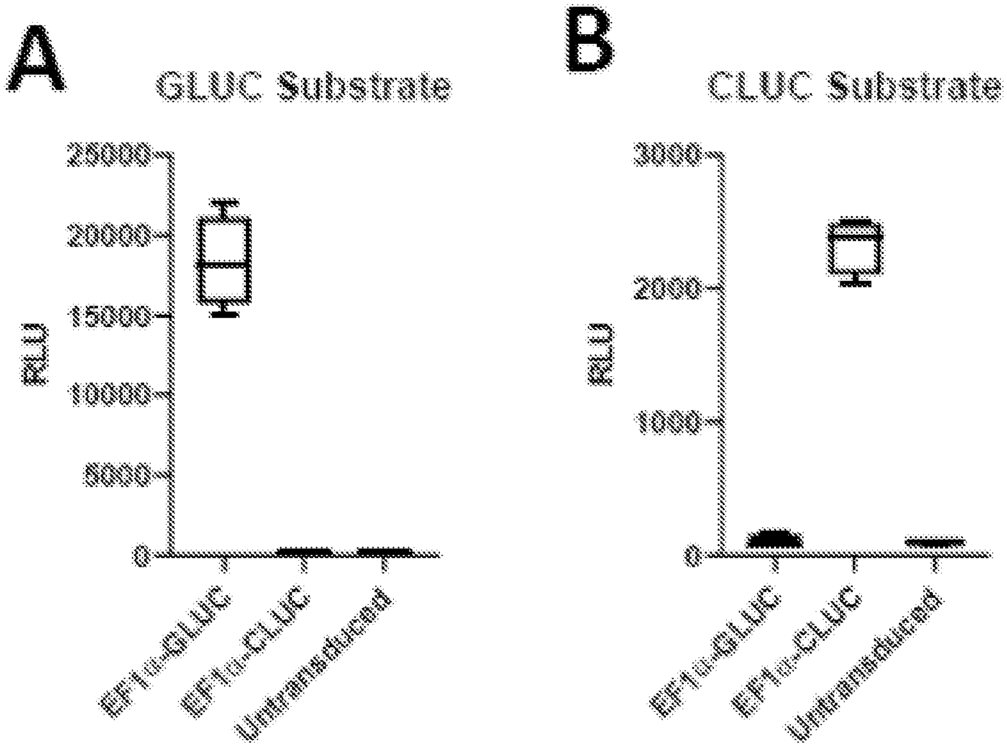
FIGs. 17A-B

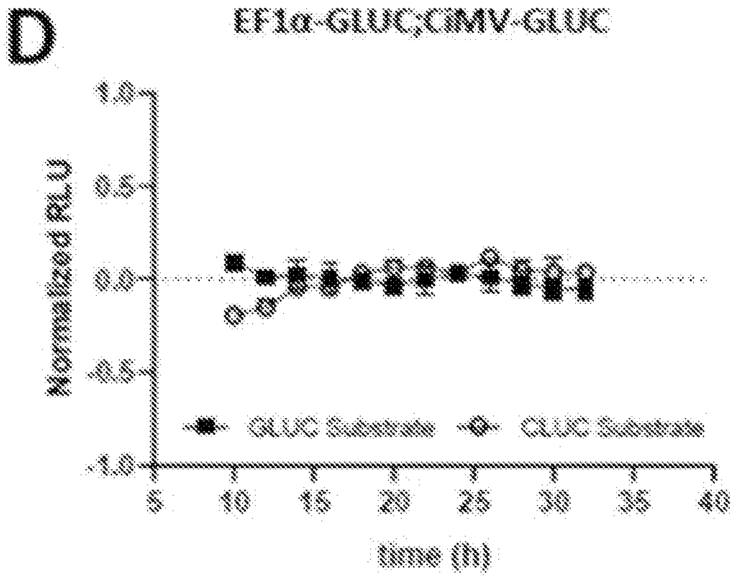
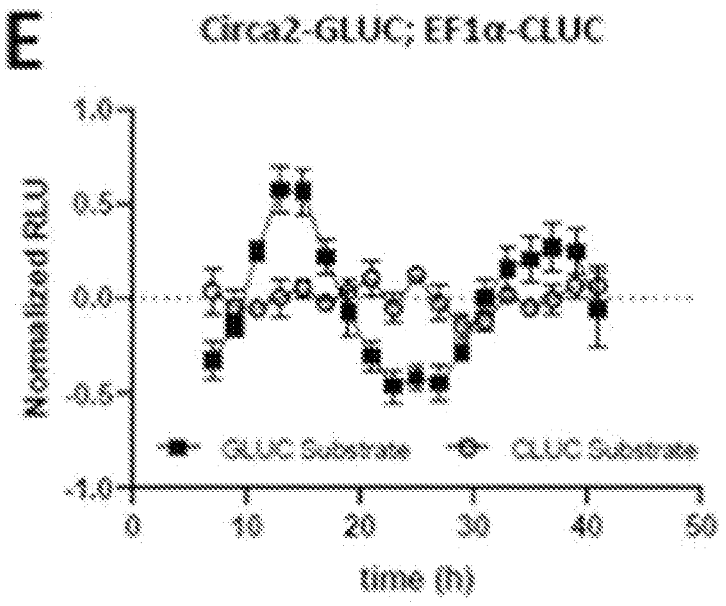
FIGs. 17D-E

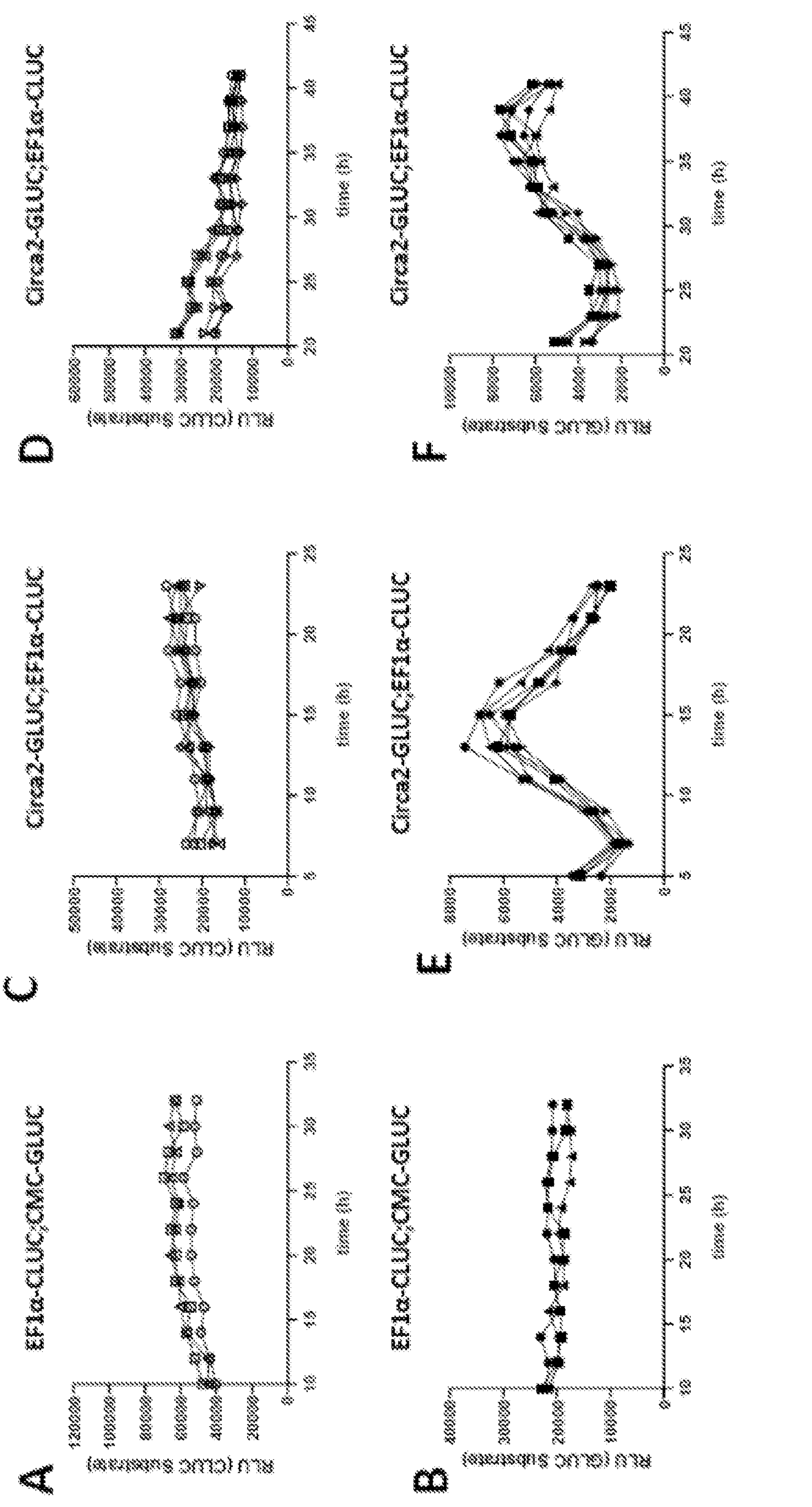
*FIGs. 18A-F*

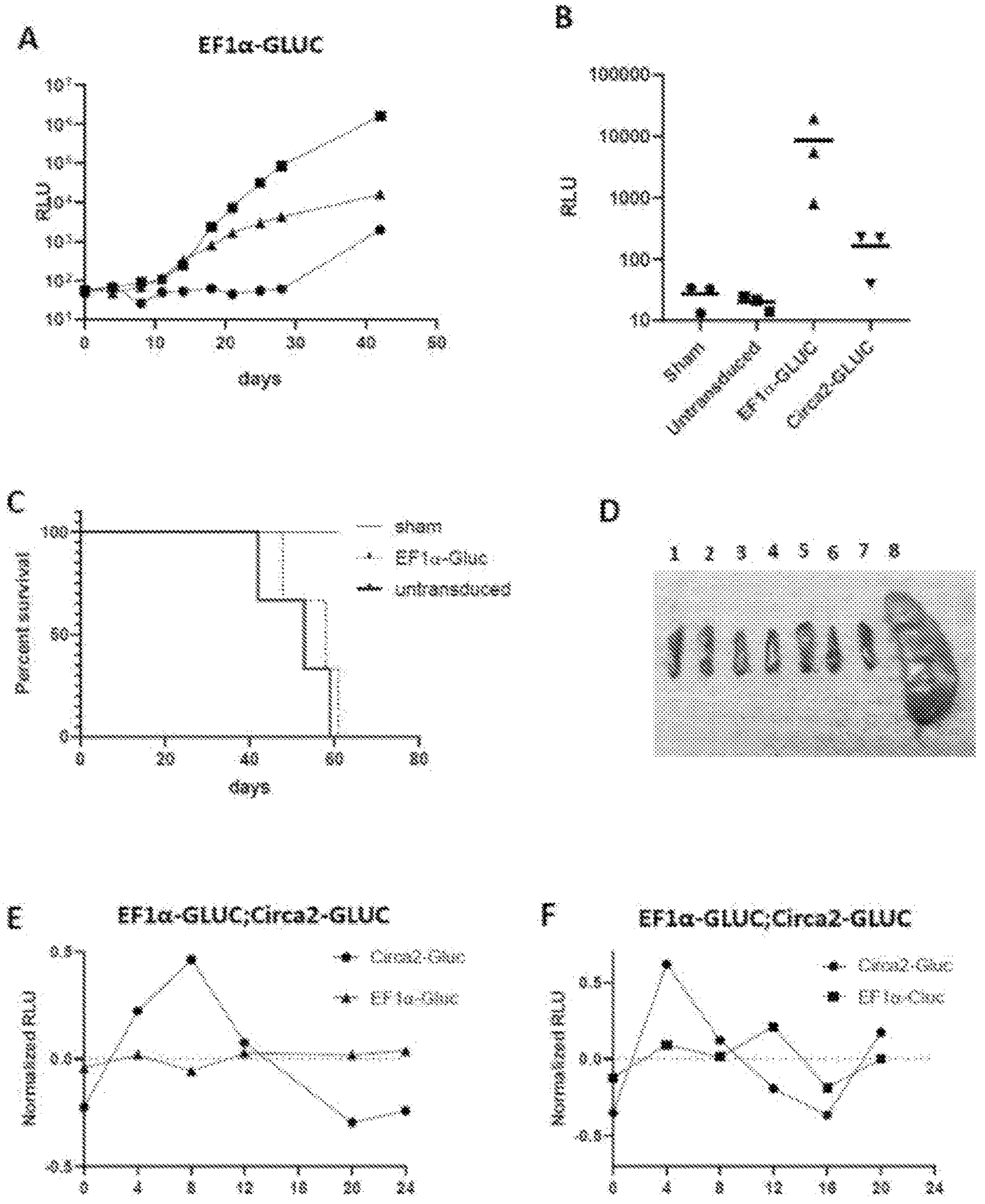
*FIGs. 20A-F*

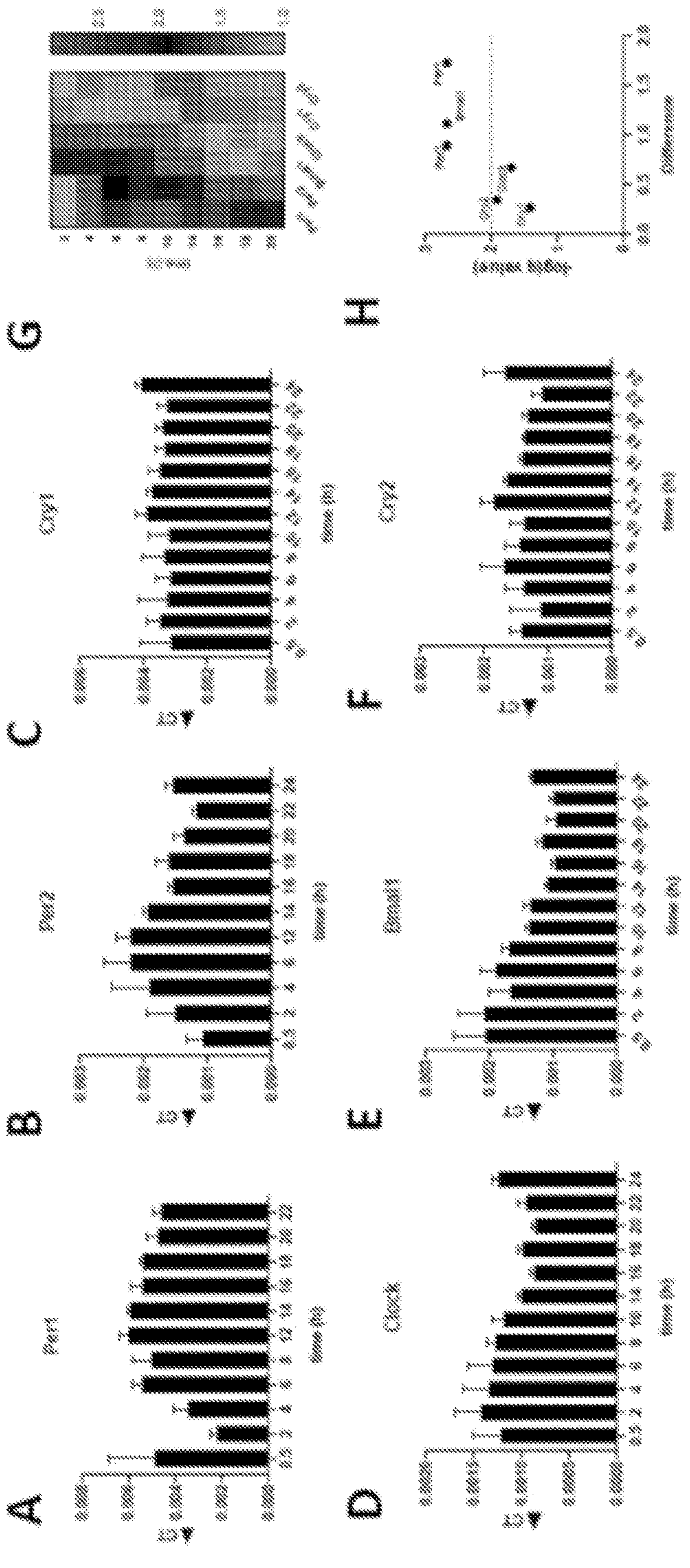
*FIGs. 23A-H*

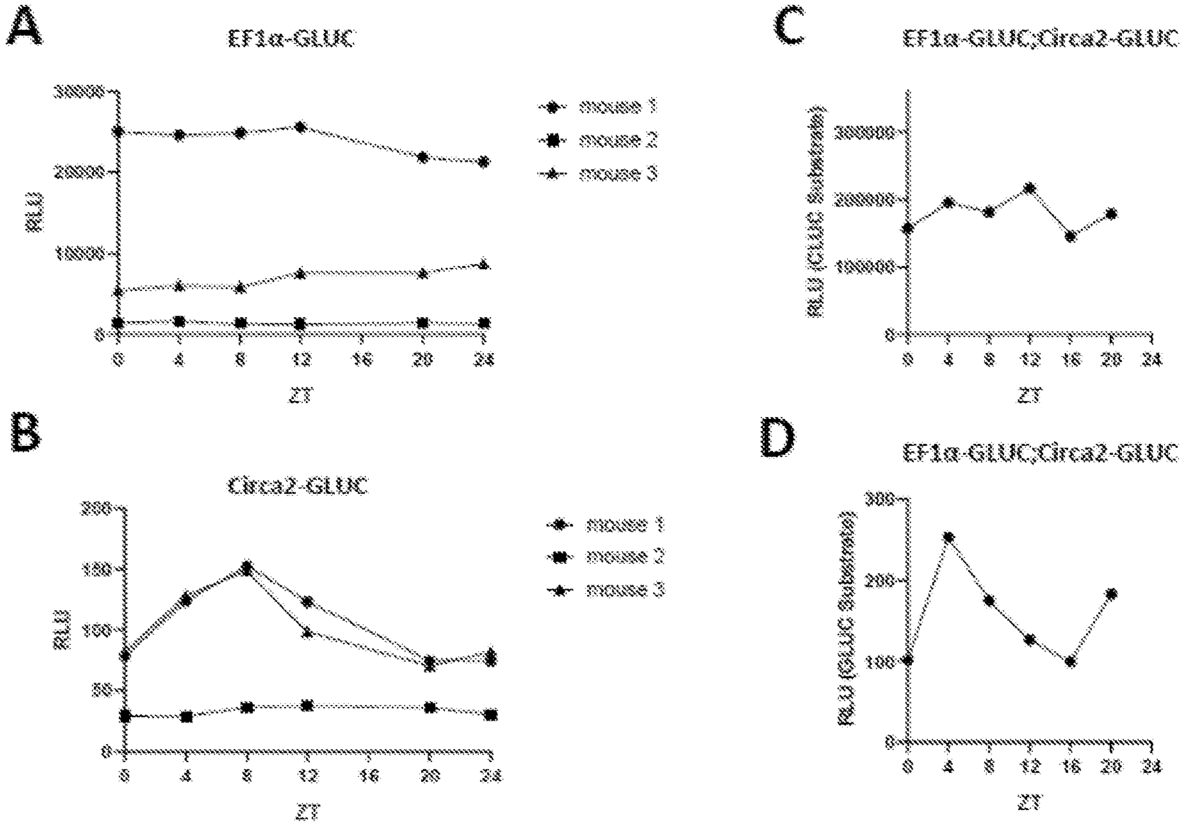
FIGs. 24A-D

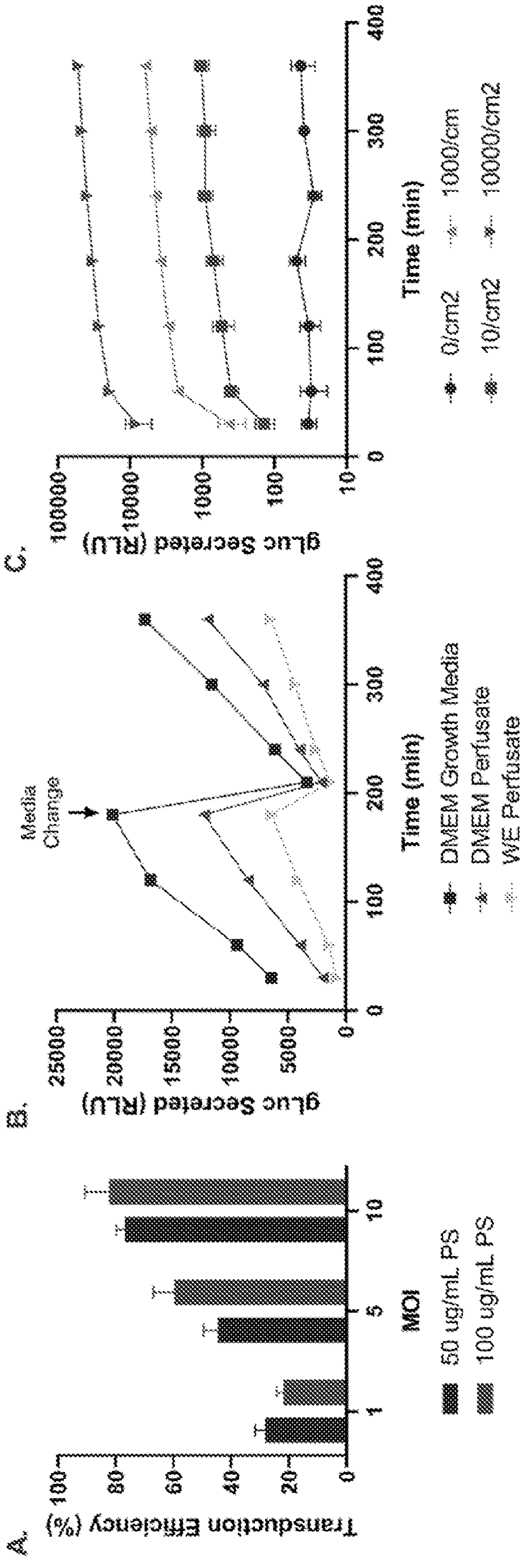
FIGs. 25A-C

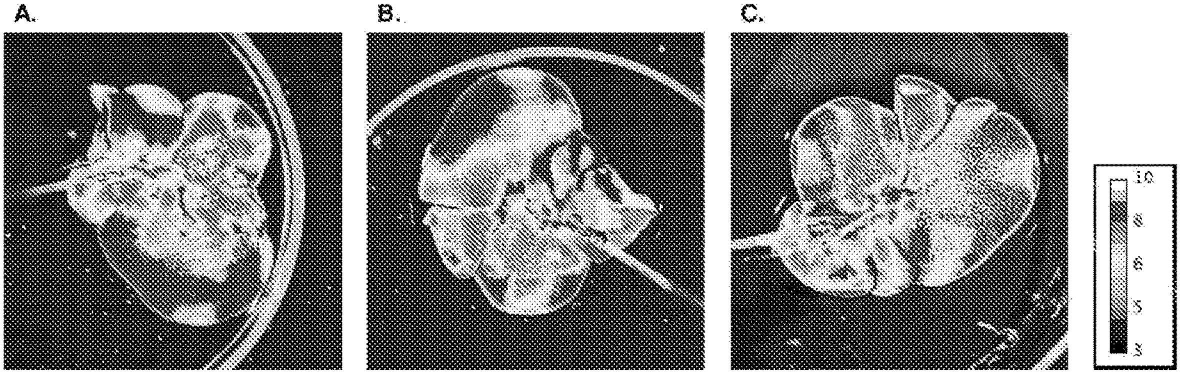
FIGs. 26A-C
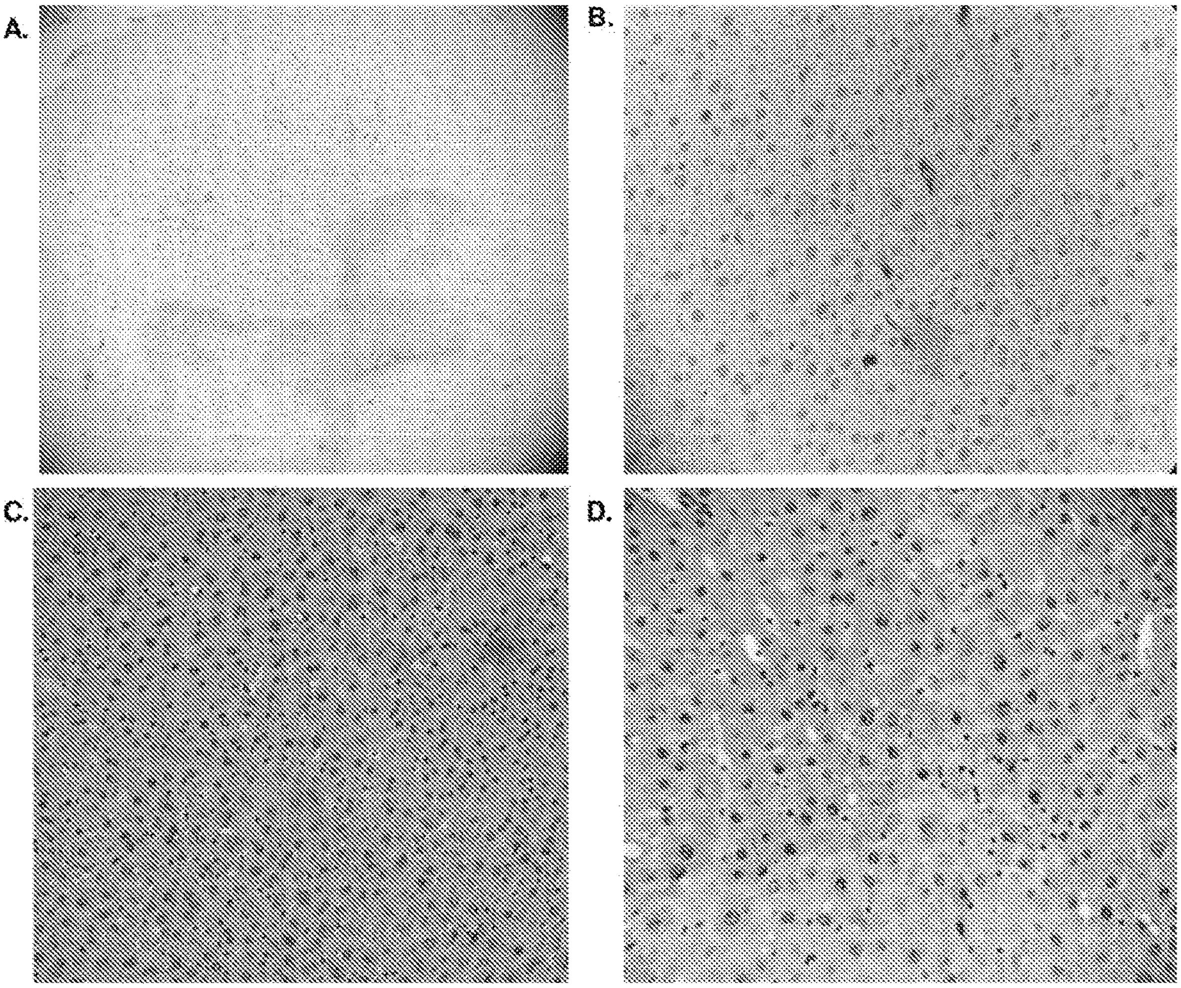
FIGs. 27A-D

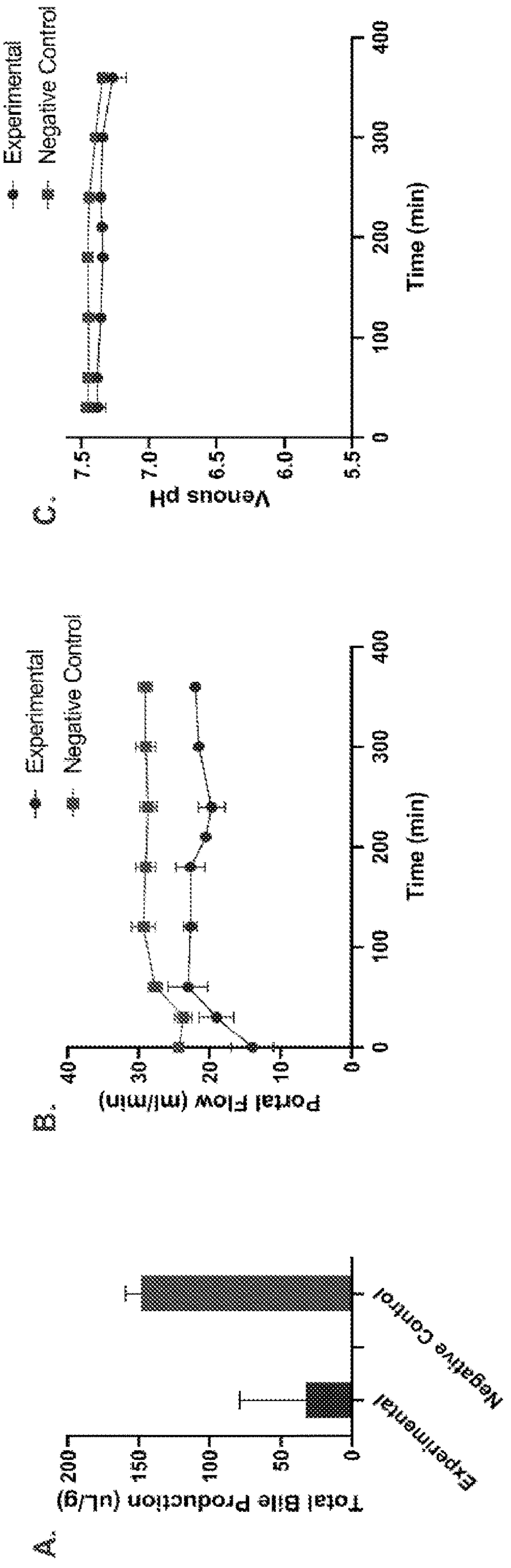
FIGs. 28A-C

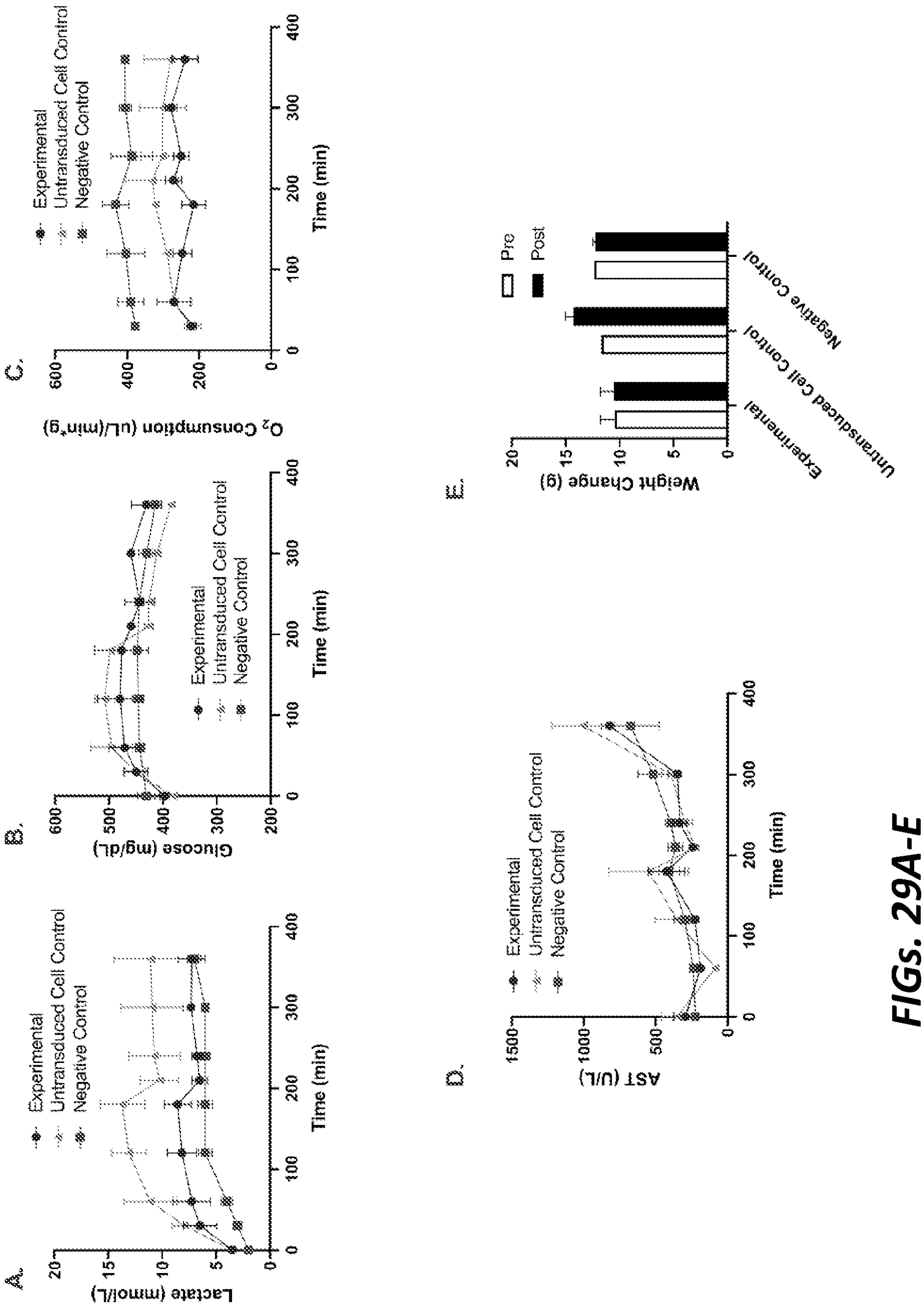
*FIGs. 29A-E*

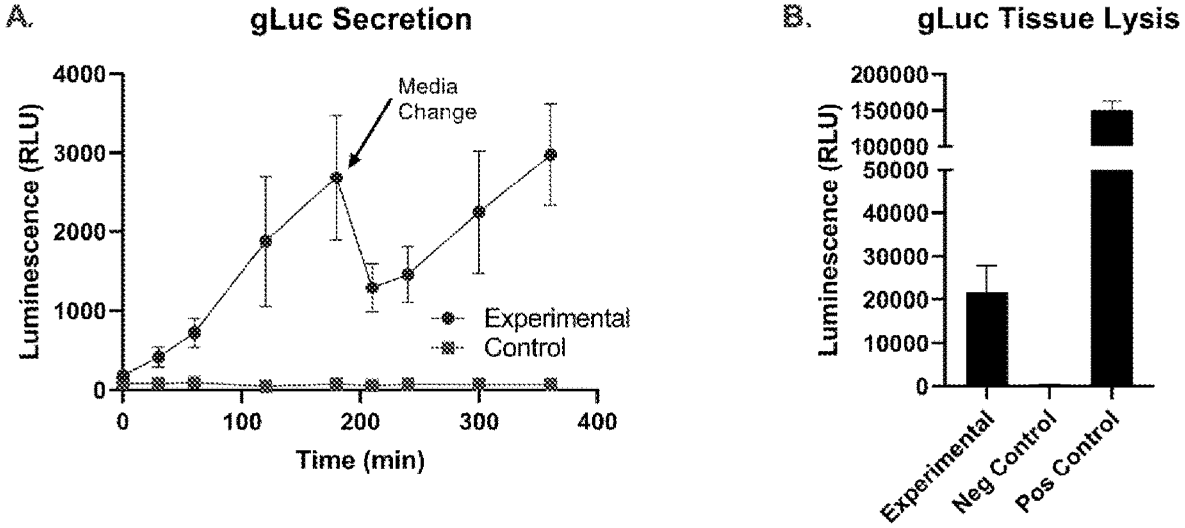
FIGs. 30A-B
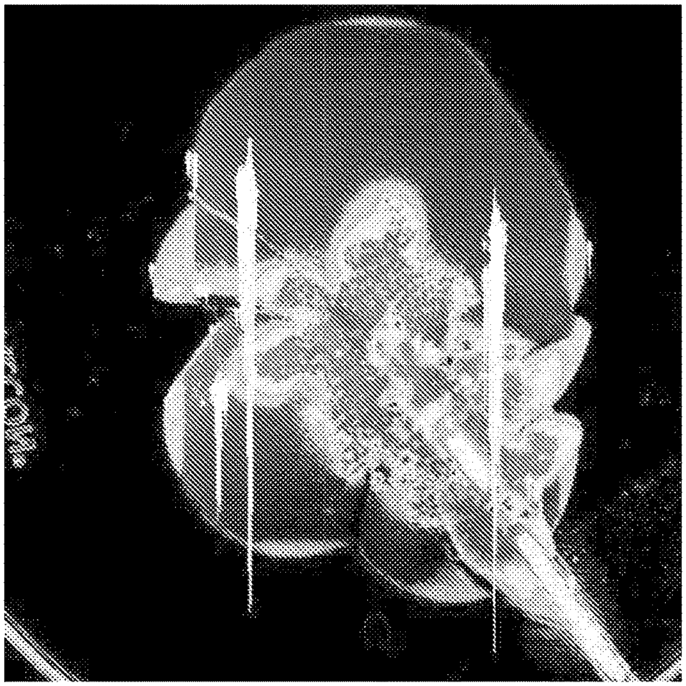
FIG. 31

SEQUENCE LISTING

```
<160> NUMBER OF SEQ ID NOS: 38

<210> SEQ ID NO 1
<211> LENGTH: 65
<212> TYPE: DNA
<213> ORGANISM: Homo sapiens

<400> SEQUENCE: 1

tcgagcagta tttagccacg tgacagtgta agcacacgtg ggccctcaag tccacgtgca      60

gggag                                                                  65


<210> SEQ ID NO 2
<211> LENGTH: 62
<212> TYPE: DNA
<213> ORGANISM: Homo sapiens

<400> SEQUENCE: 2

gggaatttcc cgggaatttc cgggactttc cgggaatttc ccgggaattt ccgggacttt      60

cc                                                                     62


<210> SEQ ID NO 3
<211> LENGTH: 70
<212> TYPE: DNA
<213> ORGANISM: Homo sapiens

<400> SEQUENCE: 3

gggaaaatga aactgggaaa acgaaactgg gaaaatgaaa gtgggaaaat gaaactggga      60

aaatgaaact                                                             70


<210> SEQ ID NO 4
<211> LENGTH: 48
<212> TYPE: DNA
```

<213> ORGANISM: Homo sapiens

<400> SEQUENCE: 4
ggacgtgcgg acgtgcgggc gtgcggacgt gcggacgtgc ggacgtgc 48

<210> SEQ ID NO 5
<211> LENGTH: 72
<212> TYPE: DNA
<213> ORGANISM: Homo sapiens

<400> SEQUENCE: 5
gggaacatta tgtcctgtgg gaacagtatg tcctgaggga acattatgtc ctgtgggaac 60
attatgtcct gt 72

<210> SEQ ID NO 6
<211> LENGTH: 71
<212> TYPE: DNA
<213> ORGANISM: Homo sapiens

<400> SEQUENCE: 6
attctagaac gttctttcca gaacgttctt tctagaacgt tctttctaga acgttctttc 60
cagaacgttc t 71

<210> SEQ ID NO 7
<211> LENGTH: 33
<212> TYPE: PRT
<213> ORGANISM: Homo sapiens

<400> SEQUENCE: 7

His Ala Glu Gly Thr Phe Thr Ser Asp Val Ser Ser Tyr Leu Glu Gly
1 5 10 15

Gln Ala Ala Lys Glu Glu Phe Ile Ile Ala Trp Leu Val Lys Gly Arg
20 25 30

Gly

<210> SEQ ID NO 8
<211> LENGTH: 34
<212> TYPE: PRT
<213> ORGANISM: Homo sapiens

<400> SEQUENCE: 8

Ser Val Ser Glu Ile Gln Leu Met His Asn Leu Gly Lys His Leu Asn
1 5 10 15

Ser Met Glu Arg Val Glu Trp Leu Arg Lys Lys Leu Gln Asp Val His
20 25 30

Asn Phe

<210> SEQ ID NO 9
<211> LENGTH: 60
<212> TYPE: PRT
<213> ORGANISM: Homo sapiens

<400> SEQUENCE: 9

Met Arg Pro Ser Gly Arg Lys Ser Ser Lys Met Gln Ala Phe Arg Ile
1 5 10 15

Trp Asp Val Asn Gln Lys Thr Phe Tyr Leu Arg Asn Asn Gln Leu Val
20 25 30

Ala Gly Tyr Leu Gln Gly Pro Asn Val Asn Leu Glu Glu Lys Ile Asp
35 40 45

Val Val Pro Ile Glu Pro His Ala Leu Phe Leu Gly
50 55 60

<210> SEQ ID NO 10
<211> LENGTH: 166
<212> TYPE: PRT
<213> ORGANISM: Homo sapiens

<400> SEQUENCE: 10

Ala Pro Pro Arg Leu Ile Cys Asp Ser Arg Val Leu Glu Arg Tyr Leu
1 5 10 15

Leu Glu Ala Lys Glu Ala Glu Asn Ile Thr Thr Gly Cys Ala Glu His
20 25 30

Cys Ser Leu Asn Glu Asn Ile Thr Val Pro Asp Thr Lys Val Asn Phe
35 40 45

Tyr Ala Trp Lys Arg Met Glu Val Gly Gln Gln Ala Val Glu Val Trp
50 55 60

Gln Gly Leu Ala Leu Leu Ser Glu Ala Val Leu Arg Gly Gln Ala Leu
65 70 75 80

Leu Val Asn Ser Ser Gln Pro Trp Glu Pro Leu Gln Leu His Val Asp
85 90 95

Lys Ala Val Ser Gly Leu Arg Ser Leu Thr Thr Leu Leu Arg Ala Leu
100 105 110

Gly Ala Gln Lys Glu Ala Ile Ser Pro Pro Asp Ala Ala Ser Ala Ala
115 120 125

Pro Leu Arg Thr Ile Thr Ala Asp Thr Phe Arg Lys Leu Phe Arg Val
130 135 140

Tyr Ser Asn Phe Leu Arg Gly Lys Leu Lys Leu Tyr Thr Gly Glu Ala
145 150 155 160

Cys Arg Thr Gly Asp Arg
165

<210> SEQ ID NO 11
<211> LENGTH: 917
<212> TYPE: PRT
<213> ORGANISM: Homo sapiens

<400> SEQUENCE: 11

Met Ser Ala Pro Arg Ile Trp Leu Ala Gln Ala Leu Leu Phe Phe Leu
1 5 10 15

Thr Thr Glu Ser Ile Gly Gln Leu Leu Glu Pro Cys Gly Tyr Ile Tyr
20 25 30

Pro Glu Phe Pro Val Val Gln Arg Gly Ser Asn Phe Thr Ala Ile Cys
35 40 45

Val Leu Lys Glu Ala Cys Leu Gln His Tyr Tyr Val Asn Ala Ser Tyr
50 55 60

Ile Val Trp Lys Thr Asn His Ala Ala Val Pro Arg Glu Gln Val Thr
65 70 75 80

Val Ile Asn Arg Thr Thr Ser Ser Val Thr Phe Thr Asp Val Val Leu
85 90 95

Pro Ser Val Gln Leu Thr Cys Asn Ile Leu Ser Phe Gly Gln Ile Glu
100 105 110

Gln Asn Val Tyr Gly Val Thr Met Leu Ser Gly Phe Pro Pro Asp Lys
115 120 125

Pro Thr Asn Leu Thr Cys Ile Val Asn Glu Gly Lys Asn Met Leu Cys
130 135 140

-continued

```
Gln Trp Asp Pro Gly Arg Glu Thr Tyr Leu Glu Thr Asn Tyr Thr Leu
145                 150                 155                 160

Lys Ser Glu Trp Ala Thr Glu Lys Phe Pro Asp Cys Gln Ser Lys His
                165                 170                 175

Gly Thr Ser Cys Met Val Ser Tyr Met Pro Thr Tyr Tyr Val Asn Ile
            180                 185                 190

Glu Val Trp Val Glu Ala Glu Asn Ala Leu Gly Lys Val Ser Ser Glu
        195                 200                 205

Ser Ile Asn Phe Asp Pro Val Asp Lys Val Lys Pro Thr Pro Pro Tyr
    210                 215                 220

Asn Leu Ser Val Thr Asn Ser Glu Glu Leu Ser Ser Ile Leu Lys Leu
225                 230                 235                 240

Ser Trp Val Ser Ser Gly Leu Gly Gly Leu Leu Asp Leu Lys Ser Asp
                245                 250                 255

Ile Gln Tyr Arg Thr Lys Asp Ala Ser Thr Trp Ile Gln Val Pro Leu
            260                 265                 270

Glu Asp Thr Met Ser Pro Arg Thr Ser Phe Thr Val Gln Asp Leu Lys
        275                 280                 285

Pro Phe Thr Glu Tyr Val Phe Arg Ile Arg Ser Ile Lys Asp Ser Gly
    290                 295                 300

Lys Gly Tyr Trp Ser Asp Trp Ser Glu Glu Ala Ser Gly Thr Thr Tyr
305                 310                 315                 320

Glu Asp Arg Pro Ser Arg Pro Pro Ser Phe Trp Tyr Lys Thr Asn Pro
                325                 330                 335

Ser His Gly Gln Glu Tyr Arg Ser Val Arg Leu Ile Trp Lys Ala Leu
            340                 345                 350

Pro Leu Ser Glu Ala Asn Gly Lys Ile Leu Asp Tyr Glu Val Ile Leu
        355                 360                 365

Thr Gln Ser Lys Ser Val Ser Gln Thr Tyr Thr Val Thr Gly Thr Glu
    370                 375                 380

Leu Thr Val Asn Leu Thr Asn Asp Arg Tyr Val Ala Ser Leu Ala Ala
385                 390                 395                 400

Arg Asn Lys Val Gly Lys Ser Ala Ala Ala Val Leu Thr Ile Pro Ser
                405                 410                 415

Pro His Val Thr Ala Ala Tyr Ser Val Val Asn Leu Lys Ala Phe Pro
            420                 425                 430

Lys Asp Asn Leu Leu Trp Val Glu Trp Thr Pro Pro Pro Lys Pro Val
        435                 440                 445

Ser Lys Tyr Ile Leu Glu Trp Cys Val Leu Ser Glu Asn Ala Pro Cys
    450                 455                 460

Val Glu Asp Trp Gln Gln Glu Asp Ala Thr Val Asn Arg Thr His Leu
465                 470                 475                 480

Arg Gly Arg Leu Leu Glu Ser Lys Cys Tyr Gln Ile Thr Val Thr Pro
                485                 490                 495

Val Phe Ala Thr Gly Pro Gly Gly Ser Glu Ser Leu Lys Ala Tyr Leu
            500                 505                 510

Lys Gln Ala Ala Pro Ala Arg Gly Pro Thr Val Arg Thr Lys Lys Val
        515                 520                 525

Gly Lys Asn Glu Ala Val Leu Ala Trp Asp Gln Ile Pro Val Asp Asp
    530                 535                 540

Gln Asn Gly Phe Ile Arg Asn Tyr Ser Ile Ser Tyr Arg Thr Ser Val
545                 550                 555                 560

Gly Lys Glu Met Val Val His Val Asp Ser Ser His Thr Glu Tyr Thr
```

-continued

```
                565                 570                 575

Leu Ser Ser Leu Ser Ser Asp Thr Leu Tyr Met Val Arg Met Ala Ala
            580                 585                 590

Tyr Thr Asp Glu Gly Gly Lys Asp Gly Pro Glu Phe Thr Phe Thr Thr
        595                 600                 605

Pro Lys Phe Ala Gln Gly Glu Ile Glu Ala Ile Val Val Pro Val Cys
    610                 615                 620

Leu Ala Phe Leu Leu Thr Thr Leu Leu Gly Val Leu Phe Cys Phe Asn
625                 630                 635                 640

Lys Arg Asp Leu Ile Lys Lys His Ile Trp Pro Asn Val Pro Asp Pro
            645                 650                 655

Ser Lys Ser His Ile Ala Gln Trp Ser Pro His Thr Pro Pro Arg His
            660                 665                 670

Asn Phe Asn Ser Lys Asp Gln Met Tyr Ser Asp Gly Asn Phe Thr Asp
        675                 680                 685

Val Ser Val Val Glu Ile Glu Ala Asn Asn Lys Lys Pro Cys Pro Asp
    690                 695                 700

Asp Leu Lys Ser Val Asp Leu Phe Lys Lys Glu Lys Val Ser Thr Glu
705                 710                 715                 720

Gly His Ser Ser Gly Ile Gly Gly Ser Ser Cys Met Ser Ser Ser Arg
            725                 730                 735

Pro Ser Ile Ser Ser Asn Glu Glu Asn Glu Ser Ala Gln Ser Thr Ala
            740                 745                 750

Ser Thr Val Gln Tyr Ser Thr Val Val His Ser Gly Tyr Arg His Gln
        755                 760                 765

Val Pro Ser Val Gln Val Phe Ser Arg Ser Glu Ser Thr Gln Pro Leu
    770                 775                 780

Leu Asp Ser Glu Glu Arg Pro Glu Asp Leu Gln Leu Val Asp Ser Val
785                 790                 795                 800

Asp Gly Gly Asp Glu Ile Leu Pro Arg Gln Ser Tyr Phe Lys Gln Asn
            805                 810                 815

Cys Ser Gln Pro Glu Ala Cys Pro Glu Ile Ser His Phe Glu Arg Ser
            820                 825                 830

Asn Gln Val Leu Ser Gly Asn Glu Glu Asp Phe Val Arg Leu Lys Gln
        835                 840                 845

Gln Gln Val Ser Asp His Ile Ser Gln Pro Tyr Gly Ser Glu Gln Arg
    850                 855                 860

Arg Leu Phe Gln Glu Gly Ser Thr Ala Asp Ala Leu Gly Thr Gly Ala
865                 870                 875                 880

Asp Gly Gln Met Glu Arg Phe Glu Ser Val Gly Met Glu Thr Thr Ile
            885                 890                 895

Asp Glu Glu Ile Pro Lys Ser Tyr Leu Pro Gln Thr Val Arg Gln Gly
            900                 905                 910

Gly Tyr Met Pro Gln
        915


<210> SEQ ID NO 12
<211> LENGTH: 22
<212> TYPE: PRT
<213> ORGANISM: Guassia princeps

<400> SEQUENCE: 12

Met Gly Val Lys Val Leu Phe Ala Leu Ile Cys Ile Ala Val Ala Glu
1               5                   10                  15
```

Ala Lys Pro Thr Gly Pro
20

<210> SEQ ID NO 13
<211> LENGTH: 22
<212> TYPE: PRT
<213> ORGANISM: Cypridina noctiluca

<400> SEQUENCE: 13

Met Lys Thr Leu Ile Leu Ala Val Ala Leu Val Tyr Cys Ala Thr Val
1 5 10 15

His Cys Gln Asp Gly Pro
20

<210> SEQ ID NO 14
<211> LENGTH: 29
<212> TYPE: PRT
<213> ORGANISM: Homo sapiens

<400> SEQUENCE: 14

Met Ala Leu Trp Met Arg Leu Leu Pro Leu Leu Ala Leu Leu Ala Leu
1 5 10 15

Trp Gly Pro Asp Pro Ala Ala Ala Phe Val Asn Gln His
20 25

<210> SEQ ID NO 15
<211> LENGTH: 31
<212> TYPE: PRT
<213> ORGANISM: Homo sapiens

<400> SEQUENCE: 15

Met Gly Val His Glu Cys Pro Ala Trp Leu Trp Leu Leu Leu Ser Leu
1 5 10 15

Leu Ser Leu Pro Leu Gly Leu Pro Val Leu Gly Ala Pro Pro Arg
20 25 30

<210> SEQ ID NO 16
<211> LENGTH: 27
<212> TYPE: PRT
<213> ORGANISM: Homo sapiens

<400> SEQUENCE: 16

Met Ala Leu Leu Leu Val Ser Leu Leu Ala Phe Leu Ser Leu Gly Ser
1 5 10 15

Gly Cys His His Arg Ile Cys His Cys Ser Asn
20 25

<210> SEQ ID NO 17
<211> LENGTH: 8147
<212> TYPE: DNA
<213> ORGANISM: Homo sapiens

<400> SEQUENCE: 17
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180
gccgcattgc agagatattg tatttaagtg cctagctcga tacataaacg ggtctctctg 240
gttagaccag atctgagcct gggagctctc tggctaacta gggaacccac tgcttaagcc 300
tcaataaagc ttgccttgag tgcttcaagt agtgtgtgcc cgtctgttgt gtgactctgg 360

```
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgatt   1800
aacttttaaa agaaaagggg ggattggggg gtacagtgca ggggaaagaa tagtagacat   1860
aatagcaaca gacatacaaa ctaaagaatt acaaaaacaa attacaaaaa ttcaaaattt   1920
tatcgatgtc gacgttaacg ctagtgatat caactttgta tagaaaagtt ggctccgaat   1980
tcgcccttag tagtgttaac cccgggctcg agcagtattt agccacgtga cagtgtaagc   2040
acacgtgggc cctcaagtcc acgtgcaggg agcctgagca ccactgagcg gtcctgagcc   2100
aagagggtat ataatggaag ctcgacttcc agaagggcga attcgaccca agtttgtaca   2160
aaaaagcagg ctccgcggcc gccccccttca ccgagctcgg atccagccac catgggagtc   2220
aaagttctgt ttgccctgat ctgcatcgct gtggccgagg ccaagcccac cgagaacaac   2280
gaagacttca acatcgtggc cgtggccagc aacttcgcga ccacggatct cgatgctgac   2340
cgcgggaagt tgcccggcaa gaagctgccg ctggaggtgc tcaaagagat ggaagccaat   2400
gcccggaaag ctggctgcac caggggctgt ctgatctgcc tgtcccacat caagtgcacg   2460
cccaagatga agaagttcat cccaggacgc tgccacacct acgaaggcga caaagagtcc   2520
gcacagggcg gcataggcga ggcgatcgtc gacattcctg agattcctgg gttcaaggac   2580
ttggagccca tggagcagtt catcgcacag gtcgatctgt gtgtggactg cacaactggc   2640
tgcctcaaag ggcttgccaa cgtgcagtgt tctgacctgc tcaagaagtg gctgccgcaa   2700
cgctgtgcga cctttgccag caagatccag ggccaggtgg acaagatcaa gggggccggt   2760
```

ggtgactaag cggccgcaat aaaatatctt tattttcatt acatctgtgt gttggttttt 2820
tgtgtgtcta gaaataataa gggtgggcgc gccgacccag ctttcttgta caaagtggtt 2880
gatatccagc acagtggcgg ccgctcgagt ctagagggcc cgcggttcga aggtaagcct 2940
atccctaacc ctctcctcgg tctcgattct acgcgtaccg gttagtaatg atcgacaatc 3000
aacctctgga ttacaaaatt tgtgaaagat tgactggtat tcttaactat gttgctcctt 3060
ttacgctatg tggatacgct gctttaatgc ctttgtatca tgctattgct tcccgtatgg 3120
ctttcatttt ctcctccttg tataaatcct ggttgctgtc tctttatgag gagttgtggc 3180
ccgttgtcag gcaacgtggc gtggtgtgca ctgtgtttgc tgacgcaacc cccactggtt 3240
ggggcattgc caccacctgt cagctccttt ccgggacttt cgctttcccc ctccctattg 3300
ccacggcgga actcatcgcc gcctgccttg cccgctgctg gacaggggct cggctgttgg 3360
gcactgacaa ttccgtggtg ttgtcgggga agctgacgtc ctttccatgg ctgctcgcct 3420
gtgttgccac ctggattctg cgcgggacgt ccttctgcta cgtcccttcg gccctcaatc 3480
cagcggacct tccttcccgc ggcctgctgc cggctctgcg gcctcttccg cgtcttcgcc 3540
ttcgccctca gacgagtcgg atctcccttt gggccgcctc cccgcctggc gatggtacct 3600
accgggtagg ggaggcgctt ttcccaaggc agtctggagc atgcgcttta gcagccccgc 3660
tgggcacttg gcgctacaca agtggcctct ggcctcgcac acattccaca tccaccggta 3720
ggcgccaacc ggctccgttc tttggtggcc ccttcgcgcc accttctact cctcccctag 3780
tcaggaagtt cccccccgcc ccgcagctcg cgtcgtgcag gacgtgacaa atggaagtag 3840
cacgtctcac tagtctcgtg cagatggaca gcaccgctga gcaatggaag cgggtaggcc 3900
tttggggcag cggccaatag cagctttgct ccttcgcttt ctgggctcag aggctgggaa 3960
ggggtgggtc cgggggcggg ctcaggggcg ggctcagggg cggggcgggc gcccgaaggt 4020
cctccggagg cccggcattc tgcacgcttc aaaagcgcac gtctgccgcg ctgttctcct 4080
cttcctcatc tccgggcctt tcgactctag acacgtgttg acaattaatc atcggcatag 4140
tatatcggca tagtataata cgacaaggtg aggaactaaa ccatggccaa gcctttgtct 4200
caagaagaat ccaccctcat tgaaagagca acggctacaa tcaacagcat ccccatctct 4260
gaagactaca gcgtcgccag cgcagctctc tctagcgacg gccgcatctt cactggtgtc 4320
aatgtatatc attttactgg gggaccttgt gcagaactcg tggtgctggg cactgctgct 4380
gctgcggcag ctggcaacct gacttgtatc gtcgcgatcg gaaatgagaa caggggcatc 4440
ttgagcccct gcggacggtg ccgacaggtg cttctcgatc tgcatcctgg gatcaaagcc 4500
atagtgaagg acagtgatgg acagccgacg gcagttggga ttcgtgaatt gctgccctct 4560
ggttatgtgt gggagggcta agcacaattc gagctcggta cctttaagac caatgactta 4620
caaggcagct gtagatctta gccacttttt aaaagaaaag gggggactgg aagggctaat 4680
tcactcccaa cgaagacaag atctgctttt tgcttgtact gggtctctct ggttagacca 4740
gatctgagcc tgggagctct ctggctaact agggaaccca ctgcttaagc ctcaataaag 4800
cttgccttga gtgcttcaag tagtgtgtgc ccgtctgttg tgtgactctg gtaactagag 4860
atccctcaga cccttttagt cagtgtggaa aatctctagc agtagtagtt catgtcatct 4920
tattattcag tatttataac ttgcaaagaa atgaatatca gagagtgaga ggaacttgtt 4980
tattgcagct tataatggtt acaaataaag caatagcatc acaaatttca caaataaagc 5040
attttttca ctgcattcta gttgtggttt gtccaaactc atcaatgtat cttatcatgt 5100
ctggctctag ctatcccgcc cctaactccg cccatcccgc ccctaactcc gcccagttcc 5160
gcccattctc cgccccatgg ctgactaatt ttttttattt atgcagaggc cgaggccgcc 5220
tcggcctctg agctattcca gaagtagtga ggaggctttt ttggaggcct agggacgtac 5280
ccaattcgcc ctatagtgag tcgtattacg cgcgctcact ggccgtcgtt ttacaacgtc 5340
gtgactggga aaaccctggc gttacccaac ttaatcgcct tgcagcacat ccccctttcg 5400
ccagctggcg taatagcgaa gaggcccgca ccgatcgccc ttcccaacag ttgcgcagcc 5460
tgaatggcga atgggacgcg ccctgtagcg gcgcattaag cgcggcgggt gtggtggtta 5520
cgcgcagcgt gaccgctaca cttgccagcg ccctagcgcc cgctcctttc gctttcttcc 5580
cttcctttct cgccacgttc gccggctttc cccgtcaagc tctaaatcgg gggctccctt 5640
tagggttccg atttagtgct ttacggcacc tcgaccccaa aaaacttgat tagggtgatg 5700
gttcacgtag tgggccatcg ccctgataga cggtttttcg ccctttgacg ttggagtcca 5760
cgttctttaa tagtggactc ttgttccaaa ctggaacaac actcaaccct atctcggtct 5820
attcttttga tttataaggg attttgccga tttcggccta ttggttaaaa aatgagctga 5880
tttaacaaaa atttaacgcg aattttaaca aaatattaac gcttacaatt taggtggcac 5940
ttttcgggga aatgtgcgcg gaacccctat ttgtttattt ttctaaatac attcaaatat 6000
gtatccgctc atgagacaat aaccctgata aatgcttcaa taatattgaa aaaggaagag 6060
tatgagtatt caacatttcc gtgtcgccct tattcccttt tttgcggcat tttgccttcc 6120
tgtttttgct cacccagaaa cgctggtgaa agtaaaagat gctgaagatc agttgggtgc 6180
acgagtgggt tacatcgaac tggatctcaa cagcggtaag atccttgaga gttttcgccc 6240
cgaagaacgt tttccaatga tgagcacttt taaagttctg ctatgtggcg cggtattatc 6300
ccgtattgac gccgggcaag agcaactcgg tcgccgcata cactattctc agaatgactt 6360
ggttgagtac tcaccagtca cagaaaagca tcttacggat ggcatgacag taagagaatt 6420
atgcagtgct gccataacca tgagtgataa cactgcggcc aacttacttc tgacaacgat 6480
cggaggaccg aaggagctaa ccgctttttt gcacaacatg ggggatcatg taactcgcct 6540
tgatcgttgg gaaccggagc tgaatgaagc cataccaaac gacgagcgtg acaccacgat 6600
gcctgtagca atggcaacaa cgttgcgcaa actattaact ggcgaactac ttactctagc 6660
ttcccggcaa caattaatag actggatgga ggcggataaa gttgcaggac cacttctgcg 6720
ctcggccctt ccggctggct ggtttattgc tgataaatct ggagccggtg agcgtgggtc 6780
tcgcggtatc attgcagcac tggggccaga tggtaagccc tcccgtatcg tagttatcta 6840
cacgacgggg agtcaggcaa ctatggatga acgaaataga cagatcgctg agataggtgc 6900
ctcactgatt aagcattggt aactgtcaga ccaagtttac tcatatatac tttagattga 6960
tttaaaactt catttttaat ttaaaaggat ctaggtgaag atcctttttg ataatctcat 7020
gaccaaaatc ccttaacgtg agttttcgtt ccactgagcg tcagaccccg tagaaaagat 7080
caaaggatct tcttgagatc ctttttttct gcgcgtaatc tgctgcttgc aaacaaaaaa 7140
accaccgcta ccagcggtgg tttgtttgcc ggatcaagag ctaccaactc tttttccgaa 7200
ggtaactggc ttcagcagag cgcagatacc aaatactgtt cttctagtgt agccgtagtt 7260
aggccaccac ttcaagaact ctgtagcacc gcctacatac ctcgctctgc taatcctgtt 7320
accagtggct gctgccagtg gcgataagtc gtgtcttacc gggttggact caagacgata 7380
gttaccggat aaggcgcagc ggtcgggctg aacggggggt tcgtgcacac agcccagctt 7440
ggagcgaacg acctacaccg aactgagata cctacagcgt gagctatgag aaagcgccac 7500
gcttcccgaa gggagaaagg cggacaggta tccggtaagc ggcagggtcg gaacaggaga 7560
gcgcacgagg gagcttccag ggggaaacgc ctggtatctt tatagtcctg tcgggtttcg 7620
ccacctctga cttgagcgtc gatttttgtg atgctcgtca ggggggcgga gcctatggaa 7680
aaacgccagc aacgcggcct ttttacggtt cctggccttt tgctggcctt ttgctcacat 7740
gttctttcct gcgttatccc ctgattctgt ggataaccgt attaccgcct ttgagtgagc 7800
tgataccgct cgccgcagcc gaacgaccga gcgcagcgag tcagtgagcg aggaagcgga 7860
agagcgccca atacgcaaac cgcctctccc cgcgcgttgg ccgattcatt aatgcagctg 7920
gcacgacagg tttcccgact ggaaagcggg cagtgagcgc aacgcaatta atgtgagtta 7980
gctcactcat taggcacccc aggctttaca ctttatgctt ccggctcgta tgttgtgtgg 8040
aattgtgagc ggataacaat ttcacacagg aaacagctat gaccatgatt acgccaagcg 8100
cgcaattaac cctcactaaa gggaacaaaa gctggagctg caagctt 8147

<210> SEQ ID NO 18
<211> LENGTH: 8147
<212> TYPE: DNA
<213> ORGANISM: Homo sapiens

<400> SEQUENCE: 18
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180
gccgcattgc agagatattg tatttaagtg cctagctcga tacataaacg ggtctctctg 240
gttagaccag atctgagcct gggagctctc tggctaacta gggaacccac tgcttaagcc 300
tcaataaagc ttgccttgag tgcttcaagt agtgtgtgcc cgtctgttgt gtgactctgg 360
taactagaga tccctcagac ccttttagtc agtgtggaaa atctctagca gtggcgcccg 420
aacagggact tgaaagcgaa agggaaacca gaggagctct ctcgacgcag gactcggctt 480
gctgaagcgc gcacggcaag aggcgagggg cggcgactgg tgagtacgcc aaaaattttg 540
actagcggag gctagaagga gagagatggg tgcgagagcg tcagtattaa gcgggggaga 600
attagatcgc gatgggaaaa aattcggtta aggccagggg gaaagaaaaa atataaatta 660
aaacatatag tatgggcaag cagggagcta gaacgattcg cagttaatcc tggcctgtta 720
gaaacatcag aaggctgtag acaaatactg ggacagctac aaccatccct tcagacagga 780
tcagaagaac ttagatcatt atataataca gtagcaaccc tctattgtgt gcatcaaagg 840
atagagataa aagacaccaa ggaagcttta gacaagatag aggaagagca aaacaaaagt 900
aagaccaccg cacagcaagc ggccgctgat cttcagacct ggaggaggag atatgaggga 960
caattggaga agtgaattat ataaatataa agtagtaaaa attgaaccat taggagtagc 1020
acccaccaag gcaaagagaa gagtggtgca gagagaaaaa agagcagtgg gaataggagc 1080
tttgttcctt gggttcttgg gagcagcagg aagcactatg ggcgcagcgt caatgacgct 1140
gacggtacag gccagacaat tattgtctgg tatagtgcag cagcagaaca atttgctgag 1200
ggctattgag gcgcaacagc atctgttgca actcacagtc tggggcatca agcagctcca 1260
ggcaagaatc ctggctgtgg aaagatacct aaaggatcaa cagctcctgg ggatttgggg 1320
ttgctctgga aaactcattt gcaccactgc tgtgccttgg aatgctagtt ggagtaataa 1380
atctctggaa cagatttgga atcacacgac ctggatggag tgggacagag aaattaacaa 1440

```
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgatt   1800
aacttttaaa agaaaagggg ggattggggg gtacagtgca ggggaaagaa tagtagacat   1860
aatagcaaca gacatacaaa ctaaagaatt acaaaaacaa attacaaaaa ttcaaaattt   1920
tatcgatgtc gacgttaacg ctagtgatat caactttgta tagaaaagtt ggctccgaat   1980
tcgcccttag tagtgttaac cccgggctcg agcagtattt agccacgtga cagtgtaagc   2040
acacgtgggc cctcaagtcc acgtgcaggg agccacgtga ccacacgtgg gtccacgtgc   2100
aagagggtat ataatggaag ctcgacttcc agaagggcga attcgaccca agtttgtaca   2160
aaaaagcagg ctccgcggcc gccccccttca ccgagctcgg atccagccac catgggagtc   2220
aaagttctgt ttgccctgat ctgcatcgct gtggccgagg ccaagcccac cgagaacaac   2280
gaagacttca acatcgtggc cgtggccagc aacttcgcga ccacggatct cgatgctgac   2340
cgcgggaagt tgcccggcaa gaagctgccg ctggaggtgc tcaaagagat ggaagccaat   2400
gcccggaaag ctggctgcac caggggctgt ctgatctgcc tgtcccacat caagtgcacg   2460
cccaagatga agaagttcat cccaggacgc tgccacacct acgaaggcga caaagagtcc   2520
gcacagggcg gcataggcga ggcgatcgtc gacattcctg agattcctgg gttcaaggac   2580
ttggagccca tggagcagtt catcgcacag gtcgatctgt gtgtggactg cacaactggc   2640
tgcctcaaag ggcttgccaa cgtgcagtgt tctgacctgc tcaagaagtg gctgccgcaa   2700
cgctgtgcga cctttgccag caagatccag ggccaggtgg acaagatcaa gggggccggt   2760
ggtgactaag cggccgcaat aaaatatctt tattttcatt acatctgtgt gttggttttt   2820
tgtgtgtcta gaaataataa gggtgggcgc gccgacccag ctttcttgta caaagtggtt   2880
gatatccagc acagtggcgg ccgctcgagt ctagagggcc cgcggttcga aggtaagcct   2940
atccctaacc ctctcctcgg tctcgattct acgcgtaccg gttagtaatg atcgacaatc   3000
aacctctgga ttacaaaatt tgtgaaagat tgactggtat tcttaactat gttgctcctt   3060
ttacgctatg tggatacgct gctttaatgc ctttgtatca tgctattgct tcccgtatgg   3120
ctttcatttt ctcctccttg tataaatcct ggttgctgtc tctttatgag gagttgtggc   3180
ccgttgtcag gcaacgtggc gtggtgtgca ctgtgtttgc tgacgcaacc cccactggtt   3240
ggggcattgc caccacctgt cagctccttt ccgggacttt cgctttcccc ctccctattg   3300
ccacggcgga actcatcgcc gcctgccttg cccgctgctg gacaggggct cggctgttgg   3360
gcactgacaa ttccgtggtg ttgtcgggga agctgacgtc ctttccatgg ctgctcgcct   3420
gtgttgccac ctggattctg cgcgggacgt ccttctgcta cgtcccttcg gccctcaatc   3480
cagcggacct tccttcccgc ggcctgctgc cggctctgcg gcctcttccg cgtcttcgcc   3540
ttcgccctca gacgagtcgg atctcccttt gggccgcctc cccgcctggc gatggtacct   3600
accgggtagg ggaggcgctt ttcccaaggc agtctggagc atgcgcttta gcagccccgc   3660
tgggcacttg gcgctacaca agtggcctct ggcctcgcac acattccaca tccaccggta   3720
ggcgccaacc ggctccgttc tttggtggcc ccttcgcgcc accttctact cctcccctag   3780
tcaggaagtt cccccccgcc ccgcagctcg cgtcgtgcag gacgtgacaa atggaagtag   3840
```

```
cacgtctcac tagtctcgtg cagatggaca gcaccgctga gcaatggaag cgggtaggcc   3900
tttggggcag cggccaatag cagctttgct ccttcgcttt ctgggctcag aggctgggaa   3960
ggggtgggtc cgggggcggg ctcaggggcg ggctcagggg cggggcgggc gcccgaaggt   4020
cctccggagg cccggcattc tgcacgcttc aaaagcgcac gtctgccgcg ctgttctcct   4080
cttcctcatc tccgggcctt tcgactctag acacgtgttg acaattaatc atcggcatag   4140
tatatcggca tagtataata cgacaaggtg aggaactaaa ccatggccaa gcctttgtct   4200
caagaagaat ccaccctcat tgaaagagca acggctacaa tcaacagcat ccccatctct   4260
gaagactaca gcgtcgccag cgcagctctc tctagcgacg gccgcatctt cactggtgtc   4320
aatgtatatc attttactgg gggaccttgt gcagaactcg tggtgctggg cactgctgct   4380
gctgcggcag ctggcaacct gacttgtatc gtcgcgatcg gaaatgagaa caggggcatc   4440
ttgagcccct gcggacggtg ccgacaggtg cttctcgatc tgcatcctgg gatcaaagcc   4500
atagtgaagg acagtgatgg acagccgacg gcagttggga ttcgtgaatt gctgccctct   4560
ggttatgtgt gggagggcta agcacaattc gagctcggta cctttaagac caatgactta   4620
caaggcagct gtagatctta gccacttttt aaaagaaaag gggggactgg aagggctaat   4680
tcactcccaa cgaagacaag atctgctttt tgcttgtact gggtctctct ggttagacca   4740
gatctgagcc tgggagctct ctggctaact agggaaccca ctgcttaagc ctcaataaag   4800
cttgccttga gtgcttcaag tagtgtgtgc ccgtctgttg tgtgactctg gtaactagag   4860
atccctcaga cccttttagt cagtgtggaa aatctctagc agtagtagtt catgtcatct   4920
tattattcag tatttataac ttgcaaagaa atgaatatca gagagtgaga ggaacttgtt   4980
tattgcagct tataatggtt acaaataaag caatagcatc acaaatttca caaataaagc   5040
atttttttca ctgcattcta gttgtggttt gtccaaactc atcaatgtat cttatcatgt   5100
ctggctctag ctatcccgcc cctaactccg cccatcccgc ccctaactcc gcccagttcc   5160
gcccattctc cgccccatgg ctgactaatt ttttttattt atgcagaggc cgaggccgcc   5220
tcggcctctg agctattcca gaagtagtga ggaggctttt ttggaggcct agggacgtac   5280
ccaattcgcc ctatagtgag tcgtattacg cgcgctcact ggccgtcgtt ttacaacgtc   5340
gtgactggga aaaccctggc gttacccaac ttaatcgcct tgcagcacat ccccctttcg   5400
ccagctggcg taatagcgaa gaggcccgca ccgatcgccc ttcccaacag ttgcgcagcc   5460
tgaatggcga atgggacgcg ccctgtagcg gcgcattaag cgcggcgggt gtggtggtta   5520
cgcgcagcgt gaccgctaca cttgccagcg ccctagcgcc cgctcctttc gctttcttcc   5580
cttcctttct cgccacgttc gccggctttc cccgtcaagc tctaaatcgg gggctccctt   5640
tagggttccg atttagtgct ttacggcacc tcgaccccaa aaaacttgat tagggtgatg   5700
gttcacgtag tgggccatcg ccctgataga cggtttttcg ccctttgacg ttggagtcca   5760
cgttctttaa tagtggactc ttgttccaaa ctggaacaac actcaaccct atctcggtct   5820
attcttttga tttataaggg attttgccga tttcggccta ttggttaaaa aatgagctga   5880
tttaacaaaa atttaacgcg aattttaaca aaatattaac gcttacaatt taggtggcac   5940
ttttcgggga aatgtgcgcg gaacccctat ttgtttattt ttctaaatac attcaaatat   6000
gtatccgctc atgagacaat aaccctgata aatgcttcaa taatattgaa aaaggaagag   6060
tatgagtatt caacatttcc gtgtcgccct tattcccttt tttgcggcat tttgccttcc   6120
tgtttttgct cacccagaaa cgctggtgaa agtaaaagat gctgaagatc agttgggtgc   6180
```

acgagtgggt tacatcgaac tggatctcaa cagcggtaag atccttgaga gttttcgccc 6240
cgaagaacgt tttccaatga tgagcacttt taaagttctg ctatgtggcg cggtattatc 6300
ccgtattgac gccgggcaag agcaactcgg tcgccgcata cactattctc agaatgactt 6360
ggttgagtac tcaccagtca cagaaaagca tcttacggat ggcatgacag taagagaatt 6420
atgcagtgct gccataacca tgagtgataa cactgcggcc aacttacttc tgacaacgat 6480
cggaggaccg aaggagctaa ccgctttttt gcacaacatg ggggatcatg taactcgcct 6540
tgatcgttgg gaaccggagc tgaatgaagc cataccaaac gacgagcgtg acaccacgat 6600
gcctgtagca atggcaacaa cgttgcgcaa actattaact ggcgaactac ttactctagc 6660
ttcccggcaa caattaatag actggatgga ggcggataaa gttgcaggac cacttctgcg 6720
ctcggccctt ccggctggct ggtttattgc tgataaatct ggagccggtg agcgtgggtc 6780
tcgcggtatc attgcagcac tggggccaga tggtaagccc tcccgtatcg tagttatcta 6840
cacgacgggg agtcaggcaa ctatggatga acgaaataga cagatcgctg agataggtgc 6900
ctcactgatt aagcattggt aactgtcaga ccaagtttac tcatatatac tttagattga 6960
tttaaaactt catttttaat ttaaaaggat ctaggtgaag atcctttttg ataatctcat 7020
gaccaaaatc ccttaacgtg agttttcgtt ccactgagcg tcagaccccg tagaaaagat 7080
caaaggatct tcttgagatc ctttttttct gcgcgtaatc tgctgcttgc aaacaaaaaa 7140
accaccgcta ccagcggtgg tttgtttgcc ggatcaagag ctaccaactc tttttccgaa 7200
ggtaactggc ttcagcagag cgcagatacc aaatactgtt cttctagtgt agccgtagtt 7260
aggccaccac ttcaagaact ctgtagcacc gcctacatac ctcgctctgc taatcctgtt 7320
accagtggct gctgccagtg gcgataagtc gtgtcttacc gggttggact caagacgata 7380
gttaccggat aaggcgcagc ggtcgggctg aacggggggt tcgtgcacac agcccagctt 7440
ggagcgaacg acctacaccg aactgagata cctacagcgt gagctatgag aaagcgccac 7500
gcttcccgaa gggagaaagg cggacaggta tccggtaagc ggcagggtcg gaacaggaga 7560
gcgcacgagg gagcttccag ggggaaacgc ctggtatctt tatagtcctg tcgggtttcg 7620
ccacctctga cttgagcgtc gatttttgtg atgctcgtca ggggggcgga gcctatggaa 7680
aaacgccagc aacgcggcct ttttacggtt cctggccttt tgctggcctt ttgctcacat 7740
gttctttcct gcgttatccc ctgattctgt ggataaccgt attaccgcct ttgagtgagc 7800
tgataccgct cgccgcagcc gaacgaccga gcgcagcgag tcagtgagcg aggaagcgga 7860
agagcgccca atacgcaaac cgcctctccc cgcgcgttgg ccgattcatt aatgcagctg 7920
gcacgacagg tttcccgact ggaaagcggg cagtgagcgc aacgcaatta atgtgagtta 7980
gctcactcat taggcacccc aggctttaca ctttatgctt ccggctcgta tgttgtgtgg 8040
aattgtgagc ggataacaat ttcacacagg aaacagctat gaccatgatt acgccaagcg 8100
cgcaattaac cctcactaaa gggaacaaaa gctggagctg caagctt 8147

<210> SEQ ID NO 19
<211> LENGTH: 10414
<212> TYPE: DNA
<213> ORGANISM: Homo sapiens

<400> SEQUENCE: 19
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180

```
gccgcattgc agagatattg tatttaagtg cctagctcga tacataaacg ggtctctctg    240
gttagaccag atctgagcct gggagctctc tggctaacta gggaacccac tgcttaagcc    300
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgatt   1800
aacttttaaa agaaaagggg ggattggggg gtacagtgca ggggaaagaa tagtagacat   1860
aatagcaaca gacatacaaa ctaaagaatt acaaaaacaa attacaaaaa ttcaaaattt   1920
tatcgatgtc gacgttaacg ctagtgatat caactttgta tagaaaagtt gcgtgaggct   1980
ccggtgcccg tcagtgggca gagcgcacat cgcccacagt ccccgagaag ttggggggag   2040
gggtcggcaa ttgaaccggt gcctagagaa ggtggcgcgg ggtaaactgg gaaagtgatg   2100
tcgtgtactg gctccgcctt tttcccgagg gtgggggaga accgtatata agtgcagtag   2160
tcgccgtgaa cgttcttttt cgcaacgggt ttgccgccag aacacaggta agtgccgtgt   2220
gtggttcccg cgggcctggc ctctttacgg gttatggccc ttgcgtgcct tgaattactt   2280
ccacctggct gcagtacgtg attcttgatc ccgagcttcg ggttggaagt gggtgggaga   2340
gttcgaggcc ttgcgcttaa ggagcccctt cgcctcgtgc ttgagttgag gcctggcctg   2400
ggcgctgggg ccgccgcgtg cgaatctggt ggcaccttcg cgcctgtctc gctgctttcg   2460
ataagtctct agccatttaa aatttttgat gacctgctgc gacgcttttt ttctggcaag   2520
```

```
atagtcttgt aaatgcgggc caagatctgc acactggtat ttcggttttt ggggccgcgg   2580
gcggcgacgg ggcccgtgcg tcccagcgca catgttcggc gaggcggggc ctgcgagcgc   2640
ggccaccgag aatcggacgg gggtagtctc aagctggccg gcctgctctg gtgcctggcc   2700
tcgcgccgcc gtgtatcgcc ccgccctggg cggcaaggct ggcccggtcg gcaccagttg   2760
cgtgagcgga aagatggccg cttcccggcc ctgctgcagg gagctcaaaa tggaggacgc   2820
ggcgctcggg agagcgggcg ggtgagtcac ccacacaaag gaaaagggcc tttccgtcct   2880
cagccgtcgc ttcatgtgac tccacggagt accgggcgcc gtccaggcac ctcgattagt   2940
tctcgagctt ttggagtacg tcgtctttag gttgggggga ggggttttat gcgatggagt   3000
ttccccacac tgagtgggtg gagactgaag ttaggccagc ttggcacttg atgtaattct   3060
ccttggaatt tgcccttttt gagtttggat cttggttcat tctcaagcct cagacagtgg   3120
ttcaaagttt ttttcttcca tttcaggtgt cgtgaggaat tagcttggta ctaatacgac   3180
tcactatagg gagacccaag ctggctaggt aagcttgatc acaagtttgt acaaaaaagc   3240
aggctccgcg gccgcccct tcacccccac tgcttactgg cttatcgaaa ttaatacgac   3300
tcactatagg gagacccaag cttggtaccg agctcggatc cgccaccatg aagaccttaa   3360
ttcttgccgt tgcattagtc tactgcgcca ctgttcattg ccaggactgt ccttacgaac   3420
ctgatccacc aaacacagtt ccaacttcct gtgaagctaa agaaggagaa tgtattgata   3480
gcagctgtgg cacctgcacg agagacatac tatcagatgg actgtgtgaa aataaaccag   3540
gaaaaacatg ttgccgaatg tgtcagtatg taattgaatg cagagtagag gccgcaggat   3600
ggtttagaac attctatgga aagagattcc agttccagga acctggtaca tacgtgttgg   3660
gtcaaggaac caagggcggc gactggaagg tgtccatcac cctggagaac ctggatggaa   3720
ccaagggggc tgtgctgacc aagacaagac tggaagtggc tggagacatc attgacatcg   3780
ctcaagctac tgagaatccc atcactgtaa acggtggagc tgaccctatc atcgccaacc   3840
cgtacaccat cggcgaggtc accatcgctg ttgttgagat gccaggcttc aacatcaccg   3900
tcattgagtt cttcaaactg atcgtgatcg acatcctcgg aggaagatct gtaagaatcg   3960
ccccagacac agcaaacaaa ggaatgatct ctggcctctg tggagatctt aaaatgatgg   4020
aagatacaga cttcacttca gatccagaac aactcgctat tcagcctaag atcaaccagg   4080
agtttgacgg ttgtccactc tatggaaatc ctgatgacgt tgcatactgc aaaggtcttc   4140
tggagccgta caaggacagc tgccgcaacc ccatcaactt ctactactac accatctcct   4200
gcgccttcgc ccgctgtatg ggtggagacg agcgagcctc acacgtgctg cttgactaca   4260
gggagacgtg cgctgctccc gaaactagag gaacctgcgt tttgtctgga catactttct   4320
acgatacatt tgacaaagca agataccaat tccagggtcc ctgcaaggag attcttatgg   4380
ccgccgactg tttctggaac acttgggatg tgaaggtttc acacaggaat gttgactctt   4440
acactgaagt agagaaagta cgaatcagga aacaatcgac tgtagtagaa ctcattgttg   4500
atggaaaaca gattctggtt ggaggagaag ccgtgtccgt cccgtacagc tctcagaaca   4560
cttccatcta ctggcaagat ggtgacatac tgactacagc catcctacct gaagctctgg   4620
tggtcaagtt caacttcaag caactgctcg tcgtacatat tagagatcca ttcgatggta   4680
agacttgcgg tatttgcggt aactacaacc aggatttcag tgatgattct tttgatgctg   4740
aaggagcctg tgatctgacc cccaacccac cgggatgcac cgaagaacag aaacctgaag   4800
ctgaacgact ctgcaatagt ctcttcgccg gtcaaagtga tcttgatcag aaatgtaacg   4860
tgtgccacaa gcctgaccgt gtcgaacgat gcatgtacga gtattgcctg aggggacaac   4920
```

```
agggtttctg tgaccacgca tgggagttca agaaagaatg ctacataaag catggagaca   4980
ccctagaagt accagatgaa tgcaaatagg cggccgcaat aaaatatctt tattttcatt   5040
acatctgtgt gttggttttt tgtgtgtcta gaaataattc ttactgtcat gccaagtaag   5100
atgctaaggg tgggcgcgcc gacccagctt tcttgtacaa agtggttgat atccagcaca   5160
gtggcggccg ctcgagtcta gagggcccgc ggttcgaagg taagcctatc cctaaccctc   5220
tcctcggtct cgattctacg cgtaccggtt agtaatgatc gacaatcaac ctctggatta   5280
caaaatttgt gaaagattga ctggtattct taactatgtt gctcctttta cgctatgtgg   5340
atacgctgct ttaatgcctt tgtatcatgc tattgcttcc cgtatggctt tcattttctc   5400
ctccttgtat aaatcctggt tgctgtctct ttatgaggag ttgtggcccg ttgtcaggca   5460
acgtggcgtg gtgtgcactg tgtttgctga cgcaaccccc actggttggg gcattgccac   5520
cacctgtcag ctcctttccg ggactttcgc tttccccctc cctattgcca cggcggaact   5580
catcgccgcc tgccttgccc gctgctggac aggggctcgg ctgttgggca ctgacaattc   5640
cgtggtgttg tcggggaagc tgacgtcctt tccatggctg ctcgcctgtg ttgccacctg   5700
gattctgcgc gggacgtcct tctgctacgt cccttcggcc ctcaatccag cggaccttcc   5760
ttcccgcggc ctgctgccgg ctctgcggcc tcttccgcgt cttcgccttc gccctcagac   5820
gagtcggatc tccctttggg ccgcctcccc gcctggcgat ggtacctacc gggtagggga   5880
ggcgcttttc ccaaggcagt ctggagcatg cgctttagca gccccgctgg gcacttggcg   5940
ctacacaagt ggcctctggc ctcgcacaca ttccacatcc accggtaggc gccaaccggc   6000
tccgttcttt ggtggcccct tcgcgccacc ttctactcct cccctagtca ggaagttccc   6060
ccccgccccg cagctcgcgt cgtgcaggac gtgacaaatg gaagtagcac gtctcactag   6120
tctcgtgcag atggacagca ccgctgagca atggaagcgg gtaggccttt ggggcagcgg   6180
ccaatagcag ctttgctcct tcgctttctg ggctcagagg ctgggaaggg gtgggtccgg   6240
gggcgggctc aggggcgggc tcaggggcgg ggcgggcgcc cgaaggtcct ccggaggccc   6300
ggcattctgc acgcttcaaa agcgcacgtc tgccgcgctg ttctcctctt cctcatctcc   6360
gggcctttcg actctagaca cgtgttgaca attaatcatc ggcatagtat atcggcatag   6420
tataatacga caaggtgagg aactaaacca tggccaagcc tttgtctcaa gaagaatcca   6480
ccctcattga aagagcaacg gctacaatca acagcatccc catctctgaa gactacagcg   6540
tcgccagcgc agctctctct agcgacggcc gcatcttcac tggtgtcaat gtatatcatt   6600
ttactggggg accttgtgca gaactcgtgg tgctgggcac tgctgctgct gcggcagctg   6660
gcaacctgac ttgtatcgtc gcgatcggaa atgagaacag gggcatcttg agcccctgcg   6720
gacggtgccg acaggtgctt ctcgatctgc atcctgggat caaagccata gtgaaggaca   6780
gtgatggaca gccgacggca gttgggattc gtgaattgct gccctctggt tatgtgtggg   6840
agggctaagc acaattcgag ctcggtacct ttaagaccaa tgacttacaa ggcagctgta   6900
gatcttagcc actttttaaa agaaaagggg ggactggaag ggctaattca ctcccaacga   6960
agacaagatc tgctttttgc ttgtactggg tctctctggt tagaccagat ctgagcctgg   7020
gagctctctg gctaactagg gaacccactg cttaagcctc aataaagctt gccttgagtg   7080
cttcaagtag tgtgtgcccg tctgttgtgt gactctggta actagagatc cctcagaccc   7140
ttttagtcag tgtggaaaat ctctagcagt agtagttcat gtcatcttat tattcagtat   7200
ttataacttg caaagaaatg aatatcagag agtgagagga acttgtttat tgcagcttat   7260
```

aatggttaca aataaagcaa tagcatcaca aatttcacaa ataaagcatt tttttcactg 7320
cattctagtt gtggtttgtc caaactcatc aatgtatctt atcatgtctg gctctagcta 7380
tcccgcccct aactccgccc atcccgcccc taactccgcc cagttccgcc cattctccgc 7440
cccatggctg actaattttt tttatttatg cagaggccga ggccgcctcg gcctctgagc 7500
tattccagaa gtagtgagga ggcttttttg gaggcctagg gacgtaccca attcgcccta 7560
tagtgagtcg tattacgcgc gctcactggc cgtcgtttta caacgtcgtg actgggaaaa 7620
ccctggcgtt acccaactta atcgccttgc agcacatccc cctttcgcca gctggcgtaa 7680
tagcgaagag gcccgcaccg atcgcccttc ccaacagttg cgcagcctga atggcgaatg 7740
ggacgcgccc tgtagcggcg cattaagcgc ggcgggtgtg gtggttacgc gcagcgtgac 7800
cgctacactt gccagcgccc tagcgcccgc tcctttcgct ttcttccctt cctttctcgc 7860
cacgttcgcc ggctttcccc gtcaagctct aaatcggggg ctccctttag ggttccgatt 7920
tagtgcttta cggcacctcg accccaaaaa acttgattag ggtgatggtt cacgtagtgg 7980
gccatcgccc tgatagacgg tttttcgccc tttgacgttg gagtccacgt tctttaatag 8040
tggactcttg ttccaaactg gaacaacact caaccctatc tcggtctatt cttttgattt 8100
ataagggatt ttgccgattt cggcctattg gttaaaaaat gagctgattt aacaaaaatt 8160
taacgcgaat tttaacaaaa tattaacgct tacaatttag gtggcacttt tcggggaaat 8220
gtgcgcggaa cccctatttg tttatttttc taaatacatt caaatatgta tccgctcatg 8280
agacaataac cctgataaat gcttcaataa tattgaaaaa ggaagagtat gagtattcaa 8340
catttccgtg tcgcccttat tccctttttt gcggcatttt gccttcctgt ttttgctcac 8400
ccagaaacgc tggtgaaagt aaaagatgct gaagatcagt tgggtgcacg agtgggttac 8460
atcgaactgg atctcaacag cggtaagatc cttgagagtt ttcgccccga agaacgtttt 8520
ccaatgatga gcacttttaa agttctgcta tgtggcgcgg tattatcccg tattgacgcc 8580
gggcaagagc aactcggtcg ccgcatacac tattctcaga atgacttggt tgagtactca 8640
ccagtcacag aaaagcatct tacggatggc atgacagtaa gagaattatg cagtgctgcc 8700
ataaccatga gtgataacac tgcggccaac ttacttctga caacgatcgg aggaccgaag 8760
gagctaaccg cttttttgca caacatgggg gatcatgtaa ctcgccttga tcgttgggaa 8820
ccggagctga atgaagccat accaaacgac gagcgtgaca ccacgatgcc tgtagcaatg 8880
gcaacaacgt tgcgcaaact attaactggc gaactactta ctctagcttc ccggcaacaa 8940
ttaatagact ggatggaggc ggataaagtt gcaggaccac ttctgcgctc ggcccttccg 9000
gctggctggt ttattgctga taaatctgga gccggtgagc gtgggtctcg cggtatcatt 9060
gcagcactgg ggccagatgg taagccctcc cgtatcgtag ttatctacac gacggggagt 9120
caggcaacta tggatgaacg aaatagacag atcgctgaga taggtgcctc actgattaag 9180
cattggtaac tgtcagacca agtttactca tatatacttt agattgattt aaaacttcat 9240
ttttaattta aaaggatcta ggtgaagatc ctttttgata atctcatgac caaaatccct 9300
taacgtgagt tttcgttcca ctgagcgtca gaccccgtag aaaagatcaa aggatcttct 9360
tgagatcctt tttttctgcg cgtaatctgc tgcttgcaaa caaaaaaacc accgctacca 9420
gcggtggttt gtttgccgga tcaagagcta ccaactcttt ttccgaaggt aactggcttc 9480
agcagagcgc agataccaaa tactgttctt ctagtgtagc cgtagttagg ccaccacttc 9540
aagaactctg tagcaccgcc tacatacctc gctctgctaa tcctgttacc agtggctgct 9600
gccagtggcg ataagtcgtg tcttaccggg ttggactcaa gacgatagtt accggataag 9660

```
gcgcagcggt cgggctgaac ggggggttcg tgcacacagc ccagcttgga gcgaacgacc   9720

tacaccgaac tgagatacct acagcgtgag ctatgagaaa gcgccacgct tcccgaaggg   9780

agaaaggcgg acaggtatcc ggtaagcggc agggtcggaa caggagagcg cacgagggag   9840

cttccagggg gaaacgcctg gtatctttat agtcctgtcg ggtttcgcca cctctgactt   9900

gagcgtcgat ttttgtgatg ctcgtcaggg gggcggagcc tatggaaaaa cgccagcaac   9960

gcggcctttt tacggttcct ggccttttgc tggccttttg ctcacatgtt ctttcctgcg  10020

ttatcccctg attctgtgga taaccgtatt accgcctttg agtgagctga taccgctcgc  10080

cgcagccgaa cgaccgagcg cagcgagtca gtgagcgagg aagcggaaga gcgcccaata  10140

cgcaaaccgc ctctccccgc gcgttggccg attcattaat gcagctggca cgacaggttt  10200

cccgactgga aagcgggcag tgagcgcaac gcaattaatg tgagttagct cactcattag  10260

gcaccccagg ctttacactt tatgcttccg gctcgtatgt tgtgtggaat tgtgagcgga  10320

taacaatttc acacaggaaa cagctatgac catgattacg ccaagcgcgc aattaaccct  10380

cactaaaggg aacaaaagct ggagctgcaa gctt                              10414
```

<210> SEQ ID NO 20
<211> LENGTH: 1601
<212> TYPE: DNA
<213> ORGANISM: Homo sapiens

<400> SEQUENCE: 20

```
aaaaggcagt gtaacacata cacacacaca catacacaca cacacacaca cacacacaca     60

cacacacaca catatacaca cacatacaaa gggtcacttt gaatccacaa cacttactta    120

attggatgac actcccaagt gtgaacagtc catttttaca acggggctac aaaaaagagg    180

tttaaagctc tcagagaatt tgtgttgacc gtaagtaatg gtgtttcttg gatatgaata    240

acatctcccc tctcacgtga tctgaaagcg gatcaacagt ggagaagaaa tcataaaagc    300

tgaggaatag gctgaatata tatatatata tatatatata tatatatata tatatatata    360

tatatatgaa tgaatggcag ttttcccctt tgtcttcagt tgacaaaagt ttcaaagacc    420

tgtctgcaaa tggcatttct gaaaggcttt tgtcaccaaa gtgtgtgaag ccactctttt    480

aagaggagtt ggaaatttta cactagccca ggatctctct tagctggcag ctgggaccca    540

tctgtaacgg tgttagctgg cctgaaaagc agaaaattag cgaccccgag aagccttggc    600

tggctgttta gtctgtagac acggtagggc ggagcagcag actctggaga aaagaaaccc    660

caagctggac ggggagcttt ctgtgagaaa ctggaccgct gccggtgacc gtcctcctca    720

ggcgtgggaa tctcccagtg caggtattag cctaggtctg atgcagagga agaggcaaca    780

gacacgtgtg ctgggaagga tggaagctcg gaggggaagg atgcggggga aggtcacctg    840

gtccacttcc ttttcagggc agcagaagaa acgtgtgacc ctctgacaga gccagacctc    900

agaaaggaag ctcagctact gtcatcccca tgagatgacc atctctctca tcagaacttt    960

acttctttgg tctttgtcaa acaggttttg aaacaccaag ctctctaggt tcatgccatc   1020

catgaaaatg ccacctcact attttaccaa ctgttaccag tacacaaact gactcaatct   1080

tttggtaaag ttcatgaaaa tgagaagcaa gcaccggaga tccgtgcgtt aagaatccag   1140

aagctaggtt ccctttggtg ttagacggaa atacggaact ttaatgtctt gctaccgtgc   1200

tgctgctgct gattatgtta aagtgtgatc aatttcaaga agccaacccc aacccccttta   1260

agtgatccct aggtttagtt tatccagaag gccaccgagc aggttaggct gcagtaaaat   1320
```

cattagcgtc aaagggacca gtaaactgca aagtgtctct agaagaaaga caagaggctt 1380
gcccagacag cccctgtggg gggttgtggt gggatatgct aataacgccc agctacaggg 1440
accaacctcc cttcccatcc cccaggaata tataaagagc cccaacctca gccactgacc 1500
gaccctggcc aacaggcatc tgtccttgtt aattacagag agacagtccc aaactccggg 1560
agctccgcct ggatttgctg gcctgcagca gccagggact g 1601

<210> SEQ ID NO 21
<211> LENGTH: 144
<212> TYPE: DNA
<213> ORGANISM: Homo sapiens

<400> SEQUENCE: 21
agtagtgtta accccgggct cgagcagtat ttagccacgt gacagtgtaa gcacacgtgg 60
gccctcaagt ccacgtgcag ggagcctgag caccactgag cggtcctgag ccaagagggt 120
atataatgga agctcgactt ccag 144

<210> SEQ ID NO 22
<211> LENGTH: 144
<212> TYPE: DNA
<213> ORGANISM: Homo sapiens

<400> SEQUENCE: 22
agtagtgtta accccgggct cgagcagtat ttagccacgt gacagtgtaa gcacacgtgg 60
gccctcaagt ccacgtgcag ggagccacgt gaccacacgt gggtccacgt gcaagagggt 120
atataatgga agctcgactt ccag 144

<210> SEQ ID NO 23
<211> LENGTH: 22
<212> TYPE: DNA
<213> ORGANISM: Homo sapiens

<400> SEQUENCE: 23
tcaactgcct ggacagcatc ct 22

<210> SEQ ID NO 24
<211> LENGTH: 22
<212> TYPE: DNA
<213> ORGANISM: Homo sapiens

<400> SEQUENCE: 24
tcagaggctg aggaggtggt at 22

<210> SEQ ID NO 25
<211> LENGTH: 22
<212> TYPE: DNA
<213> ORGANISM: Homo sapiens

<400> SEQUENCE: 25
agctgcttgg acagcgtcat ca 22

<210> SEQ ID NO 26
<211> LENGTH: 22
<212> TYPE: DNA
<213> ORGANISM: Homo sapiens

<400> SEQUENCE: 26
ccttccgctt atcactggac ct 22

<210> SEQ ID NO 27
<211> LENGTH: 22
<212> TYPE: DNA
<213> ORGANISM: Homo sapiens

<400> SEQUENCE: 27
gcagttgctt gcttcctgac ac 22

<210> SEQ ID NO 28
<211> LENGTH: 22
<212> TYPE: DNA
<213> ORGANISM: Homo sapiens

<400> SEQUENCE: 28
gacagccaca tccaacttcc ag 22

<210> SEQ ID NO 29
<211> LENGTH: 22
<212> TYPE: DNA
<213> ORGANISM: Homo sapiens

<400> SEQUENCE: 29
aggagaacca cgacgagacc ta 22

<210> SEQ ID NO 30
<211> LENGTH: 22
<212> TYPE: DNA
<213> ORGANISM: Homo sapiens

<400> SEQUENCE: 30
ccgttccaag tgcttatcca gg 22

<210> SEQ ID NO 31
<211> LENGTH: 23
<212> TYPE: DNA
<213> ORGANISM: Homo sapiens

<400> SEQUENCE: 31
caggcagcat ttaccagctc atg 23

<210> SEQ ID NO 32
<211> LENGTH: 23
<212> TYPE: DNA
<213> ORGANISM: Homo sapiens

<400> SEQUENCE: 32
gtagcttgag acatcactgg ctg 23

<210> SEQ ID NO 33
<211> LENGTH: 22
<212> TYPE: DNA
<213> ORGANISM: Homo sapiens

<400> SEQUENCE: 33
gctcaggaga acccaggtta tc 22

<210> SEQ ID NO 34
<211> LENGTH: 22
<212> TYPE: DNA
<213> ORGANISM: Homo sapiens

<400> SEQUENCE: 34
gcatctgctt ccaagaggct ca 22

```
<210> SEQ ID NO 35
<211> LENGTH: 22
<212> TYPE: DNA
<213> ORGANISM: Homo sapiens

<400> SEQUENCE: 35

gtctcctctg acttcaacag cg                                          22


<210> SEQ ID NO 36
<211> LENGTH: 22
<212> TYPE: DNA
<213> ORGANISM: Homo sapiens

<400> SEQUENCE: 36

accaccctgt tgctgtagcc aa                                          22


<210> SEQ ID NO 37
<211> LENGTH: 22
<212> TYPE: DNA
<213> ORGANISM: Homo sapiens

<400> SEQUENCE: 37

caccattggc aatgagcggt tc                                          22


<210> SEQ ID NO 38
<211> LENGTH: 22
<212> TYPE: DNA
<213> ORGANISM: Homo sapiens

<400> SEQUENCE: 38

aggtctttgc ggatgtccac gt                                          22
```

PERSONALIZED AND TIMED RELEASE OF BIOMOLECULES

CLAIM OF PRIORITY

This application is a National Stage application under 35 U.S.C. § 371 of International Application No. PCT/US2020/020125, having an International Filing Date of Feb. 27, 2020, which claims the benefit of U.S. Provisional Application Ser. No. 62/811,497, filed on Feb. 27, 2019. The entire contents of the foregoing are incorporated herein by reference.

STATEMENT OF FEDERALLY SPONSORED RESEARCH

This invention was made with government support under Grant Nos. DK087770, GM127353, and EB012521 awarded by the National Institutes of Health. The government has certain rights in the invention.

SEQUENCE LISTING

This application contains a Sequence Listing that has been submitted electronically as an ASCII text file named '29539 0379US1 Sequence_Listing.txt'. The ASCII text file, created on Aug. 25, 2021, is 52.6 KB (53,928 bytes) in size. The material in the ASCII text file is hereby incorporated by reference in its entirety.

TECHNICAL FIELD

The present invention deals with methods and compositions for use in engineering cells to secrete therapeutic biomolecules into the blood stream in vivo in response to an individual's clinical needs.

BACKGROUND

Protein based therapeutics are powerful medicines, however their use is often hampered by very short half-lives and the necessity for intravenous or subcutaneous injections. Cell based therapeutics are ushering in the next wave of biomedical breakthroughs, with a predicted market size of 7.92 billion dollars by 2025 (Cell Therapy Market Size, Share, & Trends Analysis Report By Use (Clinical, Research), By Type (Stem & Non-stem Cells) By Therapy Type (Autologous, Allogenic), By Region, And Segment Forecasts, 2018-2025, Grand View Research, Report ID: GVR-2-68038-701-8; November 2018).

SUMMARY

Described herein are methods and compositions for engineering cells (via gene therapy, e.g., using AAV) or cell-based therapies that have been genetically engineered ex vivo to dynamically secrete therapeutic proteins and/or peptides in one of three ways: 1.) As a response to a normal physiological cue for optimal drug delivery; 2.) In response to disease related molecular signals; and/or 3.) In response to an external stimuli. To date, no cell or gene therapeutic offers therapeutic peptide release dictated by the unique biology of the patient or the self-administration of a drug release trigger. Additionally, this invention obviates the need for recombinant protein production and frequent intravenous or subcutaneous injections; a common method of administration of therapeutic proteins or peptides due to poor stability as compared to small molecule drugs.

Thus, described herein are isolated nucleic acids comprising a sequence encoding a therapeutic protein, a promoter for expression of the therapeutic protein, and a response element that directs expression of the therapeutic protein in response to a physiological stimulus, optionally wherein the therapeutic protein further comprises a secretion signal, e.g., a secretion signal from *Guassia princeps* or *Cypridina noctiluca* luciferase, erythropoietin, follicle stimulating hormone, or insulin. The protein, promoter, and response element are not naturally associated in a living organism, and/or the secretion signal is exogenous, not normally associated with the protein, as a fusion protein.

Also provided herein are methods of treating a subject who has had or will have an organ transplant, the method comprising administering to the subject an organ that has been perfused with an effective amount of isolated cells comprising an isolated nucleic acid comprising a sequence encoding a therapeutic protein, a promoter for expression of the therapeutic protein, and a response element that directs expression of the therapeutic protein in response to a physiological stimulus, optionally wherein the therapeutic protein further comprises a secretion signal, e.g., a secretion signal from *Guassia princeps* or *Cypridina noctiluca* luciferase, erythropoietin, follicle stimulating hormone, or insulin.

Also provided are methods of monitoring post-transplantation surgical outcome in a subject who has had an organ transplant, the method comprising administering to the subject an organ that has been perfused with an effective amount of isolated cells comprising an isolated nucleic acid comprising a sequence encoding a therapeutic protein, a promoter for expression of the therapeutic protein, and a response element that directs expression of the therapeutic protein in response to a physiological stimulus, optionally wherein the therapeutic protein further comprises a secretion signal, e.g., a secretion signal from *Guassia princeps* or *Cypridina noctiluca* luciferase, erythropoietin, follicle stimulating hormone, or insulin.

Also provided herein are organs for implantation into a subject undergoing a solid organ transplant comprising, wherein the organ comprises an effective amount of isolated cells comprising an isolated nucleic acid comprising a sequence encoding a therapeutic protein, a promoter for expression of the therapeutic protein, and a response element that directs expression of the therapeutic protein in response to a physiological stimulus, optionally wherein the therapeutic protein further comprises a secretion signal, e.g., a secretion signal from *Guassia princeps* or *Cypridina noctiluca* luciferase, erythropoietin, follicle stimulating hormone, or insulin.

In some embodiments, the therapeutic protein is GLP1 (glucagon-like petide-1), IL-1RA (Interleukin-1 receptor antagonist), GP130, EPO (erythropoietin), or PTH (parathyroid hormone). Also provided is the use thereof, or an isolated cell comprising the isolated nucleic acid, in treating a subject who has rheumatoid arthritis, or who has had or will have an organ transplant.

In some embodiments, the therapeutic protein is IL-1RA or GP130 and the response element is from NFkB or Heat Shock Factor. Also provided is the use thereof, or an isolated cell comprising the isolated nucleic acid, in treating a subject who has rheumatoid arthritis, or who has had or will have an organ transplant. In subjects who will have an organ transplant, the organ can be treated with the nucleic acids or exogenously administered genetically-modified cells expressing the nucleic acids.

In some embodiments, the therapeutic protein is GLP1 and the response element is from Core Clock (i.e., the mammalian circadian clock transcriptional feedback loop). Also provided is the use thereof, or an isolated cell comprising the isolated nucleic acid, in treating a subject who has diabetes.

In some embodiments, the therapeutic protein is EPO and the response element is from Hypoxia Inducible Factor. Also provided is the use thereof, or an isolated cell comprising the isolated nucleic acid, in treating a subject who has chronic kidney disease-related anemia.

In some embodiments, the therapeutic protein is PTH and the response element is a calcium response element. Also provided is the use thereof, or an isolated cell comprising the isolated nucleic acid, in treating a subject who has hypoparathyroidism.

Also provided herein are vectors comprising the isolated nucleic acids described herein, and isolated cells comprising the isolated nucleic acids, and optionally expressing the therapeutic proteins.

Also provided are methods comprising administering to the subject an effective amount of the isolated nucleic acid, or isolated cells comprising the isolated nucleic acid, for treating diabetes, chronic kidney disease-related anemia, hypoparathyroidism, rheumatoid arthritis, or organ transplant rejection.

Also provided herein are methods of treating a subject who will have an organ transplant, the method comprising administering to the subject an effective amount of isolated cells comprising the isolated nucleic acids described herein, and isolated cells comprising the isolated nucleic acids, and optionally expressing the therapeutic proteins.

Also provided are methods of monitoring post-transplantation surgical outcome in a subject who has had an organ transplant, the method comprising administering to the subject an effective amount of isolated cells comprising the isolated nucleic acids described herein, and isolated cells comprising the isolated nucleic acids, and optionally expressing the therapeutic proteins, prior to receiving the organ transplant.

Herein, a "subject" and a "patient" are interchangeable and refer to any mammalian subject, e.g., a human or non-human (e.g., veterinary) subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 2. Summary of molecular signal transduction pathways coupled to therapeutic peptides and their clinical indications (upper panel). Diagrams of exemplary RED therapeutic peptide delivery genetic constructs (right) along with the reporter constructs used for experimental validation of dynamic secretion (left). In addition, therapeutic peptides modified with a Gluc or Cluc N-terminal secretion signal (not shown) can be paired with the commonly used constitutive promoter/enhancer EF1a (not shown), e.g., for comparison and other potential applications. Other secretion signal peptides and promoters are also envisioned for further customization of the release kinetics. GLP1 (glucagon-like petide-1), IL-1RA (Interleukin-1 receptor antagonist), GP130, EPO (erythropoietin) and PTH (parathyroid hormone).

Gluc were tracked over time for expression through facial bleed sampling in triplicates. Signal took around 30 days before reaching highest strength and was maintained for about 3 months.

FIGS. 6A-D. Release of a biomolecule with other response elements. MSCs were transduced with lentiviral particles encoding for NF-kB response element driving a biomolecule in human MSCs. A) Fluorescence imaging of the 3 lentiviral constructs. B) In vitro release of gLuc in a NF-kB responsive manner when engineered MSCs were exposed to different levels of TNF-a as an activating agent. C) rat fibroblasts engineered with a NF-kB response element driving gLuc and in vitro release data when engineered cells were exposed to differing levels of LPS as an activating agent. D) Engineering of Jurkat T cells via transfection with plasmids encoding for responsive elements for NFkB, GR (glucocorticoid) response, IFN-g or STAT1 driving the in vitro release of gLuc for their given induction agent. The data shows specificity of the engineered cells type for a specific stimuli. Heat shock factor (HSF) response element and Hypoxia inducible factor (HIF) were serving as a negative control.

FIGS. 7A-D. A) Lentiviral gLuc secretion vector for constitutive secretion B) Synthetic circadian promoter vector promoting gLuc secretion. C) Backbone of AAV vector where GP130 (5342 bp) is inserted downstream of a CMV promoter D) Backbone of AAV vector where PTH (348 bp) is inserted downstream of an EF1a promoter FIGS. 8A-B. A) Release of gLuc from engineered rat fibroblasts that were perfused into a liver ex vivo. gLuc was detected in the perfusate and after 3 hours of cell perfusion, the perfusate was replaced with a non-cellullar perfusate suspension and showed a washout signal that then increased over time showing that the signal is due to engineered cells still embedded in the organ. All liver perfusions displayed a consistent pattern of gLuc secretion both before and after the perfusate change. B) Near infrared imaging of engineered cells labeled with a dye that demonstrates the distribution of engineered cells in the organ. Longer perfusion times correlated with increased distribution of cells in the vasculature.

Figure 9:
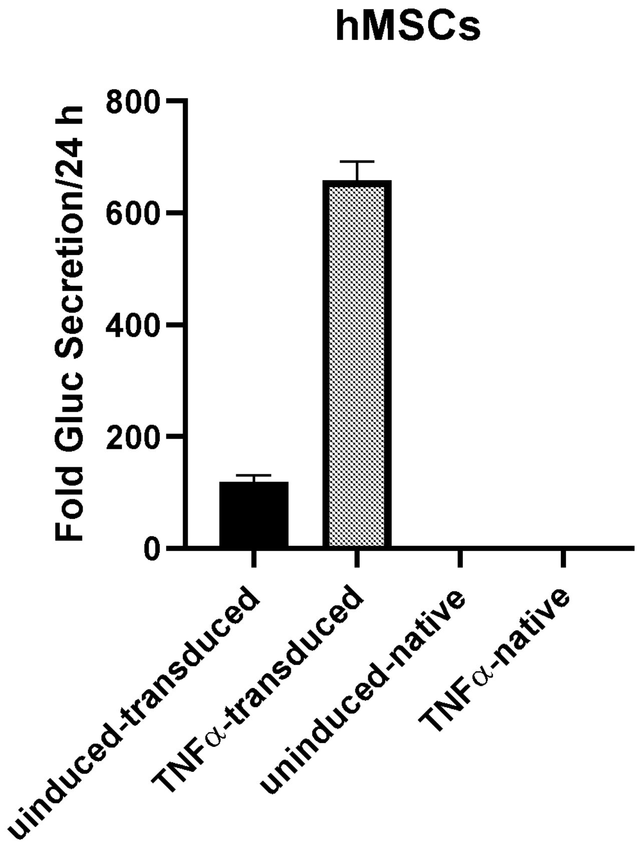

FIG. 9 shows fold differences in Gluc secretion signal with and without virial transduction and with and without TNFα induction of hMSCs lentiviral transduced with an NFκB-Gluc expression vector. Cells were transduced cells were washed thouroughly with media, then media with or without TNFα, was tested for Gluc activity. Cells were then allowed to incubate for 24 hours before testing media for Gluc activity. Untransduced or native cells were treated identically. Left panel shows an image of hMSCs transduced with an NFκB-Gluc construct containing a GFP marker. Right panel shows fold differences in Gluc secretion signal with and without virial transduction and with and without TNFα induction.

Figure 10:
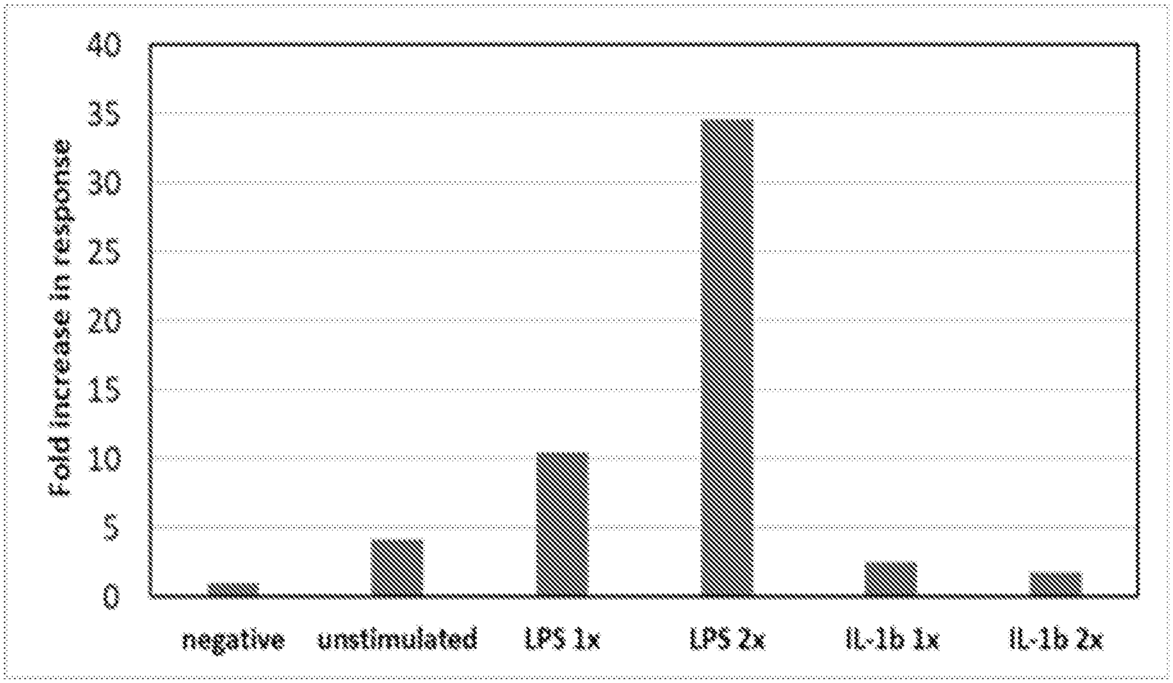

FIG. 10 shows relative GLuc signal increased dose dependently for LPS stimulation but was not stimulated by IL-1b which acts on a different response element (MAPK) endogenously in HepG2 hepatocytes that were engineered with the NFkB-GLuc construct and stimulated with either inflammatory LPS or IL-1b at two different doses. This shows that the GLuc secretion is due specifically to NfkB activity and stimulation.

Figure 11A:
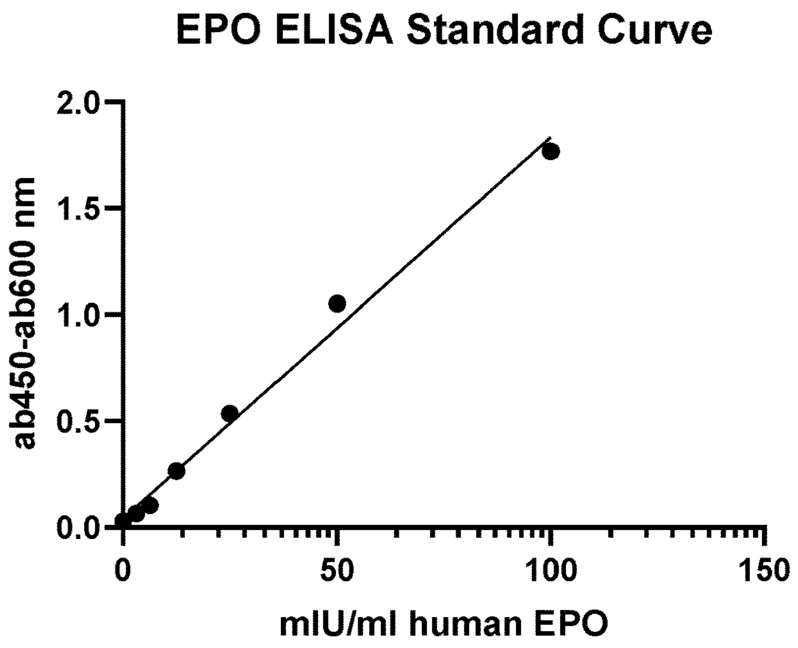
Figure 11B:
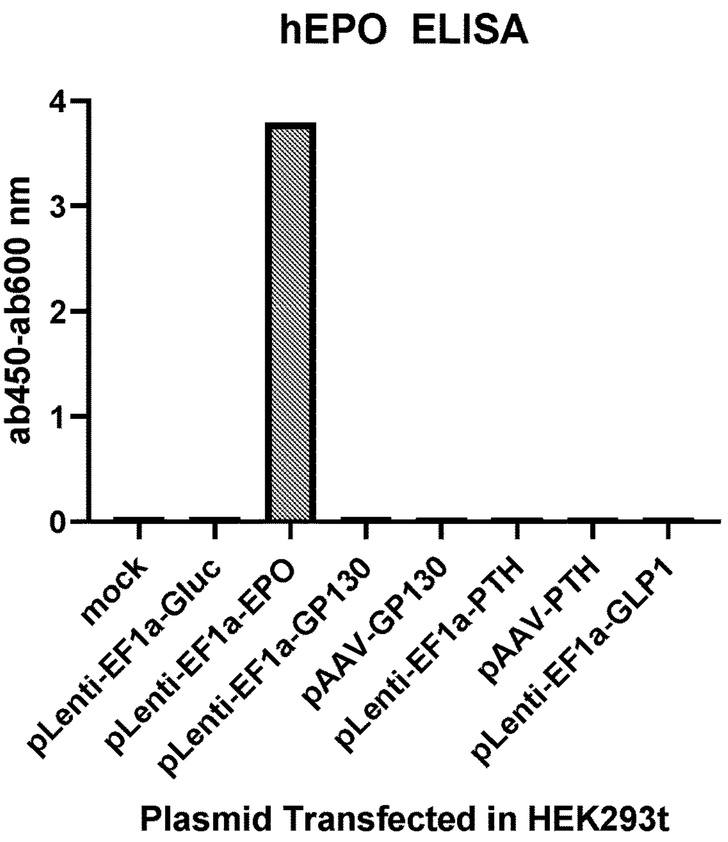
Figure 12:
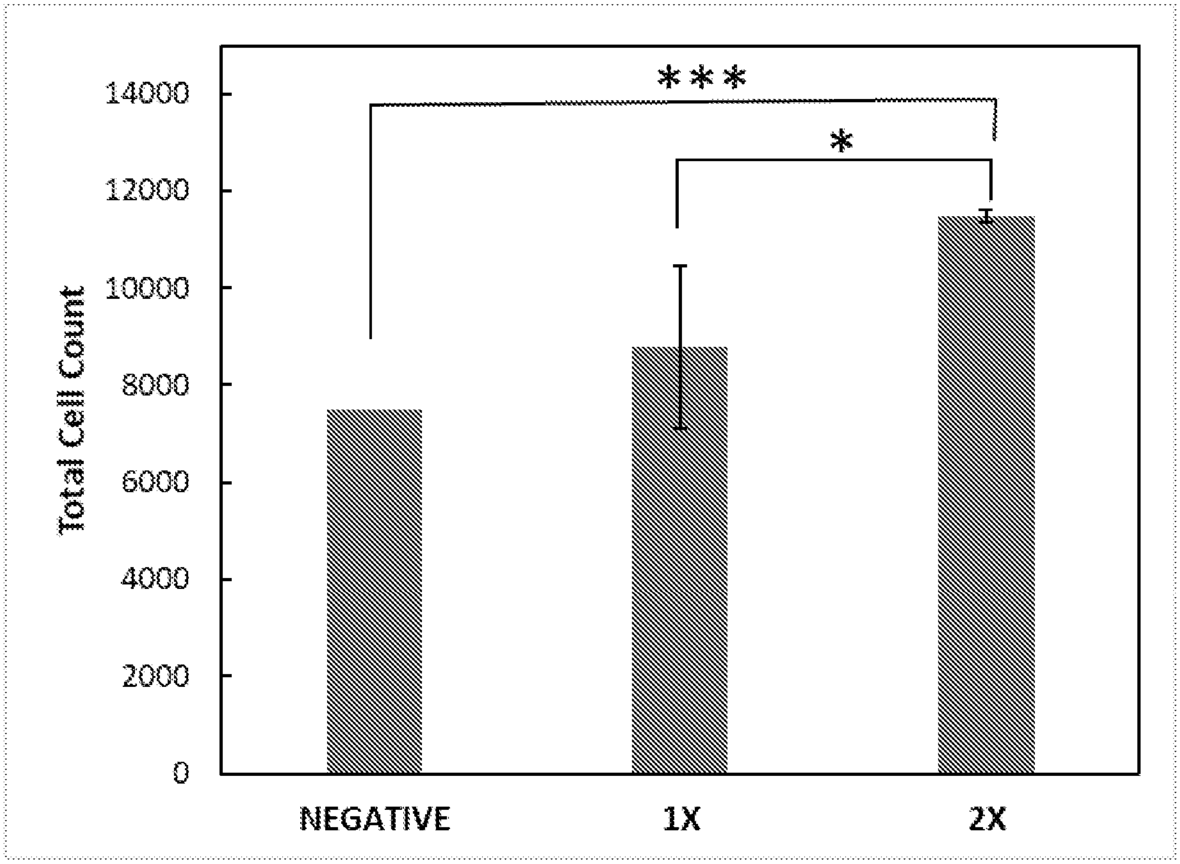
Figure 13A:
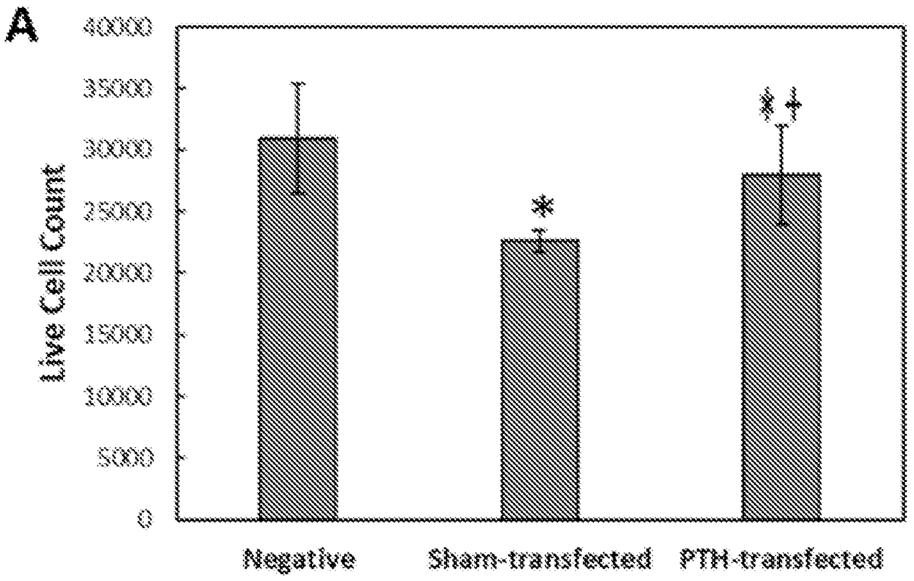
Figure 13B:
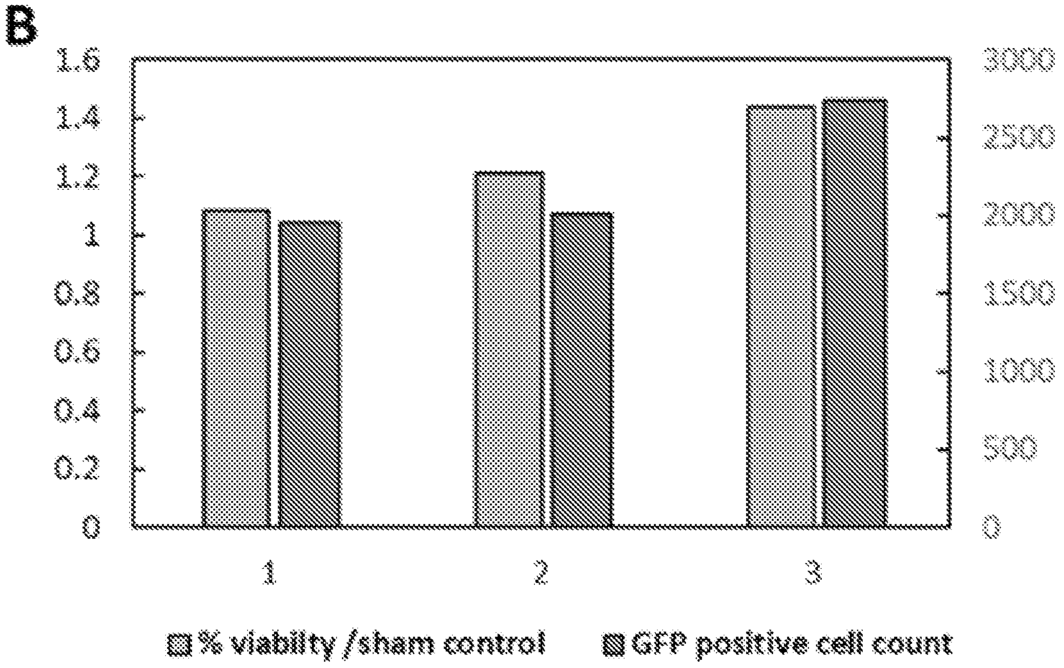

FIGS. 11A-B. FIG. 11A shows standard curve of human EPO ELISA. FIG. 11B shows the various plasmid constructs that were transfected into HEK293t cells. Media was collected 24-48 hours post transfection and assayed for human EPO by ELISA. Secreted EPO signal was detected only from cells transfected with a construct containing EPO FIG. 12. Osteoblast cells proliferate in response to PTH secreted from engineered cells. HepG2 cells were transfected at either a 1× of 2× dose of AAV-EF1a-PTH and PTH was allowed to accumulate in the supernatant for 3 days. The conditioned media was then exposed to Saos-2 osteoblasts, an osteosarcoma-derived cell line that proliferates in response to PTH. As shown in the figure, there is a dose-dependent increase in proliferation for groups exposed to PTH-conditioned media from HepG2 cells. Both the 1× and 2× dosing group proliferated significantly more than the negative control after 3 days of incubation FIGS. 13A-B. Saos-2 osteosarcoma-derived osteoblasts were transfected with EF1a-PTH construct or a sham transfection (EF1a-GLuc). Groups transfected with a PTH construct proliferated significantly more than sham-transfected groups (FIG. 13A). The level of proliferation directly correlated to the number of transfected cells (FIG. 13B), due to presumably increased PTH concentration in the media.

Figure 14:
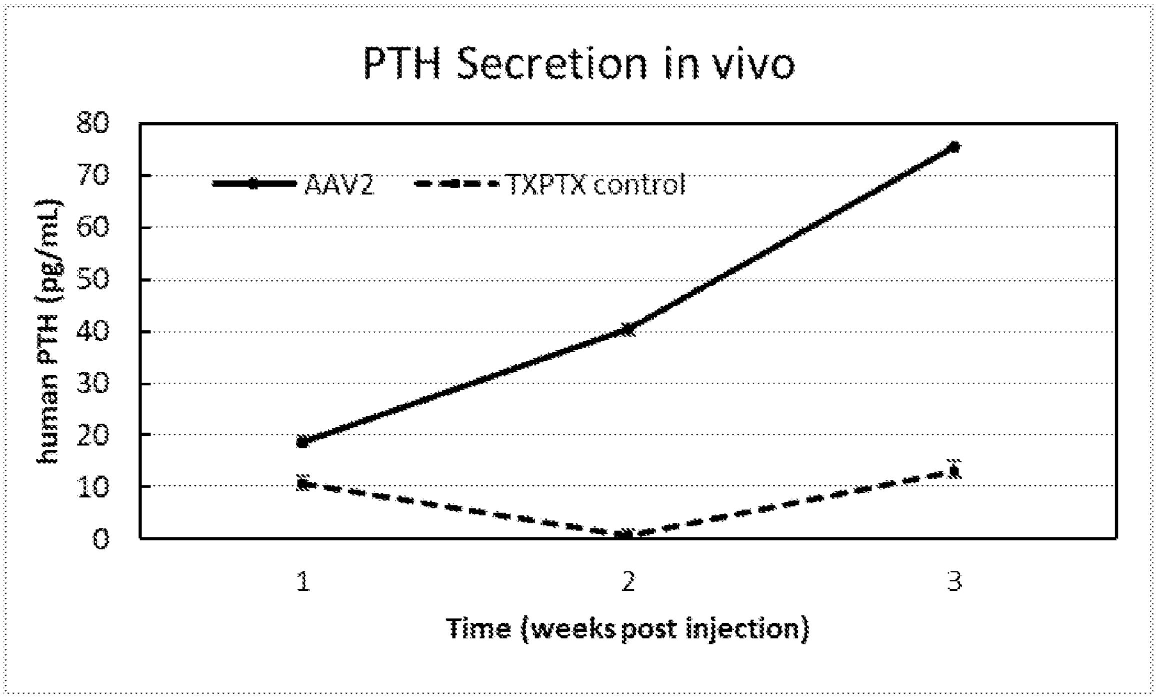

FIG. 14 AAV vectors administered in vivo result in detectable levels of human PTH in the plasma 3 weeks post injection. AAV2 vectors encoding EF1a-PTH were produced and concentrated in sterile saline at a concentration of $10^{10}$ vg/mL. Male C57B1 mice underwent thyroid/parathyroidectomy surgery and PTH levels were measured in the plasma to ensure levels were below detection limit. Each group consisted of n=2 animals and AAV2 animals received 100 uL of vector solution via intraperitoneal injection. 100 uL of whole blood was sampled via tail vein once per week at the same time of day and plasma was isolated for PTH measurement by ELISA. As shown in the figure, PTH levels increase with time reaching around 80 pg/mL which is on the same order of normal PTH concentrations.

Figure 15A:
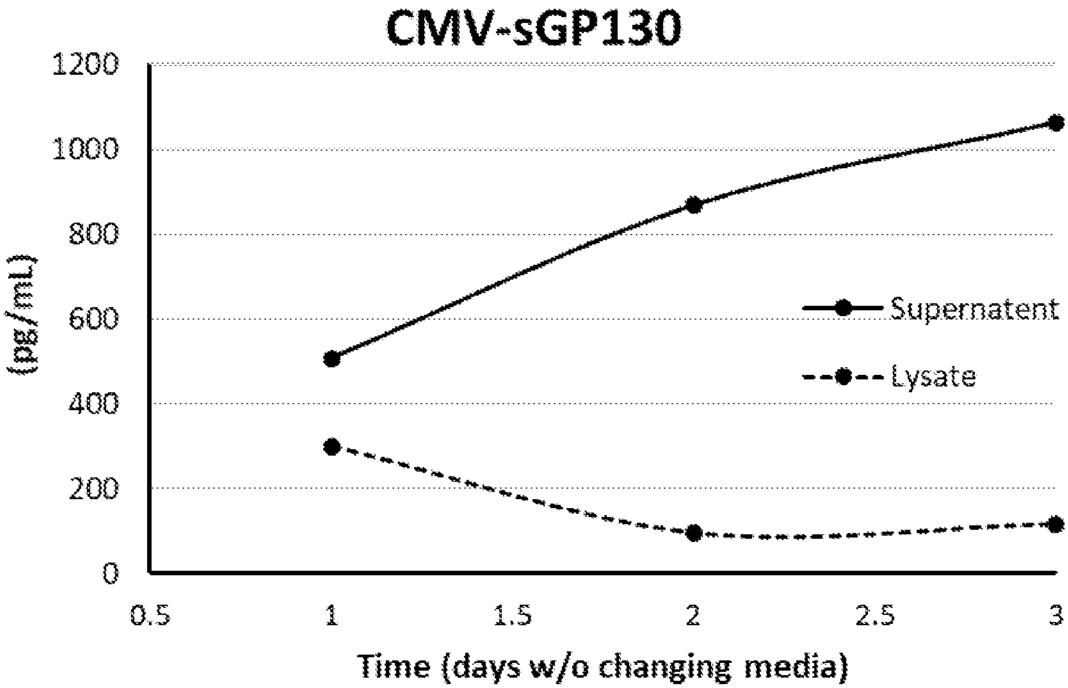
Figure 15B:
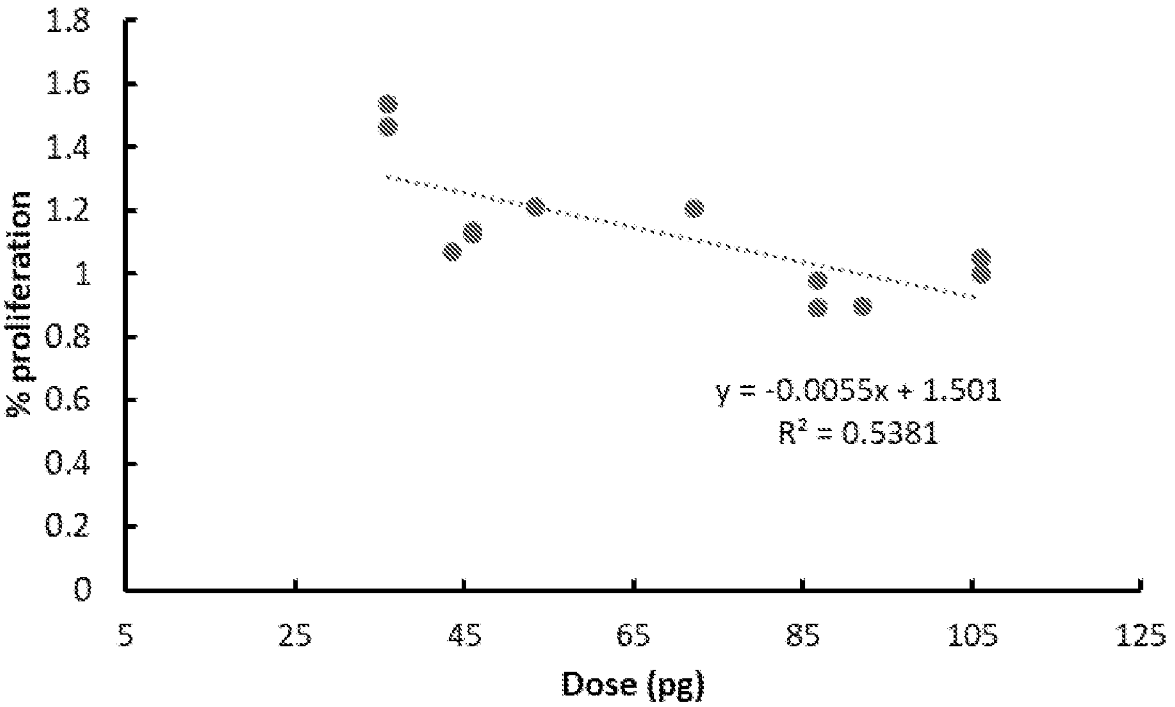

FIGS. 15A-B. Engineered cells secrete soluble GP130 into the media and suppress IL-6-dependent proliferation in DS-1 cells. Media from cells engineered with EF1a-sGP130 constructs was sampled, along with cell lysate, showing that measurable protein levels increase over time (FIG. 15A). FIG. 15B shows relationship between proliferation and dose. DS-1 cells were incubated in the conditioned media from the engineered cells which contained varying concentrations of sGP130. Using the volume added, the total sGP130 content was compared to the proliferation in that well and shows function sGP130 inhibition of IL-6 on the DS-1 cells.

Figure 16:
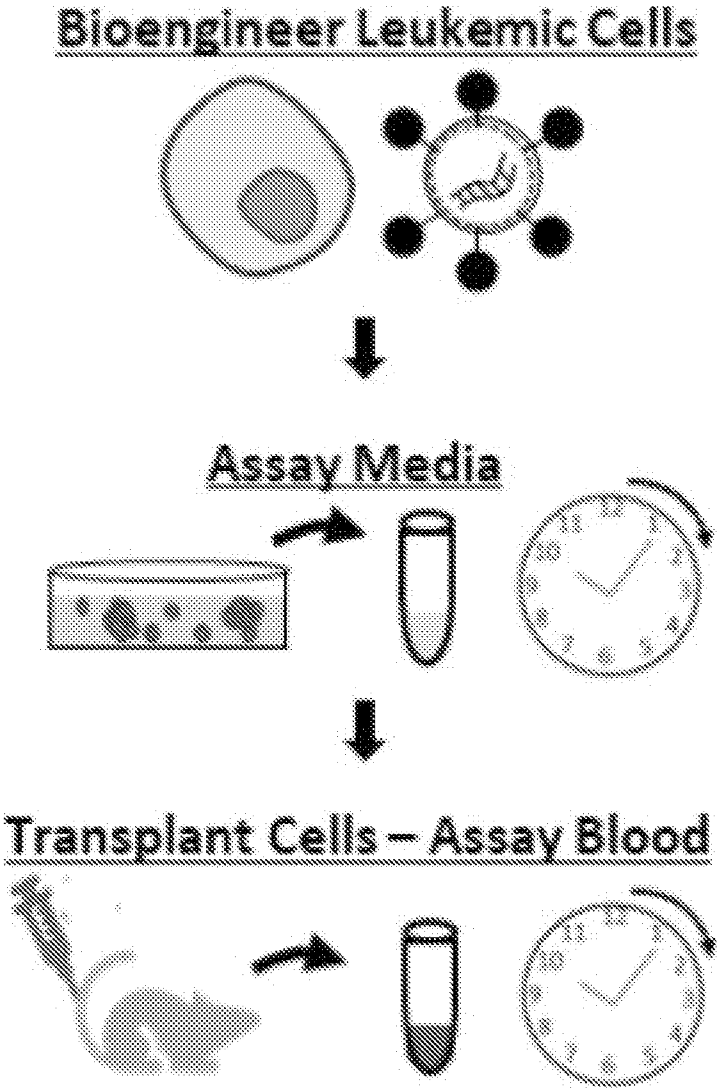

FIG. 16 is a schematic of experimental approach. Recombinant DNA was introduced into lymphoblastic leukemic T-cells (Jurkat). Secretion of luciferases in the media in vitro were monitored for 24 to 48 hours. Cells were engrafted into animals and blood was assayed for luciferase over the course of a day.

FIGS. 17A-F show rhythmic and constitutive secretion of GLUC and CLUC from lymphoblastic leukemic T-cells cells in a suspension cell flow collection system. Media conditioned with EF1α-GLUC, EF1α-CLUC or unmodified (untransduced) Jurkat cells was assayed using (A) GLUC substrate or (B) CLUC substrate separately. (C) Schematic of a continuous flow system in which Jurkat cell secretion was monitored. Jurkat cell secretions were collected from synchronized (D) EF1α-CLUC; CMV-GLUC or (E) Circa2-GLUC; EF1α-CLUC cells, linear detrended (Period: ~21.3 h) and amplitude normalized (s.d.; N=6). (F) Circa2-GLUC signals were normalized to EF1α-CLUC signals and an undamped 24-hour Sine wave was fitted to the data (Prism, least squares method, degrees of freedom: 14, R squared: 0.7777, sum of squares: 0.4124).

FIGS. 18A-F show underlying data for rhythmic and constitutive secretion of GLUC and CLUC from Jurkat cells in a suspension cell flow collection system. Jurkat cell secretions were collected from synchronized EF1α-CLUC; CMV-GLUC and assayed for (A) CLUC or (B) GLUC. Circa2-GLUC; EF1α-CLUC cell secretions were collected beginning 7 hours post-synchronization and assayed for (C) CLUC or (E) GLUC, or beginning 23 hours post-synchronization and assayed for (D) CLUC or (F) GLUC. Each line represents a replicate (N=6).

Figure 19A:
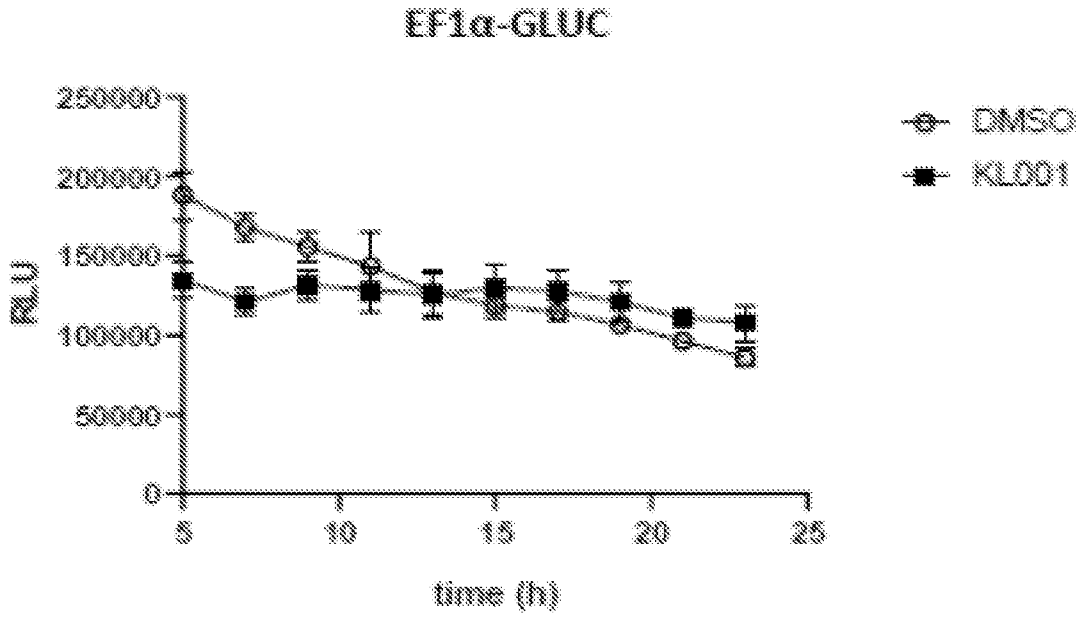
Figure 19B:
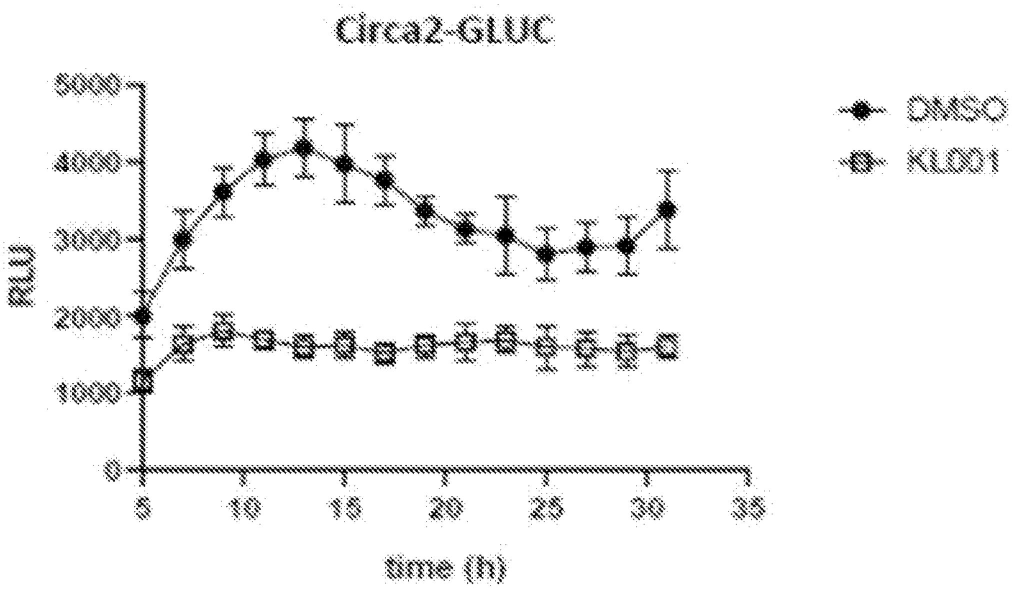

FIGS. 19A-B show pharmacological disruption of circadian clocks abolishes dynamic nature of Circa2 driven GLUC secretion in leukemic T-cells. (A) EF1α-GLUC or (B) Circa2-GLUC cells were treated with DMSO (vehicle) or 20 μM KL001 for 24 hours prior to synchronization and seeding for cell secretion analysis (GLUC substrate) using continuous flow (s.d.; N=3).

FIGS. 20A-F show constitutive and circadian clock reporter dynamics of leukemic T-cells infiltrating immuno-compromised mice. (A) Blood was collected from NSG/SCID mice were injected with EF1α-GLUC Jurkat cells every few days and assayed for GLUC (5 μl blood). Each marker represents an individual mouse. Time 0 was measured before mice were injected. (B) Mice were injected with sham (PBS vehicle), unmodified (untransduced), EF1α-GLUC, or Circa2-GLUC Jurkat cells, and blood was assayed or GLUC 40 days later. Each marker represents a single mouse. (C) Survival curve of mice injected with sham (PBS vehicle), EF1α-GLUC or unmodified (untransduced) Jurkat cells over a period of 61 days. (D) Spleens were collected from mice injected with sham (1,2), EF1α-GLUC (3,4,5) and untransduced (6,7,8) Jurkat cells. (E) Blood was collected approximately every 4 hours from mice injected with either EF1α-GLUC or Circa2-GLUC Jurkat cells and assayed for GLUC. (N=2). (F) EF1α-CLUC and Circa2-GLUC Jurkat cells were co-injected into a single mouse, then blood was collected every 4 hours and assayed for GLUC and CLUC. Lights on at ZT0 and lights off at ZT12. Raw RLU counts (5 μl blood) were amplitude normalized.

Figure 21A:
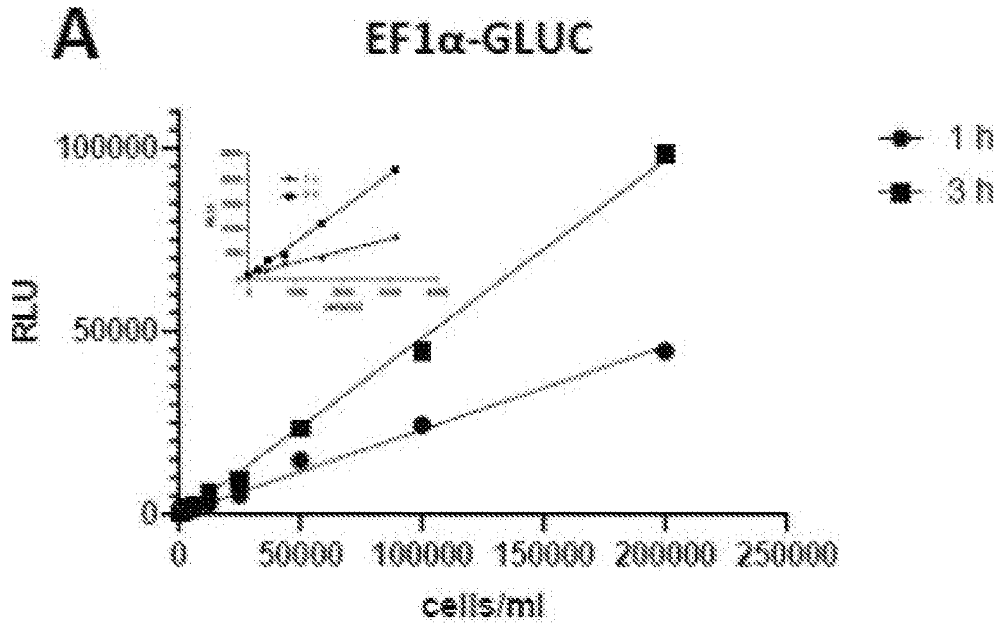
Figure 21B:
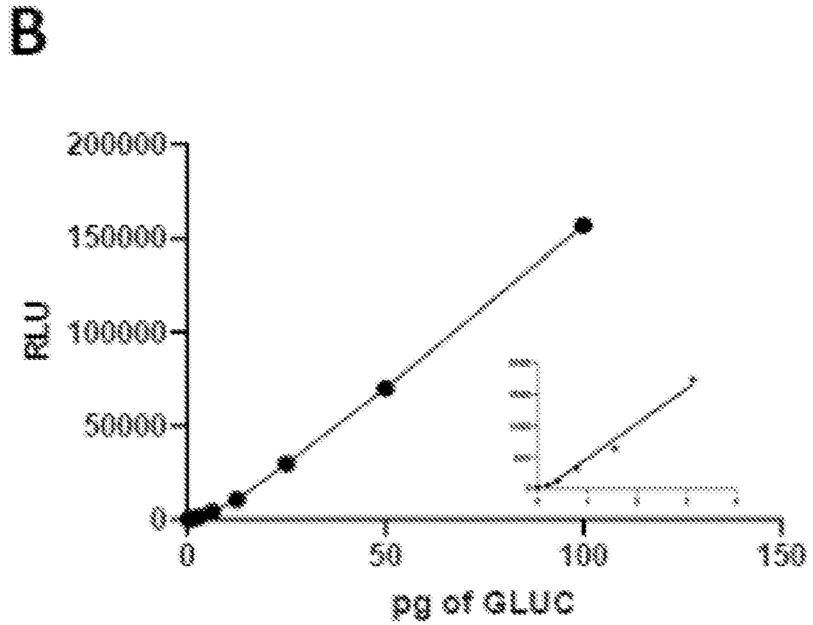

FIGS. 21A-B show sensitivity of GLUC luciferase detection secreted from cells and purified GLUC. (A) EF1α-GLUC cells seeded at various densities were incubated for 1 hour or 3 hours, and conditioned media was assayed for GLUC secretion. Inset contains lower cell densities. Linear regression fit, R squared=0.9934. (B) Standard curve of GLUC. Inset contains lower GLUC amounts. Linear regression fit, R squared=0.9938.

Figure 22A:
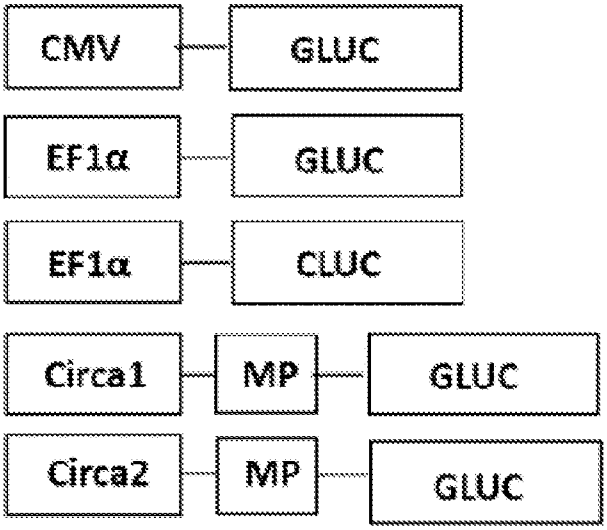
Figure 22B:
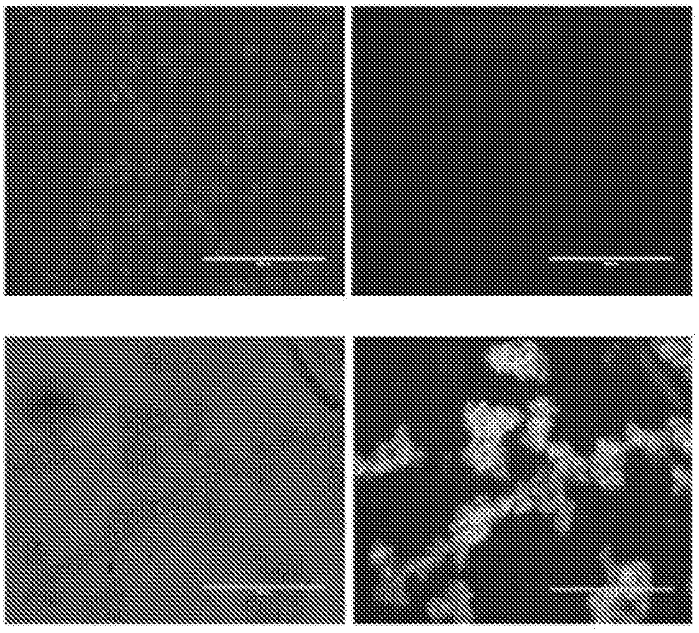
Figure 22C:
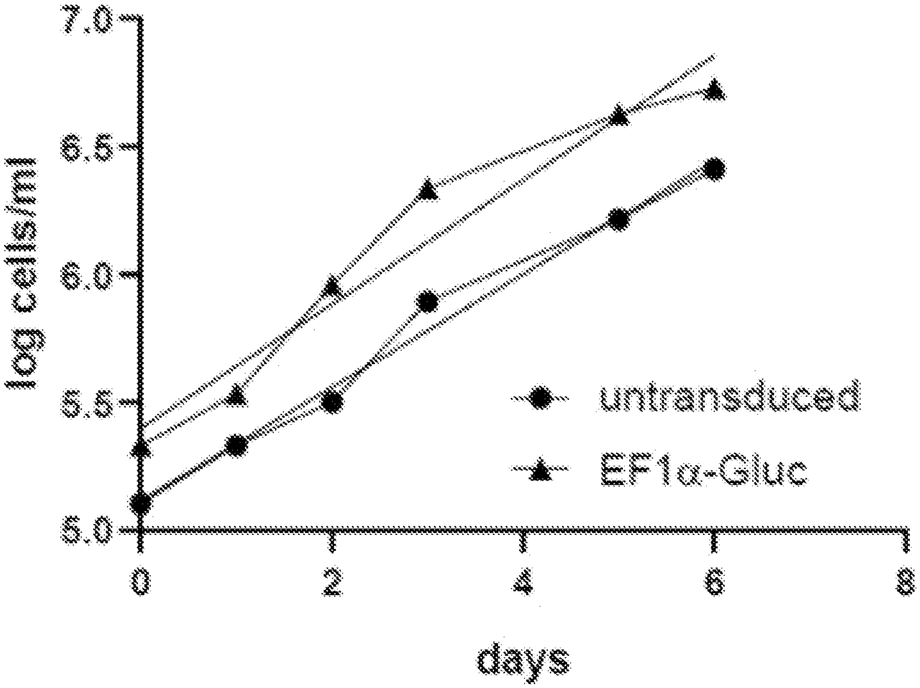

FIGS. 22A-C. Jurkat cell engineering with recombinant DNA and effects on growth rate. (A) Schematics of DNA constructs driving constitutive and circadian secretion of luciferases used in this study. (B) Untransduced (upper top panels) versus transduced (lower panels) leukemic T-cells with a GFP selective marker. (C) Growth rates of untransduced versus EF1α-GLUC cells. Starting densities of each cell type were different as noted on the Y-axis at time 0. Linear regression fit, R squared=0.9870 and 0.9508 respectively.

FIGS. 23A-H. Endogenous circadian gene expression in Jurkat leukemic T-cells. Synchronized Jurkat cells were collected approximately every 2 hours and RNA was isolated. RT-qPCR using primers specific for (A) Perl, (B) Per2, (C) Cry1, (D) Cry2, (E) Bmall and (F) Cry2 was performed and the ΔCt was calculate using GAPDH a reference gene (s.d.; N=3). (G) The lowest ΔCt values were normalized (to 1) for each gene. (H) Differences between lowest and highest normalized ΔCt values for each gene were statistically significant if q-value was <1=0.001 (−log>1=2).

FIGS. 24A-D. Underlying data for constitutive and circadian clock reporter dynamics of leukemic T-cells infiltrating immuno-compromised mice. Blood was collected approximately every 4 hours from mice injected with either EF1α-GLUC (A) or Circa2-GLUC (B). (C) EF1α-GLUC and Circa2-GLUC and (D) EF1α-CLUC and Circa2-GLUC Jurkat cells were co-injected into a single mouse, then blood was collected every 4 hours and assayed for GLUC and CLUC. Lights on at ZT0 and lights off at ZT12. Raw RLU counts ar shown (5 μl blood).

FIGS. 25A-C. Characterization and optimization of secreted luciferase reporter system in engineered rat fibroblasts. (A) Transduction efficiency measured by GFP expression using flow cytometry of Rat2 cells cultured for 24 h in DMEM with different lentiviral particles per cell (MOI) or protamine sulfate (PS) concentrations. (B) In vitro gLuc secretion under different media conditions. A media exchange was performed to wash out accumulated gLuc and fresh media was provided to detect continued secretion. A DMEM base resulted in higher gLuc secretion than the previously-used perfusate with a Williams E base. (C) Release of gLuc under different cell seeding densities. Secretion of engineered rat fibroblasts was stable and increase linearly with seeding density in vitro.

FIGS. 26A-C. Cells successfully engrafted into livers and longer perfusion times correlated with increased distribution in the vasculature. Near-infrared imaging of cells after infusion into livers under (A) 2-hour total perfusion, (B) 4-hour total perfusion, (C) 6-hour total perfusion. Pseudo-color indicates arbitrary intensity of cells in a given region with red-to-blue corresponding to highest-to-lowest intensity.

FIGS. 27A-D. Histology of liver tissue after cell infusion. Paraffin embedded liver tissue samples taken post perfusion and stained using an Anti-GFP antibody for the presence of GFP in the tissue stained brown at (A) 10× or (B) 40× magnification. Hematoxylin and eosin stain of paraffin embedded liver tissue samples taken post perfusion to check for endothelial cell damage cause by perfusion or the addition of biosensor cells at (C) 10× magnification or (D) 40× magnification.

FIGS. 28A-C. Transplant viability assessment for biosensor engrafted livers. (A) Total bile collected during perfusion. (B) Portal flow rates. (C) Venous pH obtained from perfusate.

FIGS. 29A-E. Engrafted biosensor cells have minimal impact on liver functionality. (A) Lactate, (B) Glucose levels, (C) Oxygen consumption, and (D) AST levels obtained from perfusate samples collected throughout perfusion. Lactate, glucose, and oxygen were measured in real time using a blood chemistry analyzer (i-STAT). (E) Weight of liver measured pre and post perfusion.

FIGS. 30A-B. Release of engineered biomarker from engrafted cells during machine perfusion. (A) Biosensor cells were infused in perfused livers for the first three hours, then swapped out for fresh perfusate to test engraftment. gLuc was measured in the collected perfusate. Livers displayed a pattern of gLuc secretion in the perfusate consistent with the experiment design. (B) Detection of gLuc from frozen tissue biopsies taken post-perfusion. Tissue lysis for gLuc demonstrates successful engraftment of biosensor cells in the liver tissue.

FIG. 31 shows the results when cells were bolus injected, with less distribution of biosensors throughout organ. Dyed cells injected directly into the cannulated lived did not distribute as well as perfused cells.

DETAILED DESCRIPTION

Figure 1A:
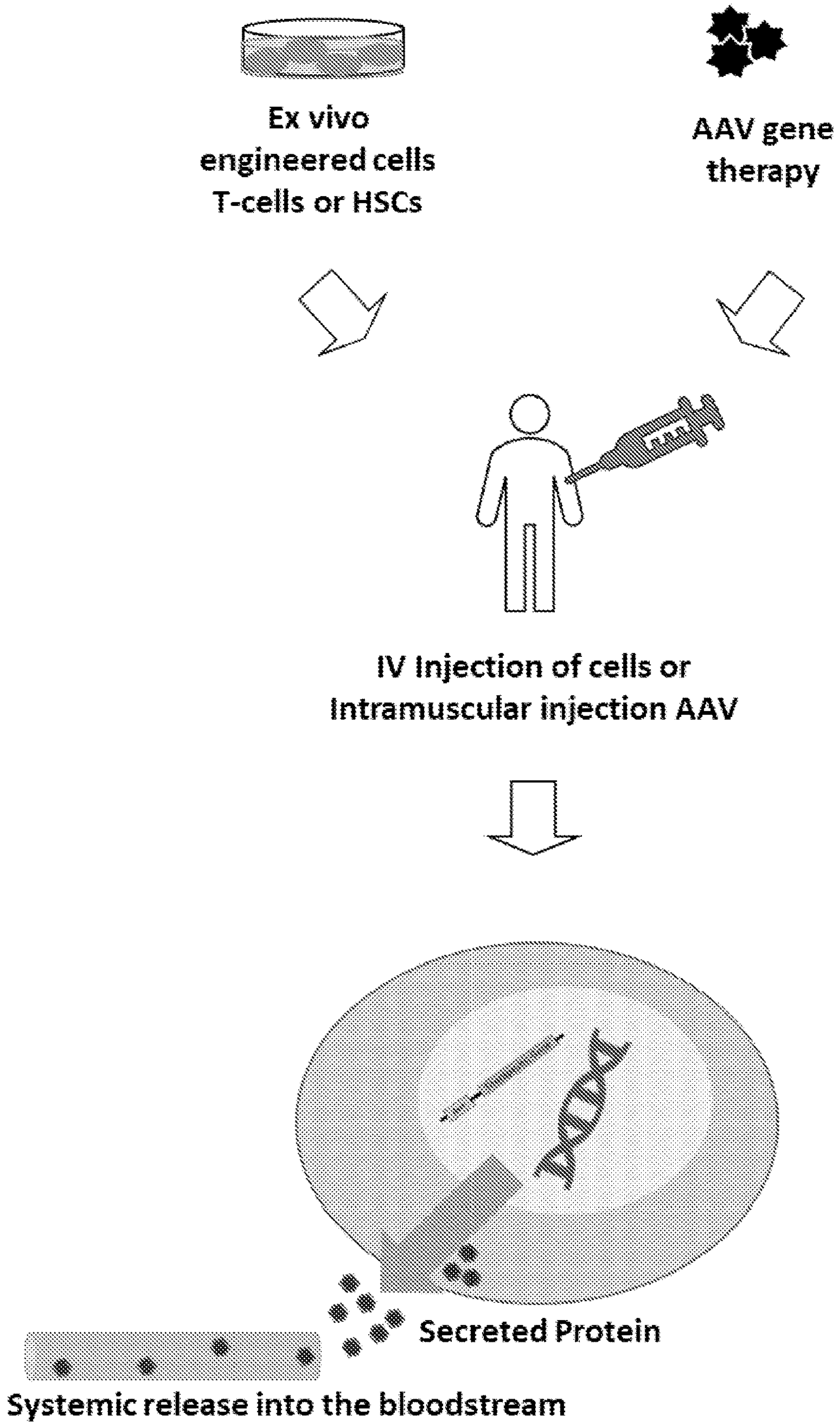
FIGS. 1A-B. (A) Schematic of an exemplary clinical application of a gene therapy or cell-based therapy that is engineered for response element driven (RED) therapeutic peptide delivery. In the case of cell therapy, RED therapeutic peptide genetic constructs are introduced to long-lived donor cells, such as B cells, NK cells, red blood cells, T cells, memory T-cells or hematopoietic stem cells, or delivered to muscle cells via an AAV viral vector as an example of a direct gene therapy. (B) These methods allow for dynamic drug secretion based on physiological cues, molecular signals of pathology or external stimuli.
Figure 1B:
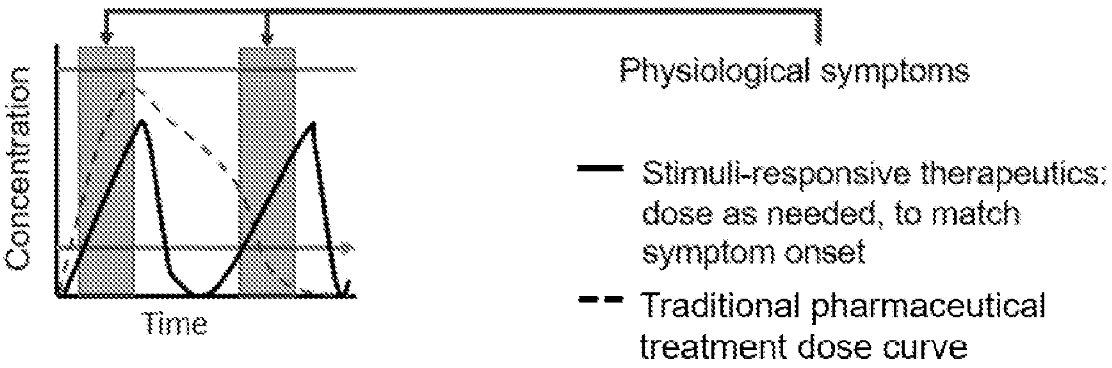

Described herein are methods and composition for use with cell therapeutics that dynamically deliver therapeutic peptides by engineering cells and viral vectors with genetic constructs (FIG. 1). All cells, including cell therapeutics, inherently sense their environments through a variety of cell signaling mechanisms, and respond to changing conditions by altering gene expression. This invention employs conserved signal transduction pathways that induce gene expression via the activation of proteins known as transcription factors. Transcription factor mediated gene activation is a central paradigm of genetic regulation. Transcription factors bind to discrete regions of DNA known as response elements within the regulatory regions of genes. Here we have generated novel genetic constructs driving therapeutic peptide expression in response to molecular and physiological cues by combining response elements with therapeutic peptide sequences.

Response Element-Driven Therapeutic Peptides

Described herein are cell therapeutics capable of adapting to a patient's body clock by using genetic sensors of circadian rhythms to drive expression of therapeutic peptides that regulate appetite and glucose levels (FIG. 2, Table 1 and Table 2). Also described herein are cell therapeutics that are activated by a patient-delivered stimulus by coupling heat-responsive genetic elements with anti-inflammatory therapeutic peptides.

Table 1 provides sequences of exemplary response elements.

TABLE 1

Exemplary Response Elements

| Pathway | Response Element Sequences | SEQ ID NO: |
|---|---|---|
| Core Clock | TCGAGCAGTATTTAGCCACGTGACAGTGTAAGCAC ACGTGGGCCCTCAAGTCCACGTGCAGGGAG | 1 |
| NFκB | GGGAATTTCCCGGGAATTTCCGGGACTTTCCGGGA ATTTCCCGGGAATTTCCGGGACTTTCC | 2 |
| Hypoxia Induible Factor | GGGAAAATGAAACTGGGAAAACGAAACTGGGAAAA TGAAAGTGGGAAAATGAAACTGGGAAAATGAAACT | 3 |
| Calcium Response | GGACGTGCGGACGTGCGGGCGTGCGGACGTGCGGAC GTGCGGACGTGC | 4 |
| Heat Shock Factor | GGGAACATTATGTCCTGTGGGAACAGTATGTCCTGA GGGAACATTATGTCCTGTGGGAACATTATGTCCTGT | 5 |
| Glucocorticoid Response | ATTCTAGAACGTICTITCCAGAACGTTCTTTCTAGA ACGTTCTTTCTAGAACGTTCTTTCCAGAACGTTCT | 6 |

Table 2 provides sequences of exemplary therapeutic peptides.

TABLE 2

Therapeutic Peptides

| Peptide Drug | Sequences | SEQ ID NO: |
|---|---|---|
| GLP-1 | HAEGTFTSDVSSYLEGQAAKEEFIIAWLVKGRG | 7 |
| PTH | SVSEIQLMHNLGKHLNSMERVEWLRKKLQDVHNF | 8 |
| IL-1RA | MRPSGRKSSKMQAFRIWDVNQKTFYLRNNQLVAGYLQ GPNVNLEEKIDVVPIEPHALFLG | 9 |
| EPO | APPRLICDSRVLERYLLEAKEAENITTGCAEHCSLNENITV PDTKVNFYAWKRMEVGQQAVEVWQGLALLSEAVLRGQ ALLVNSSQPWEPLQLHVDKAVSGLRSLTTLLRALGAQKE AISPPDAASAAPLRTITADTFRKLFRVYSNFLRGKLKLYTG EACRTGDR | 10 |
| GP130 | MSAPRIWLAQALLFFLTTESIGQLLEPCGYIYPEFPVVQRGSNFTAICVLKEACLQHY YVNASYIVWKTNHAAVPREQVTVINRTTSSVTFTDVVLPSVQLTCNILSFGQIEQNVY GVTMLSGFPPDKPTNLTCIVNEGKNMLCQWDPGRETYLETNYTL KSEWATEKFPDCQSKHGTSCMVSYMPTYYVNIEVWVEAENALGKVSSESINFDPVDKV KPTPPYNLSVTNSEELSSILKLSWVSSGLGGLLDLKSDIQYRTKDASTWIQVPLEDTM SPRTSFTVQDLKPFTEYVFRIRSIKDSGKGYWSDWSEEASGTTYEDRPSRPPSFWYKT NPSHGQEYRSVRLIWKALPLSEANGKILDYEVILTQSKSVSQTYTVTGTELTVNLTND RYVASLAARNKVGKSAAAVLTIPSPHVTAAYSVVNLKAFPKDNLLWVEWTPPPKPVSK YILEWCVLSENAPCVEDWQQEDATVNRTHLRGRLLESKCYQITVTPVFATGPGGSESL KAYLKQAAPARGPTVRTKKVGKNEAVLAWDQIPVDDQNGFIRNYSISYRTSVGKEMVV HVDSSHTEYTLSSLSSDTLYMVRMAAYTDEGGKDGPEFTFTTPKFAQGEIEAIVVPVC LAFLLTTLLGVLFCFNKRDLIKKHIWPNVPDPSKSHIAQWSPHTPPRHNFNSKDQMYS | 11 |

TABLE 2-continued

| Therapeutic Peptides | | |
|---|---|---|
| Peptide Drug | Sequences | SEQ ID NO: |
| | DGNFTDVSVVEIEANNKKPCPDDLKSVDLFKKEKVSTEGHSSGIGGSSCMSSSRPSIS SNEENESAQSTASTVQYSTVVHSGYRHQVPSVQVFSRSESTQPLLDSEERPEDLQLVD SVDGGDEILPRQSYFKQNCSQPEACPEISHFERSNQVLSGNEEDFVRLKQQQVSDHIS QPYGSEQRRLFQEGSTADALGTGADGQMERFESVGMETTIDEEIPKSYLPQTVRQGGY MPQ | |

Exemplary combinations of response elements and therapeutic peptides are shown in FIG. 2.

Also provided herein are therapeutic peptides engineered for secretion from cell therapeutics. The molecules are created by fusing therapeutic peptides to secretion signals of previously characterized luciferases (FIG. 3). *Guassia princeps* and *Cypridina noctiluca* are sea borne bioluminescent organisms from which recombinant versions of luciferases are produced for research purposes. *Guassia* and *Cypridina* luciferase, Gluc and Cluc respectively, are naturally secreted when expressed in most if not all human cells tested. As described herein, therapeutic peptides for secretion from cell therapeutics were genetically engineered by fusing the therapeutic peptides to the Gluc and Cluc peptide secretion signals.

Table 3 provides sequences of exemplary peptide secretion signals.

TABLE 3

| Exemplary Peptide Secretion Signals | | | |
|---|---|---|---|
| Source | Sequence | ACCESSION NO. | SEQ ID NO: |
| *Guassia princeps* Luciferase | MGVKVLFALICIAVAEAKPTGP | AAG54095 | 12 |
| *Cypridina noctiluca* Luciferase | MKTLILAVALVYCATVHCQDGP | BAD08210 | 13 |
| Insulin | MALWMRLLPLLALLALWGPDPAAAFVNQH | P01308 | 14 |
| Erythropoietin | MGVHECPAWLWLLLSLLSLPLGLPVLGAP PR | P01588 | 15 |
| Follicle Stimulating Hormone | MALLLVSLLAFLSLGSGCHHRICHCSN | P23945 | 16 |

The peptide secretion signal can be fused to the N or C terminus of therapeutic peptide.

Nucleic Acids

Also described herein are nucleic acid molecules comprising response elements and sequences encoding a therapeutic peptide sequence, optionally including a peptide secretion signal, as described herein. Nucleic acid molecules comprising expression vectors can be used, e.g., for in vitro expression of the therapeutic peptide.

The nucleic acids encoding the selected therapeutic peptide can be inserted in an expression vector, to make an expression construct. A number of suitable vectors are known in the art, e.g., viral vectors including recombinant retroviruses, adenovirus, adeno-associated virus, and herpes simplex virus 1, adenovirus-derived vectors, or recombinant bacterial or eukaryotic plasmids. For example, the expression construct includes a response element and a coding region encoding the therapeutic peptide as described herein, as well as one of more of a promoter sequence, e.g., a promoter sequence that restricts expression to a selected cell type, a conditional promoter, or a strong general promoter; another enhancer sequence; untranslated regulatory sequences, e.g., a 5' untranslated region (UTR), a 3'UTR; a polyadenylation site; and/or an insulator sequence. Such sequences are known in the art, and the skilled artisan would be able to select suitable sequences. See, e.g., *Current Protocols in Molecular Biology*, Ausubel, F. M. et al. (eds.) Greene Publishing Associates, (1989), Sections 9.10-9.14; Vancura (ed.), *Transcriptional Regulation: Methods and Protocols* (Methods in Molecular Biology (Book 809)) Humana Press; 2012 edition (2011) and other standard laboratory manuals.

Expression constructs can be administered in any biologically effective carrier, e.g., any formulation or composition capable of effectively delivering the component gene to cells in vivo. Viral vectors transfect cells directly; plasmid DNA can be delivered with the help of, for example, cationic liposomes (e.g., LIPOFECTIN) or derivatized (e.g. antibody conjugated), polylysine conjugates, gramicidin S, artificial viral envelopes or other such intracellular carriers, as well as direct injection of the gene construct or $CaPO_4$ precipitation. In some embodiments, the nucleic acid is applied "naked" to a cell, i.e., is applied in a simple buffer without the use of any additional agents to enhance uptake. See, e.g., Current Protocols in Molecular Biology, Ausubel, F. M. et al. (eds.) Greene Publishing Associates, (1989), Sections 9.10-9.14 and other standard laboratory manuals.

Methods of Use

The dynamic and inducible gene or cell therapeutics described herein have a number of applications. For example, diseases that involve inflammation, such as rheumatoid arthritis, can be treated by injecting the patient with cells or a viral vector, administered either locally (i.e., by injection into a joint) or systemically driving an anti-inflammatory therapeutic peptide from an inflammatory cytokine response element. The drug dosage delivered will depend on the severity of the inflammation, which correlates with the cytokine exposure of the therapeutic. The present therapeutics can also sense healthy physiological cues. For example, a person's body clock strongly regulates metabolic pathways at the transcriptional level, but it is also influenced by eating, travel across time zones, and other behaviors, making it very difficult to synchronize therapies to an individual's clock. The present methods can include delivering cells or nucleic acids engineered to express a response element-driven therapeutic peptide, optionally with a secretion signal as described herein.

Cell Therapy

In some embodiments, the methods include delivering therapeutic cells. Primary and secondary cells to be genetically engineered can be obtained from a variety of tissues and can include cell types that can be maintained and propagated in culture. For example, primary and secondary cells include pancreatic islet β cells, adipose cells, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells, dendritic cells, natural killer cells (Hölsken et al., Journal der Deutschen Dermatologischen Gesellschaft 2015, 23-28), cytotoxic T lymphocytes (Cooper et al. Cytotherapy 2006, 8(2):105-17), muscle cells (myoblasts) and precursors of these somatic cell types. The generation of adult cells that have been engineered from iPS or embryonic stem cells (e.g., differentiation of embryonic stem cells into mesenchymal stem cells) are also envisioned as a cell source for dynamically drug secreting cells. Primary cells are preferably obtained from the individual to whom the genetically engineered primary or secondary cells will be administered. However, primary cells may be obtained from a donor (i.e., an individual other than the recipient).

The term "primary cell" includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of primary cells which have been passaged one or more times.

Primary or secondary cells of vertebrate, particularly mammalian, origin can be transfected with an exogenous nucleic acid sequence as described herein, and produce the encoded therapeutic peptide product in response to the appropriate physiological signal in vitro and in vivo, over extended periods of time.

The nucleic acid sequence can be introduced into a primary or a secondary cell, e.g., by homologous recombination as described, for example, in U.S. Pat. No. 5,641,670, the contents of which are incorporated herein by reference. In some embodiments, viral vectors, e.g., lentiviral expression vectors, are used. Viral vectors for use in the present methods and compositions include recombinant retroviruses, adenovirus, adeno-associated virus, alphavirus, and lentivirus, e.g., as described herein or known in the art.

The transfected primary or secondary cells can also include DNA encoding a selectable marker, which confers a selectable phenotype upon them, facilitating their identification and isolation.

Vertebrate tissue can be obtained by standard methods such a punch biopsy or other surgical methods of obtaining a tissue source of the primary cell type of interest. For example, a biopsy can be used to obtain bone marrow, as a source of cells, e.g. hematopoietic stem cells. A mixture of primary cells can be obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly, or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection, electroporation or genome-editing using zinc-finger nucleases, transcription activator-like effector nuclease or the CRIPSR-Cas system, all of which are routine in the art (Kim et al (2010) Anal Bioanal Chem 397(8): 3173-3178; Hockemeyer et al. (2011) Nat. Biotechnol. 29:731-734; Feng, Z et al. (2013) Cell Res 23(10): 1229-1232; Jinek, M. et al. (2013) eLife 2:e00471; Wang et al (2013) Cell. 153(4): 910-918).

Transfected primary or secondary cells can be allowed to undergo sufficient numbers of doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of RED-peptide expression in the transfected cells, the site of implantation of the transfected cells (for example, the number of cells that can be used is limited by the anatomical site of implantation), and the age, surface area, and clinical condition of the patient.

As an alternative to primary or secondary differentiated cells, the methods can include using adult stem cells or induced pluripotent stem cells.

Adult Stem-Cell Based Therapy

Adult stem cell-based therapeutics offer an alternative strategy to modulating impaired function as described above, and have already been safely and successfully used in the clinic for certain hematopoietic diseases (Gratwohl et al., JAMA 2010, 303 (16): 1617-24; Mahla et al., International Journal of Cell Biology. 2016 (7): 1-24; Maguire et al., ACS Medicinal Chemistry Letters. 7 (5): 441-43). Adult stem cells have the ability to self-renew and to differentiate into specialized cell-types within the lineage of their tissue of origin. Adult stem cells, and the specialized cell-derived from them, are believed to be less likely rejected by the host immune system from which they originated, i.e., autologous stem cells. Stem cells have been identified and isolated from almost all tissues based on their expression of cell-surface proteins and in vitro characterization. Briefly, the tissue of interest can be obtained by standard methods such a punch biopsy or other surgical methods of obtaining a tissue source of the primary cell type of interest. The tissue of interest is then dissociated or homogenized by enzymatic digestion and/or physical dissociation using equipment that is commercially available and is generally known to those skilled in the art. If enzymatic digestion is used, enzymes such as collagenase, hyaluronidase, dispase, pronase, trypsin, elastase and chymotrypsin can be used, along with DNAses and RNAses. Purification of stem cells from the resulting cell mixture is now routinely accomplished by completing several rounds of fluorescent activated cell sorting (FACS) (Bosio et al., Adv. Biochem Engin, 2009, 114:23-72). Prior to being analyzed by flow cytometry, the resulting cell mixture is incubated for a set amount of time in the presence of antibodies conjugated to fluorescent dyes that can bind specific proteins solely expressed on the cell surface of the cell of interest or magnetic beads. For example, mesenchymal stem cells can be isolated from bone marrow, adipose tissue, and umbilical cord, using a combination of these specific cellular markers, e.g. Stro-1, CD146, CD106, CD271, and/or MSCA-1. Other cell types can be used, including T cells, HSCs, fibroblasts, and iPS cells.

The sorting results in a high number of viable adult stem cells that can be passaged in culture, and further enriched by undergoing multiple rounds of FACS. The enriched adult stem cells can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Once implanted in an individual, the adult stem cells survive, migrate to their appropriate anatomical site, optionally differentiate into a specialized cell-type and express the therapeutic peptide in response to the appropriate physiological stimulus.

Induced Pluripotent Stem (iPs) Cells and Trans-Differentiated Cells for Cell-Based Therapy Within the field of stem cell biology, embryonic stem cells are considered the golden standard, as embryonic stem cells have the potential to differentiate into cells derived from any of the three germ layers, except for extraembryonic trophoblasts. Embryonic stem cells are therefore considered to be pluripotent. In recent years, it has been reported that induced pluripotent stem (iPS) cells can be established by introducing certain particular nuclear reprogramming substances to adult somatic cells in the form of DNA or protein (Takahashi, K et al., Cell (2007), 131, 131:861-872; Yu et al., Science 2007, 318:1917-1920; Takahashi and Yamanaka, Development 2013 140: 2457-2461; Martin, Front Med (Lausanne). 2017; 4: 229). iPS cells have properties almost equivalent to those of embryonic stem cells, such as pluripotency and growth capacity by self-renewal (Nakagawa, M. et al., Nat Biotech 2008, 26:101-106.

Briefly, adult somatic cells, preferentially keratinocytes, are isolated from the patient by biopsy or plucked hair (Aasen T. et al., Nat Protoc 2010, 5:371-382) and reprogrammed into iPS cells as described above. The cells are engineered by transfection with a construct as described herein. Before or after transfection, the iPS cells can be differentiated in vitro into a specialized cell-type of interest by culturing the cells under very specific conditions that are unique to each specialized cell type and known to those skilled in the art (Meng, G. et al Stem Cells Dev 2012, 21:2036-2048; Nakagawa, M. et al., Sci Rep 2014, 4:3594; Fitzsimmons et al., Stem Cells International, Volume 2018, Article ID 8031718, doi.org/10.1155/2018/8031718). Differentiated iPS cells can be introduced into an individual to whom the product is to be delivered. Various routes of administration and various sites (e.g., renal sub capsular, subcutaneous, central nervous system (including intrathecal), intravascular, intrahepatic, intra-splanchnic, intraperitoneal (including intraomental), intramuscularly implantation) can be used. Once implanted in an individual, the differentiated iPS cells survive, migrate to their appropriate anatomical site, and express cell type-specific proteins corresponding to the specialized cell-type (Hanna, J. et al. Science 2007, 318, 1920-1923; Nelson, T. J. et al., Circulation 2009, 120:408-416; Homma, K. et al., Stem Cells 2013, 1149-1159).

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Once implanted in an individual, the transfected cells produce the RED-peptide product in response to the appropriate physiological cue.

The choice of cell type and method of delivering response element-driven therapeutic peptide genetic constructs to a patient can be selected depending on the specific clinical application targeted. Adoptive cell transfer strategies, which are already in clinical use, can be used to genetically integrate response element driven therapeutic peptide constructs into long-lived cells such as memory T-cells or hematopoietic stem cells for systemic drug administration. As another example, genetically engineered mesenchymal stem cells can be used for localized secretion into joint interstitial spaces.

For example, an individual who suffers from an inflammatory disorder (e.g., rheumatoid arthritis) is a candidate for implantation of cells producing a compound described herein, e.g., NF-kB inflammatory response driven expression of cytokine inhibitors IL1RA or GP130. The following provides additional examples of uses for the present compositions and methods.

Gene Therapy

The use of viral vectors, e.g., adenoassociated viral (AAV) vectors, is an alternative approach to systemically and dynamically release therapeutic peptides. Viral (e.g., AAV) particles carrying response element therapeutic peptide constructs within their genomic payloads can delivered directly into a patient via intramuscular injection, temporarily inducing dynamic peptide expression and secretion.

The nucleic acids described herein, e.g., nucleic acids encoding a therapeutic protein, a promoter for expression of the therapeutic protein, and a response element that directs expression of the therapeutic protein in response to a physiological stimulus, optionally wherein the therapeutic protein comprises a secretion signal, e.g., from *Guassia princeps* or *Cypridina noctiluca*, can be incorporated into a gene construct to be used as a part of a gene therapy protocol. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (LIPOFECTAMINE™) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein (e.g., a therapeutic protein, a promoter for expression of the therapeutic protein, and a response element that directs expression of the therapeutic protein in response to a physiological stimulus, optionally wherein the therapeutic protein comprises a secretion signal) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21):1867-74 (2000).

In some embodiments, a nucleic acid encoding a therapeutic protein, a promoter for expression of the therapeutic protein, and a response element that directs expression of the therapeutic protein in response to a physiological stimulus, optionally wherein the therapeutic protein comprises a secretion signal, is entrapped in liposomes bearing positive charges on their surface (e.g., LIPOFECTIN™ (s)), which can be tagged with antibodies against cell surface antigens of the target tissue (Mizuno et al., No Shinkei Geka 20:547-

551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Synchronizing GLP1 Delivery with Body Clocks to Improve Glycemic Control and Weight Loss Circadian clocks are complex molecular architectures that control circadian rhythms of physiology through various molecular processes, but prominently metabolic gene regulation. Clocks have been shown to heavily influence blood glucose regulation and obesity in animal models. Underlying circadian rhythms are oscillations of gene expression occurring in nearly all tissues and cells observed to date, which ultimately give rise to an individual's body clock. An essential component of circadian clocks is the CLOCK-BMAL1 heterodimeric transcription factor, which bind to E-box response elements within the promoter regions of clock regulated genes. Transcriptional reporter assays have shown that these promoter elements are sufficient to recapitulate circadian gene regulation. A patient's body clock can be linked to cell therapeutic drug delivery by engineering constructs that drive therapeutic peptide expression from circadian clock promoter elements.

GLP1 is a circadian appetite suppressing peptide hormone secreted by the gut as a response to eating. It has been shown to be elevated upon gastric bypass and reduce food intake when injected into humans (Hutchinson et al 2017, DaSilva and Bloom 2012). Their clinical use has been hampered by poor stability (GLP1: 30 minute half-life upon injection) and inability to be administered orally. Subcutaneous injection of a long-acting analog of GLP1 (liraglutide/VICTOZA®, Novo Nordisk) is currently approved for use in type 2 diabetic patients as an adjunctive therapy to improve glycemic control and weight loss, and as treatment for obesity (SAXENDA®, Novo Nordisk). A cell based therapy approach using GLP1 secreting cells may avoid issues of stability, administration and side effects by providing sustained and controlled secretion of peptide hormones. Using circadian clock promoter elements to drive GLP1 will ensure coordination of appetite suppression and glycemic regulation with an individual's body clock (FIG. 3, Table 1 and Table 2), which has been shown to be a key element of weight loss (Garaulet et al., Int J Obes (Lond). 2013 April; 37(4):604-11. Erratum in: Int J Obes (Lond). 2013 April; 37(4):624).

Figure 3:
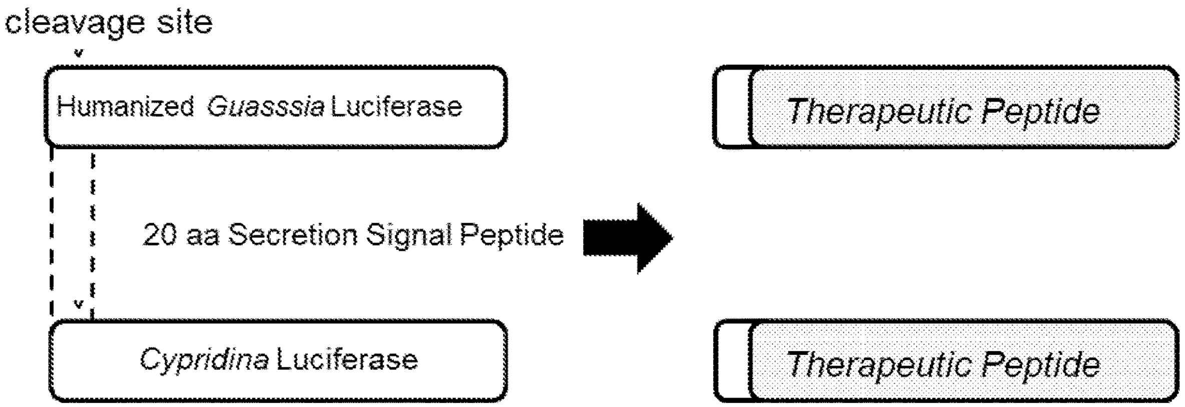
FIG. 3. Engineering therapeutic peptides for ectopic secretion with luciferase secretion signals. *Guassia* and *Cypridina* Luciferase are both luminescence generating enzymes naturally secreted (~80%). Their secretion signals are mapped to approximately the N-terminal 20 amino acids and end with a conserved cleavage site (Nielsen, "Predicting Secretory Proteins with SignalP," In Kihara, D (ed): *Protein Function Prediction* (Methods in Molecular Biology vol. 1611) pp. 59-73, Springer 2017. doi: 10.1007/978-1-4939-7015-5_6). Exemplary therapeutic peptides were designed with these secretion signals to ensure secretion from a broad range of cell types.

Oxygen Sensing Cell Therapeutics to Treat Chronic Kidney Disease Related Anemia with EPO Hypoxia is defined as a decrease oxygen concentrations detrimental to organismal or cellular health. Molecular pathways that sense and respond to hypoxia via gene expression are well characterized, ubiquitous and highly conserved. Hypoxia inducible factors or HIFs are a family of oxygen sensing transcription factors that bind to hypoxia response elements (HREs) and activate adaptive gene expression. Transcriptional reporter experiments have shown that HREs are sufficient to trigger hypoxia induced gene expression. This invention involves engineering oxygen sensing cell therapeutics by introducing synthetic HREs that drive therapeutic peptide expression (FIG. 3 and Table 1).

Erythropoietin (EPO) expression and secretion increases under hypoxic conditions as a result of HIF dependent transcriptional regulation. EPO is a peptide hormone produced largely by the kidneys to increase hematocrit levels, and recombinant EPO is used as an injectable treatment for anemia related to chronic kidney disease (CKD) (e.g., darbapoietin alfa, Amgen). Anemia is a hallmark of advanced CKD, likely due to impaired renal EPO secretion. EPO treatment has been shown to improve morbidity, cognitive function and overall quality of life in CKD patients. Genetic constructs can be used that direct cell therapeutics to secrete EPO under hypoxic conditions by driving EPO expression from synthetic HREs (FIG. 3 and Table 2). The present method allows for adaptive and minimal dosing of EPO, likely decreasing the incidence of severe adverse effects, which include cardiovascular problems.

Employing the NF-kB Inflammatory Response Pathway to Drive a Cytokine Inhibitors IL1RA or GP130 in the Treatment of Rheumatoid Arthritis or Transplant Rejection In patients with chronic inflammatory diseases such as rheumatoid arthritis and osteoarthritis, proinflammatory cytokines are a major target for therapeutics (Jones et al, 2011). A number of successful treatments currently target these cytokines to prevent downstream signaling cascades within the cell that activate inflammation. One recent therapy, tocilizumab, works through blocking the IL-6 receptors. IL-6 is a strong candidate for targeting inflammation because it is involved in both acute phase inflammatory responses, as well as homeostatic functions such as regulation of glucose metabolism (Heinrich et al, 2003). During inflammation IL-6 is highly expressed and plasma cytokine levels can reach up to several ug/mL in severe cases (Waage, 1989). IL-6 contains a receptor subunit gp130 or CD130 which important for binding the IL-6 receptors. While it is expressed in all cells, circulating levels of these soluble protein are too low to act on IL-6 receptors to mediate inflammatory. However, it has been shown that delivering a soluble form of the gp130 allows selective inhibition of the IL-6 signaling (Atreya, 2000). In vivo studies show promise for gp130 as a treatment for arthritis, colitis, infection, allergies and cancer (Hurst, 2001). The goal of this therapy is to deliver a gene construct encoding for the gp130 soluble protein, which is capable of binding to IL-6 receptors and blocking inflammatory pathways.

One pathway that is widely explored for its role in inflammation is the nuclear factor NF-κB. It is activated by cytokines such as IL-1 and TNFalpha and microbial products through canonical pathways as well as an alternative pathway through TNF-family cytokines such as lymphotoxin beta, CD40 ligands, and B cell activating factor (Lawrence, 2009). Studies in vitro and in animal models have shown correlation of NF-κB activation in inflammatory disease contexts (Miagkov et al, 1998). This has been linked to not only rheumatoid arthritis, but atherosclerosis, COPD, asthma, multiple sclerosis, IBD and ulcerative colitis as well (Tak et al 2001). Furthermore, its role in expression of anti-inflammatory genes has been established as well through antiapoptotic mechanisms in prolonged inflammation (Greten et al, 2007). Using the response element on NF-κB to drive gp130 secretion, the therapeutic biomolecule is administered in response to inflammatory activation.

Another example is the creation of biosensing cell or gene therapies for reducing transplant rejection. A technology that is sensitive enough to detect signs of graft failure or rejection early, while it is still a local response and before it become a rejection event detectable at systemic levels can be used as a powerful early warning system that indicates impending rejection. Furthermore, it may offer an opportunity to combine therapy with biomarker measurements (known as theranostics), or even trigger the release of an anti-inflammatory through the diagnostic sensor itself, locally at the site of rejection and in a dose sensitive manner. The engineered cells describe herein can be engrafted into an organ prior to transplant to act as an in situ cell-based biosensor for reporting and responding to the state of a graft. These biosensor cells can be genetically engineered with a transcription factor response element, for example NF-kB, as a gene promoter to serve as a theranostic, simultaneously driving the secretion of a blood-based biomarker, for example SEAP, and a therapeutic protein, for example sgp130 or IL-1RA, to attenuate a rejection response.

Heat Triggered Release of IL1RA or GP130 as a Self-Administered Treatment for Rheumatoid Arthritis Patients with chronic inflammatory conditions have elevated levels of IL-1 receptor antagonist (IL-1RA), a naturally occurring anti-inflammatory protein that binds competitively with IL-1a and IL-1beta to IL-1 receptors (Gabay, 1997). Levels rise dramatically in conditions such as sepsis, rheumatic disease, and noninflammatory tissue injury (al-Janadi, 1993). In these diseases, the main mediators of inflammatory are IL-1beta and TNF-alpha. IL-1RA has been shown in animal models to not only bind IL-1, but to prevent the onset of experimental arthritis and reduce severity in disease models (Arend, 1993). It has been shown specifically to exhibit efficacy when delivered to the site of injury or pathology such as the knee joint (Ghivizzani, 1998). The IL1RA analog (KINERET®) is an approved second line treatment for a subset of rheumatoid arthritis patients.) This shows that IL-1RA may need to be localized for therapeutic effect and doing so through a gene therapy, such as adenovirus into the paws of mice to express the therapeutic intra-articularly has shown promise (Whalen, 1999). While systemic levels of the protein were not measurable in vivo, using rabbit models Kim et al showed that treatment of inflammation in joints was mediated with local injection of adenovirus expressing IL-1RA and local levels of IL-1RA were maintained (Kim, 2002). Similarly, this method delivers a gene construct encoding for the IL-1RA gene.

For delivering a local therapeutic, a locally controlled response element, e.g., heat shock transcription factor (HSF), can be used. HSF is an innate response to elevated temperatures which increases the synthesis of heat shock proteins. The regulation of this protein is driven by a highly conserved HSF which can be activated through a number of stress signals (Morimoto, 1993). Heat shock proteins serve to protein cells from lethal exposures of environmental factors such as reactive oxygen specific, chemical toxins, and extreme temperatures (Parsell et al, 1994). There are four different HSFs that provide diversity and specialization in responding to stress signals, and HSF1 activates in responses to a variety of conditions such as heat shock, oxidative stress and foreign amino acids (Morimoto et al, 1998). HSF does not solely detect temperature changes, but in vitro data has shown that reticulocytes can be activated by heat shock and that human HSF1 can acquire DNA binding upon in vitro heat shock (Mosser et al 1990; Zhong et al 1998). Based on this response mechanism, an HSF1 response element can be used to drive IL-1RA or other inflammatory-related therapeutics. It is especially applicable for a therapy in which a local therapeutic is administered because a local activation stimulant can also be administered, such as a heating pad. Using HSF1 to drive IL-1RA could locally activate cells to secrete the therapeutic within the joint where a concentrated response is necessary.

Calcium Responsive Parathyroid Hormone (PTH) Replacement Therapy for Hypoparathyroidism Hypoparathyroidism as a result of thyroidectomy, congenital defects, or idiopathic causes results in abnormalities in mineral metabolism. In addition, when parathyroid hormone plasma levels are below the average range of 10-60 pg/mL, patients have increased calcium levels and decreased phosphate levels, vitamin D levels and bone mineral density. PTH therapy has also been explored for patients with osteoporosis as it has been shown to increase bone mineralization (Winer et al, 2003). PTH is an 84 amino acid peptide and currently two formulations of the recombinant peptide are available for treatment: the full-length molecule Natpara (1-84) as well as a shortened Teriparatide (1-34) (Marcucci et al, 2012). In both treatment regimens, additional supplementation with vitamin D and calcium is required, which may be due to inability to meet the therapeutic range for extended periods of time. Natpara and Teriparatide are administered through subcutaneous injection at least once daily. The present methods deliver a gene construct encoding for the full-length PTH hormone driven by a dynamic response element.

Endogenously, PTH secretion is driven by a calcium response element, where small decreases in serum calcium stimulate the parathyroid to secrete PTH. Additionally, presence of vitamin D provides negative feedback for PTH secretion. PTH has a short half-life of around 5 minutes in vivo and using an endogenous response element to drive PTH secretion may provide more accurate level restoration. The calcium receptor or CaR is a G-protein couple receptor on which calcium acts to halt PTH secret on parathyroid cells (Silver et al, 2005). The response element has been studied extensively in animal models to show that hypocalcaemia increases transcription of PTH. By using the calcium response element CaSR to drive PTH synthesis, transcription of the PTH gene will take place until calcium levels have been restored.

Synchronizing PTH Delivery with Body Clocks

As noted above, circadian clocks are complex molecular architectures that control circadian rhythms of physiology through various molecular processes. Various bone turnover markers and bone metabolism-regulating hormones such as melatonin and parathyroid hormone (PTH) display diurnal rhythmicity. It has been shown that disruption of the circadian clock due to shift work, sleep restriction, or clock gene knockout is associated with osteoporosis or other abnormal bone metabolism, showing the importance of the circadian clock system for maintaining homeostasis of bone metabolism. Moreover, common causes of osteoporosis, including postmenopausal status and aging, are associated with changes in the circadian clock. Research has shown that agonism of the circadian regulators REV-ERBs inhibits osteoclast differentiation and ameliorates ovariectomy-induced bone loss in mice, suggesting that clock genes may be promising intervention targets for abnormal bone metabolism. Moreover, osteoporosis interventions at different time points can provide varying degrees of bone protection, showing the importance of accounting for circadian rhythms for optimal curative effects in clinical treatment of osteoporosis (see, e.g., Song, C., et al, "Insights into the Role of Circadian Rhythms in Bone Metabolism: A Promising Intervention Target?," Hindawi, Volume 2018, Article ID 9156478, 11 pages).

PTH exhibits a moderate increase between 16:00 and 19:00 and a broader, longer-lasting increase from late evening to early morning, reaching its peak between 02:00 and 06:00 (J. Redmond, A. J. Fulford, L. Jarjou, B. Zhou, A. Prentice, and I. Schoenmakers, "Diurnal rhythms of bone turnover markers in three ethnic groups," The Journal of Clinical Endocrinology & Metabolism, vol. 101, no. 8, pp. 3222-3230, 2016; W. D. Fraser, A. M. Ahmad, and J. P. Vora, "The physiology of the circadian rhythm of parathyroid hormone and its potential as a treatment for osteoporosis," Current Opinion in Nephrology and Hypertension, vol. 13, no. 4, pp. 437-444, 2004). The direct connection between SCN and PTH secretion remains uncharacterized. Constitutively active PTH receptors expressed in osteoblasts promote PER1 expression (R. Hanyu, T. Hayata, M. Nagao et al., "Per-1 is a specific clock gene regulated by parathyroid hormone (PTH) signaling in osteoblasts and is functional for the transcriptional events induced by PTH," Journal of Cellular Biochemistry, vol. 112, no. 2, pp. 433-438, 2011). In organ-cultured murine femur, Okubo et al. revealed that PTH reset the circadian oscillation of PER2::luciferase activity in a time- and dose-dependent manner (N. Okubo, H. Fujiwara, Y. Minami et al., "Parathyroid hormone resets the cartilage circadian clock of the organ-cultured murine femur," Acta Orthopaedica, vol. 86, no. 5, pp. 627-631, 2015). Moreover, PTH administration shifts the peak time of PER2::luciferase activity in fracture sites and growth plates (T. Kunimoto, N. Okubo, Y. Minami et al., "A PTH-responsive circadian clock operates in ex vivo mouse femur fracture healing site," Scientific Reports, vol. 6, 2016). PTH is an approved FDA anabolic drug for osteoporosis. Accordingly, using circadian clock promoter elements to drive PTH is a potential means for preventing bone decay/osteoporosis.

Targeted Cell Type-Specific Expression Through Promoter Elements

An attractive feature being explored for viral vectors that will be directly injected in vivo is the ability to tune expression to only the targeted cell type. For example, viral particles injected intramuscularly can be engineered to contain an additional promoter upstream of the applicable response element that is specific to muscle cells. Myf5, a gene that is only expressed by activated muscle stem cells, is a good target for muscle cell AAV transduction. For this reason, we are exploring the promoter region −1500 bp from the transcriptional start site of Myf5 to be inserted into the vector. This region has been successfully isolated and cloned into a luciferase vector to report out Myf5 expression by Zhang et al.

There are a number of promoter regions that have been identified for different cell types that have been shown to facilitate cell type-specific expression when inserted upstream of a reporter in viral vectors. Depending on the target for viral injection, this could be adapted to minimize off-target effects.

TABLE 4

Exemplary promoters to drive cell type-specific expression of reporter vectors

| Gene promoter | Targeted cell type | Source |
|---|---|---|
| Myf5 | Muscle stem cells | Zhang, 2018 |
| Cola2 | Cartilage | Yi, 2001 |
| Albumin | Hepatocyte | Huang, 2017 |
| Insulin Production Factor 1 (IPF1) | Beta islet cells (pancreas) | Serup, 1996 |
| Ta1 tubulin | Neurons | Wang,1998 |
| Flk-1 | Hematopoietic cells | Kappel, 1999 |
| CD45 | Hematopoietic cells | Timon, 2001 |
| CD19 | B cells | Kozmik, 1992 |
| CMV | Constitutive, non-specific | Qin, 2010 |
| EF-1a | Constitutive, non-specific | Qin, 2010 |

EXAMPLES

The invention is further described in the following examples, which do not limit the scope of the invention described in the claims.

Figure 4A:
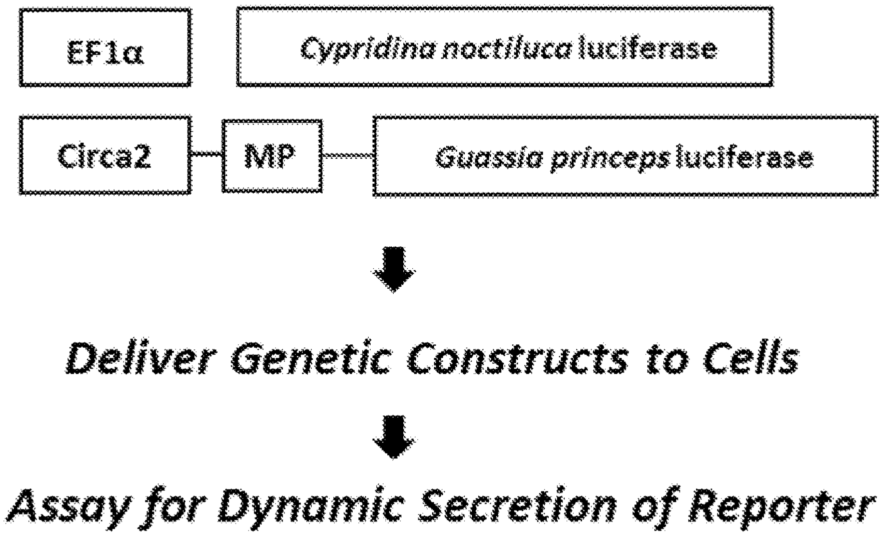
FIGS. 4A-E. Circadian secretion of luciferase in a cell culture model of acute T-cell leukemia. A.) DNA constructs used and experimental workflow. Circa2=144 bp recombined fragment of a circadian gene promoter containing E-box response elements. MP=minimal promoter B.) Suspension cell laminar flow collection system. Suspension cells are allowed to settle the bottom of a gas permeable bag for several hours before beginning to flow media. C.) GPL=*Guassia princeps* Luciferase, CNL=*Cypridinia noctiluca* Luciferase. Jurkat cells expressing CNL (upper) and GPL (lower) from EF1a or Circa1 promoters respectively were synchronized with dexamethasone for 30 minutes prior to seeding onto the laminar flow collection system, and fractions were assayed with appropriate substrate every two hours. Replicates are distinguished by color. D.) RLU values were normalized to the mean of all fractions, linear detrended and represented on one plot. E.) NSG animals were IP injected with Jurkat cells stably expressing CnL (upper) and GpL (middle) from the EF1a and Circa2 promoters respectively. After ~60 days, tail vein blood plasma samples were collected every 4 hours for 24 hours, and assayed for GpL or CnL bioluminescence activity. ZT or Zeitgeber time indicates the subjective day and night hours, with lights coming on at ZT0 and turning off at ZT12. RLU values (lower) were normalized to the mean of all fractions, linear detrended and represented on one plot.
Figure 4B:
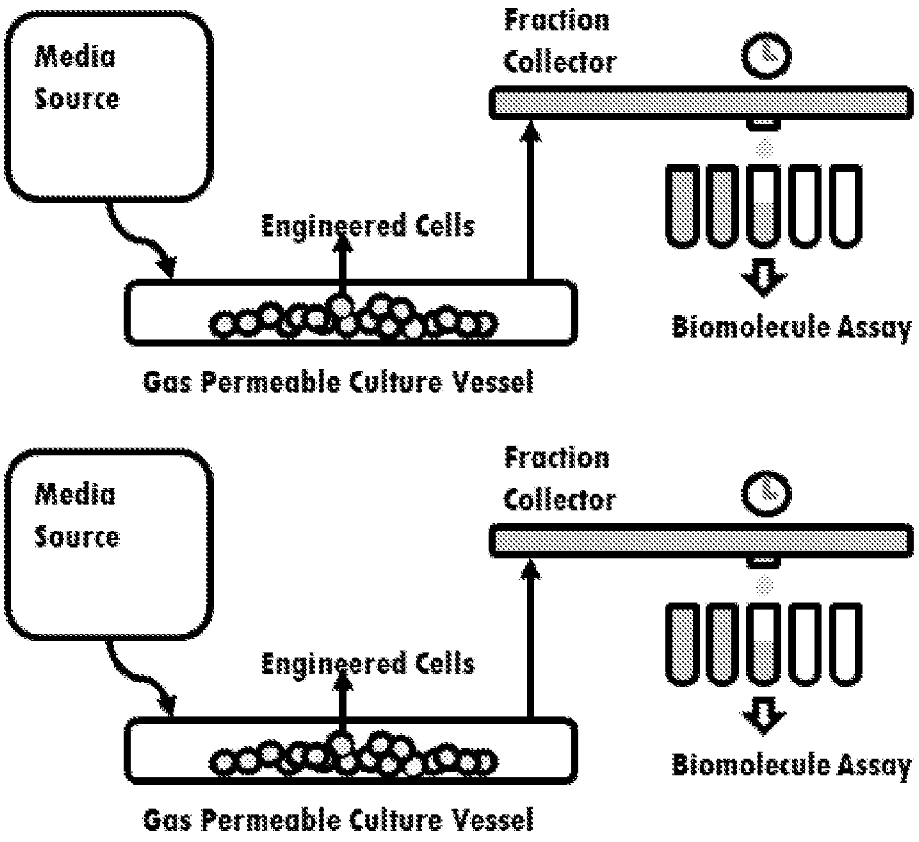
Figure 4C:
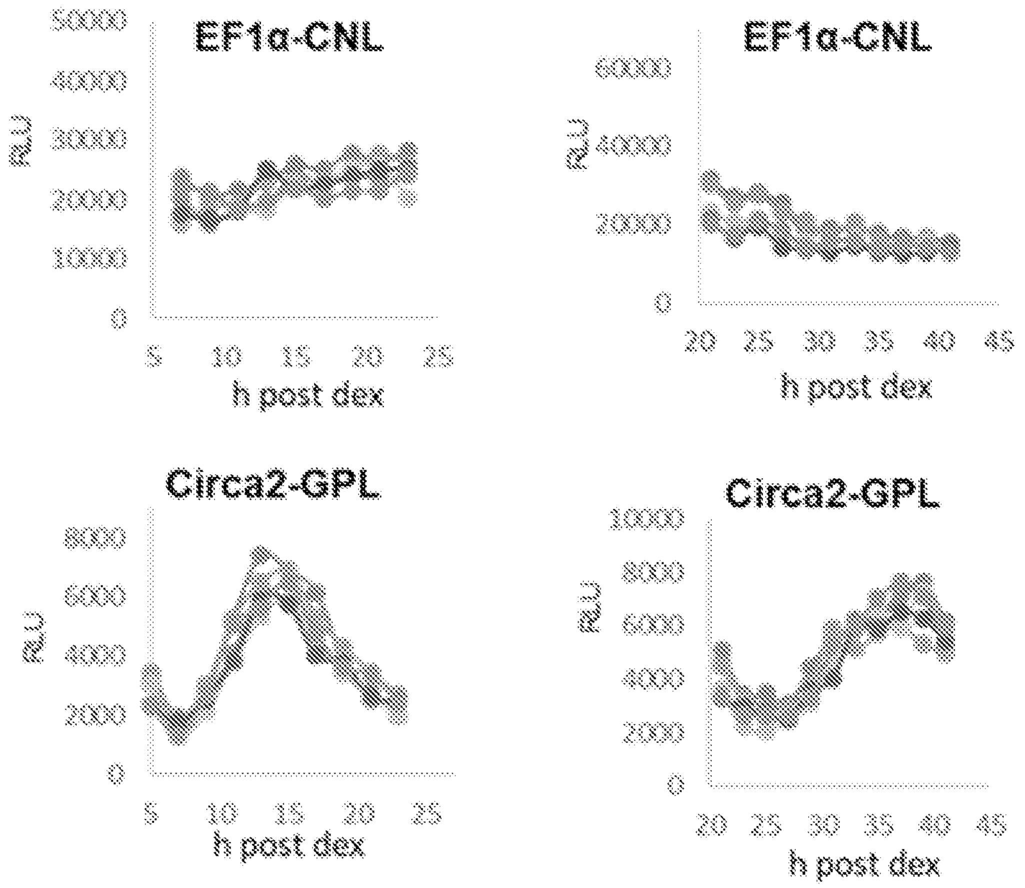

Example 1: Synchronizing GLP1 Delivery with Body Clocks to Improve Glycemic Control and Weight Loss Circadian clock promoter element driven expression of a secreted luciferase reporter protein (FIG. 2 and Table 1) demonstrates that dynamic peptide secretion can be directed by the genetic constructs described herein (FIG. 4). Circadian secretion of luciferase in a cell culture model of acute T-cell leukemia. Promoters, reporters and peptide drugs were cloned into Gateway entry vectors (designed for multisite cloning) from blunt ended PCR amplicons or custom synthesized double stranded DNA fragments (IDT) using the TOPO-isomerase cloning system (pENTR 5' TOPO TA and pENTR/TEV/D-TOPO, Thermo). PCR/Restriction digestion and sequencing were used to verify entry clone identity and orientation. Performed multisite Gateway cloning into a promoterless Lentiviral construct (pLenti6.4/R4R2N5-DEST, Thermo) with desired promoter/reporter or peptide drug combination. Cells were transduced and antibiotic selected or electroporated with DNA constructs. FIG. 4A depicts the experimental workflow. Circa2 is a 100 bp recombined fragment of a circadian gene promoter containing E-box response elements, while EF1a is standard constitutive promoter. FIG. 4B describes the suspension cell laminar flow collection system. Suspension cells are allowed to settle the bottom of a gas permeable bag for several hours before beginning to flow media. C.) GPL=*Guassia princeps* Luciferase, CNL=*Cypridinia noctiluca* Luciferase. FIG. 4C demonstrates Jurkat (human T-cell leukemia) cells expressing CNL (*Cypridinia noctiluca* Luciferase) and GPL (*Guassia princeps* Luciferase) from EF1a or Circa2 promoters respectively were synchronized with dexamethasone for 30 minutes prior to seeding onto the laminar flow collection system, and fractions were assayed with appropriate substrate every two hours. Replicates are distinguished by color. RLU values were normalized to the mean of all fractions, linear detrended and represented on one plot.

Figure 4D:
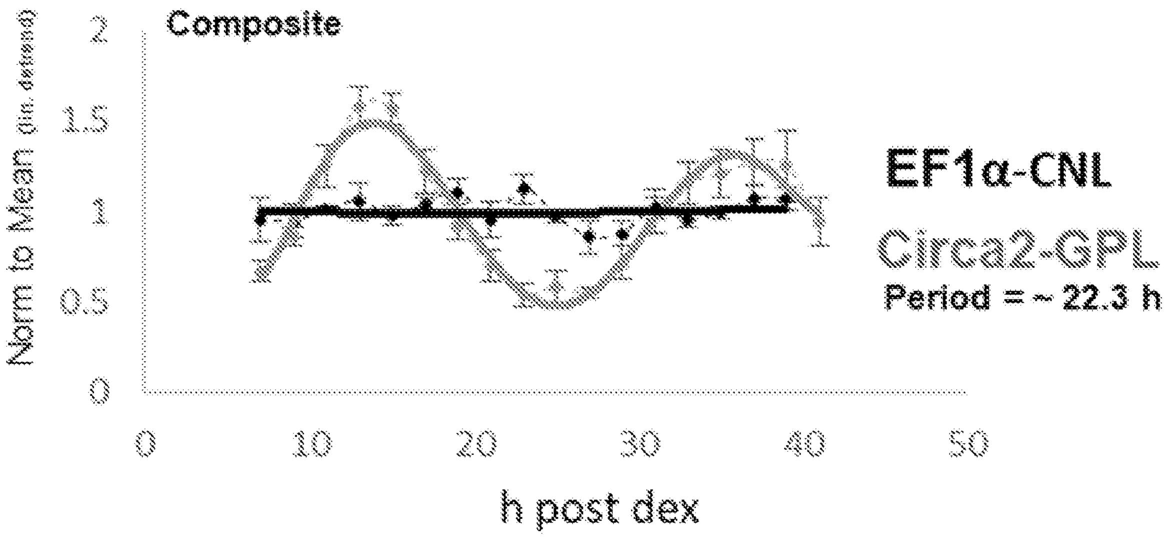
Figure 4E:
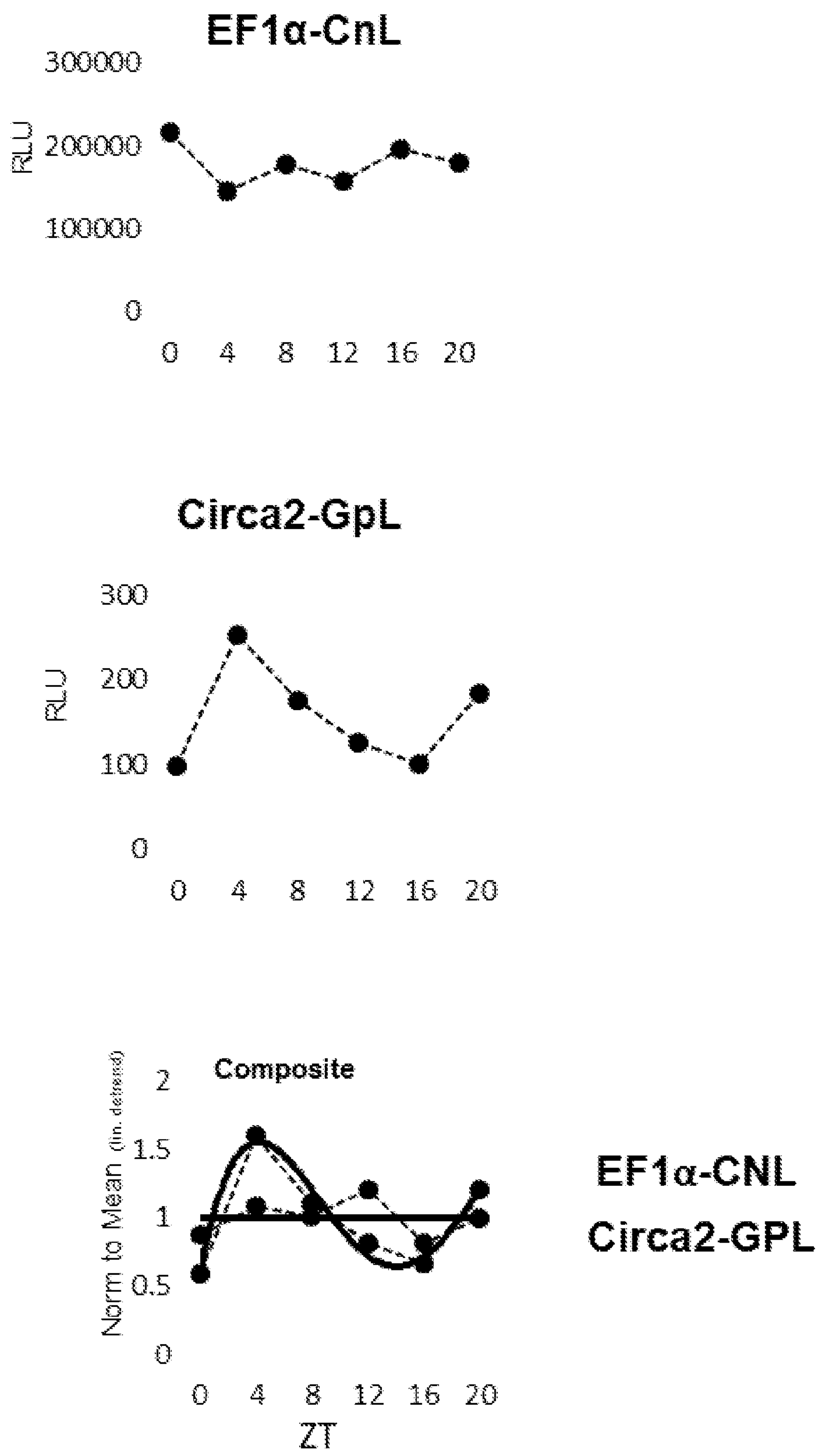

FIG. 4D demonstrated NSG animals IP injected with Jurkat cells stably expressing CnL (upper) and GpL (lower) from the EF1a and Circa2 promoters respectively. After ~60 days, tail vein blood plasma samples were collected every 4 hours for 24 hours, and assayed for GpL or CnL bioluminescence activity. ZT or Zeitgeiber time indicates the subjective day and night hours, with lights coming on at ZT0 and turning off at ZT12. RLU values were normalized to the mean of all fractions, linear detrended and represented on one plot.

Figure 5A:
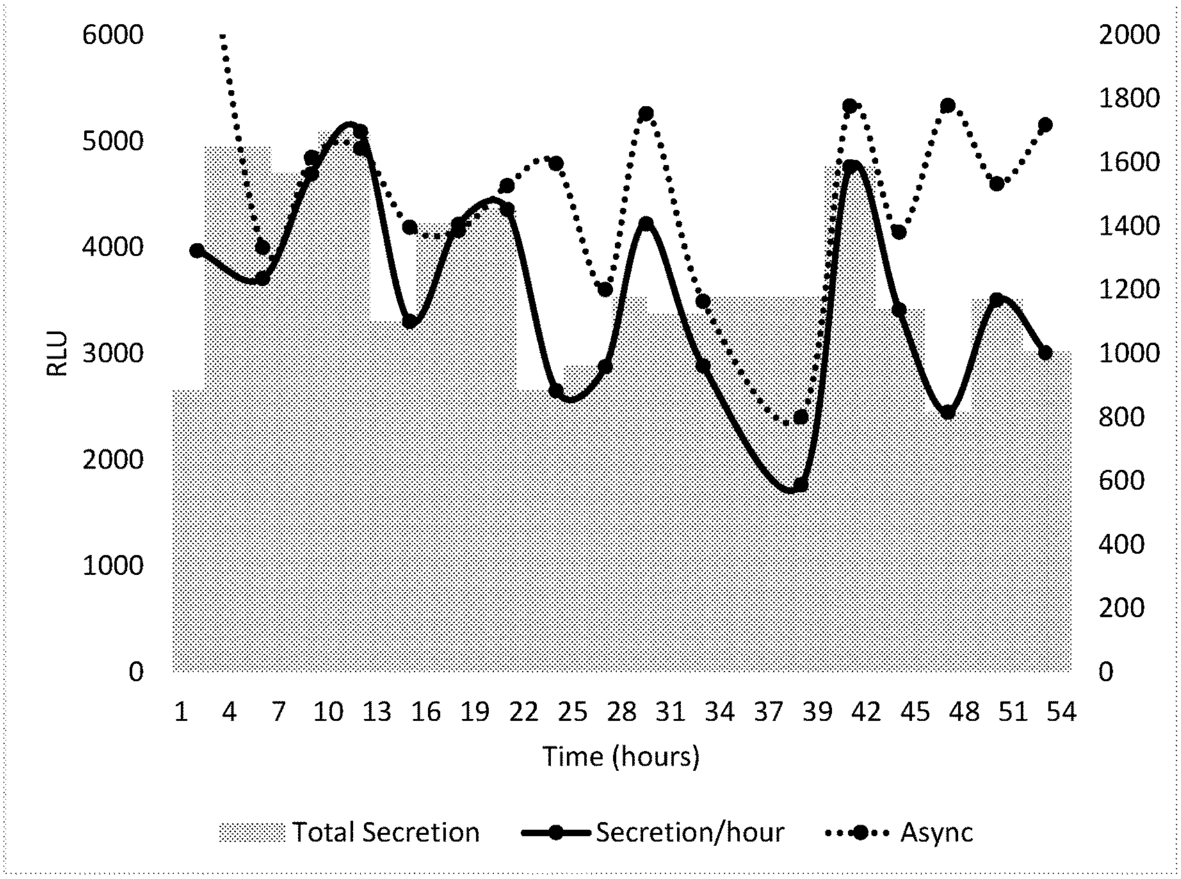
FIGS. 5A-B. Circadian secretion of luciferase in vitro and in vivo. A) Adeno-associated viral particles encoding Per2-Gluc were used to transduce HEK293 cells in cultures and supernatant was samples every 3 hours using a *Gaussia* luciferase assay. Cells were either synchronized with dexamethasone treatment prior to sampling or controlled (async). Total secretion over each time period was used to calculate secretion per hour. B) Transduction of mouse via intramuscular injection with AAV particles encoding Per2-
Figure 5B:
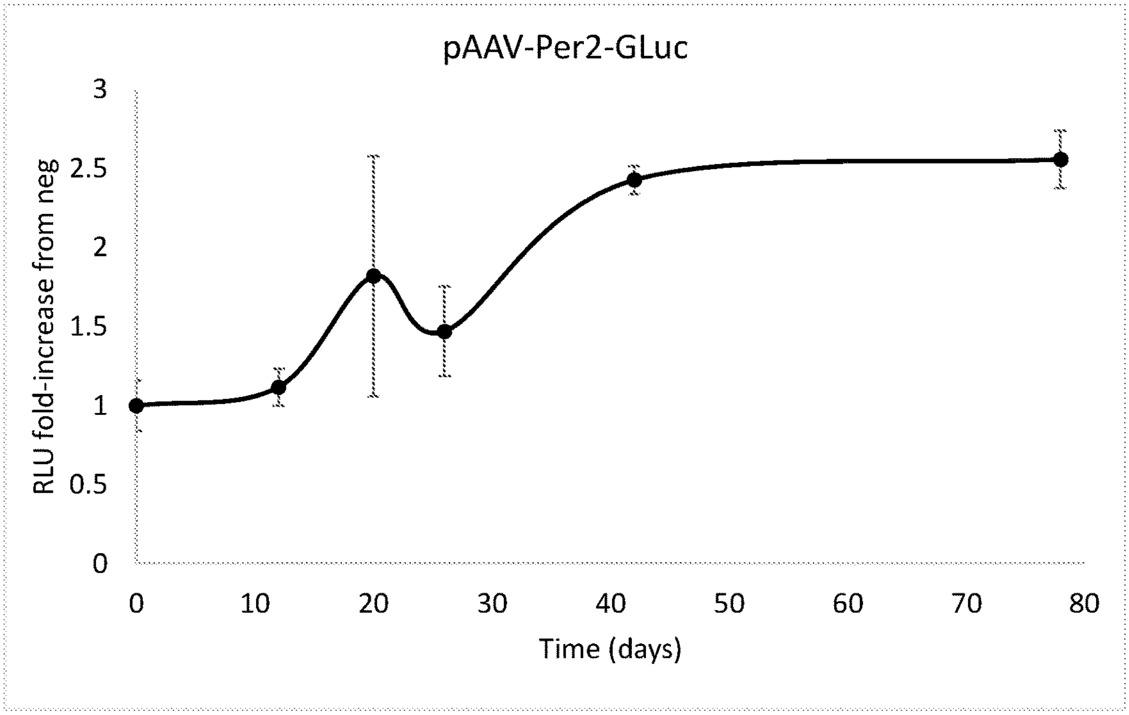

Example 2: Circadian AAV Constructs to Secrete Luciferase are Expressed Rhythmically in Murine Muscle Cells In Vitro and In Vivo Circadian clock promoter element driving expression of a secreted luciferase reporter protein in AAV demonstrate oscillation in vitro in murine myoblast cell line, C2C12 (FIG. 5A) The in vitro transductions are done by adding viral particles at an MOI of 50 and then synchronizing the endogenous clocks of the C2C12 cells with dexamethasone for 4 hours before supernatant samples are analyzed. AAV viral particles are injected in the anterior tibialis muscle of mice and show GLuc expression after around 1 month and continue to be expressed after 2-3 months (FIG. 5B).

Figure 6B:
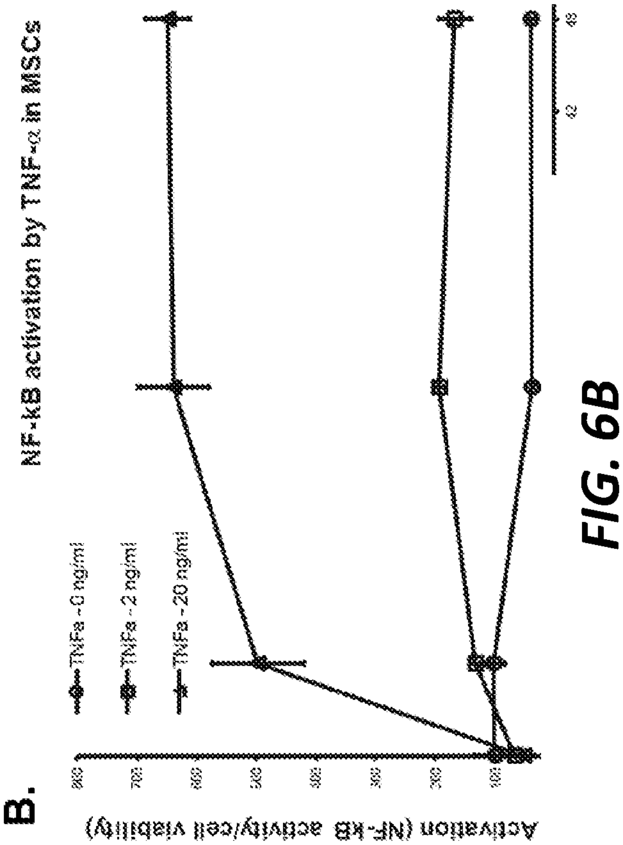
Figure 6A:
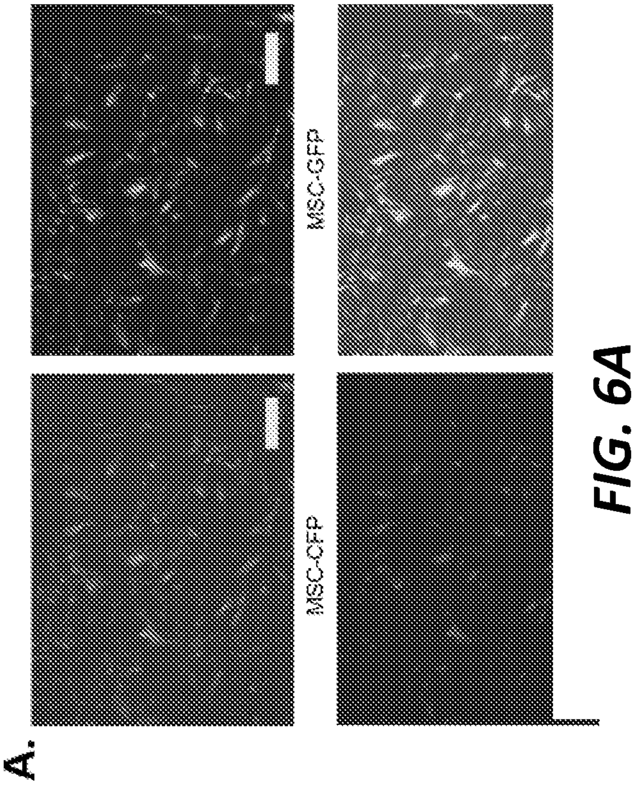
Figure 6C:
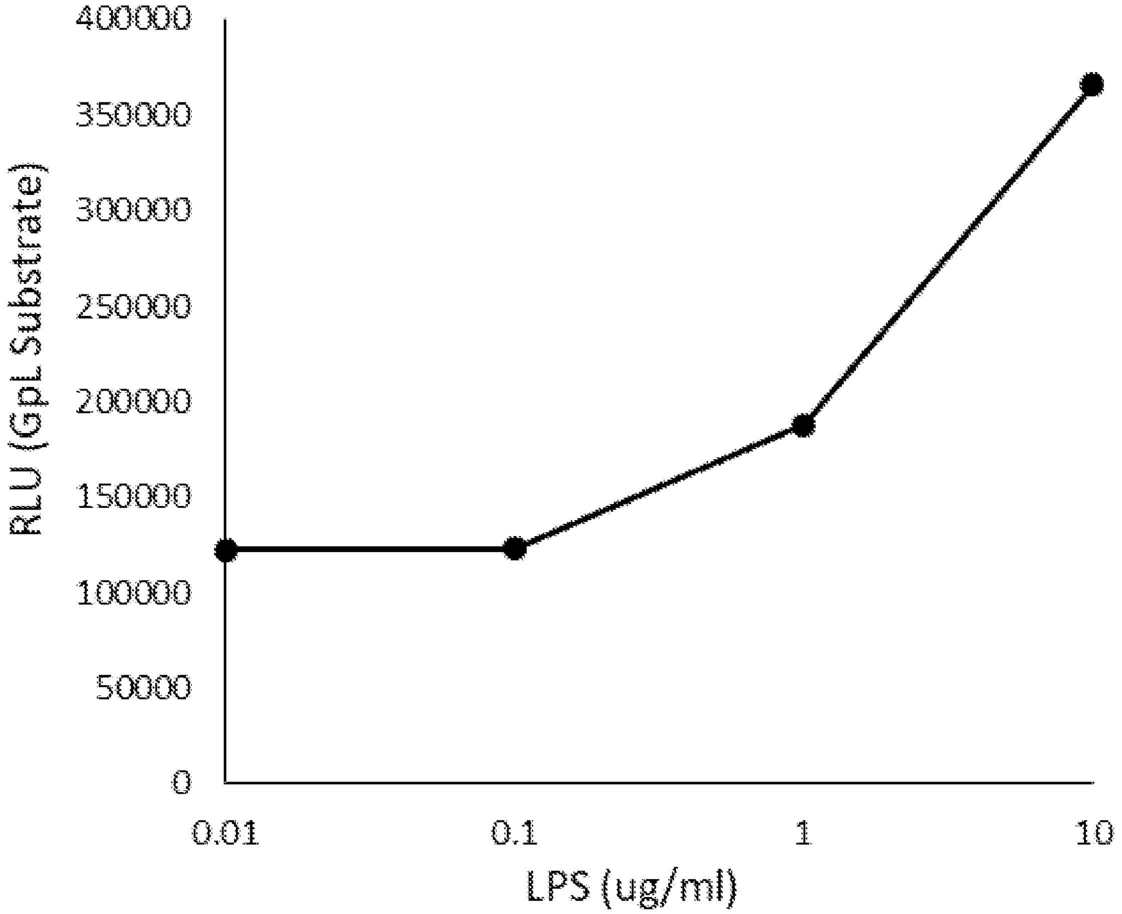
Figure 6D:
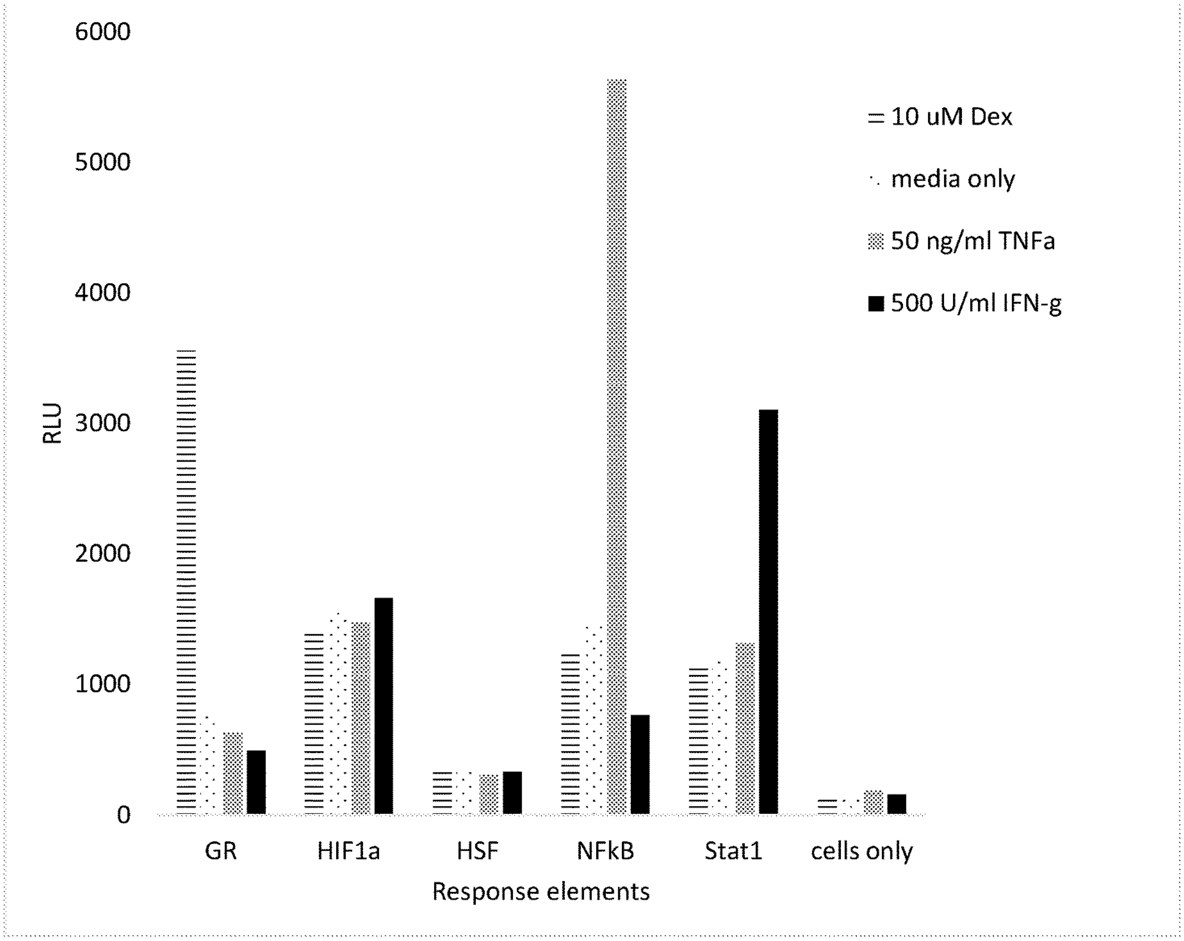
Figure 7A:
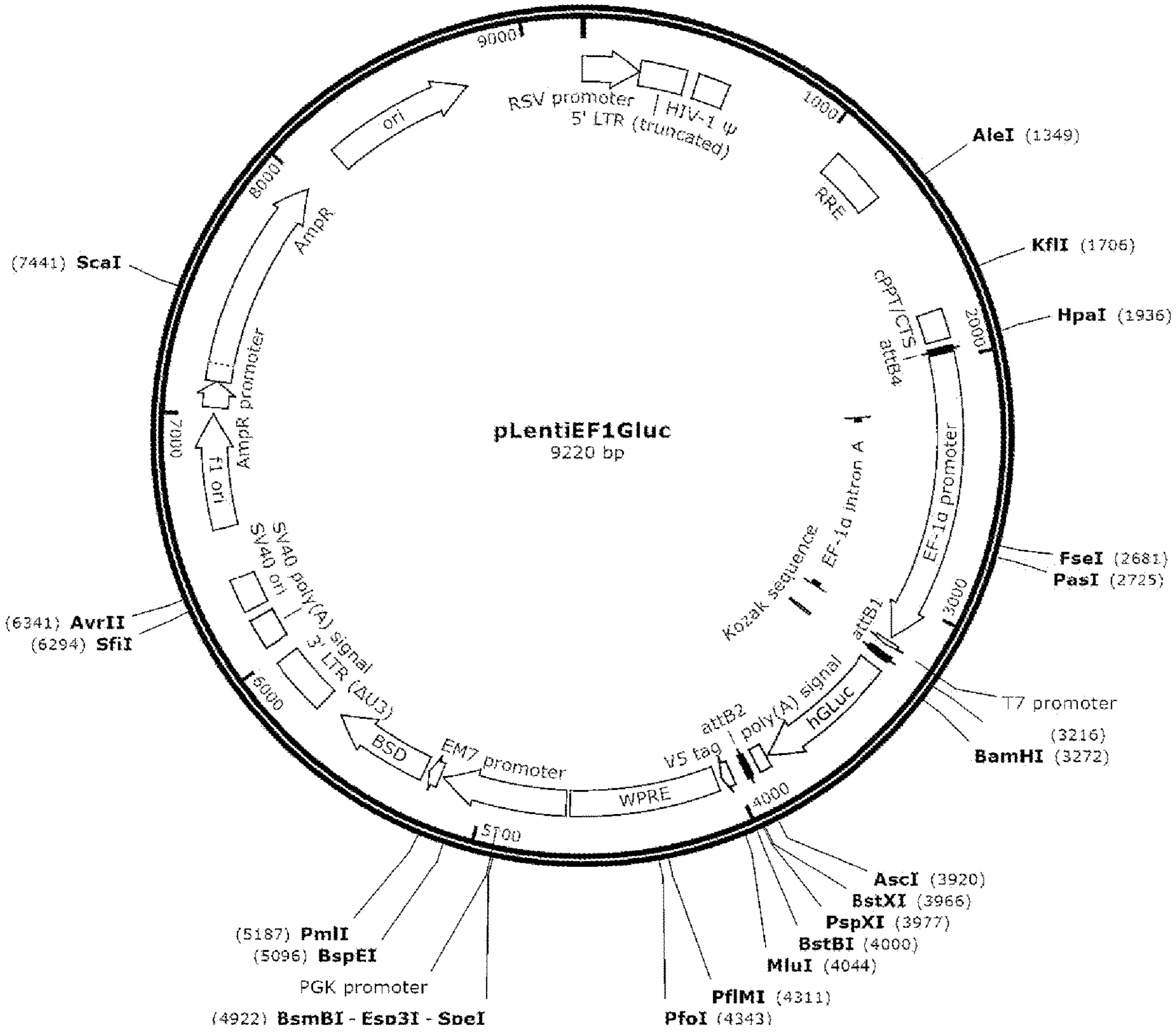
Figure 7B:
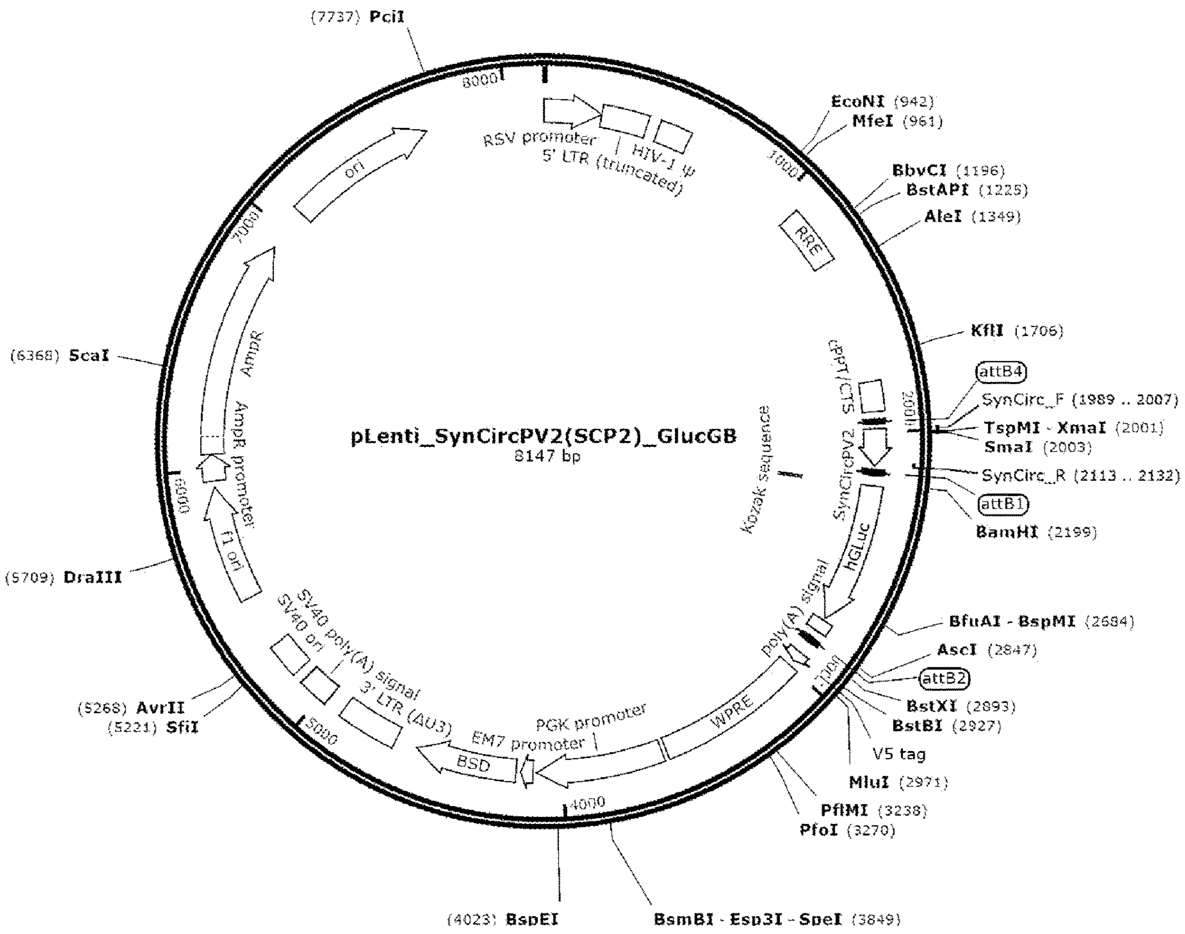
Figure 7C:
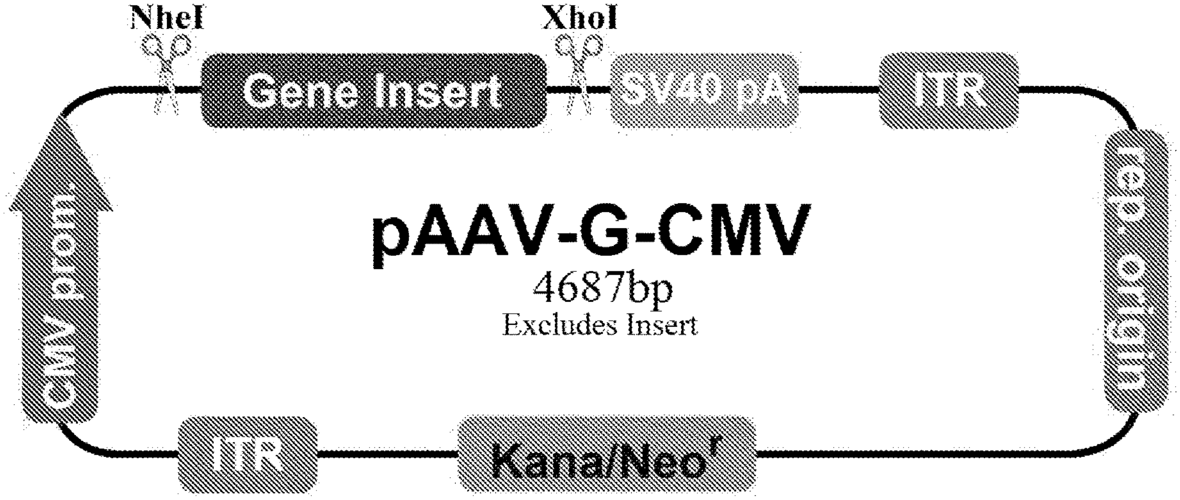
Figure 7D:
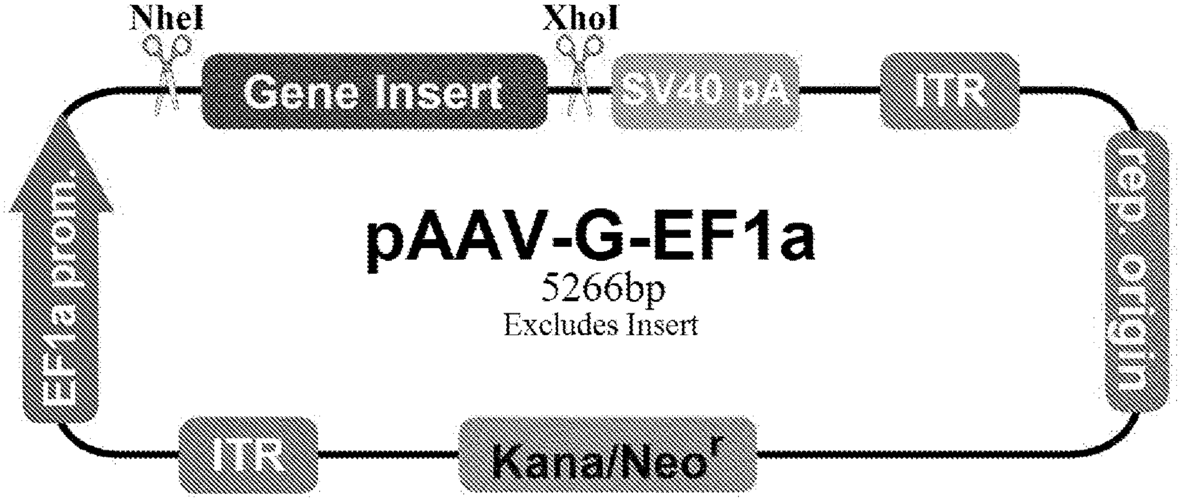

Example 3: Employing the NF-kB, Stat1, GR Inflammatory Response Pathway to Drive a Cytokine Inhibitors IL1RA or GP130 in the Treatment of Rheumatoid Arthritis We have begun to employ genetic constructs which direct cell or gene therapeutics to secrete a luciferase reporter protein when exposed to pro-inflammatory cytokines. (FIG. 6A) Human Mesenchymal Stem cells were infected with 3 lentivirus vector expressing NFkB-Gluc-CFP, CMV-SEAP-IYFP and CMV-Vluc-ImCherry. 48 hrs later, MSCs were analyzed by fluorescence microscopy for all FPs showing efficient transduction efficiency of all 3 reporters. (FIG. 6B) Cells were plated in a 96-well plate and treated with different amounts of TNFalpha or PBS in 5 replicates. Aliquots of conditioned medium were assayed for Gluc (NFkB activity) and SEAP (cell viability). Data presented as average ratio of Gluc/SEAP (NFkB activation ratio)+/−SD. Secondarily, Rat2 fibroblasts were transduced with lentiviral particles containing an NF-kB promoter fused to *Gaussia princeps* luciferase (plasmid CSW-NF-tata-Gluc-CHS4 obtained from the MGH vector core) to show that different species can also accept these gene constructs. Rat cells were exposed to bacterial lipopolysaccharide (LPS) as a different inflammatory stimuli at varying concentrations for 24 hours prior to assaying for bioluminescent activity (FIG. 6C). As shown in FIG. 6D, plasmids containing the glucocorticoid receptor (GR), HSF, HIF1α, NFκB or STAT1 response elements were constructed as described above and transfected into 293t cells. After 72 hours, cells were stimulated with the indicated treatment for 18 hours prior to assaying for luciferase activity. These experiments indicate a highly specific 4-6 fold induction by response elements GR, NFκB and STAT1.

Example 4: Transplanting Engineered Cell Biosensors into Livers Ex Vivo Prior to Organ Transplantation in the Detection and Treatment of Organ Rejection A rat fibroblast cell line from ATCC (CRL-1764) was engineered with a lentivirus to express a green fluorescent protein (GFP) gene in addition to the *gaussia* luciferase reporter gene. Rat2 cells were cultured for 24 h in DMEM with increasing concentrations of lentiviral particles per cell (MOI) and protamine sulfate (PS), a cationic vehicle. Conditions with high concentrations of lentiviral particle multiplicity of infection (MOI) and the cationic vehicle protamine sulfate (PS) had the highest transduction efficiency. Transduced GFP-positive cells were sorted using a BD FACS Aria III (BD Biosciences) cell sorter. GFP-positive cells were then cultured, expanded and used for subsequent studies.

Figure 8A:
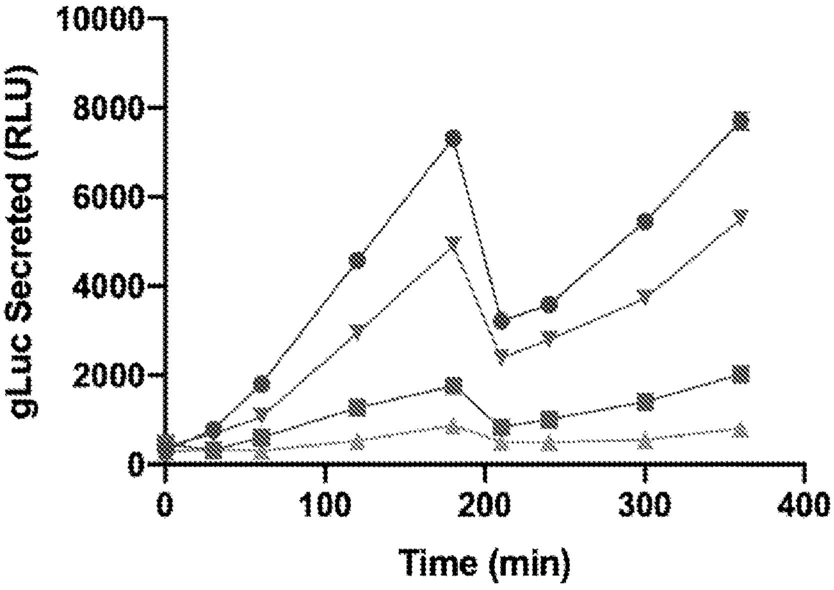
Figure 8B:
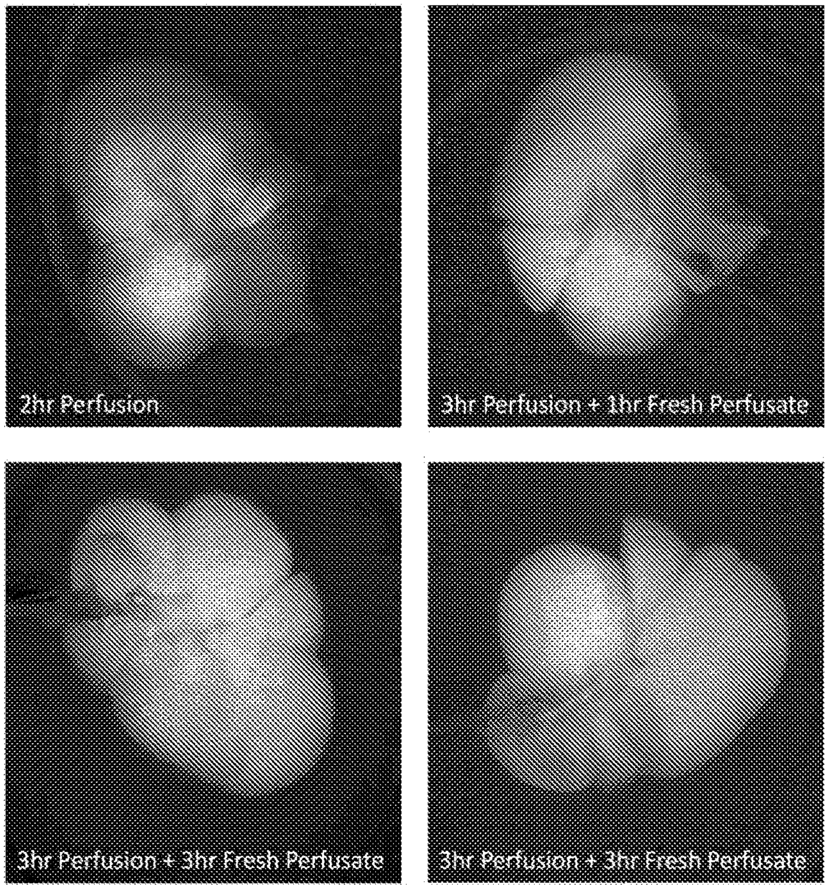

Livers were perfused ex vivo for three hours, then replaced with fresh perfusate to test the engraftment of the biosensor cells. Throughout the perfusion, assays were performed to demonstrate the viability of the perfused rat livers in the control and experimental groups. Assays of liver function conclusively showed that the engrafted biosensor cells did not negatively impact liver function and bode well for future transplantation. The perfusate was sampled for gLuc to determine if cells engrafted by indirect means. All the liver perfusions displayed a consistent pattern of gLuc secretion both before and after the perfusate change (FIG. 8A). In order to confirm engraftment within the livers, the biosensor cells were dyed with a near-IR dye and imaged using a near-infrared imaging system. Longer perfusion times correlated with increased distribution of the cells within the vasculature (FIG. 8B). Altogether, these results establish the successful engraftment of our biosensor cells in donor livers, with a robust blood-based biomarker signal and minimal impact on the organ.

Example 5: hMSCs Lentiviral Transduced with an NFκB-Gluc Expression Vector

Human MSCs were transduced with lentiviral particles containing an NFκB-Gluc expression constructs. Cells were transduced cells were washed thouroughly with media, then media with or without TNFα, was tested for Gluc activity. Cells were then allowed to incubate for 24 hours before testing media for Gluc activity. Untransduced or native cells were treated identically. FIG. 9 shows fold differences in Gluc secretion signal with and without virial transduction and with and without TNFα induction.

Example 6: Liver Cells Engineered with Inflammatory Response Element NFkB Respond Selectively HepG2 hepatocytes were engineered with the NFkB-GLuc construct and stimulated with either inflammatory LPS or IL-1b at two different doses. Media was sampled for GLuc activity after 12 hours. Relative GLuc signal increased dose dependently for LPS stimulation but was not stimulated by IL-1b which acts on a different response element (MAPK) endogenously (FIG. 10). This shows NFkB cells are selective to expected simulants.

Example 7: Human Erythropoietin (EPO) Secretion by HEK293t Cells Transfected Lentiviral Constructs HEK293ts were transfected with various plasmid constructs as indicated on y-axis in FIG. 11B. FIG. 11A shows standard curve of human EPO ELISA. Media was collected 24-48 hours post transfection and assayed for human EPO by ELISA. Secreted EPO signal was detected only from cells transfected with a construct containing EPO.

Example 8: Osteoblast Cells Proliferate in Response to PTH Secreted from Engineered Cells Liver cells were engineered with the EF1α-PTH construct and supernatant was collected. In response to the PTH-containing conditioned media, Saos-2 osteoblasts proliferated in a dose-dependent manner. Both the 1× and 2× dosing group proliferated significantly more than the negative control after 3 days of incubation (FIG. 12).

Alternatively, Saos-2 osteosarcoma-derived osteoblasts were transfected with EF1α-PTH construct or a sham transfection (EF1α-GLuc). Despite transfection having a negative impact on cell viability, groups transfected with a PTH construct proliferated significantly more than sham-transfected groups (FIG. 13A). Additionally, the level of proliferation directly correlated to the number of transfected cells (FIG. 13B), due to presumably increased PTH concentration in the media.

Example 9: Measurable Levels of Human PTH are Detected In Vivo Following AAV Injection AAV vectors administered in vivo result in detectable levels of human PTH in the plasma 3 weeks post injection. AAV2 vectors encoding EF1a-PTH were produced and concentrated in sterile saline at a concentration of $10^{10}$ vg/mL. Male C57/B1 mice underwent thyroid/parathyroidectomy surgery and PTH levels were measured in the plasma to ensure levels were below detection limit. Each group consisted of n=2 animals and AAV2 animals received 100 uL of vector solution via intraperitoneal injection. 100 uL of whole blood was sampled via tail vein once per week at the same time of day and plasma was isolated for PTH measurement by ELISA. As shown in FIG. 14, PTH levels increase with time reaching around 80 pg/mL which is on the same order of normal PTH concentrations.

Example 10: Engineered Cells Secrete Soluble GP130 into the Media and Suppress IL-6-Dependent Proliferation in DS-1 Cells Media from cells engineered with EF1α-sGP130 constructs was sampled, along with cell lysate, showing that measurable protein levels increase over time (FIG. 15A). Conditioned media containing secreted sGP130 from engineered cells was exposed to DS-1 cells, an IL-6 dependent cell line. The resulting proliferation had an inverse relationship to the dose of sGP130 in the sample, showing proliferation is suppressed via the presence of secreted sGP130 (FIG. 15B).

Example 11: Materials and Methods for Examples 12 and 13

The following serves as Materials and Methods for Examples 12 and 13 below.

Plasmid Construction

Circa promoters are synthetic circadian response elements based on our previous work (Tamayo et al. 2015; Gillessen et al. 2017), upstream of a minimal promoter. Source DNA sequence for minimal promoter was pGL4.24[luc2P/minP] (Promega). Sequences can be found in Table 5. Source DNA sequences for constitutive promoter/enhancers were pENTR-5-EF1ap (Thermo cat #A11145) and pMAXGFP (Lonza) for EF1a and CMV respectively. Source DNA sequences for reporters were pCMV-Gluc2 (NEB cat #8081S) and pCMV-Cluc2 (NEB cat #N0321) for GLUC and CLUC respectively. PCR amplicons or custom synthesized double stranded DNA fragments (IDT) or promoters and reporters were cloned into pENTR TOPO-TA (Thermo cat #EP0402) and pENTR d-TOPO (Thermo cat #K252520) entry vectors respectively. Multisite Gateway cloning into a promoterless lentiviral plasmid pLenti6.4/R4R2/V5-DEST (Thermo cat #A11146) with desired promoter/reporter combination using LR clonase enzyme mix II (Thermo cat #11791100) according to manufacturer's instructions. DNA was isolated using PUREYIELD™ (Promega cat #A1222) and PURELINK™ (Thermo cat #K210017). Standard procedures were performed to verify clones, including PCR, restriction enzyme digestion and sequencing. Clones were further selected on their ability to express reporters when transfected using LIPOFECTAMINE™ 3000 (Thermo cat #L3000015) in 293t cells (ATCC cat #CRL-3216).

Cell Engineering

Jurkat E6-1 cells (ATCC cat #TIB-152) are derived from T lymphocytes originally isolated from a child patient with acute T-cell leukemia (Schneider et al. 1977). Jurkat cells were passaged as indicated by vendor (RPMI). Lentiviral particles were produced using a protocol modified from the manufacturer of LIPOFECTAMINE™ 3000 (thermofisher-.com/content/dam/LifeTech/global/life-sciences/CellCul-tureandTransfection/pdfs/Lipofectamine3000-Lenti Virus-AppNote-Global-FHR.pdf). Briefly, 293t cells grown to 85-95% confluency in a 75 cm2 flask (Corning) were transfected with 2 μg pVSVG, 5 μg pPMDL, 2 μg pRSV and 10 ug lentiviral transfer plasmid using LIPOFECTAMINE™ 3000 in OPTI-MEM™ (Thermo cat #51985091) containing 5% FBS. Lentiviral particles were harvested 24 to 48 hours post transfection, spun at 5000×g, filtered through a 40 μm basket filter (Millipore), concentrated at 25,000 RPM using a BECKMAN COULTER® swing bucket rotor (SW-28) and resuspended in OPTI-MEM™ without FBS. Functional titers were determined by transducing 293t cells. Transduced Jurkat cells were selected by blasticidin (Thermo cat #R21001) resistance or by fluorescence activated cell sorting (FACS). For blasticidin selection, cells were incubated in media containing 10 μg/ml blasticidin for 5 days, and media was replaced with fresh blasticidin containing media as needed for 2 weeks. CMV-GLUC;EF1α-CLUC cells were generated by transducing EF1α-CLUC blasticidin resistant cells with Gluc-IRES-eGFP (Partners Research Viral Vector Core, Boston, MA) and selecting for GFP positive cells by FACS (sorting was performed by the HSCI-CRM Partners Research Core Facility, Boston, MA). Circa1/2-GLUC;EF1α-CLUC cells were generated by electroporating EF1α-CLUC blasticidin resistant cells with Circa1/2-GLUC lentiviral transfer plasmids using an ECM 399 electroporator (BTX). In a 2 mm cuvette (BTX), $3\times10^6$ cells resuspended in 200 μl OPTI-MEM™ were electroporated with 8 μg lentiviral transfer plasmid DNA at 500V, 700 us, single pulse, then immediately resuspended in standard media. Cells recovered for 24 hours prior to further experiments.

Monitoring Secretion of Luciferase

For both GLUC and CLUC assays, up to 20 μl of conditioned media from engineered cells, mouse plasma or purified GLUC (Nanolight cat #321) was loaded onto a 96-well black plate prior to adding working concentration of substrate. A volume of 100 μl of GLUC substrate (coelenterazine) (Nanolight cat #303-500) or CLUC substrate (Cypridina Luciferase Substrate) (Nanolight cat #305-500) at a concentration of 12.5 ng/ml in PBS were added to wells and immediately read with microplate reader (BIOTEK® SYNERGY™ 2) with an integration time of 0.1 s. Luminescence was recorded by the device as relative luminescence units (RLU). Continuous monitoring of plasma luciferase from mice is described in a separate section below. To monitor continuous secretion of luciferase from cells in vitro over time, cells were seeded onto a custom-made constant flow cell culture and collection device. For each experiment, $16\times10^6$ cells in approximately 2 ml of media were injected into a tube-like bag made from air permeable material (Rogers Corporation HT-6240 Transparent 0.010") with approximate dimensions of 20 cm in length and 0.6 cm in diameter. We have previously shown that vessels made from this material are optimal for the expansion of human T-cells (Li et al. 2018). Silicone tubing (Platinum LS14 MASTERFLEX® cat #96410-14) was used to connect the cell containing vessel to media filled syringes operated by a PHD 2000 syringe pump (Harvard Apparatus) and to a Biologic BIOFRAC™ fraction collector (BIO-RAD®). Cells were allowed to settle for 3-4 hours prior to flowing media at 3.8 ml/hour. Fractions were collected every hour and 20 µl of every other fraction was assayed for GLUC and/or CLUC using a maximum of 12 fractions per 24-hour period of collection. For circadian experiments, cells were synchronized with 10 µM dexamethasone (Sigma cat #D4902) for 30 minutes, washed 3 times with PBS and seeded onto a continuous flow vessel either immediately or after a 24-hour incubation. For KL001 (Sigma cat #SML1032) experiments, $1\times10^6$ cells/ml EF1α-GLUC or Circa2-GLUC stable cells selected by blasticidin resistance were incubated with 20 µM KL001 or DMSO (vehicle) for 24 hours prior to washing, synchronization, and continuous flow monitoring as described above. Underlying RLU data was normalized to 0 by dividing raw data points by the average of the data set, then subtracting quotient by the average of the data set. All line fitting was performed using GRAPHPAD PRISM® 8. Linear detrending and period determination of circadian data was performed using BioDare2 (Zielinski et al. 2014; biodare2.ed.ac.uk).

RT-qPCR

Jurkat cells were synchronized as described above then seeded in a 24-well plate at $1\times10^6$ cells/well, and one well was harvested and washed 30 minutes and then every 2 hours post synchronization for 24 hours. Cells were snap frozen and stored in $N_2$(l) until all cells were collected. Samples for each replicate set were processed simultaneously. RNA was isolated from each sample using the PURELINK™ RNA Mini Kit (Thermo cat #12183025) and A260/280 ratios were determined using a NANODROP™ ND-1000 (Thermo). Each sample was used to generate cDNA using the iScript-ISCRIPT™ cDNA Synthesis Kit (BIO-RAD® cat #170-8891), and the POWERUP™ SYBR™ Green Master Mix (Applied Biosystems cat #A25742) was used to perform qPCR according to the manufacturer's instructions using a ViiA 7 Real-Time PCR System (Applied Biosystems). Primer sequences can be found in Table 5. Ct values were automatically generated by the VIIA™ 7 software. The ΔCt values of each gene at each time point corresponds to the average Ct value subtracted by the average Ct value of GAPDH at the same time point, then transformed by 2^-ΔCt. For heat map representation and statistical analysis, each gene's data set between 2 h and 20 h post-synchronization was normalized to the lowest value of the set. To determine if the lowest and highest values (presumably peaks and troughs) were statistically significant, q-values were calculated using GRAPHPAD PRISM® 8.

Animal Procedures

In all experiments, female NSG (NOD.Cg-Prkdcscid Il2rgtm1Wjl/SzJ, Jackson Laboratory stock #005557) mice less than 6 months old were used, and they were housed in a 12 hours on/12 hours off facility fed ad libitum. Jurkat cells were washed 4-5 times with PBS and resuspended in 500 µl PBS before their intraperitoneal injection at $5\times10^5$ cells per animal. For all experiments, less than 10% of the animal's total blood volume was drawn by tail snip within a 24 hour period around 40 days post injection. Immediately upon drawing blood, heparin sodium (McKesson cat #916396) was added at a final concentration of 0.002 U/ml and spun at 2,000×g for 10 min at 4° C. The plasma supernatant was stored −80° C. Using methods described above, 5 µl of plasma was assayed for GLUC or CLUC activity. Animals were euthanized when they showed clear signs of engraftment related disease as compared to control animals. All animal work was performed in accordance with the ethical standards of the Institutional Animal Care and Use Committee (IACUC).

Data Analysis and Statistics

All line fitting was performed using GRAPHPAD PRISM® 8. Linear detrending and period determination of circadian data was performed using BioDare2 (Zielinski et al. 2014; biodare2.ed.ac.uk). For FIG. 17F, an undamped 24-hour Sine wave was fitted to the data (Prism, least squares method, degrees of freedom: 14, R squared: 0.7777, sum of squares: 0.4124). To determine if the lowest and highest values (presumably peaks and troughs) were statistically significant, q-values were calculated using GRAPHPAD PRISM® 8.

Example 12: Clock Driven Secretion of Luciferase from Human Leukemic T-Cells in Cell Culture Destabilized firefly luciferase, which is largely cytosolic, has traditionally been used to monitor circadian clocks (Vollmers et al. 2008; Zhang et al. 2009). *Gaussia princeps* and *Cypridina noctiluca* luciferases, GLUC and CLUC respectively, (Verhaegent and Christopoulos 2002; Nakajima et al. 2004) are naturally secreted forms of luciferase and allow for easy, real-time monitoring in vivo through blood sample collection. GLUC has been used in previous studies to monitor cell expansion of solid tumor xenografts in living animals and has a half-life of ~20 minutes in mouse plasma, allowing for the monitoring of dynamic secretion (Badr et al. 2009; Chung et al. 2009). In fact, these luciferases have been used to track circadian expression in the plasma of transgenic mice and in fibroblasts in vitro (Yamada et al. 2013; Watanabe et al. 2010). GLUC and CLUC have been shown to catalyze distinct substrates to generate light, which allows for their use as dual luciferase reporters (Wu et al. 2007). We engineered human leukemic T-cells (Jurkat E6-1) to express GLUC and CLUC from constitutive and circadian clock response elements (further discussed below) to first detect secretion rhythms in cell culture before testing them in a xenotransplantation model (FIG. 16).

We used EF1α, a strong, constitutive promoter to validate our assays as a reference promoter, and as an indicator of basal transcription and protein synthesis (Wang et al. 2017). Jurkat human leukemic T-cells were transduced and made stable by negative (blasticidin) and/or positive (GFP) selection. Stable cell lines or parental Jurkat cells (untransduced)

were then incubated in standard media for 2 hours, at which point media was collected and assayed using either GLUC substrate (coelenterazine) or CLUC substrate (FIGS. 17A-B). While positive signals were several orders of magnitude above background, we observed no significant difference in signal between untransduced and CLUC expressing cell-conditioned media when incubated with GLUC substrate, and the converse was true for GLUC expressing cell-conditioned media incubated with CLUC substrate. These results confirm that the Jurkat cell secreted GLUC and CLUC maintain exclusive substrate specificity.

Luciferase enzymes have long been a staple choice for monitoring gene transcriptional reporters due to their extraordinary sensitivity and dynamic range (Ghim et al. 2010). We characterized the ability of GLUC secretion to correlate with cell number by conditioning media with varying concentrations of stably secreting Jurkat cells (EF1α-GLUC). Remarkably, cell concentrations of less than 1000 cells/ml (FIG. 21A) and sub-picogram amounts of GLUC were detected with linear correlations (FIG. 21B). We developed lentiviral constructs with constitutive and circadian promoter elements driving GLUC or CLUC expression (FIG. 22A), and showed that these constructs were competent for transduction using GFP markers (FIG. 22B). Additionally, GLUC expression did not affect cell growth parameters (FIG. 22C). The ultra-sensitivity of GLUC should allow for the detection of a very small number of actively secreting cells; a potential constraint in animal models.

Figure 17C:
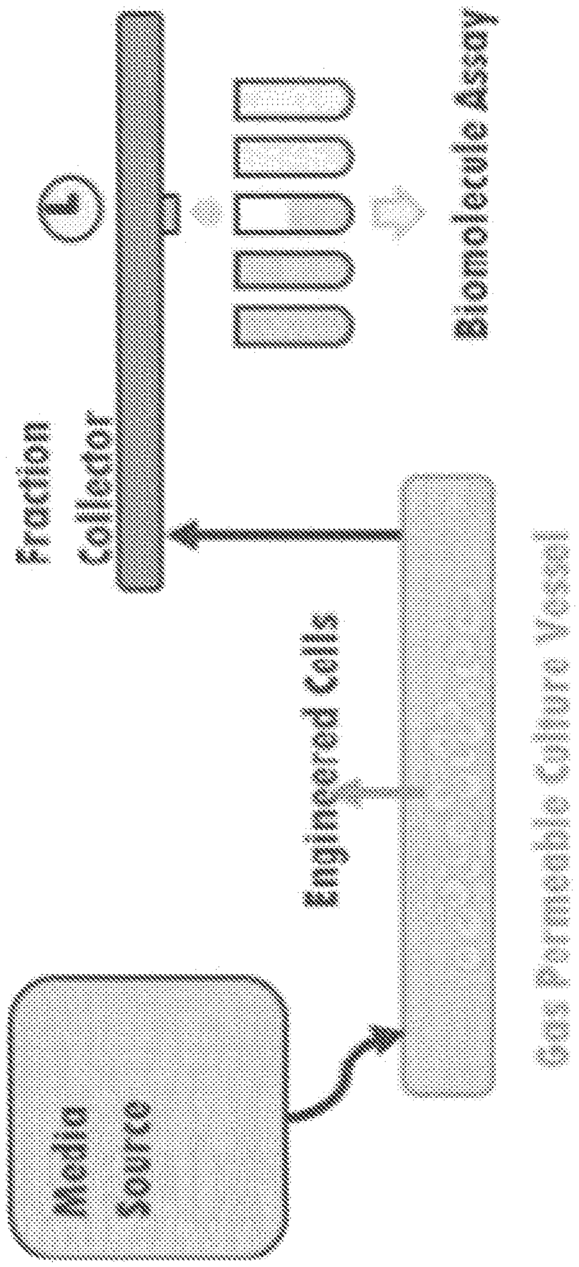

To characterize the dynamic nature of response element secretion over at least 24 hours, we created a system to flow media over sediment suspension cells followed by automated collection of media (FIG. 17C). To examine constitutive reporters, we transduced Jurkat cells with constructs driving GLUC and CLUC expression from CMV and EF1α promoters respectively. Cells were seeded onto an air permeable tubular vessel and allowed to settle for 3 to 4 hours before flowing media through the vessel at 3.8 milliliters per hour, and media outflow was collected at a rate of one fraction per hour. Individual fractions were then assayed (20 μl of 3.8 ml fractions) for CLUC and GLUC activity. In order to compare rhythmicity on similar scales of amplitude, each raw data set was then normalized to the mean of all data points and set to 0 and linear detrended before plotting both GLUC and CLUC data sets on a single graph (FIG. 17D). These results demonstrate that both CMV and EF1α promoters could drive stable expression with minimal fluctuation over a 24-hour period.

The core circadian clock response element consists of a palindromic 6-base pair sequence known as the E-box (Partch et al. 2016). E-box sequences are high-affinity binding sites of the CLOCK-BMAL1 transcription factor heterodimer within clock regulated gene promoters. Studies have shown that E-box sequences from promoter regions of clock-regulated genes are sufficient to drive rhythmic gene expression (Vollmers et al. 2008; Zhang et al. 2009). Response element (RE) compactness was a factor we considered since large RE-gene cassettes may hinder viral production, and poorly characterized DNA sequences may be a source of noise or toxicity. We based the designs of clock response elements on our previous work showing that three to six much abbreviated portions of the Per1 gene promoter containing E-box sequences (16-21 base pairs) specifically bind CLOCK-BMAL1 and recapitulate circadian promoter binding in vitro (Tamayo et al. 2015; Gillessen et al. 2017). This synthetic clock reporter, we call Circa2, contains six E-box sequences respectively, flanked by 12 base pairs of Per1 promoter sequence and followed by a short 31 base pair minimal promoter (MP) base pairs, with total size of 144 base pairs.

Figure 17F:
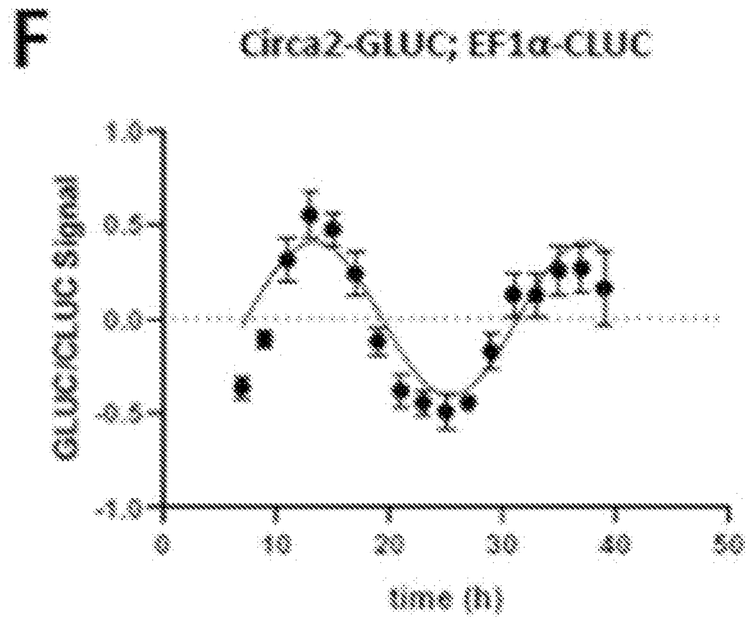

Lentiviral plasmids containing Circa2 driving GLUC expression were electroporated into Jurkat cells constitutively expressing CLUC from the EF1α promoter. Cells were allowed to recover overnight before synchronizing with dexamethasone treatment for 30 minutes (Balsalobre et al. 2000), washing then loading onto the laminar flow system as described above. Fractions were collected every hour and analyzed for GLUC and CLUC activity with a 2-hour resolution and raw data was normalized to the mean of all data points, detrended and set to 0 as before (FIG. 17E). In addition, Circa-2 driven GLUC data was normalized to EF1α driven CLUC to which sine curve with a 24-h wavelength constraint could be fitted with confidence (FIG. 17F). This normalized data was used to calculate an approximate period length of 21.3 hours. These results demonstrate that circadian promoter elements can drive rhythmic gene expression and secretion from human leukemic T-cells. Raw data plots of CLUC (FIGS. 18A, 18C, 18D) and GLUC (FIGS. 18B, 18E, 18F) are shown for cells that expressed GLUC from Circa2 and CLUC from EF1α or CMV, and expectedly revealed higher concentrations of GLUC secreted from EF1a promoters than from Circa2/minimal promoter constructs. Similar results were obtained using a construct containing three E-box sequences (data not shown).

To confirm that the oscillatory nature of gene expression was circadian clock related, we next treated cells with a pharmacological agent previously shown to disrupt circadian clocks. KL001 has been shown to stabilize CRY1 protein, a CLOCK-BMAL1 repressor, leading to a dysfunctional transcriptional feedback loop (Hirota et al. 2012). Stable Jurkat cell lines expressing GLUC driven by Circa2 or EF1α as a reference, were treated with a sublethal dose of KL001 (20 μM) or vehicle (DMSO) for 24 hours before dexamethasone synchronization and seeding on the laminar flow system as described above. KL001 treatment had little to no effect on EF1α driven GLUC secretion as shown by raw and normalized data (FIG. 19A), while severely disrupting the dynamic nature of Circa2 driven GLUC secretion (FIG. 19B). These results show that the endogenous circadian clocks of Jurkat human leukemic T-cells are responsible for the dynamic secretion of GLUC from synthetic clock response elements.

To better understand the nature of Jurkat cell endogenous clocks, we measured the expression of core clock controlled genes every 2 hours upon synchronization with dexamethasone in untransduced Jurkat cells. We show by RT-qPCR that Per1, Per2, Bmal1, Clock, Cry1 and Cry2 mRNA transcripts were all detectable, suggesting a rhythmic pattern of expression for Per1, Per2, Bmal1 and Clock (FIGS. 23A-F). Per1 and Per2 peaked at around 12 hours post synchronization (FIG. 23G), consistent with our reporters, which are based on promoter elements found in those genes. Clock and Bmal1 are controlled by a different arm of the clock (Partch et al. 2016), and expectedly yielded an antiphasic pattern of expression, peaking nearly 12 hours earlier than Per1 and Per2. The differences in mRNA expression between the peaks and troughs of Per1, Per2 and Bmal1 were statistically significant (FIG. 23H). It is unclear why Cry1 and Cry2 expressions rhythms were too weak to observe. These results demonstrate that endogenous circadian genes are weakly rhythmic at the mRNA level in Jurkat cells, consistent with our observations using secreted luciferase reporters.

Example 13: Constitutive and Dynamic Luciferase Secretion from Xenotransplanted Cells in Mice We next set out to determine if clock driven secretion from human leukemic T-cells would persist in animals upon transplantation. We first used EF1α driven GLUC expression to determine the optimal time post-transplantation for data collection. Stably transduced Jurkat cells were injected into immune-compromised mice (NSG), and plasma GLUC activity was monitored (5 μl plasma assayed) for 42 days post-transplantation. Animals expressed plasma EF1α driven GLUC levels above pre-bleed levels (time 0) between 10 and 30 days with variable kinetic profiles (FIG. 20A). Animals injected with Circa2-GLUC expressing cells required at least 40 days to express plasma levels of GLUC above background (FIG. 20B), likely because they are expressing far lower levels of GLUC, as predicted by our in vitro observations. We estimate that these signals correspond to between approximately 200 ng/ml to 0.1 ng/ml of GLUC per milliliter of blood based on a GLUC standard curve).

The delay in plasma GLUC concentration when driven by Circa2 presented a challenge because mice transplanted with Jurkat cells began showing signs of disease around 43 days post-transplantation, at which point they were euthanized in accordance with the animal protocol. About 30% of animals transplanted with Circa2-GLUC cells were healthy enough to undergo further experiments when plasma GLUC concentrations were detected. Most animals were euthanized by 61 days, with one animal found dead at 43 days (FIG. 20C). We observed variable cancer associated pathologies including lower limb paralysis, lethargy, weight loss, tumors and a case of splenomegaly (FIG. 20D).

Mice (NSG) were injected with stably selected Jurkat cells expressing GLUC from the Circa2 synthetic clock response element or from the EF1α promoter as a reference. Plasma GLUC signals were measured every 4 hours for 24 hours. We observed that Circa2 driven GLUC levels in plasma have a dynamic profile consistent with circadian clock dependent transcription, as compared to EF1α driven secretion (FIG. 20E). Raw data points were normalized to the mean signal set to 0, averaged for each set. In a separate experiment, immuno-compromised mice (NSG) were injected with two different stably selected cell lines expressing GLUC from Circa2 or CLUC from EF1α as an internal reference. Similarly, EF1α driven plasma CLUC signals were stable as compared to Circa2 driven GLUC signals (FIG. 20F). These data clearly demonstrate the use of this approach to study transcriptional dynamics of cancer cells in vivo.

Furthermore, given that our cell culture results indicate that the clocks of Jurkat cells are not strongly coupled, these experiments suggest that Jurkat human leukemic T-cells synchronize to mouse physiological time-setting cues. As shown in FIGS. 19E and 19F, the secretion of clock-driven cells peak around hour 4-8 ZT and are at a minimum around hour 16-20 ZT. Underlying data for circadian time dependent analysis of plasma GLUC and CLUC signals are also reported (FIG. 24).

Example 14: Materials and Methods for Examples 15-19

The following serves as Materials and Methods for Examples 15-19 below.

Rat Fibroblast Culture and Expansion

Frozen vials of Rat2 fibroblast cell line were purchased from American Type Culture Collection (Manassas, VA, USA). Cells were thawed and cultured in Dulbecco Modified Eagle Medium (DMEM) composed of 10% fetal bovine serum (FBS) and 2% penicillin and streptomycin. Media was changed every 3-4 days and incubated at 37° C., 5% carbon dioxide. Cells were subcultured when they reached 80-90% confluence.

Genetic Engineering of Rat Fibroblasts

Rat fibroblasts were harvested at passage 2 for lentiviral infection. A lentivirus vector expressing gLuc (Tannous B A, Kim D E, Fernandez J L, Weissleder R, Breakefield X O. Mol Ther. 2005; 11(3):435-43; Tannous BA. Nat Protoc. 2009; 4(4):582-91. doi: 10.1038/nprot.2009.28) and green fluorescent protein (GFP) under the control of the CMV promoter was obtained from the Massachusetts General Hospital Vector Core (funded by NIH/NINDS P30NS045776). Cells were cultured for 24 h in DMEM with increasing concentrations of lentiviral particles per cell and protamine sulfate, a cationic vehicle (Lin P, Lin Y, Lennon D P, Correa D, Schluchter M, Caplan A I. Efficient lentiviral transduction of human mesenchymal stem cells that preserves proliferation and differentiation capabilities. Stem Cells Transl Med. 2012; 1(12):886-97. Epub 2013 Jan. 4). Transduced GFP-positive cells were sorted using a BD FACSARIA™ III (BD Biosciences) cell sorter (Harvard Stem Cell Institute Flow Cytometry Core at Massachusetts General Hospital, Boston, MA, USA). GFP-positive cells were then cultured, expanded and used for subsequent studies. Only passages 3-5 rat fibroblasts were used for experiments.

Animals

Male Lewis rats weighing 200 g-250 g were housed in standard conditions (Charles River Laboratories, Boston, MA, USA). The animals were kept in accordance with the National Research Council guidelines. The experimental protocol was approved by the Institutional Animal Care and Use Committee, Massachusetts General Hospital.

Liver Procurement

All procurements were performed using the technique of Delriviere et al (Delriviere L, Gibbs P, Kobayashi E, Goto S, Kamada N, Gianello P. Detailed modified technique for safer harvesting and preparation of liver graft in the rat. Microsurgery. 1996; 17(12):690-6. Epub 1996 Jan. 1). Animals were anesthetized using inhalation of 3-5% isoflurane (Forane, Deerfield, IL, USA) with 1 L/min 95%/5% oxygen-carbon dioxide gas. The animal's abdomen was shaved and a transverse laparotomy was made. Intestines were moved to expose the entirety of the liver, portal vein, common bile duct, and inferior vena cava. The common bile duct was cannulated using a ~6 cm 28-gauge polyethylene tube (SURFLO®, Terumo, Somerset, NJ, USA) to collect bile throughout the perfusion. Via the infrahepatic vena cava (IHVC), 300U of heparin was administered and 3 minutes were allowed for circulation. The portal vein was cannulated using a 16-gauge catheter and IHVC was transected for exsanguination. All cannulas were secured with 7-0 silk suture. The liver was immediately flushed in situ via the portal vein cannula with 50 mL of 0.9% NaCl at 4° C. The liver was freed from its ligamentous attachments, weighed, and placed in ice-cold saline prior to being connected to the perfusion circuit.

Perfusate Composition

Perfusate composition consisted of a base of DMEM supplemented with 200 mM L-glutamine (Invitrogen), 10% v/v FBS (Thermo Scientific), 5% with bovine serum albumin (BSA; Sigma-Aldrich), 8 mg/L dexamethasone (Sigma-Aldrich), 2000 U/L heparin (APP Pharmaceuticals), and 2 U/L insulin (Humulin, Eli Lily).

A determined concentration of $5\times10^6$ engineered rat fibroblasts was added to 150 mL of perfusate to circulate through the system for the initial three hours. At hour three, the perfusate was switched to media without any rat fibroblasts and perfused for an additional three hours.

Normothermic Machine Perfusion

Normothermic machine perfusion (NMP) was chosen to maintain the liver at a metabolically active state, similar to in vivo conditions (Tolboom et al. Tissue Eng. 2007; 13(8): 2143-51. Epub 2007 Jun. 29; Berendsen et al. Transplant Res. 2012; 1(1):6. Epub 2013 Feb. 2). The NMP circuit used was comprised of an organ reservoir, bubble trap, membrane oxygenator, roller pump, water bath, and series of silicon tubing. Prior to liver procurement, the perfusion system was first flushed with ultrapure water and warmed to 37° C. before perfusate was circulated.

Immediately after procurement, the liver was transferred to the organ reservoir and perfused through the portal vein cannula. The liver was perfused with partial oxygen pressure ($pO_2$) above 400 mmHg. The flow rate of the system was manually altered according to target a portal pressure of 5 mmHg, measured using a water column manometer. Flow rates initiated at 5 mL/min and were increased to maintain an absolute pressure of 5 mmHg inside the liver.

Perfusate Analysis

Samples of perfusate were taken at time points 0, 30, 60, 120, 180, 210, 240, 300, and 360 minutes and stored at −80° C. Serum chemistry and blood gas analyses were performed during perfusion using CG4+ and CHEM8+ i-STAT cartridges (Abbott Point of Care Inc., Princeton, NJ, USA). Liver biopsies were taken post-perfusion and either snap-frozen in liquid nitrogen or fixed in 10% formalin. Assays for aspartate aminotransferase (AST; TR70121, Thermo Scientific) were performed following perfusion according to the manufacturer's instructions.

Bioluminescence Assays

Bioluminescence assays were performed by pipetting 10 μL of sample into a black-walled 96-well plate (Corning) and adding 1000 μL of coelenterazine native substrate (NanoLight Technology) at 100 μmol/L diluted in phosphate buffered saline. Samples were read immediately using a BIOTEK® SYNERGY™ 2 Multi-Mode Reader for 10s at a gain of 100-200 (BIOTEK®).

Ex Vivo Liver Imaging

Prior to perfusion, $5\times10^6$ Rat2 fibroblasts were labeled with a near infrared fluorescent membrane dye (QTRACKER™ 705 Cell Labeling Kit, Invitrogen). Ex vivo fluorescence imaging with the 665 excitation and 680 emission filter set was performed using the Olympus OV110 (Olympus Corporation) to visualize engraftment in liver. Image visualizations were performed in ImageJ software.

Cell Lysis of gLuc-Secreting Cells in Liver Tissue

Tissue biopsied post perfusion and stored in −80° C. was lysed for Gaussia Luciferase activity using NanoFuel FLASH Assay for Gaussia Luciferase (NanoLight Technology, 319). Approximately 100 mg rat liver tissue was homogenized in 200 uL lysis buffer, the samples were vortexed and kept on ice. After 15 minutes, 200 uL of *Gaussia* dilution buffer was added to the samples and they were vortexed once more. *Gaussia*-expressing cells were used as a positive control and were prepared in the same sequence. Tissue perfused with non-transduced cells was used as a negative control. The sample volume for each well was 20 uL with N=4. Finally, 50 uL of Coelenterazine buffer was injected into each well and read for Luminescence with an integration time of 10 seconds.

Histological Evaluation

Once perfusion was completed tissue samples were taken from three different lobe locations. The collected samples were formalin-fixed to be paraffin-embedded. The tissue was cut into 4-micrometer sections, mounted on a glass slide, and stained for hematoxylin-eosin and/or anti-GFP antibody (Abcam ab1218).

Example 15: Optimization and Characterization of Engineered Biosensor Cells

We utilized self-inactivating lentiviral vectors as previously described (Wurdinger T et al. Nat Methods. 2008; 5(2):171-3. Epub 2008/01/22) to integrate transgenes into the genome of dividing as well as non-dividing cells and pass them onto daughter cells; hence, cells will be stably expressing all genetic reporters. The lentivirus was engineered to contain a GFP gene for purifying engineered cells by FACS. In addition, a secreted gLuc reporter gene was inserted. gLuc enzyme activity can be specifically and easily quantified in a small aliquot of volume (5 μl) ex vivo by adding its respective substrate and measuring enzymatic conversion. gLuc has been used for high sensitivity detection (Tannous et al. Mol Ther. 2005; 11(3):435-43. Tannous B A. Nat Protoc. 2009; 4(4):582-91) with a half-life of 5-10 minutes in mouse circulation and from as few ~1000 cells in an entire mouse (Wurdinger et al. Nat Methods. 2008; 5(2):171-3. Epub 2008 Jan. 22; Teng et al. Stem Cells. 2014; 32(8):2021-32. Epub 2014 May 8). Since these probes are secreted, accumulate in the blood, and are specific to their corresponding substrates, the signal intensity is very specific and amplified such that even a few dispersed cells can be detected using a simple bioluminescent blood test. This reporter system could enable the indirect observation, in real-time, of cell fate within an organ transplant in vivo by measuring biomarker levels in circulating fluids.

Conditions with high concentrations of lentiviral particle MOI and the cationic vehicle had the highest transduction efficiency (FIG. 25A). Once rat fibroblasts were transduced with lentiviral particles, gLuc secretion was characterized during a 6-hour in vitro experiment modeled on the planned perfusion with a washout period (FIG. 25B). As expected, gLuc secretion rose after cell seeding, was reduced after media exchange, and rose again with a similar rate in fresh media. When transitioning from an in vitro to an ex vivo organ perfusion model, the typical organ perfusate solution would be the vehicle that engineered cells would be circulating in. We explored gLuc release in vitro between typical fibroblast growth media (DMEM), perfusate using a DMEM base, and perfusate using a Williams E base (as previously utilized for liver perfusion). Perfusate utilizing a DMEM base resulted in higher gLuc secretion (FIG. 25B) and was used for subsequent perfusions. The production of gLuc was stable, independent of cell density, and was more sensitive to the concentration of cells per $cm^2$ (FIG. 25C) when plotted on a log scale.

Example 16: Biosensor Cells Successfully Engraft in Ex Vivo Rat Livers by Machine Perfusion A six-hour perfusion was previously established as a benchmark for rat liver normothermic perfusion (NMP) to preserve liver metabolic function before successful transplant into recipient rats (Tolboom et al. Tissue Eng. 2007; 13(8):2143-51. Epub 2007 Jun. 29). Given the eventual aim of these biosensor cells to monitor and regulate transplanted livers, we chose to use the same six-hour perfusion in our experiments. In order to confirm successful engraftment of the biosensor cells into the liver, we infused the cells for the first three hours of the perfusion, then used fresh perfusate to check if the cells washed out. An initial cell mass of $5\times10^6$ engineered rat fibroblasts was chosen at a concentration of approximately $30\times10^3$ cells/mL to have a dilute cell suspension well below physiological circulating cell numbers.

To confirm the location of the biosensor cells within the liver, they were treated with a near-infrared (NIR) dye prior to perfusion. Cells injected directly through the cannulated liver did not distribute as thoroughly as perfused cells (FIG. 31), justifying the need for a continuous flow-based seeding process for improved biodistribution of engineered cells within the tissue. As the length of perfusion increased from 2 hours (FIG. 26A) to 4 hours (FIG. 26B) to 6 hours (FIG. 26C), we found that longer perfusions corresponded with qualitatively improved distribution of the cells across the organ bed even after a washout period and addition of fresh perfusate. The 6-hour perfusion time qualitatively enabled distribution of cells into the periphery, which was not clearly populated in livers perfused for 2-4 hours.

Example 17: Histological Confirmation of Biosensor Cell Engraftment

NIR tracking of engineered cells helped initially verify cell engraftment, though could not resolve microscopic resolution of cell localization within the tissue. Histological analysis was further performed to assess the presence of the biosensor cells embedded in the tissue by staining GFP+ cells using for anti-GFP antibody 9F9.F9 (FIGS. 27A and 27B). Engineered cells contained both GFP and gLuc genes and therefore the location of the cells can be tracked via GFP presence as well. The brown staining in tissue samples indicated GFP+ cells present in the tissue. Cell localization was generally near sinusoidal endothelium near portal veins. Hematoxylin-eosin (H&E) staining was used initially to histologically assess preservation injury and endothelial cell damage in liver tissue. Confluence of cells and absence of neutrophils is an indication of little to no damage caused due to the perfusion and/or addition of cells (Schofield et al. Shock. 2013; 40(6):463-70. Epub 2013 Oct. 4). Biopsies (FIGS. 27C and 27D) from different liver perfusions were shown to have no major pathological damage based on these criteria.

Example 18: Engrafted Biosensor Cells have Minimal Impact on Liver Viability Functionality Liver functionality after cell engraftment was further assessed at the organ level by comparing the biochemistries of an experimental group perfused with transduced cells, a group containing un-transduced cells, and a negative control group perfused with no cells. These groups could isolate the effect of cells alone compared to the transgene to identify a root cause of any observed effects.

To assess viability of the perfused grafts, we used the composite viability criterion of Mergental et al which were established to clinically predict primary nonfunction in normothermically perfused human livers (Mergental et al. Liver Transpl. 2018; 24(10):1453-69. Epub 2018 Oct. 26). Briefly, one major and two minor criteria must be met in order to deem the liver clinically viable. As shown in FIG. 28, perfused livers containing engineered sensor cells produce bile (FIG. 28A), a major criterion; show stable flow rates (FIG. 28B) and stable perfusate pH (FIG. 28C), two minor criteria. Therefore, it can be suggested that the cell infusion and engraftment would not have an impact on the ability of the liver to successfully survive and function after transplant.

To further assess if the cell infusion did affect function, we assessed several additional parameters during perfusion: Metabolic activity of the liver was additionally tested using glucose stability (Delriviere et al. Microsurgery. 1996; 17(12):690-6. Epub 1996/01/01) as well as oxygen consumption rate. Hepatocellular damage was further assessed using and aspartate transaminase (AST) release (Imber et al., Transplantation. 2002; 73(5):701-9. Epub 2002/03/22) which we have also shown to be correlated to transplant success in similar normothermic rat liver perfusions systems (Uygun et al., Transplant Proc. 2010; 42(7):2463-7. Epub 2010/09/14). Finally, we measured liver weight before and after perfusion to evaluate if there was any edema. In all three groups lactate (FIG. 29A) and glucose (FIG. 29B) values rose initially but began to stabilize after the perfusate switch at T=3 hrs. Oxygen consumption (FIG. 29C) was calculated using $$O_2 \text{ Consumption} = \text{portal flow} * S * \frac{pO_{2inflow} - pO_{2outFlow}}{g \text{ liver weight}}$$

(S, the solubility constant of water at 37° C.=0.031 μL/mL/mm Hg (Reinders et al. J Stem Cell Res Ther. 2014; 4(2):1000166. Epub 2014 Jun. 6). Oxygen consumption was found to be higher in the control group due to the higher portal flows. AST production, known to correlate with liver damage, followed a similar trend for all three groups throughout perfusion (FIG. 29D). Finally, weight change (FIG. 29E) pre- and post-perfusion showed that the engineered fibroblasts did not cause any edema to the liver. Overall, these assays show conclusively that the engrafted biosensor cells did not any negatively impact liver function.

Example 19: Biosensor Cells Remain Viable and Secrete Detectable gLuc in External Circulation Fluids Biosensor cells were added to perfusate to circulate and engraft in liver, and fresh perfusate without cells was swapped in after 180 minutes to test for engraftment. gLuc has been used as a highly sensitive reporter for assessment of cells in vivo, so levels in the perfusate allow us to track its activity within the rat livers (Elman et al., PLoS One. 2014; 9(2):e89882. Epub 2014/03/04; Singleton et al., Cytotherapy. 2017; 19(12):1537-45. Epub 2017/09/18; Tannous, Nat Protoc. 2009; 4(4):582-91). There was a consistent pattern of gLuc secretion: an initial buildup in the first three hours, then a drop at the time of switching to fresh perfusate, and resumption of increase during hours 4-6 (FIG. 30A). Given that the rate of production was similar after the washout period, the data suggest that the initial release of gLuc during the engraftment period represented the adherent, engineered cells within the organ itself rather than being derived from circulating cells.

In order to approximate the number of engrafted cells per tissue, we measured intra-tissue gLuc levels from frozen tissue biopsies compared to a known control sample of pure engineered gLuc fibroblasts. Tissue samples were lysed and the transduced cell group, in comparison to the un-transduced cell group (Negative Control), had significantly higher levels of gLuc secretion (FIG. 30B). When compared to a positive control of $1\times10^6$ pure gLuc cells, the signal coming from a 100 mg tissue biopsy was ~13% to that of the positive control. This equates to $\sim1.3\times10^3$ engineered cells per mg of tissue. When scaled to a 10 g liver, the order of magnitude of engineered cells approaches $10^7$ cells which suggests that nearly the entirety of the infused cell population likely engrafted, albeit greater than expected and likely due to the variability of the assay and assumptions herein.

| Exemplary Sequences |
|---|
| Circa1-Gluc<br>5'AATGTAGTCTTATGCAATACTCTTGTAGTCTTGCAACATGGTAACGATGAGTTAG<br>CAACATGCCTTACAAGGAGAGAAAAAGCACCGTGCATGCCGATTGGTGGAAGTAAGG<br>TGGTACGATCGTGCCTTATTAGGAAGGCAACAGACGGGTCTGACATGGATTGGACGA<br>ACCACTGAATTGCCGCATTGCAGAGATATTGTATTTAAGTGCCTAGCTCGATACATA<br>AACGGGTCTCTCTGGTTAGACCAGATCTGAGCCTGGGAGCTCTCTGGCTAACTAGGG<br>AACCCACTGCTTAAGCCTCAATAAAGCTTGCCTTGAGTGCTTCAAGTAGTGTGTGCC<br>CGTCTGTTGTGTGACTCTGGTAACTAGAGATCCCTCAGACCCTTTTAGTCAGTGTGG<br>AAAATCTCTAGCAGTGGCGCCCGAACAGGGACTTGAAAGCGAAAGGGAAACCAGAGG<br>AGCTCTCTCGACGCAGGACTCGGCTTGCTGAAGCGCGCACGGCAAGAGGCGAGGGGC<br>GGCGACTGGTGAGTACGCCAAAAATTTTGACTAGCGGAGGCTAGAAGGAGAGAGATG<br>GGTGCGAGAGCGTCAGTATTAAGCGGGGGAGAATTAGATCGCGATGGGAAAAAATTC<br>GGTTAAGGCCAGGGGGAAAGAAAAAATATAAATTAAAACATATAGTATGGGCAAGCA<br>GGGAGCTAGAACGATTCGCAGTTAATCCTGGCCTGTTAGAAACATCAGAAGGCTGTA<br>GACAAATACTGGGACAGCTACAACCATCCCTTCAGACAGGATCAGAAGAACTTAGAT<br>CATTATATAATACAGTAGCAACCCTCTATTGTGTGCATCAAAGGATAGAGATAAAAG<br>ACACCAAGGAAGCTTTAGACAAGATAGAGGAAGAGCAAAACAAAAGTAAGACCACCG<br>CACAGCAAGCGGCCGCTGATCTTCAGACCTGGAGGAGGAGATATGAGGGACAATTGG<br>AGAAGTGAATTATATAAATATAAAGTAGTAAAAATTGAACCATTAGGAGTAGCACCC<br>ACCAAGGCAAAGAGAAGAGTGGTGCAGAGAGAAAAAAGAGCAGTGGGAATAGGAGCT<br>TTGTTCCTTGGGTTCTTGGGAGCAGCAGGAAGCACTATGGGCGCAGCGTCAATGACG<br>CTGACGGTACAGGCCAGACAATTATTGTCTGGTATAGTGCAGCAGCAGAACAATTTG<br>CTGAGGGCTATTGAGGCGCAACAGCATCTGTTGCAACTCACAGTCTGGGGCATCAAG<br>CAGCTCCAGGCAAGAATCCTGGCTGTGGAAAGATACCTAAAGGATCAACAGCTCCTG<br>GGGATTTGGGGTTGCTCTGGAAAACTCATTTGCACCACTGCTGTGCCTTGGAATGCT<br>AGTTGGAGTAATAAATCTCTGGAACAGATTTGGAATCACACGACCTGGATGGAGTGG<br>GACAGAGAAATTAACAATTACACAAGCTTAATACACTCCTTAATTGAAGAATCGCAA<br>AACCAGCAAGAAAAGAATGAACAAGAATTATTGGAATTAGATAAATGGGCAAGTTTG<br>TGGAATTGGTTTAACATAACAAATTGGCTGTGGTATATAAAATTATTCATAATGATA<br>GTAGGAGGCTTGGTAGGTTTAAGAATAGTTTTTGCTGTACTTTCTATAGTGAATAGA<br>GTTAGGCAGGGATATTCACCATTATCGTTTCAGACCCACCTCCCAACCCCGAGGGGA<br>CCCGACAGGCCCGAAGGAATAGAAGAAGAAGGTGGAGAGAGAGACAGAGACAGATCC<br>ATTCGATTAGTGAACGGATCTCGACGGTATCGATTAACTTTTAAAAGAAAAGGGGGG<br>ATTGGGGGGTACAGTGCAGGGGAAAGAATAGTAGACATAATAGCAACAGACATACAA<br>ACTAAAGAATTACAAAAACAAATTACAAAAATTCAAAATTTTATCGATGTCGACGTT<br>AACGCTAGTGATATCAACTTTGTATAGAAAAGTTGGCTCCGAATTCGCCCTTAGTAG<br>TGTTAACCCCGGGCTCGAGCAGTATTTAGCCACGTGACAGTGTAAGCACACGTGGGC<br>CCTCAAGTCCACGTGCAGGGAGCCTGAGCACCACTGAGCGGTCCTGAGCCAAGAGGG<br>TATATAATGGAAGCTCGACTTCCAGAAGGGCGAATTCGACCCAAGTTTGTACAAAAA<br>AGCAGGCTCCGCGGCCGCCCCCTTCACCGAGCTCGGATCCAGCCACCATGGGAGTCA<br>AAGTTCTGTTTGCCCTGATCTGCATCGCTGTGGCCGAGGCCAAGCCCACCGAGAACA<br>ACGAAGACTTCAACATCGTGGCCGTGGCCAGCAACTTCGCGACCACGGATCTCGATG<br>CTGACCGCGGGAAGTTGCCCGGCAAGAAGCTGCCGCTGGAGGTGCTCAAAGAGATGG<br>AAGCCAATGCCCGGAAAGCTGGCTGCACCAGGGGCTGTCTGATCTGCCTGTCCCACA<br>TCAAGTGCACGCCCAAGATGAAGAAGTTCATCCCAGGACGCTGCCACACCTACGAAG<br>GCGACAAAGAGTCCGCACAGGGCGGCATAGGCGAGGCGATCGTCGACATTCCTGAGA<br>TTCCTGGGTTCAAGGACTTGGAGCCCATGGAGCAGTTCATCGCACAGGTCGATCTGT<br>GTGTGGACTGCACAACTGGCTGCCTCAAAGGGCTTGCCAACGTGCAGTGTTCTGACC<br>TGCTCAAGAAGTGGCTGCCGCAACGCTGTGCGACCTTTGCCAGCAAGATCCAGGGCC<br>AGGTGGACAAGATCAAGGGGGCCGGTGGTGACTAAGCGGCCGCAATAAAATATCTTT<br>ATTTTCATTACATCTGTGTGTTGGTTTTTTGTGTGTCTAGAAATAATAAGGGTGGGC<br>GCGCCGACCCAGCTTTCTTGTACAAAGTGGTTGATATCCAGCACAGTGGCGGCCGCT<br>CGAGTCTAGAGGGCCCGCGGTTCGAAGGTAAGCCTATCCCTAACCCTCTCCTCGGTC<br>TCGATTCTACGCGTACCGGTTAGTAATGATCGACAATCAACCTCTGGATTACAAAAT<br>TTGTGAAAGATTGACTGGTATTCTTAACTATGTTGCTCCTTTTACGCTATGTGGATA<br>CGCTGCTTTAATGCCTTTGTATCATGCTATTGCTTCCCGTATGGCTTTCATTTTCTC<br>CTCCTTGTATAAATCCTGGTTGCTGTCTCTTTATGAGGAGTTGTGGCCCGTTGTCAG<br>GCAACGTGGCGTGGTGTGCACTGTGTTTGCTGACGCAACCCCCACTGGTTGGGGCAT<br>TGCCACCACCTGTCAGCTCCTTTCCGGGACTTTCGCTTTCCCCCTCCCTATTGCCAC<br>GGCGGAACTCATCGCCGCCTGCCTTGCCCGCTGCTGGACAGGGGCTCGGCTGTTGGG<br>CACTGACAATTCCGTGGTGTTGTCGGGGAAGCTGACGTCCTTTCCATGGCTGCTCGC<br>CTGTGTTGCCACCTGGATTCTGCGCGGGACGTCCTTCTGCTACGTCCCTTCGGCCCT<br>CAATCCAGCGGACCTTCCTTCCCGCGGCCTGCTGCCGGCTCTGCGGCCTCTTCCGCG<br>TCTTCGCCTTCGCCCTCAGACGAGTCGGATCTCCCTTTGGGCCGCCTCCCCGCCTGG<br>CGATGGTACCTACCGGGTAGGGGAGGCGCTTTTCCCAAGGCAGTCTGGAGCATGCGC<br>TTTAGCAGCCCCGCTGGGCACTTGGCGCTACACAAGTGGCCTCTGGCCTCGCACACA<br>TTCCACATCCACCGGTAGGCGCCAACCGGCTCCGTTCTTTGGTGGCCCCTTCGCGCC<br>ACCTTCTACTCCTCCCCTAGTCAGGAAGTTCCCCCCCGCCCCGCAGCTCGCGTCGTG<br>CAGGACGTGACAAATGGAAGTAGCACGTCTCACTAGTCTCGTGCAGATGGACAGCAC<br>CGCTGAGCAATGGAAGCGGGTAGGCCTTTGGGGCAGCGGCCAATAGCAGCTTTGCTC<br>CTTCGCTTTCTGGGCTCAGAGGCTGGGAAGGGGTGGGTCCGGGGGCGGGCTCAGGGG<br>CGGGCTCAGGGGCGGGGCGGGCGCCCGAAGGTCCTCCGGAGGCCCGGCATTCTGCAC<br>GCTTCAAAAGCGCACGTCTGCCGCGCTGTTCTCCTCTTCCTCATCTCCGGGCCTTTC<br>GACTCTAGACACGTGTTGACAATTAATCATCGGCATAGTATATCGGCATAGTATAAT<br>ACGACAAGGTGAGGAACTAAACCATGGCCAAGCCTTTGTCTCAAGAAGAATCCACCC<br>TCATTGAAAGAGCAACGGCTACAATCAACAGCATCCCCATCTCTGAAGACTACAGCG<br>TCGCCAGCGCAGCTCTCTCTAGCGACGGCCGCATCTTCACTGGTGTCAATGTATATC<br>ATTTTACTGGGGGACCTTGTGCAGAACTCGTGGTGCTGGGCACTGCTGCTGCTGCGG<br>CAGCTGGCAACCTGACTTGTATCGTCGCGATCGGAAATGAGAACAGGGGCATCTTGA |

-continued

| Exemplary Sequences |
|---|
| GCCCCTGCGGACGGTGCCGACAGGTGCTTCTCGATCTGCATCCTGGGATCAAAGCCA<br>TAGTGAAGGACAGTGATGGACAGCCGACGGCAGTTGGGATTCGTGAATTGCTGCCCT<br>CTGGTTATGTGTGGGAGGGCTAAGCACAATTCGAGCTCGGTACCTTTAAGACCAATG<br>ACTTACAAGGCAGCTGTAGATCTTAGCCACTTTTTAAAAGAAAAGGGGGGACTGGAA<br>GGGCTAATTCACTCCCAACGAAGACAAGATCTGCTTTTTGCTTGTACTGGGTCTCTC<br>TGGTTAGACCAGATCTGAGCCTGGGAGCTCTCTGGCTAACTAGGGAACCCACTGCTT<br>AAGCCTCAATAAAGCTTGCCTTGAGTGCTTCAAGTAGTGTGTGCCCGTCTGTTGTGT<br>GACTCTGGTAACTAGAGATCCCTCAGACCCTTTTAGTCAGTGTGGAAAATCTCTAGC<br>AGTAGTAGTTCATGTCATCTTATTATTCAGTATTTATAACTTGCAAAGAAATGAATA<br>TCAGAGAGTGAGAGGAACTTGTTTATTGCAGCTTATAATGGTTACAAATAAAGCAAT<br>AGCATCACAAATTTCACAAATAAAGCATTTTTTTCACTGCATTCTAGTTGTGGTTTG<br>TCCAAACTCATCAATGTATCTTATCATGTCTGGCTCTAGCTATCCCGCCCCTAACTC<br>CGCCCATCCCGCCCCTAACTCCGCCCAGTTCCGCCCATTCTCCGCCCCATGGCTGAC<br>TAATTTTTTTTATTTATGCAGAGGCCGAGGCCGCCTCGGCCTCTGAGCTATTCCAGA<br>AGTAGTGAGGAGGCTTTTTTGGAGGCCTAGGGACGTACCCAATTCGCCCTATAGTGA<br>GTCGTATTACGCGCGCTCACTGGCCGTCGTTTTACAACGTCGTGACTGGGAAAACCC<br>TGGCGTTACCCAACTTAATCGCCTTGCAGCACATCCCCCTTTCGCCAGCTGGCGTAA<br>TAGCGAAGAGGCCCGCACCGATCGCCCTTCCCAACAGTTGCGCAGCCTGAATGGCGA<br>ATGGGACGCGCCCTGTAGCGGCGCATTAAGCGCGGCGGGTGTGGTGGTTACGCGCAG<br>CGTGACCGCTACACTTGCCAGCGCCCTAGCGCCCGCTCCTTTCGCTTTCTTCCCTTC<br>CTTTCTCGCCACGTTCGCCGGCTTTCCCCGTCAAGCTCTAAATCGGGGGCTCCCTTT<br>AGGGTTCCGATTTAGTGCTTTACGGCACCTCGACCCCAAAAAACTTGATTAGGGTGA<br>TGGTTCACGTAGTGGGCCATCGCCCTGATAGACGGTTTTTCGCCCTTTGACGTTGGA<br>GTCCACGTTCTTTAATAGTGGACTCTTGTTCCAAACTGGAACAACACTCAACCCTAT<br>CTCGGTCTATTCTTTTGATTTATAAGGGATTTTGCCGATTTCGGCCTATTGGTTAAA<br>AAATGAGCTGATTTAACAAAAATTTAACGCGAATTTTAACAAAATATTAACGCTTAC<br>AATTTAGGTGGCACTTTTCGGGGAAATGTGCGCGGAACCCCTATTTGTTTATTTTTC<br>TAAATACATTCAAATATGTATCCGCTCATGAGACAATAACCCTGATAAATGCTTCAA<br>TAATATTGAAAAAGGAAGAGTATGAGTATTCAACATTTCCGTGTCGCCCTTATTCCC<br>TTTTTTGCGGCATTTTGCCTTCCTGTTTTTGCTCACCCAGAAACGCTGGTGAAAGTA<br>AAAGATGCTGAAGATCAGTTGGGTGCACGAGTGGGTTACATCGAACTGGATCTCAAC<br>AGCGGTAAGATCCTTGAGAGTTTTCGCCCCGAAGAACGTTTTCCAATGATGAGCACT<br>TTTAAAGTTCTGCTATGTGGCGCGGTATTATCCCGTATTGACGCCGGGCAAGAGCAA<br>CTCGGTCGCCGCATACACTATTCTCAGAATGACTTGGTTGAGTACTCACCAGTCACA<br>GAAAAGCATCTTACGGATGGCATGACAGTAAGAGAATTATGCAGTGCTGCCATAACC<br>ATGAGTGATAACACTGCGGCCAACTTACTTCTGACAACGATCGGAGGACCGAAGGAG<br>CTAACCGCTTTTTTGCACAACATGGGGGATCATGTAACTCGCCTTGATCGTTGGGAA<br>CCGGAGCTGAATGAAGCCATACCAAACGACGAGCGTGACACCACGATGCCTGTAGCA<br>ATGGCAACAACGTTGCGCAAACTATTAACTGGCGAACTACTTACTCTAGCTTCCCGG<br>CAACAATTAATAGACTGGATGGAGGCGGATAAAGTTGCAGGACCACTTCTGCGCTCG<br>GCCCTTCCGGCTGGCTGGTTTATTGCTGATAAATCTGGAGCCGGTGAGCGTGGGTCT<br>CGCGGTATCATTGCAGCACTGGGGCCAGATGGTAAGCCCTCCCGTATCGTAGTTATC<br>TACACGACGGGGAGTCAGGCAACTATGGATGAACGAAATAGACAGATCGCTGAGATA<br>GGTGCCTCACTGATTAAGCATTGGTAACTGTCAGACCAAGTTTACTCATATATACTT<br>TAGATTGATTTAAAACTTCATTTTTAATTTAAAAGGATCTAGGTGAAGATCCTTTTT<br>GATAATCTCATGACCAAAATCCCTTAACGTGAGTTTTCGTTCCACTGAGCGTCAGAC<br>CCCGTAGAAAAGATCAAAGGATCTTCTTGAGATCCTTTTTTTCTGCGCGTAATCTGC<br>TGCTTGCAAACAAAAAAACCACCGCTACCAGCGGTGGTTTGTTTGCCGGATCAAGAG<br>CTACCAACTCTTTTTCCGAAGGTAACTGGCTTCAGCAGAGCGCAGATACCAAATACT<br>GTTCTTCTAGTGTAGCCGTAGTTAGGCCACCACTTCAAGAACTCTGTAGCACCGCCT<br>ACATACCTCGCTCTGCTAATCCTGTTACCAGTGGCTGCTGCCAGTGGCGATAAGTCG<br>TGTCTTACCGGGTTGGACTCAAGACGATAGTTACCGGATAAGGCGCAGCGGTCGGGC<br>TGAACGGGGGGTTCGTGCACACAGCCCAGCTTGGAGCGAACGACCTACACCGAACTG<br>AGATACCTACAGCGTGAGCTATGAGAAAGCGCCACGCTTCCCGAAGGGAGAAAGGCG<br>GACAGGTATCCGGTAAGCGGCAGGGTCGGAACAGGAGAGCGCACGAGGGAGCTTCCA<br>GGGGGAAACGCCTGGTATCTTTATAGTCCTGTCGGGTTTCGCCACCTCTGACTTGAG<br>CGTCGATTTTTGTGATGCTCGTCAGGGGGGCGGAGCCTATGGAAAAACGCCAGCAAC<br>GCGGCCTTTTTACGGTTCCTGGCCTTTTGCTGGCCTTTTGCTCACATGTTCTTTCCT<br>GCGTTATCCCCTGATTCTGTGGATAACCGTATTACCGCCTTTGAGTGAGCTGATACC<br>GCTCGCCGCAGCCGAACGACCGAGCGCAGCGAGTCAGTGAGCGAGGAAGCGGAAGAG<br>CGCCCAATACGCAAACCGCCTCTCCCCGCGCGTTGGCCGATTCATTAATGCAGCTGG<br>CACGACAGGTTTCCCGACTGGAAAGCGGGCAGTGAGCGCAACGCAATTAATGTGAGT<br>TAGCTCACTCATTAGGCACCCCAGGCTTTACACTTTATGCTTCCGGCTCGTATGTTG<br>TGTGGAATTGTGAGCGGATAACAATTTCACACAGGAAACAGCTATGACCATGATTAC<br>GCCAAGCGCGCAATTAACCCTCACTAAAGGGAACAAAAGCTGGAGCTGCAAGCTT3'<br>SEQ ID NO: 17<br><br>Circa2-Gluc<br>5'AATGTAGTCTTATGCAATACTCTTGTAGTCTTGCAACATGGTAACGATGAGTTAG<br>CAACATGCCTTACAAGGAGAGAAAAAGCACCGTGCATGCCGATTGGTGGAAGTAAGG<br>TGGTACGATCGTGCCTTATTAGGAAGGCAACAGACGGGTCTGACATGGATTGGACGA<br>ACCACTGAATTGCCGCATTGCAGAGATATTGTATTTAAGTGCCTAGCTCGATACATA<br>AACGGGTCTCTCTGGTTAGACCAGATCTGAGCCTGGGAGCTCTCTGGCTAACTAGGG<br>AACCCACTGCTTAAGCCTCAATAAAGCTTGCCTTGAGTGCTTCAAGTAGTGTGTGCC<br>CGTCTGTTGTGTGACTCTGGTAACTAGAGATCCCTCAGACCCTTTTAGTCAGTGTGG<br>AAAATCTCTAGCAGTGGCGCCCGAACAGGGACTTGAAAGCGAAAGGGAAACCAGAGG<br>AGCTCTCTCGACGCAGGACTCGGCTTGCTGAAGCGCGCACGGCAAGAGGCGAGGGGC |

-continued

| Exemplary Sequences |
|---|
| GGCGACTGGTGAGTACGCCAAAAATTTTGACTAGCGGAGGCTAGAAGGAGAGAGATG<br>GGTGCGAGAGCGTCAGTATTAAGCGGGGGAGAATTAGATCGCGATGGGAAAAAATTC<br>GGTTAAGGCCAGGGGGAAAGAAAAAATATAAATTAAAACATATAGTATGGGCAAGCA<br>GGGAGCTAGAACGATTCGCAGTTAATCCTGGCCTGTTAGAAACATCAGAAGGCTGTA<br>GACAAATACTGGGACAGCTACAACCATCCCTTCAGACAGGATCAGAAGAACTTAGAT<br>CATTATATAATACAGTAGCAACCCTCTATTGTGTGCATCAAAGGATAGAGATAAAAG<br>ACACCAAGGAAGCTTTAGACAAGATAGAGGAAGAGCAAAACAAAAGTAAGACCACCG<br>CACAGCAAGCGGCCGCTGATCTTCAGACCTGGAGGAGGAGATATGAGGGACAATTGG<br>AGAAGTGAATTATATAAATATAAAGTAGTAAAAATTGAACCATTAGGAGTAGCACCC<br>ACCAAGGCAAAGAGAAGAGTGGTGCAGAGAGAAAAAAGAGCAGTGGGAATAGGAGCT<br>TTGTTCCTTGGGTTCTTGGGAGCAGCAGGAAGCACTATGGGCGCAGCGTCAATGACG<br>CTGACGGTACAGGCCAGACAATTATTGTCTGGTATAGTGCAGCAGCAGAACAATTTG<br>CTGAGGGCTATTGAGGCGCAACAGCATCTGTTGCAACTCACAGTCTGGGGCATCAAG<br>CAGCTCCAGGCAAGAATCCTGGCTGTGGAAAGATACCTAAAGGATCAACAGCTCCTG<br>GGGATTTGGGGTTGCTCTGGAAAACTCATTTGCACCACTGCTGTGCCTTGGAATGCT<br>AGTTGGAGTAATAAATCTCTGGAACAGATTTGGAATCACACGACCTGGATGGAGTGG<br>GACAGAGAAATTAACAATTACACAAGCTTAATACACTCCTTAATTGAAGAATCGCAA<br>AACCAGCAAGAAAAGAATGAACAAGAATTATTGGAATTAGATAAATGGGCAAGTTTG<br>TGGAATTGGTTTAACATAACAAATTGGCTGTGGTATATAAAATTATTCATAATGATA<br>GTAGGAGGCTTGGTAGGTTTAAGAATAGTTTTTGCTGTACTTTCTATAGTGAATAGA<br>GTTAGGCAGGGATATTCACCATTATCGTTTCAGACCCACCTCCCAACCCCGAGGGGA<br>CCCGACAGGCCCGAAGGAATAGAAGAAGAAGGTGGAGAGAGAGACAGAGACAGATCC<br>ATTCGATTAGTGAACGGATCTCGACGGTATCGATTAACTTTTAAAAGAAAAGGGGGG<br>ATTGGGGGGTACAGTGCAGGGGAAAGAATAGTAGACATAATAGCAACAGACATACAA<br>ACTAAAGAATTACAAAAACAAATTACAAAAATTCAAAATTTTATCGATGTCGACGTT<br>AACGCTAGTGATATCAACTTTGTATAGAAAAGTTGGCTCCGAATTCGCCCTTAGTAG<br>TGTTAACCCCGGGCTCGAGCAGTATTTAGCCACGTGACAGTGTAAGCACACGTGGGC<br>CCTCAAGTCCACGTGCAGGGAGCCACGTGACCACACGTGGGTCCACGTGCAAGAGGG<br>TATATAATGGAAGCTCGACTTCCAGAAGGGCGAATTCGACCCAAGTTTGTACAAAAA<br>AGCAGGCTCCGCGGCCGCCCCCTTCACCGAGCTCGGATCCAGCCACCATGGGAGTCA<br>AAGTTCTGTTTGCCCTGATCTGCATCGCTGTGGCCGAGGCCAAGCCCACCGAGAACA<br>ACGAAGACTTCAACATCGTGGCCGTGGCCAGCAACTTCGCGACCACGGATCTCGATG<br>CTGACCGCGGGAAGTTGCCCGGCAAGAAGCTGCCGCTGGAGGTGCTCAAAGAGATGG<br>AAGCCAATGCCCGGAAAGCTGGCTGCACCAGGGGCTGTCTGATCTGCCTGTCCCACA<br>TCAAGTGCACGCCCAAGATGAAGAAGTTCATCCCAGGACGCTGCCACACCTACGAAG<br>GCGACAAAGAGTCCGCACAGGGCGGCATAGGCGAGGCGATCGTCGACATTCCTGAGA<br>TTCCTGGGTTCAAGGACTTGGAGCCCATGGAGCAGTTCATCGCACAGGTCGATCTGT<br>GTGTGGACTGCACAACTGGCTGCCTCAAAGGGCTTGCCAACGTGCAGTGTTCTGACC<br>TGCTCAAGAAGTGGCTGCCGCAACGCTGTGCGACCTTTGCCAGCAAGATCCAGGGCC<br>AGGTGGACAAGATCAAGGGGGCCGGTGGTGACTAAGCGGCCGCAATAAAATATCTTT<br>ATTTTCATTACATCTGTGTGTTGGTTTTTTGTGTGTCTAGAAATAATAAGGGTGGGC<br>GCGCCGACCCAGCTTTCTTGTACAAAGTGGTTGATATCCAGCACAGTGGCGGCCGCT<br>CGAGTCTAGAGGGCCCGCGGTTCGAAGGTAAGCCTATCCCTAACCCTCTCCTCGGTC<br>TCGATTCTACGCGTACCGGTTAGTAATGATCGACAATCAACCTCTGGATTACAAAAT<br>TTGTGAAAGATTGACTGGTATTCTTAACTATGTTGCTCCTTTTACGCTATGTGGATA<br>CGCTGCTTTAATGCCTTTGTATCATGCTATTGCTTCCCGTATGGCTTTCATTTTCTC<br>CTCCTTGTATAAATCCTGGTTGCTGTCTCTTTATGAGGAGTTGTGGCCCGTTGTCAG<br>GCAACGTGGCGTGGTGTGCACTGTGTTTGCTGACGCAACCCCCACTGGTTGGGGCAT<br>TGCCACCACCTGTCAGCTCCTTTCCGGGACTTTCGCTTTCCCCCTCCCTATTGCCAC<br>GGCGGAACTCATCGCCGCCTGCCTTGCCCGCTGCTGGACAGGGGCTCGGCTGTTGGG<br>CACTGACAATTCCGTGGTGTTGTCGGGGAAGCTGACGTCCTTTCCATGGCTGCTCGC<br>CTGTGTTGCCACCTGGATTCTGCGCGGGACGTCCTTCTGCTACGTCCCTTCGGCCCT<br>CAATCCAGCGGACCTTCCTTCCCGCGGCCTGCTGCCGGCTCTGCGGCCTCTTCCGCG<br>TCTTCGCCTTCGCCCTCAGACGAGTCGGATCTCCCTTTGGGCCGCCTCCCCGCCTGG<br>CGATGGTACCTACCGGGTAGGGGAGGCGCTTTTCCCAAGGCAGTCTGGAGCATGCGC<br>TTTAGCAGCCCCGCTGGGCACTTGGCGCTACACAAGTGGCCTCTGGCCTCGCACACA<br>TTCCACATCCACCGGTAGGCGCCAACCGGCTCCGTTCTTTGGTGGCCCCTTCGCGCC<br>ACCTTCTACTCCTCCCCTAGTCAGGAAGTTCCCCCCCGCCCCGCAGCTCGCGTCGTG<br>CAGGACGTGACAAATGGAAGTAGCACGTCTCACTAGTCTCGTGCAGATGGACAGCAC<br>CGCTGAGCAATGGAAGCGGGTAGGCCTTTGGGGCAGCGGCCAATAGCAGCTTTGCTC<br>CTTCGCTTTCTGGGCTCAGAGGCTGGGAAGGGGTGGGTCCGGGGGCGGGCTCAGGGG<br>CGGGCTCAGGGGCGGGGCGGGCGCCCGAAGGTCCTCCGGAGGCCCGGCATTCTGCAC<br>GCTTCAAAAGCGCACGTCTGCCGCGCTGTTCTCCTCTTCCTCATCTCCGGGCCTTTC<br>GACTCTAGACACGTGTTGACAATTAATCATCGGCATAGTATATCGGCATAGTATAAT<br>ACGACAAGGTGAGGAACTAAACCATGGCCAAGCCTTTGTCTCAAGAAGAATCCACCC<br>TCATTGAAAGAGCAACGGCTACAATCAACAGCATCCCCATCTCTGAAGACTACAGCG<br>TCGCCAGCGCAGCTCTCTCTAGCGACGGCCGCATCTTCACTGGTGTCAATGTATATC<br>ATTTTACTGGGGGACCTTGTGCAGAACTCGTGGTGCTGGGCACTGCTGCTGCTGCGG<br>CAGCTGGCAACCTGACTTGTATCGTCGCGATCGGAAATGAGAACAGGGGCATCTTGA<br>GCCCCTGCGGACGGTGCCGACAGGTGCTTCTCGATCTGCATCCTGGGATCAAAGCCA<br>TAGTGAAGGACAGTGATGGACAGCCGACGGCAGTTGGGATTCGTGAATTGCTGCCCT<br>CTGGTTATGTGTGGGAGGGCTAAGCACAATTCGAGCTCGGTACCTTTAAGACCAATG<br>ACTTACAAGGCAGCTGTAGATCTTAGCCACTTTTTAAAAGAAAAGGGGGGACTGGAA<br>GGGCTAATTCACTCCCAACGAAGACAAGATCTGCTTTTTGCTTGTACTGGGTCTCTC<br>TGGTTAGACCAGATCTGAGCCTGGGAGCTCTCTGGCTAACTAGGGAACCCACTGCTT<br>AAGCCTCAATAAAGCTTGCCTTGAGTGCTTCAAGTAGTGTGTGCCCGTCTGTTGTGT<br>GACTCTGGTAACTAGAGATCCCTCAGACCCTTTTAGTCAGTGTGGAAAATCTCTAGC |

-continued

| Exemplary Sequences |
|---|
| AGTAGTAGTTCATGTCATCTTATTATTCAGTATTTATAACTTGCAAAGAAATGAATA<br>TCAGAGAGTGAGAGGAACTTGTTTATTGCAGCTTATAATGGTTACAAATAAAGCAAT<br>AGCATCACAAATTTCACAAATAAAGCATTTTTTTCACTGCATTCTAGTTGTGGTTTG<br>TCCAAACTCATCAATGTATCTTATCATGTCTGGCTCTAGCTATCCCGCCCCTAACTC<br>CGCCCATCCCGCCCCTAACTCCGCCCAGTTCCGCCCATTCTCCGCCCCATGGCTGAC<br>TAATTTTTTTTATTTATGCAGAGGCCGAGGCCGCCTCGGCCTCTGAGCTATTCCAGA<br>AGTAGTGAGGAGGCTTTTTTGGAGGCCTAGGGACGTACCCAATTCGCCCTATAGTGA<br>GTCGTATTACGCGCGCTCACTGGCCGTCGTTTTACAACGTCGTGACTGGGAAAACCC<br>TGGCGTTACCCAACTTAATCGCCTTGCAGCACATCCCCCTTTCGCCAGCTGGCGTAA<br>TAGCGAAGAGGCCCGCACCGATCGCCCTTCCCAACAGTTGCGCAGCCTGAATGGCGA<br>ATGGGACGCGCCCTGTAGCGGCGCATTAAGCGCGGCGGGTGTGGTGGTTACGCGCAG<br>CGTGACCGCTACACTTGCCAGCGCCCTAGCGCCCGCTCCTTTCGCTTTCTTCCCTTC<br>CTTTCTCGCCACGTTCGCCGGCTTTCCCCGTCAAGCTCTAAATCGGGGGCTCCCTTT<br>AGGGTTCCGATTTAGTGCTTTACGGCACCTCGACCCCAAAAAACTTGATTAGGGTGA<br>TGGTTCACGTAGTGGGCCATCGCCCTGATAGACGGTTTTTCGCCCTTTGACGTTGGA<br>GTCCACGTTCTTTAATAGTGGACTCTTGTTCCAAACTGGAACAACACTCAACCCTAT<br>CTCGGTCTATTCTTTTGATTTATAAGGGATTTTGCCGATTTCGGCCTATTGGTTAAA<br>AAATGAGCTGATTTAACAAAAATTTAACGCGAATTTTAACAAAATATTAACGCTTAC<br>AATTTAGGTGGCACTTTTCGGGGAAATGTGCGCGGAACCCCTATTTGTTTATTTTTC<br>TAAATACATTCAAATATGTATCCGCTCATGAGACAATAACCCTGATAAATGCTTCAA<br>TAATATTGAAAAAGGAAGAGTATGAGTATTCAACATTTCCGTGTCGCCCTTATTCCC<br>TTTTTTGCGGCATTTTGCCTTCCTGTTTTTGCTCACCCAGAAACGCTGGTGAAAGTA<br>AAAGATGCTGAAGATCAGTTGGGTGCACGAGTGGGTTACATCGAACTGGATCTCAAC<br>AGCGGTAAGATCCTTGAGAGTTTTCGCCCCGAAGAACGTTTTCCAATGATGAGCACT<br>TTTAAAGTTCTGCTATGTGGCGCGGTATTATCCCGTATTGACGCCGGGCAAGAGCAA<br>CTCGGTCGCCGCATACACTATTCTCAGAATGACTTGGTTGAGTACTCACCAGTCACA<br>GAAAAGCATCTTACGGATGGCATGACAGTAAGAGAATTATGCAGTGCTGCCATAACC<br>ATGAGTGATAACACTGCGGCCAACTTACTTCTGACAACGATCGGAGGACCGAAGGAG<br>CTAACCGCTTTTTTGCACAACATGGGGGATCATGTAACTCGCCTTGATCGTTGGGAA<br>CCGGAGCTGAATGAAGCCATACCAAACGACGAGCGTGACACCACGATGCCTGTAGCA<br>ATGGCAACAACGTTGCGCAAACTATTAACTGGCGAACTACTTACTCTAGCTTCCCGG<br>CAACAATTAATAGACTGGATGGAGGCGGATAAAGTTGCAGGACCACTTCTGCGCTCG<br>GCCCTTCCGGCTGGCTGGTTTATTGCTGATAAATCTGGAGCCGGTGAGCGTGGGTCT<br>CGCGGTATCATTGCAGCACTGGGGCCAGATGGTAAGCCCTCCCGTATCGTAGTTATC<br>TACACGACGGGGAGTCAGGCAACTATGGATGAACGAAATAGACAGATCGCTGAGATA<br>GGTGCCTCACTGATTAAGCATTGGTAACTGTCAGACCAAGTTTACTCATATATACTT<br>TAGATTGATTTAAAACTTCATTTTTAATTTAAAAGGATCTAGGTGAAGATCCTTTTT<br>GATAATCTCATGACCAAAATCCCTTAACGTGAGTTTTCGTTCCACTGAGCGTCAGAC<br>CCCGTAGAAAAGATCAAAGGATCTTCTTGAGATCCTTTTTTTCTGCGCGTAATCTGC<br>TGCTTGCAAACAAAAAAACCACCGCTACCAGCGGTGGTTTGTTTGCCGGATCAAGAG<br>CTACCAACTCTTTTTCCGAAGGTAACTGGCTTCAGCAGAGCGCAGATACCAAATACT<br>GTTCTTCTAGTGTAGCCGTAGTTAGGCCACCACTTCAAGAACTCTGTAGCACCGCCT<br>ACATACCTCGCTCTGCTAATCCTGTTACCAGTGGCTGCTGCCAGTGGCGATAAGTCG<br>TGTCTTACCGGGTTGGACTCAAGACGATAGTTACCGGATAAGGCGCAGCGGTCGGGC<br>TGAACGGGGGGTTCGTGCACACAGCCCAGCTTGGAGCGAACGACCTACACCGAACTG<br>AGATACCTACAGCGTGAGCTATGAGAAAGCGCCACGCTTCCCGAAGGGAGAAAGGCG<br>GACAGGTATCCGGTAAGCGGCAGGGTCGGAACAGGAGAGCGCACGAGGGAGCTTCCA<br>GGGGGAAACGCCTGGTATCTTTATAGTCCTGTCGGGTTTCGCCACCTCTGACTTGAG<br>CGTCGATTTTTGTGATGCTCGTCAGGGGGGCGGAGCCTATGGAAAAACGCCAGCAAC<br>GCGGCCTTTTTACGGTTCCTGGCCTTTTGCTGGCCTTTTGCTCACATGTTCTTTCCT<br>GCGTTATCCCCTGATTCTGTGGATAACCGTATTACCGCCTTTGAGTGAGCTGATACC<br>GCTCGCCGCAGCCGAACGACCGAGCGCAGCGAGTCAGTGAGCGAGGAAGCGGAAGAG<br>CGCCCAATACGCAAACCGCCTCTCCCCGCGCGTTGGCCGATTCATTAATGCAGCTGG<br>CACGACAGGTTTCCCGACTGGAAAGCGGGCAGTGAGCGCAACGCAATTAATGTGAGT<br>TAGCTCACTCATTAGGCACCCCAGGCTTTACACTTTATGCTTCCGGCTCGTATGTTG<br>TGTGGAATTGTGAGCGGATAACAATTTCACACAGGAAACAGCTATGACCATGATTAC<br>GCCAAGCGCGCAATTAACCCTCACTAAAGGGAACAAAAGCTGGAGCTGCAAGCTT3′<br>SEQ ID NO: 18<br><br>EF1a-Cluc<br>AATGTAGTCTTATGCAATACTCTTGTAGTCTTGCAACATGGTAACGATGAGTTAGCA<br>ACATGCCTTACAAGGAGAGAAAAAGCACCGTGCATGCCGATTGGTGGAAGTAAGGTG<br>GTACGATCGTGCCTTATTAGGAAGGCAACAGACGGGTCTGACATGGATTGGACGAAC<br>CACTGAATTGCCGCATTGCAGAGATATTGTATTTAAGTGCCTAGCTCGATACATAAA<br>CGGGTCTCTCTGGTTAGACCAGATCTGAGCCTGGGAGCTCTCTGGCTAACTAGGGAA<br>CCCACTGCTTAAGCCTCAATAAAGCTTGCCTTGAGTGCTTCAAGTAGTGTGTGCCCG<br>TCTGTTGTGTGACTCTGGTAACTAGAGATCCCTCAGACCCTTTTAGTCAGTGTGGAA<br>AATCTCTAGCAGTGGCGCCCGAACAGGGACTTGAAAGCGAAAGGGAAACCAGAGGAG<br>CTCTCTCGACGCAGGACTCGGCTTGCTGAAGCGCGCACGGCAAGAGGCGAGGGGCGG<br>CGACTGGTGAGTACGCCAAAAATTTTGACTAGCGGAGGCTAGAAGGAGAGAGATGGG<br>TGCGAGAGCGTCAGTATTAAGCGGGGGAGAATTAGATCGCGATGGGAAAAAATTCGG<br>TTAAGGCCAGGGGGAAAGAAAAAATATAAATTAAAACATATAGTATGGGCAAGCAGG<br>GAGCTAGAACGATTCGCAGTTAATCCTGGCCTGTTAGAAACATCAGAAGGCTGTAGA<br>CAAATACTGGGACAGCTACAACCATCCCTTCAGACAGGATCAGAAGAACTTAGATCA<br>TTATATAATACAGTAGCAACCCTCTATTGTGTGCATCAAAGGATAGAGATAAAAGAC<br>ACCAAGGAAGCTTTAGACAAGATAGAGGAAGAGCAAAACAAAAGTAAGACCACCGCA<br>CAGCAAGCGGCCGCTGATCTTCAGACCTGGAGGAGGAGATATGAGGGACAATTGGAG |

-continued

| Exemplary Sequences |
|---|
| AAGTGAATTATATAAATATAAAGTAGTAAAAATTGAACCATTAGGAGTAGCACCCAC<br>CAAGGCAAAGAGAAGAGTGGTGCAGAGAGAAAAAAGAGCAGTGGGAATAGGAGCTTT<br>GTTCCTTGGGTTCTTGGGAGCAGCAGGAAGCACTATGGGCGCAGCGTCAATGACGCT<br>GACGGTACAGGCCAGACAATTATTGTCTGGTATAGTGCAGCAGCAGAACAATTTGCT<br>GAGGGCTATTGAGGCGCAACAGCATCTGTTGCAACTCACAGTCTGGGGCATCAAGCA<br>GCTCCAGGCAAGAATCCTGGCTGTGGAAAGATACCTAAAGGATCAACAGCTCCTGGG<br>GATTTGGGGTTGCTCTGGAAAACTCATTTGCACCACTGCTGTGCCTTGGAATGCTAG<br>TTGGAGTAATAAATCTCTGGAACAGATTTGGAATCACACGACCTGGATGGAGTGGGA<br>CAGAGAAATTAACAATTACACAAGCTTAATACACTCCTTAATTGAAGAATCGCAAAA<br>CCAGCAAGAAAAGAATGAACAAGAATTATTGGAATTAGATAAATGGGCAAGTTTGTG<br>GATTGGTTTAACATAACAAATTGGCTGTGGTATATAAAATTATTCATAATGATAGT<br>AGGAGGCTTGGTAGGTTTAAGAATAGTTTTTGCTGTACTTTCTATAGTGAATAGAGT<br>TAGGCAGGGATATTCACCATTATCGTTTCAGACCCACCTCCCAACCCCGAGGGGACC<br>CGACAGGCCCGAAGGAATAGAAGAAGAAGGTGGAGAGAGAGACAGAGACAGATCCAT<br>TCGATTAGTGAACGGATCTCGACGGTATCGATTAACTTTTAAAAGAAAAGGGGGGAT<br>TGGGGGGTACAGTGCAGGGGAAAGAATAGTAGACATAATAGCAACAGACATACAAAC<br>TAAAGAATTACAAAAACAAATTACAAAAATTCAAAATTTTATCGATGTCGACGTTAA<br>CGCTAGTGATATCAACTTTGTATAGAAAAGTTGCGTGAGGCTCCGGTGCCCGTCAGT<br>GGGCAGAGCGCACATCGCCCACAGTCCCCGAGAAGTTGGGGGGAGGGGTCGGCAATT<br>GAACCGGTGCCTAGAGAAGGTGGCGCGGGGTAAACTGGGAAAGTGATGTCGTGTACT<br>GGCTCCGCCTTTTTCCCGAGGGTGGGGGAGAACCGTATATAAGTGCAGTAGTCGCCG<br>TGAACGTTCTTTTTCGCAACGGGTTTGCCGCCAGAACACAGGTAAGTGCCGTGTGTG<br>GTTCCCGCGGGCCTGGCCTCTTTACGGGTTATGGCCCTTGCGTGCCTTGAATTACTT<br>CCACCTGGCTGCAGTACGTGATTCTTGATCCCGAGCTTCGGGTTGGAAGTGGGTGGG<br>AGAGTTCGAGGCCTTGCGCTTAAGGAGCCCCTTCGCCTCGTGCTTGAGTTGAGGCCT<br>GGCCTGGGCGCTGGGGCCGCCGCGTGCGAATCTGGTGGCACCTTCGCGCCTGTCTCG<br>CTGCTTTCGATAAGTCTCTAGCCATTTAAAATTTTTGATGACCTGCTGCGACGCTTT<br>TTTTCTGGCAAGATAGTCTTGTAAATGCGGGCCAAGATCTGCACACTGGTATTTCGG<br>TTTTTGGGGCCGCGGGCGGCGACGGGGCCCGTGCGTCCCAGCGCACATGTTCGGCGA<br>GGCGGGGCCTGCGAGCGCGGCCACCGAGAATCGGACGGGGGTAGTCTCAAGCTGGCC<br>GGCCTGCTCTGGTGCCTGGCCTCGCGCCGCCGTGTATCGCCCCGCCCTGGGCGGCAA<br>GGCTGGCCCGGTCGGCACCAGTTGCGTGAGCGGAAAGATGGCCGCTTCCCGGCCCTG<br>CTGCAGGGAGCTCAAAATGGAGGACGCGGCGCTCGGGAGAGCGGGCGGGTGAGTCAC<br>CCACACAAAGGAAAAGGGCCTTTCCGTCCTCAGCCGTCGCTTCATGTGACTCCACGG<br>AGTACCGGGCGCCGTCCAGGCACCTCGATTAGTTCTCGAGCTTTTGGAGTACGTCGT<br>CTTTAGGTTGGGGGGAGGGGTTTTATGCGATGGAGTTTCCCCACACTGAGTGGGTGG<br>AGACTGAAGTTAGGCCAGCTTGGCACTTGATGTAATTCTCCTTGGAATTTGCCCTTT<br>TTGAGTTTGGATCTTGGTTCATTCTCAAGCCTCAGACAGTGGTTCAAAGTTTTTTTC<br>TTCCATTTCAGGTGTCGTGAGGAATTAGCTTGGTACTAATACGACTCACTATAGGGA<br>GACCCAAGCTGGCTAGGTAAGCTTGATCACAAGTTTGTACAAAAAAGCAGGCTCCGC<br>GGCCGCCCCCTTCACCCCCACTGCTTACTGGCTTATCGAAATTAATACGACTCACTA<br>TAGGGAGACCCAAGCTTGGTACCGAGCTCGGATCCGCCACCATGAAGACCTTATTC<br>TTGCCGTTGCATTAGTCTACTGCGCCACTGTTCATTGCCAGGACTGTCCTTACGAAC<br>CTGATCCACCAAACACAGTTCCAACTTCCTGTGAAGCTAAAGAAGGAGAATGTATTG<br>ATAGCAGCTGTGGCACCTGCACGAGAGACATACTATCAGATGGACTGTGTGAAAATA<br>AACCAGGAAAAACATGTTGCCGAATGTGTCAGTATGTAATTGAATGCAGAGTAGAGG<br>CCGCAGGATGGTTTAGAACATTCTATGGAAAGAGATTCCAGTTCCAGGAACCTGGTA<br>CATACGTGTTGGGTCAAGGAACCAAGGGCGGCGACTGGAAGGTGTCCATCACCCTGG<br>AGAACCTGGATGGAACCAAGGGGGCTGTGCTGACCAAGACAAGACTGGAAGTGGCTG<br>GAGACATCATTGACATCGCTCAAGCTACTGAGAATCCCATCACTGTAAACGGTGGAG<br>CTGACCCTATCATCGCCAACCCGTACACCATCGGCGAGGTCACCATCGCTGTTGTTG<br>AGATGCCAGGCTTCAACATCACCGTCATTGAGTTCTTCAAACTGATCGTGATCGACA<br>TCCTCGGAGGAAGATCTGTAAGAATCGCCCCAGACACAGCAAACAAAGGAATGATCT<br>CTGGCCTCTGTGGAGATCTTAAAATGATGGAAGATACAGACTTCACTTCAGATCCAG<br>AACAACTCGCTATTCAGCCTAAGATCAACCAGGAGTTTGACGGTTGTCCACTCTATG<br>GAAATCCTGATGACGTTGCATACTGCAAAGGTCTTCTGGAGCCGTACAAGGACAGCT<br>GCCGCAACCCCATCAACTTCTACTACTACACCATCTCCTGCGCCTTCGCCCGCTGTA<br>TGGGTGGAGACGAGCGAGCCTCACACGTGCTGCTTGACTACAGGGAGACGTGCGCTG<br>CTCCCGAAACTAGAGGAACCTGCGTTTTGTCTGGACATACTTTCTACGATACATTTG<br>ACAAAGCAAGATACCAATTCCAGGGTCCCTGCAAGGAGATTCTTATGGCCGCCGACT<br>GTTTCTGGAACACTTGGGATGTGAAGGTTTCACACAGGAATGTTGACTCTTACACTG<br>AAGTAGAGAAAGTACGAATCAGGAAACAATCGACTGTAGTAGAACTCATTGTTGATG<br>GAAAACAGATTCTGGTTGGAGGAGAAGCCGTGTCCGTCCCGTACAGCTCTCAGAACA<br>CTTCCATCTACTGGCAAGATGGTGACATACTGACTACAGCCATCCTACCTGAAGCTC<br>TGGTGGTCAAGTTCAACTTCAAGCAACTGCTCGTCGTACATATTAGAGATCCATTCG<br>ATGGTAAGACTTGCGGTATTTGCGGTAACTACAACCAGGATTTCAGTGATGATTCTT<br>TTGATGCTGAAGGAGCCTGTGATCTGACCCCCAACCCACCGGGATGCACCGAAGAAC<br>AGAAACCTGAAGCTGAACGACTCTGCAATAGTCTCTTCGCCGGTCAAAGTGATCTTG<br>ATCAGAAATGTAACGTGTGCCACAAGCCTGACCGTGTCGAACGATGCATGTACGAGT<br>ATTGCCTGAGGGGACAACAGGGTTTCTGTGACCACGCATGGGAGTTCAAGAAAGAAT<br>GCTACATAAAGCATGGAGACACCCTAGAAGTACCAGATGAATGCAAATAGGCGGCCG<br>CAATAAAATATCTTTATTTTCATTACATCTGTGTGTTGGTTTTTTGTGTGTCTAGAA<br>ATAATTCTTACTGTCATGCCAAGTAAGATGCTAAGGGTGGGCGCGCCGACCCAGCTT<br>TCTTGTACAAAGTGGTTGATATCCAGCACAGTGGCGGCCGCTCGAGTCTAGAGGGCC<br>CGCGGTTCGAAGGTAAGCCTATCCCTAACCCTCTCCTCGGTCTCGATTCTACGCGTA<br>CCGGTTAGTAATGATCGACAATCAACCTCTGGATTACAAAATTTGTGAAAGATTGAC<br>TGGTATTCTTAACTATGTTGCTCCTTTTACGCTATGTGGATACGCTGCTTTAATGCC |

-continued

| Exemplary Sequences |
| --- |
| TTTGTATCATGCTATTGCTTCCCGTATGGCTTTCATTTTCTCCTCCTTGTATAAATC<br>CTGGTTGCTGTCTCTTTATGAGGAGTTGTGGCCCGTTGTCAGGCAACGTGGCGTGGT<br>GTGCACTGTGTTTGCTGACGCAACCCCCACTGGTTGGGGCATTGCCACCACCTGTCA<br>GCTCCTTTCCGGGACTTTCGCTTTCCCCCTCCCTATTGCCACGGCGGAACTCATCGC<br>CGCCTGCCTTGCCCGCTGCTGGACAGGGGCTCGGCTGTTGGGCACTGACAATTCCGT<br>GGTGTTGTCGGGGAAGCTGACGTCCTTTCCATGGCTGCTCGCCTGTGTTGCCACCTG<br>GATTCTGCGCGGGACGTCCTTCTGCTACGTCCCTTCGGCCCTCAATCCAGCGGACCT<br>TCCTTCCCGCGGCCTGCTGCCGGCTCTGCGGCCTCTTCCGCGTCTTCGCCTTCGCCC<br>TCAGACGAGTCGGATCTCCCTTTGGGCCGCCTCCCCGCCTGGCGATGGTACCTACCG<br>GGTAGGGGAGGCGCTTTTCCCAAGGCAGTCTGGAGCATGCGCTTTAGCAGCCCCGCT<br>GGGCACTTGGCGCTACACAAGTGGCCTCTGGCCTCGCACACATTCCACATCCACCGG<br>TAGGCGCCAACCGGCTCCGTTCTTTGGTGGCCCCTTCGCGCCACCTTCTACTCCTCC<br>CCTAGTCAGGAAGTTCCCCCCCGCCCCGCAGCTCGCGTCGTGCAGGACGTGACAAAT<br>GGAAGTAGCACGTCTCACTAGTCTCGTGCAGATGGACAGCACCGCTGAGCAATGGAA<br>GCGGGTAGGCCTTTGGGGCAGCGGCCAATAGCAGCTTTGCTCCTTCGCTTTCTGGGC<br>TCAGAGGCTGGGAAGGGGTGGGTCCGGGGGCGGGCTCAGGGGCGGGCTCAGGGGCGG<br>GGCGGGCGCCCGAAGGTCCTCCGGAGGCCCGGCATTCTGCACGCTTCAAAAGCGCAC<br>GTCTGCCGCGCTGTTCTCCTCTTCCTCATCTCCGGGCCTTTCGACTCTAGACACGTG<br>TTGACAATTAATCATCGGCATAGTATATCGGCATAGTATAATACGACAAGGTGAGGA<br>ACTAAACCATGGCCAAGCCTTTGTCTCAAGAAGAATCCACCCTCATTGAAAGAGCAA<br>CGGCTACAATCAACAGCATCCCCATCTCTGAAGACTACAGCGTCGCCAGCGCAGCTC<br>TCTCTAGCGACGGCCGCATCTTCACTGGTGTCAATGTATATCATTTTACTGGGGGAC<br>CTTGTGCAGAACTCGTGGTGCTGGGCACTGCTGCTGCTGCGGCAGCTGGCAACCTGA<br>CTTGTATCGTCGCGATCGGAAATGAGAACAGGGGCATCTTGAGCCCCTGCGGACGGT<br>GCCGACAGGTGCTTCTCGATCTGCATCCTGGGATCAAAGCCATAGTGAAGGACAGTG<br>ATGGACAGCCGACGGCAGTTGGGATTCGTGAATTGCTGCCCTCTGGTTATGTGTGGG<br>AGGGCTAAGCACAATTCGAGCTCGGTACCTTTAAGACCAATGACTTACAAGGCAGCT<br>GTAGATCTTAGCCACTTTTTAAAAGAAAAGGGGGGACTGGAAGGGCTAATTCACTCC<br>CAACGAAGACAAGATCTGCTTTTTGCTTGTACTGGGTCTCTCTGGTTAGACCAGATC<br>TGAGCCTGGGAGCTCTCTGGCTAACTAGGGAACCCACTGCTTAAGCCTCAATAAAGC<br>TTGCCTTGAGTGCTTCAAGTAGTGTGTGCCCGTCTGTTGTGTGACTCTGGTAACTAG<br>AGATCCCTCAGACCCTTTTAGTCAGTGTGGAAAATCTCTAGCAGTAGTAGTTCATGT<br>CATCTTATTATTCAGTATTTATAACTTGCAAAGAAATGAATATCAGAGAGTGAGAGG<br>AACTTGTTTATTGCAGCTTATAATGGTTACAAATAAAGCAATAGCATCACAAATTTC<br>ACAAATAAAGCATTTTTTTCACTGCATTCTAGTTGTGGTTTGTCCAAACTCATCAAT<br>GTATCTTATCATGTCTGGCTCTAGCTATCCCGCCCCTAACTCCGCCCATCCCGCCCC<br>TAACTCCGCCCAGTTCCGCCCATTCTCCGCCCCATGGCTGACTAATTTTTTTTATTT<br>ATGCAGAGGCCGAGGCCGCCTCGGCCTCTGAGCTATTCCAGAAGTAGTGAGGAGGCT<br>TTTTTGGAGGCCTAGGGACGTACCCAATTCGCCCTATAGTGAGTCGTATTACGCGCG<br>CTCACTGGCCGTCGTTTTACAACGTCGTGACTGGGAAAACCCTGGCGTTACCCAACT<br>TAATCGCCTTGCAGCACATCCCCCTTTCGCCAGCTGGCGTAATAGCGAAGAGGCCCG<br>CACCGATCGCCCTTCCCAACAGTTGCGCAGCCTGAATGGCGAATGGACGCGCCCTG<br>TAGCGGCGCATTAAGCGCGGCGGGTGTGGTGGTTACGCGCAGCGTGACCGCTACACT<br>TGCCAGCGCCCTAGCGCCCGCTCCTTTCGCTTTCTTCCCTTCCTTTCTCGCCACGTT<br>CGCCGGCTTTCCCCGTCAAGCTCTAAATCGGGGGCTCCCTTTAGGGTTCCGATTTAG<br>TGCTTTACGGCACCTCGACCCCAAAAAACTTGATTAGGGTGATGGTTCACGTAGTGG<br>GCCATCGCCCTGATAGACGGTTTTTCGCCCTTTGACGTTGGAGTCCACGTTCTTTAA<br>TAGTGGACTCTTGTTCCAAACTGGAACAACACTCAACCCTATCTCGGTCTATTCTTT<br>TGATTTATAAGGGATTTTGCCGATTTCGGCCTATTGGTTAAAAAATGAGCTGATTTA<br>ACAAAAATTTAACGCGAATTTTAACAAAATATTAACGCTTACAATTTAGGTGGCACT<br>TTTCGGGGAAATGTGCGCGGAACCCCTATTTGTTTATTTTTCTAAATACATTCAAAT<br>ATGTATCCGCTCATGAGACAATAACCCTGATAAATGCTTCAATAATATTGAAAAAGG<br>AAGAGTATGAGTATTCAACATTTCCGTGTCGCCCTTATTCCCTTTTTTGCGGCATTT<br>TGCCTTCCTGTTTTTGCTCACCCAGAAACGCTGGTGAAAGTAAAAGATGCTGAAGAT<br>CAGTTGGGTGCACGAGTGGGTTACATCGAACTGGATCTCAACAGCGGTAAGATCCTT<br>GAGAGTTTTCGCCCCGAAGAACGTTTTCCAATGATGAGCACTTTTAAAGTTCTGCTA<br>TGTGGCGCGGTATTATCCCGTATTGACGCCGGGCAAGAGCAACTCGGTCGCCGCATA<br>CACTATTCTCAGAATGACTTGGTTGAGTACTCACCAGTCACAGAAAAGCATCTTACG<br>GATGGCATGACAGTAAGAGAATTATGCAGTGCTGCCATAACCATGAGTGATAACACT<br>GCGGCCAACTTACTTCTGACAACGATCGGAGGACCGAAGGAGCTAACCGCTTTTTTG<br>CACAACATGGGGGATCATGTAACTCGCCTTGATCGTTGGGAACCGGAGCTGAATGAA<br>GCCATACCAAACGACGAGCGTGACACCACGATGCCTGTAGCAATGGCAACAACGTTG<br>CGCAAACTATTAACTGGCGAACTACTTACTCTAGCTTCCCGGCAACAATTAATAGAC<br>TGGATGGAGGCGGATAAAGTTGCAGGACCACTTCTGCGCTCGGCCCTTCCGGCTGGC<br>TGGTTTATTGCTGATAAATCTGGAGCCGGTGAGCGTGGGTCTCGCGGTATCATTGCA<br>GCACTGGGGCCAGATGGTAAGCCCTCCCGTATCGTAGTTATCTACACGACGGGGAGT<br>CAGGCAACTATGGATGAACGAAATAGACAGATCGCTGAGATAGGTGCCTCACTGATT<br>AAGCATTGGTAACTGTCAGACCAAGTTTACTCATATATACTTTAGATTGATTTAAAA<br>CTTCATTTTTAATTTAAAAGGATCTAGGTGAAGATCCTTTTTGATAATCTCATGACC<br>AAAATCCCTTAACGTGAGTTTTCGTTCCACTGAGCGTCAGACCCCGTAGAAAAGATC<br>AAAGGATCTTCTTGAGATCCTTTTTTTCTGCGCGTAATCTGCTGCTTGCAAACAAAA<br>AAACCACCGCTACCAGCGGTGGTTTGTTTGCCGGATCAAGAGCTACCAACTCTTTTT<br>CCGAAGGTAACTGGCTTCAGCAGAGCGCAGATACCAAATACTGTTCTTCTAGTGTAG<br>CCGTAGTTAGGCCACCACTTCAAGAACTCTGTAGCACCGCCTACATACCTCGCTCTG<br>CTAATCCTGTTACCAGTGGCTGCTGCCAGTGGCGATAAGTCGTGTCTTACCGGGTTG<br>GACTCAAGACGATAGTTACCGGATAAGGCGCAGCGGTCGGGCTGAACGGGGGGTTCG<br>TGCACACAGCCCAGCTTGGAGCGAACGACCTACACCGAACTGAGATACCTACAGCGT |

-continued

| Exemplary Sequences |
|---|
| GAGCTATGAGAAAGCGCCACGCTTCCCGAAGGGAGAAAGGCGGACAGGTATCCGGTA<br>AGCGGCAGGGTCGGAACAGGAGAGCGCACGAGGGAGCTTCCAGGGGGAAACGCCTGG<br>TATCTTTATAGTCCTGTCGGGTTTCGCCACCTCTGACTTGAGCGTCGATTTTTGTGA<br>TGCTCGTCAGGGGGGCGGAGCCTATGGAAAAACGCCAGCAACGCGGCCTTTTTACGG<br>TTCCTGGCCTTTTGCTGGCCTTTTGCTCACATGTTCTTTCCTGCGTTATCCCCTGAT<br>TCTGTGGATAACCGTATTACCGCCTTTGAGTGAGCTGATACCGCTCGCCGCAGCCGA<br>ACGACCGAGCGCAGCGAGTCAGTGAGCGAGGAAGCGGAAGAGCGCCCAATACGCAAA<br>CCGCCTCTCCCCGCGCGTTGGCCGATTCATTAATGCAGCTGGCACGACAGGTTTCCC<br>GACTGGAAAGCGGGCAGTGAGCGCAACGCAATTATGTGAGTTAGCTCACTCATTAG<br>GCACCCCAGGCTTTACACTTTATGCTTCCGGCTCGTATGTTGTGTGGAATTGTGAGC<br>GGATAACAATTTCACACAGGAAACAGCTATGACCATGATTACGCCAAGCGCGCAATT<br>AACCCTCACTAAAGGGAACAAAAGCTGGAGCTGCAAGCTT SEQ ID<br>NO: 19 |
| MYF5 Promoter<br>AAAAGGCAGTGTAACACATACACACACACACATACACACACACACACAC<br>ACACACACACACACACACACACATATACACACACATACAAAGGGTCACTT<br>TGAATCCACAACACTTACTTAATTGGATGACACTCCCAAGTGTGAACAGT<br>CCATTTTTACAACGGGGCTACAAAAAAGAGGTTTAAAGCTCTCAGAGAAT<br>TTGTGTTGACCGTAAGTAATGGTGTTTCTTGGATATGAATAACATCTCCCC<br>TCTCACGTGATCTGAAAGCGGATCAACAGTGGAGAAGAAATCATAAAAG<br>CTGAGGAATAGGCTGAATATATATATATATATATATATATATATATATATA<br>TATATATATATATATATGAATGAATGGCAGTTTTCCCCTTTGTCTTCAGTTG<br>ACAAAAGTTTCAAAGACCTGTCTGCAAATGGCATTTCTGAAAGGCTTTTGT<br>CACCAAAGTGTGTGAAGCCACTCTTTTAAGAGGAGTTGGAAATTTTACAC<br>TAGCCCAGGATCTCTCTTAGCTGGCAGCTGGGACCCATCTGTAACGGTGTT<br>AGCTGGCCTGAAAAGCAGAAAATTAGCGACCCCGAGAAGCCTTGGCTGG<br>CTGTTTAGTCTGTAGACACGGTAGGGCGGAGCAGCAGACTCTGGAGAAAA<br>GAAACCCCAAGCTGGACGGGGAGCTTTCTGTGAGAAACTGGACCGCTGCC<br>GGTGACCGTCCTCCTCAGGCGTGGGAATCTCCCAGTGCAGGTATTAGCCT<br>AGGTCTGATGCAGAGGAAGAGGCAACAGACACGTGTGCTGGGAAGGATG<br>GAAGCTCGGAGGGGAAGGATGCGGGGGAAGGTCACCTGGTCCACTTCCTT<br>TTCAGGGCAGCAGAAGAAACGTGTGACCCTCTGACAGAGCCAGACCTCAG<br>AAAGGAAGCTCAGCTACTGTCATCCCCATGAGATGACCATCTCTCTCATC<br>AGAACTTTACTTCTTTGGTCTTTGTCAAACAGGTTTTGAAACACCAAGCTC<br>TCTAGGTTCATGCCATCCATGAAAATGCCACCTCACTATTTTACCAACTGT<br>TACCAGTACACAAACTGACTCAATCTTTTGGTAAAGTTCATGAAAATGAG<br>AAGCAAGCACCGGAGATCCGTGCGTTAAGAATCCAGAAGCTAGGTTCCCT<br>TTGGTGTTAGACGGAAATACGGAACTTTAATGTCTTGCTACCGTGCTGCTG<br>CTGCTGATTATGTTAAAGTGTGATCAATTTCAAGAAGCCAACCCCAACCC<br>CTTTAAGTGATCCCTAGGTTTAGTTTATCCAGAAGGCCACCGAGCAGGTTA<br>GGCTGCAGTAAAATCATTAGCGTCAAAGGGACCAGTAAACTGCAAAGTGT<br>CTCTAGAAGAAAGACAAGAGGCTTGCCCAGACAGCCCCTGTGGGGGGTTG<br>TGGTGGGATATGCTAATAACGCCCAGCTACAGGGACCAACCTCCCTTCCC<br>ATCCCCCAGGAATATATAAAGAGCCCCAACCTCAGCCACTGACCGACCCT<br>GGCCAACAGGCATCTGTCCTTGTTAATTACAGAGAGACAGTCCCAAACTC<br>CGGGAGCTCCGCCTGGATTTGCTGGCCTGCAGCAGCCAGGGACTG<br>SEQ ID NO: 20 |

TABLE 5

DNA Sequences. All sequences shown in 5′ to 3′. E-box sequences are double underlined and minimal promoters are in bold. Forward and reverse RT-qPCR primers are shown paired

| Name | Sequence | SEQ ID NO: |
|---|---|---|
| Circa1 | AGTAGTGTTAACCCCGGGCTCGAGCAGTATTTAGCCACGTGACA<br>GTGTAAGCACACGTGGGCCCTCAAGTCCACGTGCAGGGAGCCT<br>GAGCACCACTGAGCGGTCCTGAGCCA**AGAGGGTATATAATGG**<br>**AAGCTCGACTTCCAG** | 21 |
| Circa2 | AGTAGTGTTAACCCCGGGCTCGAGCAGTATTTAGCCACGTGACA<br>GTGTAAGCACACGTGGGCCCTCAAGTCCACGTGCAGGGAGCCA<br>CGTGACCACACGTGGGTCCACGTGCA**AGAGGGTATATAATGGA**<br>**AGCTCGACTTCCAG** | 22 |
| Per1 | TCAACTGCCTGGACAGCATCCT<br>TCAGAGGCTGAGGAGGTGGTAT | 23<br>24 |
| Per2 | AGCTGCTTGGACAGCGTCATCA<br>CCTTCCGCTTATCACTGGACCT | 25<br>26 |

TABLE 5-continued

DNA Sequences. All sequences shown in 5′ to 3′. E-box sequences are double underlined and minimal promoters are in bold. Forward and reverse RT-qPCR primers are shown paired

| Name | Sequence | SEQ ID NO: |
|---|---|---|
| Cry1 | GCAGTTGCTTGCTTCCTGACAC | 27 |
| | GACAGCCACATCCAACTTCCAG | 28 |
| Cry2 | AGGAGAACCACGACGAGACCTA | 29 |
| | CCGTTCCAAGTGCTTATCCAGG | 30 |
| Clock | CAGGCAGCATTTACCAGCTCATG | 31 |
| | GTAGCTTGAGACATCACTGGCTG | 32 |
| Bmal1 | GCTCAGGAGAACCCAGGTTATC | 33 |
| | GCATCTGCTTCCAAGAGGCTCA | 34 |
| Gapdh | GTCTCCTCTGACTTCAACAGCG | 35 |
| | ACCACCCTGTTGCTGTAGCCAA | 36 |
| β-Actin | CACCATTGGCAATGAGCGGTTC | 37 |
| | AGGTCTTTGCGGATGTCCACGT | 38 |

REFERENCES

1. Jones, S. A., Scheller, J., & Rose-John, S. (2011). Therapeutic strategies for the clinical blockade of IL-6/gp130 signaling. The Journal of clinical investigation, 121(9), 3375-3383.
2. Heinrich, P. C., Behrmann, I., Serge, H., Hermanns, H. M., Müller-Newen, G., & Schaper, F. (2003). Principles of interleukin (IL)-6-type cytokine signalling and its regulation. Biochemical journal, 374(1), 1-20.
3. Waage, A., Kaufmann, C., Espevik, T., & Husby, G. (1989). Interleukin-6 in synovial fluid from patients with arthritis. Clinical immunology and immunopathology, 50(3), 394-398.
4. Atreya, R., Mudter, J., Finotto, S., Müllberg, J., Jostock, T., Wirtz, S., . . . & Strand, D. (2000). Blockade of interleukin 6 trans signaling suppresses T-cell resistance against apoptosis in chronic intestinal inflammation: evidence in crohn disease and experimental colitis in vivo. Nature medicine, 6(5), 583.
5. Hurst, S. M., Wilkinson, T. S., McLoughlin, R. M., Jones, S., Horiuchi, S., Yamamoto, N., . . . & Jones, S. A. (2001). 11-6 and its soluble receptor orchestrate a temporal switch in the pattern of leukocyte recruitment seen during acute inflammation. Immunity, 14(6), 705-714.
6. Lawrence, T. (2009). The nuclear factor NF-κB pathway in inflammation. Cold Spring Harbor perspectives in biology, a001651.
7. Miagkov, A. V., Kovalenko, D. V., Brown, C. E., Didsbury, J. R., Cogswell, J. P., Stimpson, S. A., . . . & Makarov, S. S. (1998). NF-κB activation provides the potential link between inflammation and hyperplasia in the arthritic joint. Proceedings of the National Academy of Sciences, 95(23), 13859-13864.
8. Tak, P. P., & Firestein, G. S. (2001). NF-κB: a key role in inflammatory diseases. The Journal of clinical investigation, 107(1), 7-11.
9. Greten, F. R., Arkan, M. C., Bollrath, J., Hsu, L. C., Goode, J., Miething, C., . . . & Van Rooijen, N. (2007). NF-κB is a negative regulator of IL-1β secretion as revealed by genetic and pharmacological inhibition of IKKβ. Cell, 130(5), 918-931.
10. Gabay, C., Smith, M. F., Eidlen, D., & Arend, W. P. (1997). Interleukin 1 receptor antagonist (IL-1Ra) is an acute-phase protein. The Journal of clinical investigation, 99(12), 2930-2940.
11. Al-Janadi, M., Al-Balla, S., Al-Dalaan, A., & Raziuddin, S. (1993). Cytokine profile in systemic lupus erythematosus, rheumatoid arthritis, and other rheumatic diseases. Journal of clinical immunology, 13(1), 58-67.
12. Arend, W. P. (1993). Interleukin-1 receptor antagonist. In Advances in immunology (Vol. 54, pp. 167-227). Academic Press.
13. Ghivizzani, S. C., Lechman, E. R., Kang, R., Tio, C., Kolls, J., Evans, C. H., & Robbins, P. D. (1998). Direct adenovirus-mediated gene transfer of interleukin 1 and tumor necrosis factor α soluble receptors to rabbit knees with experimental arthritis has local and distal anti-arthritic effects. Proceedings of the National Academy of Sciences, 95(8), 4613-4618.
14. Whalen, J. D., Lechman, E. L., Carlos, C. A., Weiss, K., Glorioso, J. C., Robbins, P. D., & Evans, C. H. (1999). Adenoviral transfer of the viral IL-10 gene periarticularly to mouse paws suppresses development of collagen-induced arthritis in both injected and uninjected paws. The journal of immunology, 162(6), 3625-3632.
15. Kim, S. H., Lechman, E. R., Kim, S., Nash, J., Oligino, T. J., & Robbins, P. D. (2002). Ex vivo gene delivery of IL-1Ra and soluble TNF receptor confers a distal synergistic therapeutic effect in antigen-induced arthritis. Molecular Therapy, 6(5), 591-600.
16. Morimoto, R. (1993). Cells in stress: transcriptional activation of heat shock genes. Science, 259(5100), 1409-1411.
17. Parsell, D. A., Kowal, A. S., Singer, M. A., & Lindquist, S. (1994). Protein disaggregation mediated by heat-shock protein Hsp104. Nature, 372(6505), 475.
18. Morimoto, R. I. (1998). Regulation of the heat shock transcriptional response: cross talk between a family of heat shock factors, molecular chaperones, and negative regulators. Genes & development, 12(24), 3788-3796.
19. Mosser, D. D., Kotzbauer, P. T., Sarge, K. D., & Morimoto, R. I. (1990). In vitro activation of heat shock transcription factor DNA-binding by calcium and biochemical conditions that affect protein conformation. Proceedings of the National Academy of Sciences, 87(10), 3748-3752.
20. Zhong, M. I. N., Orosz, A., & Wu, C. (1998). Direct sensing of heat and oxidation by *Drosophila* heat shock transcription factor. Molecular cell, 2(1), 101-108.

21. Winer, K. K., Ko, C. W., Reynolds, J. C., Dowdy, K., Keil, M., Peterson, D., . . . & Cutler Jr, G. B. (2003). Long-term treatment of hypoparathyroidism: a randomized controlled study comparing parathyroid hormone-(1-34) versus calcitriol and calcium. The Journal of Clinical Endocrinology & Metabolism, 88(9), 4214-4220.

22. Marcucci, G., Della Pepa, G., & Brandi, M. L. (2016). Natpara for the treatment of hypoparathyroidism. Expert opinion on biological therapy, 16(11), 1417-1424.

23. Silver, J., & Levi, R. (2005). Regulation of PTH synthesis and secretion relevant to the management of secondary hyperparathyroidism in chronic kidney disease. Kidney International, 67, S8-S12.

24. Zhang, P., Li, W., Wang, L., Liu, H., Gong, J., Wang, F., & Chen, X. (2018). Salidroside Inhibits Myogenesis by Modulating p-Smad3-Induced Myf5 Transcription. Frontiers in pharmacology, 9, 209.

25. Yi, T., Choi, H. M., Park, R. W., Sohn, K. Y., & Kim, I. S. (2001). Transcriptional repression of type I procollagen genes during adipocyte differentiation. Experimental & molecular medicine, 33(4), 269.

26. Huang, W., Liu, X., Queen, N. J., & Cao, L. (2017). Targeting Visceral Fat by Intraperitoneal Delivery of Novel AAV Serotype Vector Restricting Off-Target Transduction in Liver. Molecular Therapy-Methods & Clinical Development, 6, 68-78.

27. Serup, P., Jensen, J., Andersen, F. G., Jørgensen, M. C., Blume, N., Holst, J. J., & Madsen, O. D. (1996). Induction of insulin and islet amyloid polypeptide production in pancreatic islet glucagonoma cells by insulin promoter factor 1. Proceedings of the National Academy of Sciences, 93(17), 9015-9020.

28. Wang, S., Wu, H., Jiang, J., Delohery, T. M., Isdell, F., & Goldman, S. A. (1998). Isolation of neuronal precursors by sorting embryonic forebrain transfected with GFP regulated by the Tal tubulin promoter. Nature biotechnology, 16(2), 196.

29. Kappel, A., Rönicke, V., Damert, A., Flamme, I., Risau, W., & Breier, G. (1999). Identification of vascular endothelial growth factor (VEGF) receptor-2 (Flk-1) promoter/enhancer sequences sufficient for angioblast and endothelial cell-specific transcription in transgenic mice. Blood, 93(12), 4284-4292

30. Timon, M., & Beverley, P. C. L. (2001). Structural and functional analysis of the human CD45 gene (PTPRC) upstream region: evidence for a functional promoter within the first intron of the gene. Immunology, 102(2), 180-189.

31. Kozmik, Z. B. Y. N. E. K., Wang, S. H. I. R. L. E. Y., Dörfler, P., Adams, B., & Busslinger, M. E. I. N. R. A. D. (1992). The promoter of the CD19 gene is a target for the B-cell-specific transcription factor BSAP. Molecular and Cellular Biology, 12(6), 2662-2672.

32. Qin, J. Y., Zhang, L., Clift, K. L., Hulur, I., Xiang, A. P., Ren, B. Z., & Lahn, B. T. (2010). Systematic comparison of constitutive promoters and the doxycycline-inducible promoter. PloS one, 5(5), e10611.

33. Thim L, Hansen M T, Norris K, Hoegh I, Boel E, Forstrom J, Ammerer G, Fiil N P. Secretion and processing of insulin precursors in yeast. Proc Natl Acad Sci USA. 1986 September; 83(18):6766-70.

34. Roh, J. Y., Koo, B. C., Kwon, M. S. et al. Modification of enhanced green fluorescent protein for secretion out of cells Biotechnol Bioproc E (2013) 18: 1135.

35. Aryal R P, Kwak P B, Tamayo A G, Gebert M, Chiu P L, Walz T, Weitz C J. Macromolecular Assemblies of the Mammalian Circadian Clock. Mol Cell. 2017 Sep. 7; 67(5):770-782.e6.

36. Badr C E, Niers J M, Tjon-Kon-Fat L A, Noske D P, Wurdinger T, Tannous B A. Real-time monitoring of nuclear factor kappaB activity in cultured cells and in animal models. Mol Imaging. 2009 September-October; 8(5):278-90.

37. Balsalobre A, Brown S A, Marcacci L, Tronche F, Kellendonk C, Reichardt H M, Schatz G, Schibler U. Resetting of circadian time in peripheral tissues by glucocorticoid signaling. Science. 2000 Sep. 29; 289(5488): 2344-7.

38. Binnewies M, Roberts E W, Kersten K, Chan V, Fearon D F, Merad M, Coussens L M, Gabrilovich D I, Ostrand-Rosenberg S, Hedrick C C, Vonderheide R H, Pittet M J, Jain R K, Zou W, Howcroft T K, Woodhouse E C, Weinberg R A, Krummel M F. Understanding the tumor immune microenvironment (TIME) for effective therapy. Nat Med. 2018 May; 24(5):541-550. doi: 10.1038/s41591-018-0014-x. Epub 2018 Apr. 23. Review.

39. Bollinger T, Leutz A, Leliayski A, Skrum L, Kovac J, Bonacina L, Benedict C, Lange T, Westermann J, Oster H, Solbach W. Circadian clocks in mouse and human CD4+ T cells. PLoS One. 2011; 6(12):e29801. doi: 10.1371/journal.pone.0029801. Epub 2011 Dec. 28.

40. Chen H, Ware T M B, Iaria J, Zhu H J. Live Cell Imaging of the TGF-β/Smad3 Signaling Pathway In Vitro and In Vivo Using an Adenovirus Reporter System. J Vis Exp. 2018 Jul. 30; (137). doi: 10.3791/57926.

41. Chung E, Yamashita H, Au P, Tannous B A, Fukumura D, Jain R K. Secreted *Gaussia* luciferase as a biomarker for monitoring tumor progression and treatment response of systemic metastases. PLoS One. 2009 Dec. 15; 4(12): e8316. doi: 10.1371/journal.pone.0008316.

42. Duarte D, Hawkins E D, Lo Celso C. The interplay of leukemia cells and the bone marrow microenvironment. Blood. 2018 Apr. 5; 131(14):1507-1511. doi:10.1182/blood-2017-12-784132. Epub 2018 Feb. 27.

43. Gaucher J, Montellier E, Sassone-Corsi P. Molecular Cogs: Interplay between Circadian Clock and Cell Cycle. Trends Cell Biol. 2018 May; 28(5):368-379. doi: 10.1016/j.tcb.2018.01.006. Epub 2018 Feb. 19.

44. Gekakis N, Staknis D, Nguyen H B, Davis F C, Wilsbacher L D, King D P, Takahashi J S, Weitz C J. Role of the CLOCK protein in the mammalian circadian mechanism. Science. 1998 Jun. 5; 280(5369):1564-9.

45. Ghim C M, Lee S K, Takayama S, Mitchell R J. The art of reporter proteins in science: past, present and future applications. BMB Rep. 2010 July; 43(7):451-60.

46. Gillessen M, Kwak P B, Tamayo A. A simple method to measure CLOCK-BMAL1 DNA binding activity in tissue and cell extracts. F1000Res. 2017 Aug. 3; 6:1316. doi: 10.12688/f1000research.11685.2.

47. Heipertz E L, Harper J, Lopez C A, Fikrig E, Hughes M E, Walker W E. Circadian Rhythms Influence the Severity of Sepsis in Mice via a TLR2-Dependent, Leukocyte-Intrinsic Mechanism. J Immunol. 2018 Jul. 1; 201(1):193-201. doi: 10.4049/jimmunol. 1701677. Epub 2018 May 14.

48. Hemmers S, Rudensky A Y. The Cell-Intrinsic Circadian Clock Is Dispensable for Lymphocyte Differentiation and Function. Cell Rep. 2015 Jun. 9; 11(9):1339-49. doi: 10.1016/j.celrep.2015.04.058. Epub 2015 May 21.

49. Hirota T, Lee J W, St John P C, Sawa M, Iwaisako K, Noguchi T, Pongsawakul P Y, Sonntag T, Welsh D K, Brenner D A, Doyle F J 3rd, Schultz P G, Kay S A. Identification of small molecule activators of cryptochrome. Science. 2012 Aug. 31; 337(6098):1094-7. doi: 10.1126/science.1223710. Epub 2012 Jul. 12.

50. Kiessling S, Beaulieu-Laroche L, Blum I D, Landgraf D, Welsh D K, Storch K F, Labrecque N, Cermakian N. Enhancing circadian clock function in cancer cells inhibits tumor growth. BMC Biol. 2017 Feb. 14; 15(1):13. doi: 10.1186/s12915-017-0349-7.

51. Krevvata M, Silva B C, Manavalan J S, Galan-Diez M, Kode A, Matthews B G, Park D, Zhang C A, Galili N, Nickolas T L, Dempster D W, Dougall W, Teruya-Feldstein J, Economides A N, Kalajzic I, Raza A, Berman E, Mukherjee S, Bhagat G, Kousteni S. Inhibition of leukemia cell engraftment and disease progression in mice by osteoblasts. Blood. 2014 Oct. 30; 124(18):2834-46. doi: 10.1182/blood-2013-07-517219. Epub 2014 Aug. 18.

52. Lamia K A. Ticking time bombs: connections between circadian clocks and cancer. F1000Res. 2017 Oct. 30; 6:1910. doi: 10.12688/f1000research.11770.1. eCollection 2017.

53. Li M, Chin L Y, Shukor S, Tamayo A, Maus M V, Parekkadan B. Closed loop bioreactor system for the ex vivo expansion of human T cells. Cytotherapy. 2019 January; 21(1):76-82. doi: 10.1016/j.jcyt.2018.10.009. Epub 2018 Nov. 27.

54. Lu P, Takai K, Weaver V M, Werb Z. Extracellular matrix degradation and remodeling in development and disease. Cold Spring Harb Perspect Biol. 2011 Dec. 1; 3(12). pii: a005058. doi: 10.1101/cshperspect.a005058.

55. McCubrey J A, Steelman L S, Chappell W H, Sun L, Davis N M, Abrams S L, Franklin R A, Cocco L, Evangelisti C, Chiarini F, Martelli A M, Libra M, Candido S, Ligresti G, Malaponte G, Mazzarino M C, Fagone P, Donia M, Nicoletti F, Polesel J, Talamini R, Bäsecke J, Mijatovic S, Maksimovic-Ivanic D, Michele M, Tafuri A, Dulińska-Litewka J, Laidler P, D'Assoro A B, Drobot L, Umezawa D, Montalto G, Cervello M, Demidenko Z N. Advances in targeting signal transduction pathways. Oncotarget. 2012 December; 3(12):1505-21. doi: 10.18632/oncotarget. 802.

56. Mei L, Fan Y, Lv X, Welsh D K, Zhan C, Zhang E E. Long-term in vivo recording of circadian rhythms in brains of freely moving mice. Proc Natl Acad Sci USA. 2018 Apr. 17; 115(16):4276-4281. doi: 10.1073/pnas.1717735115. Epub 2018 Apr. 2.

57. Mure L S, Le H D, Benegiamo G, Chang M W, Rios L, Jillani N, Ngotho M, Kariuki T, Dkhissi-Benyahya O, Cooper H M, Panda S. Diurnal transcriptome atlas of a primate across major neural and peripheral tissues. Science. 2018 Mar. 16; 359(6381). pii: eaao0318. doi: 10.1126/science.aao0318. Epub 2018 Feb. 8.

58. Padmanabhan K, Billaud M. Desynchronization of Circadian Clocks in Cancer: A Metabolic and Epigenetic Connection. Front Endocrinol (Lausanne). 2017 Jun. 19; 8:136. doi: 10.3389/fendo.2017.00136. eCollection 2017.

59. Nakajima Y, Kobayashi K, Yamagishi K, Enomoto T, Ohmiya Y. cDNA cloning and characterization of a secreted luciferase from the luminous Japanese ostracod, *Cypridina noctiluca*. Biosci Biotechnol Biochem. 2004 March; 68(3):565-70.

60. Nobis C C, Dubeau Laramée G, Kervezee L, Maurice De Sousa D, Labrecque N, Cermakian N. The circadian clock of CD8 T cells modulates their early response to vaccination and the rhythmicity of related signaling pathways. Proc Natl Acad Sci USA. 2019 Oct. 1; 116(40):20077-20086. doi: 10.1073/pnas.1905080116. Epub 2019 Sep. 16.

61. Partch C L, Green C B, Takahashi J S. Molecular architecture of the mammalian circadian clock. Trends Cell Biol. 2014 February; 24(2):90-9. doi: 10.1016/j.tcb.2013.07.002. Epub 2013 Aug. 1. Review.

62. Pick R, He W, Chen C S, Scheiermann C. Time-of-Day-Dependent Trafficking and Function of Leukocyte Subsets. Trends Immunol. 2019 June; 40(6):524-537. doi: 10.1016/j.it.2019.03.010. Epub 2019 May 17.

63. Puram R V, Kowalczyk M S, de Boer C G, Schneider R K, Miller P G, McConkey M, Tothova Z, Tejero H, Heckl D, Jaras M, Chen M C, Li H, Tamayo A, Cowley G S, Rozenblatt-Rosen O, Al-Shahrour F, Regev A, Ebert B L. Core Circadian Clock Genes Regulate Leukemia Stem Cells in AML. Cell. 2016 Apr. 7; 165(2):303-16. doi: 10.1016/j.cell.2016.03.015.

64. Richmond R C, Anderson E L, Dashti H S, Jones S E, Lane J M, Strand L B, Brumpton B, Rutter M K, Wood A R, Straif K, Relton C L, Munafò M, Frayling T M, Martin R M, Saxena R, Weedon M N, Lawlor D A, Smith G D. Investigating causal relations between sleep traits and risk of breast cancer in women: mendelian randomisation study. BMJ. 2019 Jun. 26; 365:12327. doi: 10.1136/bmj.12327

65. Saland E, Boutzen H, Castellano R, Pouyet L, Griessinger E, Larrue C, de Toni F, Scotland S, David M, Danet-Desnoyers G, Vergez F, Barreira Y, Collette Y, Récher C, Sarry J E. A robust and rapid xenograft model to assess efficacy of chemotherapeutic agents for human acute myeloid leukemia. Blood Cancer J. 2015 Mar. 20; 5(3):e297. doi: 10.1038/bcj.2015.19.

66. Schneider U, Schwenk H U, Bornkamm G. Characterization of EBV-genome negative "null" and "T" cell lines derived from children with acute lymphoblastic leukemia and leukemic transformed non-Hodgkin lymphoma. Int J Cancer. 1977 May 15; 19(5):621-6.

67. Sever R, Brugge J S. Signal transduction in cancer. Cold Spring Harb Perspect Med. 2015 Apr. 1; 5(4):a006098. doi: 10.1101/cshperspect.a006098

68. Shen K, Luk S, Elman J, Murray R, Mukundan S, Parekkadan B. Suicide Gene-Engineered Stromal Cells Reveal a Dynamic Regulation of Cancer Metastasis. Sci Rep. 2016 Feb. 19; 6:21239. doi: 10.1038/srep21239.

69. Silver A C, Arjona A, Hughes M E, Nitabach M N, Fikrig E. Circadian expression of clock genes in mouse macrophages, dendritic cells, and B cells. Brain Behav Immun. 2012 March; 26(3):407-13. doi: 10.1016/j.bbi.2011.10.001. Epub 2011 Oct. 13.

70. Sulli G, Rommel A, Wang X, Kolar M J, Puca F, Saghatelian A, Plikus M V, Verma I M, Panda S. Pharmacological activation of REV-ERBs is lethal in cancer and oncogene-induced senescence. Nature. 2018 Jan. 18; 553(7688):351-355. doi: 10.1038/nature25170. Epub 2018 Jan. 10.

71. Tamayo A G, Duong H A, Robles M S, Mann M, Weitz C J. Histone monoubiquitination by Clock-Bmall complex marks Perl and Per2 genes for circadian feedback. Nat Struct Mol Biol. 2015 October; 22(10):759-66. doi: 10.1038/nsmb.3076. Epub 2015 Aug. 31.

72. Verhaegent M, Christopoulos T K. Recombinant *Gaussia* luciferase. Overexpression, purification, and analytical application of a bioluminescent reporter for DNA hybridization. Anal Chem. 2002 Sep. 1; 74(17):4378-85.

73. Verlande A, Masri S. Circadian Clocks and Cancer: Timekeeping Governs Cellular Metabolism. Trends Endocrinol Metab. 2019 July; 30(7):445-458. doi: 10.1016/j.tem.2019.05.001. Epub 2019 May 30.

74. Vollmers C, Panda S, DiTacchio L. A high-throughput assay for siRNA-based circadian screens in human U2OS cells. PLoS One. 2008; 3(10):e3457. doi: 10.1371/journal.pone.0003457. Epub 2008 Oct. 20. Erratum in: PLoS ONE. 2009; 4(2).doi:10.1371/annotation/42c80798-20f2-4a1f-8c1d-290631231cf5.
75. Wang X, Xu Z, Tian Z, Zhang X, Xu D, Li Q, Zhang J, Wang T. The EF-1α promoter maintains high-level transgene expression from episomal vectors in transfected CHO-K1 cells. J Cell Mol Med. 2017 November; 21(11): 3044-3054. doi: 10.1111/jcmm.13216. Epub 2017 May 30.
76. Watanabe T, Enomoto T, Takahashi M, Honma S, Honma K, Ohmiya Y. Multichannel perfusion culture bioluminescence reporter system for long-term detection in living cells. Anal Biochem. 2010 Jul. 1; 402(1):107-9. doi: 10.1016/j.ab.2010.03.014. Epub 2010 Mar. 15.
77. Wu C, Suzuki-Ogoh C, Ohmiya Y. Dual-reporter assay using two secreted luciferase genes. Biotechniques. 2007 March; 42(3):290, 292.
78. Yamada Y, Nishide S Y, Nakajima Y, Watanabe T, Ohmiya Y, Honma K, Honma S. Monitoring circadian time in rat plasma using a secreted *Cypridina* luciferase reporter. Anal Biochem. 2013 Aug. 15; 439(2):80-7. doi: 10.1016/j.ab.2013.04.019. Epub 2013 Apr. 25.
79. Yu X, Rollins D, Ruhn K A, Stubblefield J J, Green C B, Kashiwada M, Rothman P B, Takahashi J S, Hooper L V. TH17 cell differentiation is regulated by the circadian clock. Science. 2013 Nov. 8; 342(6159):727-30. doi: 10.1126/science.1243884.
80. Zhang E E, Liu A C, Hirota T, Miraglia L J, Welch G, Pongsawakul P Y, Liu X, Atwood A, Huss J W 3rd, Janes J, Su A I, Hogenesch J B, Kay S A. A genome-wide RNAi screen for modifiers of the circadian clock in human cells. Cell. 2009 Oct. 2; 139(1):199-210. doi: 10.1016/j.cell.2009.08.031. Epub 2009 Sep. 17.
81. Zhang R, Lahens N F, Ballance H I, Hughes M E, Hogenesch J B. A circadian gene expression atlas in mammals: implications for biology and medicine. Proc Natl Acad Sci USA. 2014 Nov. 11; 111(45):16219-24. doi: 10.1073/pnas.1408886111. Epub 2014 Oct. 27.
82. Zielinski T, Moore A M, Troup E, Halliday K J, Millar A J. Strengths and limitations of period estimation methods for circadian data. PLoS One. 2014 May 8; 9(5): e96462. doi: 10.1371/journal.pone.0096462. eCollection 2014.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid comprising a sequence encoding parathyroid hormone (PTH), wherein the PTH sequence is downstream of a synthetic promoter comprising: (1) a Core Clock response element comprising SEQ ID NO: 1 and (2) a minimal promoter derived from CMV that is downstream of the Core Clock response element.

2. A vector comprising the isolated nucleic acid of claim 1.

3. An isolated cell comprising the isolated nucleic acid of claim 1, wherein the isolated cell expresses PTH.

4. The isolated nucleic acid of claim 1, wherein the Core Clock response element further comprises sequences from a Per1 promoter that flank the E-box elements.

5. The isolated nucleic acid of claim 1, wherein the minimal promoter comprises 31 base pairs.

6. The isolated nucleic acid of claim 1, wherein the synthetic promoter comprises SEQ ID NO:21.

7. The isolated nucleic acid of claim 1, wherein the synthetic promoter comprises SEQ ID NO:22.

8. The isolated nucleic acid of claim 1, wherein the nucleic acid further encodes a secretion signal.

9. The isolated nucleic acid of claim 8, wherein the secretion signal is from *Gaussia princeps* or *Cypridina noctiluca* luciferase, erythropoietin, follicle stimulating hormone, or insulin.

* * * * *